United States Patent
Pahutski, Jr. et al.

(10) Patent No.: US 9,113,631 B2
(45) Date of Patent: Aug. 25, 2015

(54) 1,3-DIARYL-SUBSTITUTED HETEROCYCLIC PESTICIDES

(71) Applicant: E I DU PONT DE NEMOURS AND COMPANY, Wilmington, DE (US)

(72) Inventors: Thomas Francis Pahutski, Jr., Elkton, MD (US); George Philip Lahm, Wilmington, DE (US); Moumita Kar, Hyderabad (IN); Omar Khaled Ahmad, Philadelphia, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/349,367

(22) PCT Filed: Oct. 25, 2012

(86) PCT No.: PCT/US2012/061948
§ 371 (c)(1),
(2) Date: Apr. 3, 2014

(87) PCT Pub. No.: WO2013/063282
PCT Pub. Date: May 2, 2013

(65) Prior Publication Data
US 2014/0249025 A1 Sep. 4, 2014

Related U.S. Application Data

(60) Provisional application No. 61/550,971, filed on Oct. 25, 2011.

(51) Int. Cl.
| | | |
|---|---|---|
| C07D 231/00 | (2006.01) |
| A01N 43/56 | (2006.01) |
| A01N 43/60 | (2006.01) |
| A01N 43/647 | (2006.01) |
| A01N 43/653 | (2006.01) |
| A01N 43/713 | (2006.01) |
| A01N 43/80 | (2006.01) |
| A01N 43/82 | (2006.01) |
| A01N 43/84 | (2006.01) |
| A01N 43/90 | (2006.01) |
| A01N 47/12 | (2006.01) |
| A01N 47/36 | (2006.01) |
| C07D 401/06 | (2006.01) |
| C07D 403/06 | (2006.01) |

(52) U.S. Cl.
CPC .......... *A01N 43/56* (2013.01); *A01N 43/60* (2013.01); *A01N 43/647* (2013.01); *A01N 43/653* (2013.01); *A01N 43/713* (2013.01); *A01N 43/80* (2013.01); *A01N 43/82* (2013.01); *A01N 43/84* (2013.01); *A01N 43/90* (2013.01); *A01N 47/12* (2013.01); *A01N 47/36* (2013.01); *C07D 401/06* (2013.01); *C07D 403/06* (2013.01)

(58) Field of Classification Search
CPC ........................................... A01N 47/36
USPC ........................................ 548/364.1
See application file for complete search history.

(56) References Cited

U.S. PATENT DOCUMENTS 7,566,709 B2 * 7/2009 Schiemann et al. ....... 514/236.5
8,742,110 B2 * 6/2014 Duffy et al. .................... 546/18

FOREIGN PATENT DOCUMENTS

| DE | 10315573 A1 * 10/2004 | ........ C07D 405/04 |
| WO | 2004089910 A1 | 10/2004 |
| WO | 2006134459 A1 | 12/2006 |

* cited by examiner

Primary Examiner — Nizal Chandrakumar
(74) Attorney, Agent, or Firm — Roman Kucharczyk

(57) ABSTRACT

Disclosed are compounds of Formula 1, N-oxides, and salts thereof,

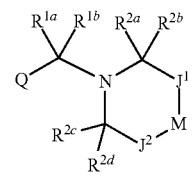

1 wherein
Q is

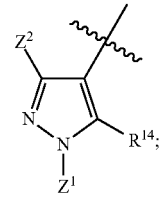

Q-1 and $Z^1$, $Z^2$, $J^1$, $J^2$, M, $R^{1a}$, $R^{1b}$, $R^{2a}$, $R^{2b}$, $R^{2c}$, $R^{2d}$ and $R^{14}$ are as defined in the disclosure. Also disclosed are compositions containing the compounds of Formula 1 and methods for controlling an invertebrate pest comprising contacting the invertebrate pest or its environment with a biologically effective amount of a compound or a composition of the invention.

9 Claims, No Drawings

1,3-DIARYL-SUBSTITUTED HETEROCYCLIC PESTICIDES

FIELD OF THE INVENTION

This invention relates to certain 1,3-diaryl-substituted heterocyclic compounds, their N-oxides, salts and their compositions suitable for agronomic and nonagronomic uses, and methods of their use for controlling invertebrate pests such as arthropods in both agronomic and nonagronomic environments.

BACKGROUND OF THE INVENTION

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, turf, wood products, and public health is also important. Many products are commercially available for these purposes, but the need continues for new compounds that are more effective, less costly, less toxic, environmentally safer or have different sites of action.

U.S. Pat. No. 7,566,709 B2 discloses pyrazole compounds of Formula i as 5-HT receptor antagonists for the treatment of psychoses and neurological disorders

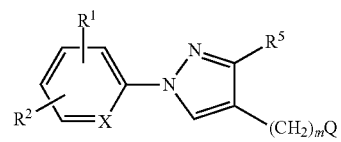

i wherein, inter alia, $R^1$ and $R^2$ are independently H, A or halogen, X is N or CH, $R^5$ is alkyl or an aromatic ring, A is alkyl, and Q is $NR^3R^4$ or a heteroatom-containing radical.

SUMMARY OF THE INVENTION

This invention is directed to a composition comprising a compound of Formula 1 (including all stereoisomers), N-oxides, and salts thereof:

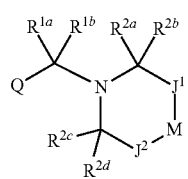

1 wherein
Q is

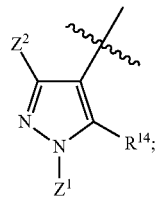

Q-1

$R^{1a}$ is H, cyano, $C_1$-$C_6$ alkyl, $C_3$-$C_6$ cycloalkyl, $C_1$-$C_6$ haloalkyl, C(O)OH, $C(O)R^{5a}$, $C(O)OR^{6a}$ or $C(O)NR^{7a}R^{8a}$;

$R^{1b}$ is H or $C_1$-$C_6$ alkyl;

$R^{2a}$ and $R^{2c}$ are each independently H, halogen, cyano, $C(X)R^5$, $C(O)OR^6$, $C(X)NR^7R^8$ or $S(O)_nR^{11}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$;

$R^{2b}$ and $R^{2d}$ are each independently H, halogen, cyano, nitro, $C(X)R^5$, $C(O)OR^6$, $C(X)NR^7R^8$, $NR^9R^{10}$, $S(O)_nR^{11}$ or $SO_2NR^9R^{10}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$; or phenyl or a 5- or 6-membered heteroaromatic ring, each ring unsubstituted or substituted with 1 to 3 $R^4$;

$J^1$ is a direct bond, $-C(R^{3a}R^{3b})-$ or $-C(R^{3a}R^{3b})C(R^{3a}R^{3b})$;

$J^2$ is a direct bond or $-C(R^{3c}R^{3d})-$;

M is $-C(R^{3e})A)-$, $-N(A^1)-$, $-O-$ or $-S(O)_n-$,

A is halogen, cyano, nitro, $C(X)R^5$, $C(O)OR^6$, $C(X)NR^7R^8$, $C(X)NR^{7b}R^8$, $NR^9R^{10}$, $S(O)_nR^{11}$ or $SO_2NR^9R^{10}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, $C_1$-$C_4$ alkyl, $C_1$-$C_4$ haloalkyl, $C(O)R^{5a}$, $C(O)OR^{6a}$, $C(O)NR^{7a}R^{8a}$, $NR^{9a}R^{10a}$, $OR^{12a}$ and $S(O)_nR^{11a}$; or phenyl, a 5- or 6-membered heteroaromatic ring or a 7- to 11-membered heteroaromatic ring system, each ring or ring system unsubstituted or substituted with 1 to 3 $R^4$;

$A^1$ is cyano, nitro, $C(X)R^5$, $C(O)OR^6$, $C(X)NR^7R^8$, $C(X)NR^{7b}R^8$, $NR^9R^{10}$, $S(O)_nR^{11}$ or $SO_2NR^9R^{10}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, $C_1$-$C_4$ alkyl, $C_1$-$C_4$ haloalkyl, $C(O)R^{5a}$, $C(O)OR^{6a}$, $C(O)NR^{7a}R^{8a}$, $NR^{9a}R^{10a}$, $OR^{12a}$ and $S(O)_nR^{11a}$; or phenyl, a 5- or 6-membered heteroaromatic ring or a 7- to 11-membered heteroaromatic ring system, each ring or ring system unsubstituted or substituted with 1 to 3 $R^4$; or benzyl unsubstituted or substituted with 1 to 3 $R^4$;

each $R^{3a}$ and $R^{3c}$ are each independently H, halogen, cyano, $C(X)R^5$, $C(O)OR^6$, $C(X)NR^7R^8$, $OR^{12}$ or $S(O)_nR^{11}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$;

each $R^{3b}$ and $R^{3d}$ are each independently H, halogen, cyano, nitro, $C(X)R^5$, $C(O)OR^6$, $C(X)NR^7R^8$, $NR^9R^{10}$, $OR^{12}$, $S(O)_nR^{11}$ or $SO_2NR^9R^{10}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$; or phenyl or a 5- or 6-membered heteroaromatic ring, each ring unsubstituted or substituted with 1 to 3 $R^4$;

$R^{3e}$ is H, halogen, cyano, nitro, $C(X)R^5$, $C(O)OR^6$, $C(X)NR^7R^8$, $NR^9R^{10}$, $OR^{12}$, $S(O)_nR^{11}$ or $SO_2NR^9R^{10}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$; or phenyl or a 5- or 6-membered heteroaromatic ring, each ring unsubstituted or substituted with 1 to 3 $R^4$; or $R^{3e}$ and A can be taken together with the carbon atom to which they are attached to form a 3- to 7-membered ring containing ring members selected from carbon atoms and up to 2 heteroatoms independently selected from one oxygen atom, one sulfur atom, and up to 2 nitrogen atoms, wherein up to 2 carbon atom ring members are independently selected from C(=O) and C(=S) and the sulfur atom ring member is selected from S, S(O) or S(O)$_2$, said ring being unsubstituted or substituted with up to 4 substituents independently selected from the group consisting of halogen, cyano and $C_1$-$C_4$ alkyl; or or when any two substituents independently selected from the group consisting of $R^{2a}$, $R^{2b}$, $R^{2c}$, $R^{2d}$, $R^{3a}$, $R^{3b}$, $R^{3c}$, $R^{3d}$ and $R^{3e}$ are $C_1$-$C_4$ alkyl, then said two substituents can be taken together to form a ring;

$Z^1$ is phenyl substituted with 1 to 4 $R^{4a}$; or $Z^1$ is a 5- or 6-membered heteroaromatic ring or an 8- to 10-membered heteroaromatic bicyclic ring system, each ring or ring system unsubstituted or substituted with 1 to 3 $R^{4a}$;

$Z^2$ is phenyl, unsubstituted or substituted with 1 to 4 $R^{4b}$; or $Z^2$ is a 5- or 6-membered heteroaromatic ring or an 8- to 10-membered heteroaromatic bicyclic ring system, each ring or ring system unsubstituted or substituted with 1 to 3 $R^{4b}$;

each $R^4$, $R^{4a}$ and $R^{4b}$ is independently halogen, cyano, nitro, $C(X)R^5$, $C(O)OR^6$, $C(X)NR^7R^8$, $NR^9R^{10}$, $OR^{12}$, $S(O)_nR^{11}$ or $SO_2NR^9R^{10}$; or $C_1$-$C_6$ alkyl, $C_2$-$C_6$ alkenyl, $C_1$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$; or phenyl or a 5- or 6-membered heteroaromatic ring, each ring unsubstituted or substituted with 1 to 3 $R^{13}$; and when two $R^4$, two $R^{4a}$ or two $R^{4b}$ groups are attached to adjacent carbon atoms, then said two $R^4$, two $R^{4a}$ or two $R^{4b}$ groups can be taken together with the carbon atoms to which they are attached to form a ring;

each $R^5$ is independently H; or $C_1$-$C_6$ alkyl, $C_2$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$; or phenyl or a 5- or 6-membered heteroaromatic ring, each ring unsubstituted or substituted with 1 to 3 $R^{13}$;

each $R^{5a}$ is independently $C_1$-$C_4$ alkyl, $C_1$-$C_4$ haloalkyl or $C_3$-$C_7$ cycloalkyl;

each $R^6$ is independently $C_1$-$C_6$ alkyl, $C_1$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$; or phenyl or a 5- or 6-membered heteroaromatic ring, each ring unsubstituted or substituted with 1 to 3 $R^{13}$;

each $R^{6a}$ is independently $C_1$-$C_4$ alkyl or $C_1$-$C_4$ haloalkyl;

each $R^7$ and $R^8$ is independently H; or $C_1$-$C_6$ alkyl, $C_2$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$; or phenyl or a 5- or 6-membered heteroaromatic ring, each ring unsubstituted or substituted with 1 to 3 $R^{13}$; or $R^7$ and $R^8$ can be taken together with the nitrogen atom to which they are attached to form a 5-, 6- or 7-membered ring;

each $R^{7a}$ and $R^{8a}$ is independently H, $C_1$-$C_4$ alkyl or $C_1$-$C_4$ haloalkyl;

$R^{7b}$ is $N(R^{7a})_2$, OH or $OR^{12a}$;

each $R^9$ and $R^{10}$ is independently H, $C(X)R^5$, $C(O)OR^6$ or $C(X)NR^7R^8$; or $C_1$-$C_6$ alkyl, $C_2$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$; or phenyl or a 5- or 6-membered heteroaromatic ring, each ring unsubstituted or substituted with 1 to 3 $R^3$; or $R^9$ and $R^{10}$ can be taken together with the nitrogen atom to which they are attached to form a 5-, 6- or 7-membered ring;

each $R^{9a}$ and $R^{10a}$ is independently H, $C(X)R^{5a}$, $C(O)OR^{6a}$, $C(X)NR^{7a}R^{8a}$, $C_1$-$C_4$ alkyl or $C_1$-$C_4$ haloalkyl;

each $R^{11}$ is independently $C_1$-$C_6$ alkyl, $C_2$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$; or phenyl or a 5- or 6-membered heteroaromatic ring, each ring unsubstituted or substituted with 1 to 3 $R^{13}$;

each $R^{11a}$ is independently $C_1$-$C_4$ alkyl or $C_1$-$C_4$ haloalkyl;

each $R^{12}$ is independently H; or $C_1$-$C_6$ alkyl, $C_2$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$; or phenyl or a 5- or 6-membered heteroaromatic ring, each ring unsubstituted or substituted with 1 to 3 $R^{13}$;

each $R^{12a}$ is independently H, $C_1$-$C_4$ alkyl or $C_1$-$C_4$ haloalkyl;

each $R^{13}$ is independently halogen, cyano, nitro, $C(X)R^{5a}$, $C(O)OR^{6a}$, $C(X)NR^{7a}R^{8a}$, $NR^{9a}R^{10a}$, $OR^{12a}$, $S(O)_nR^{11a}$ or $SO_2NR^{9a}R^{10a}$; or $C_1$-$C_6$ alkyl, $C_2$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$; provided that when two $R^{13}$ groups are attached to adjacent carbon atoms, then said two $R^{13}$ groups can be taken together with the carbon atoms to which they are attached to form a ring;

$R^{14}$ is H, halogen, cyano, nitro, $C(X)R^5$, $C(O)OR^6$, $C(X)NR^7R^8$, $NR^9R^{10}$, $OR^{12}$, $S(O)_nR^{11}$ or $SO_2NR^9R^{10}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$;

each X is independently O or S; and each n is independently 0, 1 or 2;

and at least one additional component selected from the group consisting of surfactants, solid diluents and liquid diluents. In one embodiment, this invention also provides a composition for controlling an invertebrate pest comprising a compound of Formula 1, an N-oxide, or a salt thereof, and at least one additional component selected from the group consisting of surfactants, solid diluents and liquid diluents, said composition further comprising at least one additional biologically active compound or agent.

This invention also provides a method for controlling an invertebrate pest comprising contacting the invertebrate pest or its environment with a biologically effective amount of a compound of Formula 1, an N-oxide, or a salt thereof (e.g., as a composition described herein). This invention also relates to such method wherein the invertebrate pest or its environment is contacted with a composition comprising a biologically effective amount of a compound of Formula 1, an N-oxide, or a salt thereof, and at least one additional component selected from the group consisting of surfactants, solid diluents and liquid diluents, said composition optionally further comprising a biologically effective amount of at least one additional biologically active compound or agent.

This invention also provides a method for controlling an invertebrate pest comprising contacting the invertebrate pest or its environment with a biologically effective amount of any of the aforesaid compositions wherein the environment is a plant.

This invention also provides a method for controlling an invertebrate pest comprising contacting the invertebrate pest or its environment with a biologically effective amount of any of the aforesaid compositions wherein the environment is an animal.

This invention also provides a method for controlling an invertebrate pest comprising contacting the invertebrate pest or its environment with a biologically effective amount of any of the aforesaid compositions wherein the environment is a seed.

This invention also provides a method for protecting a seed from an invertebrate pest comprising contacting the seed with a biologically effective amount of a compound of Formula 1, an N-oxide, or a salt thereof (e.g., as a composition described herein). This invention also relates to the treated seed.

This invention is also directed to compounds of Formula 1 (including all stereoisomers), N-oxides, and salts thereof, as described above, wherein $J^1$ is —$C(R^{3a}R^{3b})$—;

$J^2$ is —$C(R^{3c}R^{3d})$—; and $M$ is —$C(R^{3e})(A)$-;

provided that when A is $C(X)NR^7R^8$ and X is O, then both $R^7$ and $R^8$ are not H.

This invention is also directed to compounds of Formula 1 (including all stereoisomers), N-oxides, and salts thereof, as described above, wherein $R^{1a}$ and $R^{1b}$ are H;

$J^1$ is —$(R^{3a}R^{3b})$;

$J^2$ is a direct bond;

$M$ is —$C(R^{3e})(A)$-;

$R^{2a}$ and $R^{2c}$ are H;

$R^{2b}$ and $R^{2d}$ are each independently H, $C_1$-$C_4$ alkyl or $C_1$-$C_4$ haloalkyl;

$R^{3a}$ and $R^{3b}$ are H;

$R^{3e}$ is H, halogen, cyano, nitro, $C(X)R^5$, $C(O)OR^6$, $C(X)NR^7R^8$, $NR^9R^{10}$, $S(O)_nR^{11}$ or $SO_2NR^9R^{10}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$; or phenyl or a 5- or 6-membered heteroaromatic ring, each ring unsubstituted or substituted with 1 to 3 $R^4$;

A is cyano, $C(X)R^5$, $C(O)OR^6$, $C(X)NR^7R^8$, $C(X)NR^{7b}R^8$, $NR^9R^{10}$, $S(O)_nR^{11}$ or $SO_2NR^9R^{10}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, $C_1$-$C_4$ alkyl, $C_1$-$C_4$ haloalkyl, $C(O)R^{5a}$, $C(O)OR^{6a}$, $C(O)NR^{7a}R^{8a}$, $NR^{9a}R^{10a}$ and $S(O)_nR^{11a}$; or phenyl, a 5- or 6-membered heteroaromatic ring or a 7- to 11-membered heteroaromatic ring system, each ring or ring system unsubstituted or substituted with 1 to 3 $R^4$; provided that when A is $NHC(O)CH_3$ and $R^{3e}$ is H, then $Z^1$ is other than 2-fluorophenyl, 3-methylphenyl, 4-methylphenyl or 2,5-dimethylphenyl; or $R^{3e}$ and A can be taken together with the carbon atom to which they are attached to form a 3- to 7-membered ring containing ring members selected from carbon atoms and up to 2 heteroatoms independently selected from one oxygen atom, one sulfur atom, and up to 2 nitrogen atoms, wherein up to 2 carbon atom ring members are independently selected from C(=O) and C(=S) and the sulfur atom ring member is selected from S, S(O) or $S(O)_2$, said ring being unsubstituted or substituted with up to 4 substituents independently selected from the group consisting of halogen, cyano and $C_1$-$C_4$ alkyl;

provided that $R^{3e}$ and A are each other than $N(CH_3)_2$.

This invention is also directed to compounds of Formula 1p (including all stereoisomers), N-oxides, and salts thereof:

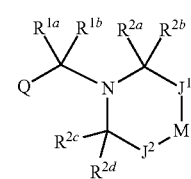

wherein
Q is

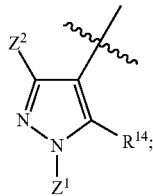

Q-1

$R^{1a}$ is H, cyano, $C_1$-$C_6$ alkyl, $C_3$-$C_6$ cycloalkyl, $C_1$-$C_6$ haloalkyl, C(O)OH, C(O)$R^{5a}$, C(O)O$R^{6a}$ or C(O)N$R^{7a}R^{8a}$;

$R^{1b}$ is H or $C_1$-$C_6$ alkyl;

$R^{2a}$ and $R^{2c}$ are each independently H, halogen, cyano, C(X)$R^5$, C(O)O$R^6$, C(X)N$R^7R^8$, O$R^{12}$ or S(O)$_n R^{11}$; or $C_1$-$C_6$ alkyl, $C_2$-$C_6$ alkenyl, $C_1$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, O$R^{12a}$, $C_1$-$C_4$ alkyl, $C_1$-$C_4$ haloalkyl and S(O)$_n R^{11a}$;

$R^{2b}$ and $R^{2d}$ are each independently H, halogen, cyano, nitro, C(X)$R^5$, C(O)O$R^6$, C(X)N$R^7R^8$, N$R^9R^{10}$, O$R^{12}$, S(O)$_n R^{11}$ or SO$_2$N$R^9R^{10}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, O$R^{12a}$, $C_1$-$C_4$ alkyl, $C_1$-$C_4$ haloalkyl and S(O)$_n R^{11a}$; or phenyl or a 5- or 6-membered heteroaromatic ring, each ring unsubstituted or substituted with 1 to 3 $R^4$;

$J^1$ is —C($R^{3a}R^{3b}$)—;

$J^2$ is C($R^{3c}R^{3d}$)—;

M is —C($R^{3e}$)(A)-;

A is cyano, nitro, C(X)$R^5$, C(O)O$R^6$, C(X)N$R^7R^8$, C(X)N$R^{7b}R^8$, N$R^9R^{10}$, S(O)$_n R^{11}$ or SO$_2$N$R^9R^{10}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, $C_1$-$C_4$ alkyl, $C_1$-$C_4$ haloalkyl, C(O)$R^{5a}$, C(O)O$R^{6a}$, C(O)N$R^{7a}R^{8a}$, N$R^{9a}R^{10a}$, O$R^{12a}$ and S(O)$_n R^{11a}$; or phenyl, a 5- or 6-membered heteroaromatic ring or a 7- to 11-membered heteroaromatic ring system, each ring or ring system unsubstituted or substituted with 1 to 3 $R^4$; provided that when A is C(X)N$R^7R^8$ and X is O, then both $R^7$ and $R^8$ are not H:

$R^{3a}$ and $R^{3c}$ are each independently H, halogen, cyano, C(X)$R^5$, C(O)O$R^6$, C(X)N$R^7R^8$, O$R^{12}$ or S(O)$_n R^{11}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, O$R^{12a}$, $C_1$-$C_4$ alkyl, $C_1$-$C_4$ haloalkyl and S(O)$_n R^{11a}$;

$R^{3b}$ and $R^{3d}$ are each independently H, halogen, cyano, nitro, C(X)$R^5$, C(O)O$R^6$, C(X)N$R^7R^8$, N$R^9R^{10}$, O$R^{12}$, S(O)$_n R^{11}$ or SO$_2$N$R^9R^{10}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, O$R^{12a}$, $C_1$-$C_4$ alkyl, $C_1$-$C_4$ haloalkyl and S(O)$_n R^{11a}$; or phenyl or a 5- or 6-membered heteroaromatic ring, each ring unsubstituted or substituted with 1 to 3 $R^4$;

$R^{3e}$ is H, halogen, cyano, nitro, C(X)$R^5$, C(O)O$R^6$, C(X)N$R^7R^8$, N$R^9R^{10}$, O$R^{12}$, N$R^9R^{10}$, S(O)$_n R^{11}$ or SO$_1$N$R^9R^{10}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, O$R^{12a}$, $C_1$-$C_4$ alkyl, $C_1$-$C_4$ haloalkyl and S(O)$_n R^{11a}$; or phenyl or a 5- or 6-membered heteroaromatic ring, each ring unsubstituted or substituted with 1 to 3 $R^4$;

or when any two substituents independently selected from the group consisting of $R^{2a}$, $R^{2b}$, $R^{2c}$, $R^{2d}$, $R^{3a}$, $R^{3b}$, $R^{3c}$, $R^{3d}$ and $R^{3e}$ are $C_1$-$C_4$ alkyl, then said two substituents can be taken together to form a ring;

$Z^1$ is phenyl substituted with 1 to 4 $R^4$; or $Z^1$ is a 5- or 6-membered heteroaromatic ring, each ring unsubstituted or substituted with 1 to 3 $R^4$;

$Z^2$ is phenyl substituted with 1 to 4 $R^4$; or $Z^2$ is a 5- or 6-membered heteroaromatic ring, each ring unsubstituted or substituted with 1 to 3 $R^4$;

each $R^4$ is independently halogen, cyano, nitro, C(X)$R^5$, C(O)O$R^6$, C(X)N$R^7R^8$, N$R^9R^{10}$, O$R^{12}$, S(O)$_n R^{11}$ or SO$_2$N$R^9R^{10}$; or $C_1$-$C_6$ alkyl, $C_2$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, O$R^{12a}$, $C_1$-$C_4$ alkyl, $C_1$-$C_4$ haloalkyl and S(O)$_n R^{11a}$;

each $R^5$ is independently H; or $C_1$-$C_6$ alkyl, $C_2$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, O$R^{12a}$, $C_1$-$C_4$ alkyl, $C_1$-$C_4$ haloalkyl and S(O)$_n R^{11a}$; or phenyl or a 5- or 6-membered heteroaromatic ring, each ring unsubstituted or substituted with 1 to 3 $R^{13}$;

each $R^{5a}$ is independently $C_1$-$C_4$ alkyl or $C_1$-$C_4$ haloalkyl;

each $R^6$ is independently $C_1$-$C_6$ alkyl, $C_2$-$C_6$ alkenyl, $C_1$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, O$R^{12a}$, $C_1$-$C_4$ alkyl, $C_1$-$C_4$ haloalkyl and S(O)$_n R^{11a}$; or phenyl or a 5- or 6-membered heteroaromatic ring, each ring unsubstituted or substituted with 1 to 3 $R^{13}$;

each $R^{6a}$ is independently $C_1$-$C_4$ alkyl or $C_1$-$C_4$ haloalkyl;

each $R^7$ and $R^8$ is independently H; or $C_1$-$C_6$ alkyl, $C_2$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, O$R^{12a}$, $C_1$-$C_4$ alkyl, $C_1$-$C_4$ haloalkyl and S(O)$_n R^{11a}$; or phenyl or a 5- or 6-membered heteroaromatic ring, each ring unsubstituted or substituted with 1 to 3 $R^{13}$;

each $R^{7a}$ and $R^{8a}$ is independently H, $C_1$-$C_4$ alkyl or $C_1$-$C_4$ haloalkyl;

each $R^{7b}$ is independently N($R^{7a}$)$_2$, OH or O$R^{12a}$;

each $R^9$ and $R^{10}$ is independently H, C(X)$R^5$, C(O)O$R^6$ or C(X)N$R^7R^8$; or $C_1$-$C_6$ alkyl, $C_2$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, O$R^{12a}$, $C_1$-$C_4$ alkyl, $C_1$-$C_4$ haloalkyl and S(O)$_n R^{11a}$; or phenyl or a 5- or 6-membered heteroaromatic ring, each ring unsubstituted or substituted with 1 to 3 $R^{13}$;

each $R^{9a}$ and $R^{10a}$ is independently H, $C(X)R^{5a}$, $C(O)OR^{6a}$, $C(X)NR^{7a}R^{8a}$, $C_1$-$C_4$ alkyl or $C_1$-$C_4$ haloalkyl;

each $R^{11}$ is independently $C_1$-$C_6$ alkyl, $C_1$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$; or phenyl or a 5- or 6-membered heteroaromatic ring, each ring unsubstituted or substituted with 1 to 3 $R^{13}$;

each $R^{11a}$ is independently $C_1$-$C_4$ alkyl or $C_1$-$C_4$ haloalkyl;

each $R^{12}$ is independently H; or $C_1$-$C_6$ alkyl, $C_2$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$; or phenyl or a 5- or 6-membered heteroaromatic ring, each ring unsubstituted or substituted with 1 to 3 $R^{13}$;

each $R^{12a}$ is independently H, $C_1$-$C_4$ alkyl or $C_1$-$C_4$ haloalkyl;

each $R^{13}$ is independently halogen, cyano, nitro, $C(X)R^{5a}$, $C(O)OR^{6a}$, $C(X)NR^{7a}R^{8a}$, $NR^{9a}R^{10a}$, $OR^{12a}$, $S(O)_nR^{11a}$ or $SO_2NR^{9a}R^{10a}$; or $C_1$-$C_6$ alkyl, $C_2$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$;

$R^{14}$ is H, halogen, cyano, nitro, $C(X)R^5$, $C(O)OR^6$, $C(X)NR^7R^8$, $NR^9R^{10}$, $OR^{12}$, $S(O)_nR^{11}$ or $SO_2NR^9R^{10}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$;

each X is independently O or S; and each n is independently 0, 1 or 2.

An embodiment of this invention also provides a composition comprising a compound of Formula 1p, an N-oxide, or a salt thereof, and at least one additional component selected from the group consisting of surfactants, solid diluents and liquid diluents. In one embodiment, this invention also provides a composition for controlling an invertebrate pest comprising a compound of Formula 1p, an N-oxide, or a salt thereof, and at least one additional component selected from the group consisting of surfactants, solid diluents and liquid diluents, said composition further comprising at least one additional biologically active compound or agent.

An embodiment of this invention provides a method for controlling an invertebrate pest comprising contacting the invertebrate pest or its environment with a biologically effective amount of a compound of Formula 1p, an N-oxide, or a salt thereof (e.g., as a composition described herein). This invention also relates to such method wherein the invertebrate pest or its environment is contacted with a composition comprising a biologically effective amount of a compound of Formula 1p, an N-oxide, or a salt thereof, and at least one additional component selected from the group consisting of surfactants, solid diluents and liquid diluents, said composition optionally further comprising a biologically effective amount of at least one additional biologically active compound or agent.

DETAILS OF THE INVENTION

As used herein, the terms "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising", it should be readily understood that (unless otherwise stated) the description should be interpreted to also describe such an invention using the terms "consisting essentially of" or "consisting of".

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" refers to a living organism of the Phylum Nematoda. The term "helminths" includes roundworms, heartworms, phytophagous nematodes (Nematoda), flukes (Tematoda), Acanthocephala and tapeworms (Cestoda).

In the context of this disclosure "invertebrate pest control" means inhibition of invertebrate pest development (including mortality, feeding reduction, and/or mating disruption), and related expressions are defined analogously.

The term "agronomic" refers to the production of field crops such as for food and fiber and includes the growth of corn, soybeans and other legumes, rice, cereal (e.g., wheat, oats, barley, rye, rice, maize), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (berries, cherries) and other specialty crops (e.g., canola, sunflower, olives).

The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

A wavy line in a structure fragment denotes the attachment point of the fragment to the remainder of the molecule. For example, when the variable Q in Formula 1 is defined as Q-1, the wavy line bisecting the bond in the 4-position of the pyrazole Q-1 means that the pyrazole Q-1 is attached to the remainder of the structure of Formula 1 at said 4-position, as shown below.

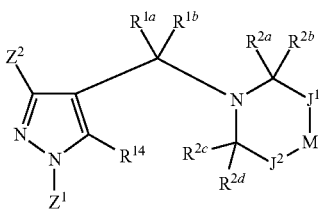

When the variable M is defined as —C($R^{3c}$)(A)-, this is equivalent to a carbon atom ring member substituted with one $R^{3c}$ and one A as shown below.

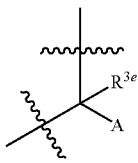

In the above recitations, the term "alkyl", used either alone or in compound words such as "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Cycloalkyl" includes, for example, cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. "Cycloalkenyl" includes groups such as cyclopentenyl and cyclohexenyl as well as groups with more than one double bond such as 1,3- and 1,4-cyclohexadienyl. The formula "C(O)CH($CH_2$)$_2$" represents a carbonyl group substituted with a cyclopropyl group.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $CF_3$, $CH_1Cl$, $CH_2CF_3$ and $CCl_2CF_3$.

The chemical abbreviations S(O) and S(=O) as used herein represent a sulfinyl moiety. The chemical abbreviations $SO_2$, S(O)$_2$ and S(=O)$_2$ as used herein represent a sulfonyl moiety. The chemical abbreviations C(O) and C(=O) as used herein represent a carbonyl moiety. The chemical abbreviations $CO_2$, C(O)O and C(=O)O as used herein represent an oxycarbonyl moiety. "CHO" means formyl.

When $A^1$ is benzyl substituted with 1 to 3 $R^4$, the $R^4$ substituent(s) may be attached to any available carbon atom of the benzyl group (i.e. the $R^4$ substituent(s) may be attached to the benzylic carbon atom or to any available carbon atom of the phenyl group).

The total number of carbon atoms in a substituent group is indicated by the "$C_i$-$C_j$" prefix where i and j are numbers from 1 to 8. For example, $C_1$-$C_4$ alkyl designates methyl through butyl.

When a group contains a substituent which can be hydrogen, for example $R^{1a}$ or $R^{1b}$, then when this substituent is taken as hydrogen, it is recognized that this is equivalent to said group being unsubstituted. When a variable group is shown to be optionally attached to a position, for example ($R^v$)$_r$ in U-36 of Exhibit 1 wherein r may be 0, then hydrogen can be at the position even if not recited in the variable group definition. When one or more positions on a group are said to be "not substituted" or "unsubstituted", then hydrogen atoms are attached to take up any free valency.

Unless otherwise indicated, a "ring" or "ring system" as a component of Formula 1 is carbocyclic or heterocyclic. The term "ring system" denotes two or more connected rings. The term "bicyclic ring system" denotes a ring system consisting of two rings sharing two or more common atoms.

A ring or a bicyclic ring system can be part of an extended ring system containing more than two rings wherein substituents on the ring or bicyclic ring system are taken together to form the additional rings, which may be in bicyclic relationships with other rings in the extended ring system.

The term "aromatic" indicates that each of the ring atoms is essentially in the same plane and has a p-orbital perpendicular to the ring plane, and that (4n+2)π electrons, where n is a positive integer, are associated with the ring or ring system to comply with Hückel's rule.

The terms "heterocyclic ring" or "heterocycle" denotes a ring wherein at least one of the atoms forming the ring backbone is other than carbon. Unless otherwise indicated, a heterocyclic ring can be a saturated, partially unsaturated, or fully unsaturated ring. "Saturated heterocyclic ring" refers to a heterocyclic ring containing only single bonds between ring members. "Partially saturated heterocyclic ring" refers a heterocyclic ring containing at least one double bond but which is not aromatic. The term "heteroaromatic ring" denotes a fully unsaturated aromatic ring in which at least one atom forming the ring backbone is not carbon. Typically a heteroaromatic ring contains no more than 4 nitrogens, no more than 1 oxygen and no more than 1 sulfur. Unless otherwise indicated, heteroaromatic rings can be attached through any available carbon or nitrogen by replacement of a hydrogen on said carbon or nitrogen. The term "heteroaromatic bicyclic ring system" denotes a ring system consisting of two fused rings, in which at least one of the two rings is a heteroaromatic ring as defined above.

When a radical is optionally substituted with listed substituents with the number of substituents stated (e.g., "up to 5"), then the radical may be unsubstituted or substituted with a number of substituents ranging up to the high number stated (e.g., "5"), and the attached substituents are independently selected from the substituents listed.

When a substituent is a ring or ring system, it can be attached to the remainder of Formula 1 through any available ring member, unless otherwise described.

The term "unsubstituted" in connection with a group such as a ring or ring system means the group does not have any substituents other than its one or more attachments to the remainder of Formula 1.

The phrase "phenyl or a 5- or 6-membered heteroaromatic ring, each ring unsubstituted or substituted with 1 to 3 $R^4$" means that each phenyl ring is unsubstituted or substituted with 1 to 3 $R^4$, each 5-membered heteroaromatic ring is unsubstituted or substituted with 1 to 3 $R^4$, and each 6-membered heteroaromatic ring is unsubstituted or substituted with 1 to 3 $R^4$.

When the number of optional substituents is not restricted by an expressed limitation (e.g., the phrase "unsubstituted or substituted with at least one substituent independently selected from"), it is understood to mean that the number of optional substituents can range from 0 up to the number of positions available. One skilled in the art will appreciate that while some substituents such as halogen can be present at every available position (for example, the $C_2F_5$ substituent is a $C_2$ alkyl group substituted with the maximum number of 5 fluorine atoms), practical factors such as cost and synthetic accessibility can limit the number of occurrences of other substituents. These limitations are part of the general synthetic knowledge known to those skilled in the art. Of note are embodiments wherein in the absence of expressed limitation of number of optional substituents, the number of optional substituents is up to 3 (i.e. 0, 1, 2 or 3) if accommodated by the number of available positions.

As noted above, substituents such as A, $Z^1$ or $Z^2$ can be (among others) a 5- or 6-membered heteroaromatic ring, optionally substituted with one or more substituents selected from a group of substituents as defined in the Summary of Invention. Examples of a 5- or 6-membered heteroaromatic ring optionally substituted with one or more substituents include the rings U-2 through U-61 illustrated in Exhibit 1 wherein $R^v$ is any substituent as defined in the Summary of the Invention (e.g., for $R^1$) and r is an integer from 0 to 5, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Exhibit 1

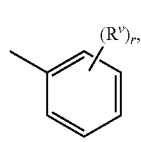
U-1

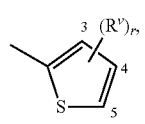
U-2

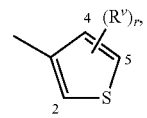
U-3

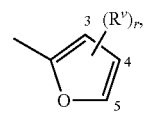
U-4

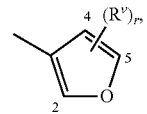
U-5

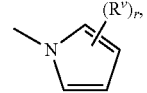
U-6

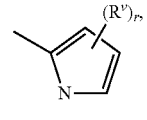
U-7

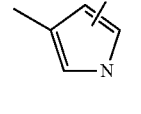
U-8

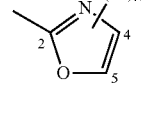
U-9

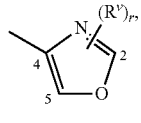
U-10

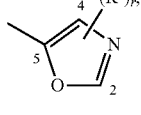
U-11

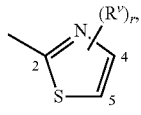
U-12

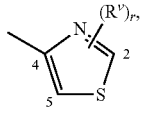
U-13

U-14

U-15 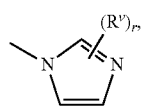
U-16 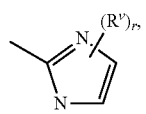
U-17 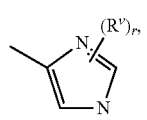
U-18 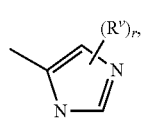
U-19 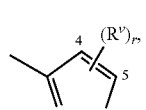
U-20 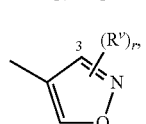
U-21 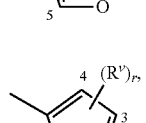
U-22 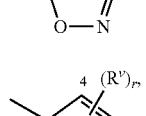
U-23 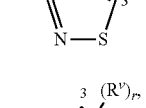
U-24 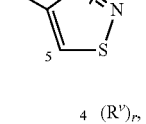
U-25 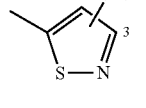
U-26 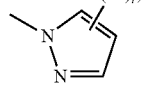
U-27 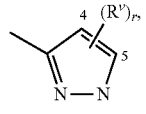
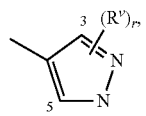
U-28 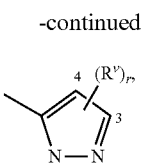
U-29 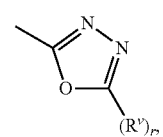
U-30 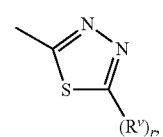
U-31 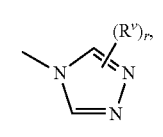
U-32 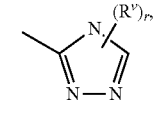
U-33 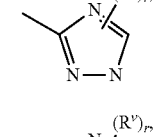
U-34 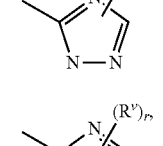
U-35 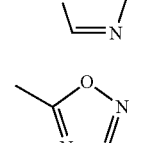
U-36 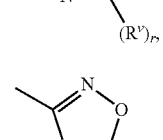
U-37 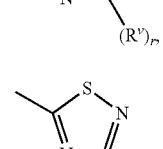
U-38 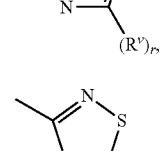
U-39

-continued

U-40 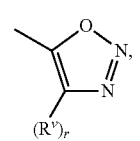

U-41 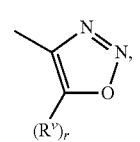

U-42 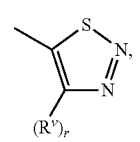

U-43 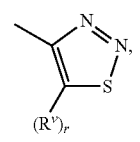

U-44 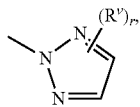

U-45 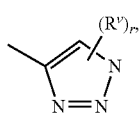

U-46 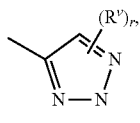

U-47 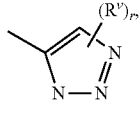

U-48 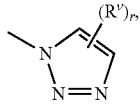

U-49 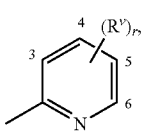

U-50 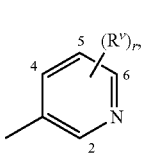

U-51 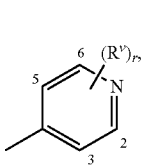

-continued

U-52 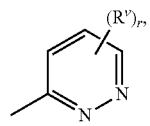

U-53 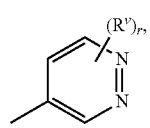

U-54 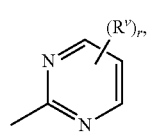

U-55 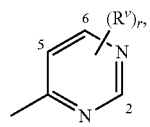

U-56 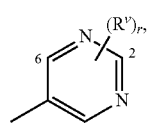

U-57 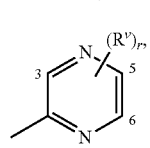

U-58 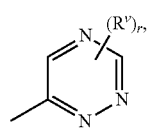

U-59 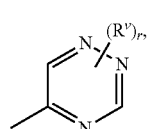

U-60 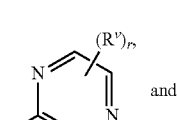 and

U-61 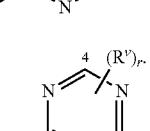

As noted above, substituents such as A can be (among others) a 7-, 8-, 9-, 10- or 11-membered heteroaromatic bicyclic ring system optionally substituted with up to 3 substituents selected from a group of substituents as defined in the Summary of Invention. Examples of an 8-, 9- or 10-membered heteroaromatic bicyclic ring system optionally substituted with up to 3 substituents include the ring systems H-1 through H-23 illustrated in Exhibit 2 wherein $R^v$ is any substituent as defined in the Summary of the Invention (e.g., for A) and r is an integer from 0 to 3, limited by the number of available positions on each H group.

Exhibit 2

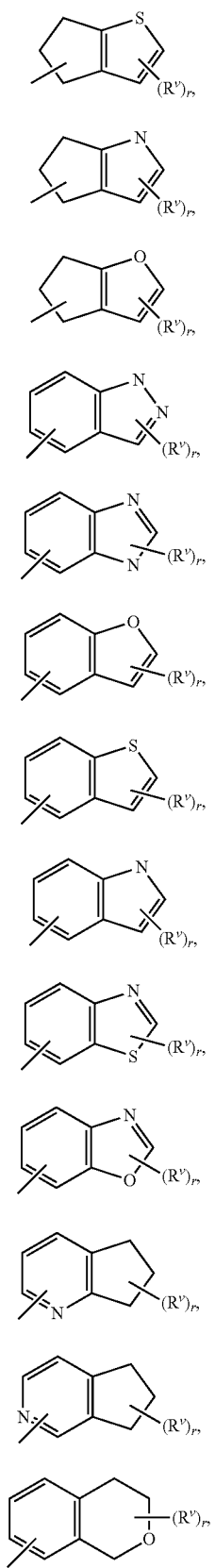

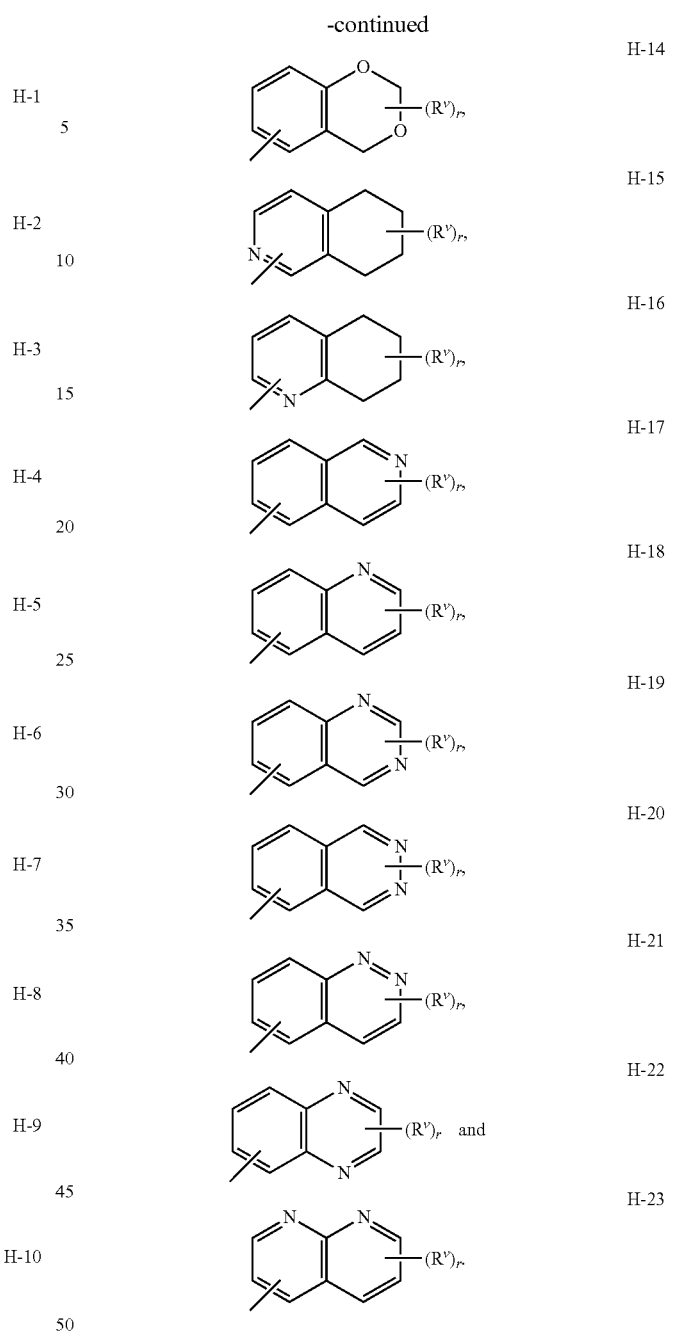

Although R$^v$ groups are shown in the structures U-1 through U-61 and H-1 through H-23, it is noted that they do not need to be present since they are optional substituents. The nitrogen atoms that require substitution to fill their valence are substituted with H or R$^v$. Note that when the attachment point between (R$^v$)$_r$ and the U or H group is illustrated as floating, (R$^v$)$_r$ can be attached to any available carbon atom or nitrogen atom of the U or H group. Note that when the attachment point on the U or H group is illustrated as floating, the U or H group can be attached to the remainder of Formula 1 through any available carbon or nitrogen of the U or H group by replacement of a hydrogen atom.

A wide variety of synthetic methods are known in the art to enable preparation of aromatic and nonaromatic heterocyclic rings and ring systems; for extensive reviews see the eight volume set of *Comprehensive Heterocyclic Chemistry*, A. R.

Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

Compounds of this invention can exist as one or more conformational isomers due to restricted bond rotation caused by steric hinderance. This invention comprises mixtures of conformational isomers. In addition, this invention includes compounds that are enriched in one conformer relative to others.

Compounds selected from Formula 1 (including all stereoisomers, N-oxides, and salts thereof) typically exist in more than one form, and Formula 1 thus includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice.

Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and 3-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry* vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding non-salt forms, salts share the biological utility of the nonsalt forms. Thus a wide variety of salts of the compounds of Formula 1 are useful for control of invertebrate pests. The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention relates to compounds selected from Formula 1, N-oxides, and salts thereof.

Embodiments of the present invention as described in the Summary of the Invention include those described below. In the following Embodiments Formula 1 includes stereoisomers, N-oxides, and salts thereof, and reference to "a compound of Formula 1" includes the definitions of substituents specified in the Summary of the Invention unless further defined in the Embodiments.

Embodiment 1

A compound of Formula 1, or a composition comprising a compound of Formula 1, wherein $R^{1a}$ is H, cyano, $C_1$-$C_6$ alkyl, $C_3$-$C_6$ cycloalkyl, $C_1$-$C_6$ haloalkyl, C(O)OH, C(O)$R^{5a}$, C(O)O$R^{6a}$ or C(O)N$R^{7a}R^{8a}$.

Embodiment 1a

A compound or composition of Embodiment 1 wherein $R^{1a}$ is H, cyano or $C_1$-$C_6$ alkyl.

Embodiment 1b

A compound or composition of Embodiment 1a wherein $R^{1a}$ is H, cyano or methyl.

Embodiment 1c

A compound or composition of Embodiment 1b wherein $R^{1a}$ is H.

Embodiment 2

A compound of Formula 1, or a composition comprising a compound of Formula 1, or any one of Embodiments 1 through 1c wherein $R^{1b}$ is H or methyl.

Embodiment 2a

A compound or composition of Embodiment 2 wherein $R^{1b}$ is H.

Embodiment 3

A compound of Formula 1, or a composition comprising a compound of Formula 1, wherein $R^{1a}$ and $R^{1b}$ are H.

Embodiment 4

A compound of Formula 1, or a composition comprising a compound of Formula 1, or any one of Embodiments 1 through 3 wherein $R^{2a}$, $R^{2b}$, $R^{2c}$, and $R^{2d}$ are each independently cyano, $C_1$-$C_6$ alkyl, $C(O)OR^6$.

Embodiment 4a

A compound of Formula 1, or a composition comprising a compound of Formula 1, or any one of Embodiments 1 through 3 wherein $R^{2a}$ and $R^{2c}$ are H; and $R^{2b}$ and $R^{2d}$ are each independently H, $C_1$-$C_4$ alkyl or $C_1$-$C_4$ haloalkyl.

Embodiment 4b

A compound or composition of Embodiment 4 wherein $R^{2a}$, $R^{2b}$, $R^{2c}$, and $R^{2d}$ are each H.

Embodiment 5

A compound of Formula 1, or a composition comprising a compound of Formula 1, or any one of Embodiments 1 through 4b wherein $J^1$ is —$C(R^{3a}R^{3b})$— and $J^2$ is a direct bond or —$C(R^{3c}R^{3d})$—.

Embodiment 5a

A compound or composition of Embodiment 5 wherein $J^1$ is —$C(R^{3a}R^{3b})$— and $J^2$ is a direct bond.

Embodiment 5b

A compound or composition of Embodiment 5 wherein $J^1$ is —$C(R^{3a}R^{3b})$— and $J^2$ is —$C(R^{3c}R^{3d})$—.

Embodiment 6

A compound of Formula 1, or a composition comprising a compound of Formula 1, or any one of Embodiments 1 through 5b wherein $R^{3a}$, $R^{3b}$, $R^{3c}$, and $R^{3d}$ are each independently H, halogen or $C_1$-$C_6$ alkyl.

Embodiment 6a

A compound or composition of Embodiment 6 wherein $R^{3a}$, $R^{3b}$, $R^{3c}$, and $R^{3d}$ are each independently H, F, Cl, Br or methyl.

Embodiment 6b

A compound or composition of Embodiment 6a wherein $R^{3a}$ and $R^{3b}$ are H.

Embodiment 6c

A compound or composition of Embodiment 6a wherein $R^{3a}$, $R^{3b}$, $R^{3c}$, and $R^{3d}$ are H.

Embodiment 7

A compound of Formula 1, or a composition comprising a compound of Formula 1, or any one of Embodiments 1 through 6c wherein M is —$C(R^{3e})(A)$- or —O—.

Embodiment 7a

A compound or composition of Embodiment 7 wherein M is —$C(R^{3e})(A)$-.

Embodiment 7b

A compound or composition of Embodiment 7a wherein M is —$C(R^{3e})(A)$-; provided that when A is $C(X)NR^7R^8$ and X is O, then both $R^7$ and $R^8$ are not H.

Embodiment 7c

A compound or composition of Embodiment 7 wherein M is —O—.

Embodiment 8

A compound of Formula 1, or a composition comprising a compound of Formula 1, or any one of Embodiments 1 through 7b wherein A is cyano, $C(X)R^5$, $C(O)OR^6$, $C(X)NR^7R^8$, $C(X)NR^{7b}R^8$, $NR^9R^{10}$, $S(O)_nR^{11}$ or $SO_2NR^9R^{10}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, $C_1$-$C_4$ alkyl, $C_1$-$C_4$ haloalkyl, $C(O)R^{5a}$, $C(O)OR^{6a}$, $C(O)NR^{7a}R^{8a}$, $NR^{9a}R^{10a}$ and $S(O)_nR^{11a}$; or phenyl, a 5- or 6-membered heteroaromatic ring or a 7- to 11-membered heteroaromatic ring system, each ring or ring system unsubstituted or substituted with 1 to 3 $R^4$; provided that when A is $NHC(O)CH_3$ and $R^{3e}$ is H, then $Z^1$ is other than 2-fluorophenyl, 3-methylphenyl, 4-methylphenyl or 2,5-dimethylphenyl; or $R^{3e}$ and A can be taken together with the carbon atom to which they are attached to form a 3- to 7-membered ring containing ring members selected from carbon atoms and up to 2 heteroatoms independently selected from one oxygen atom, one sulfur atom, and up to 2 nitrogen atoms, wherein up to 2 carbon atom ring members are independently selected from $C(=O)$ and $C(=S)$ and the sulfur atom ring member is selected from S, S(O) or $S(O)_2$, said ring being unsubstituted or substituted with up to 4 substituents independently selected from the group consisting of halogen, cyano and $C_1$-$C_4$ alkyl; provided that $R^{3e}$ and A are each other than $N(CH_3)_2$.

Embodiment 8a

A compound of Formula 1, or a composition comprising a compound of Formula 1, or any one of Embodiments 1 through 7b wherein A is cyano, $C(X)R^5$, $C(O)OR^6$, $C(X)NR^7R^8$ or $NR^9R^{10}$; or $C_1$-$C_6$ alkyl, $C_3$-$C_7$ cycloalkyl or $C_4$-$C_8$ cycloalkylalkyl, each unsubstituted or substituted with at least one substituent independently selected from the group consisting of halogen, cyano, nitro, $OR^{12a}$, $C_1$-$C_4$ alkyl, $C_1$-$C_4$ haloalkyl, $C(O)R^{5a}$, $C(O)OR^{6a}$, $C(O)NR^{7a}R^{8a}$ and $S(O)_nR^{11a}$; or phenyl or a 5- or 6-membered heteroaromatic ring, each ring unsubstituted or substituted with 1 to 3 $R^4$.

Embodiment 8b

A compound or composition of Embodiment 8a wherein A is cyano, $C(X)R^5$, $C(O)OR^6$, $C(X)NR^7R^8$ or $NR^9R^{10}$; or phenyl or a 5- or 6-membered heteroaromatic ring, each ring unsubstituted or substituted with 1 to 3 $R^4$.

Embodiment 8c

A compound or composition of Embodiment 8a wherein A is cyano, $C(X)R^5$, $C(O)OR^6$ or $NR^9R^{10}$; or phenyl or a 5- or 6-membered heteroaromatic ring, each ring unsubstituted or substituted with 1 to 3 $R^4$.

Embodiment 8d

A compound or composition of Embodiment 8c wherein A is cyano, $C(X)R^5$, $C(O)OR^6$ or $NR^9R^{10}$.

Embodiment 8e

A compound or composition of Embodiment 8d wherein A is cyano, $C(O)OR^{6a}$, $NHC(O)R^{5a}$ or $NHC(O)OR^{6a}$.

Embodiment 8f

A compound or composition of Embodiment 8c wherein A is cyano, $C(O)OR^{6a}$ or $NHC(O)R^{5a}$; or a 5-membered heteroaromatic ring, unsubstituted or substituted with 1 to 3 $R^4$.

Embodiment 8g

A compound or composition of Embodiment 8c wherein A is $NHC(O)R^{5a}$; or a 5- or 6-membered heteroaromatic ring, unsubstituted or substituted with 1 to 3 $R^4$.

Embodiment 8h

A compound or composition of Embodiment 8c wherein A is cyano, $NHC(O)R^{5a}$ or 1,3,4-oxadiazol-2-yl.

Embodiment 9

A compound of Formula 1, or a composition comprising a compound of Formula 1, or any one of Embodiments 1 through 8h wherein $R^{3e}$ is H, halogen, cyano, nitro, $C(X)R^5$, $C(O)OR^6$, $C(X)NR^7R^8$, $NR^9R^{10}$, $S(O)_nR^{11}$ or $SO_2NR^9R^{10}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$; or phenyl or a 5- or 6-membered heteroaromatic ring, each ring unsubstituted or substituted with 1 to 3 $R^4$.

Embodiment 9a

A compound or composition of Embodiment 9 wherein $R^{3e}$ is H, halogen, $C(X)R^5$ or $C(O)OR^6$; or $C_1$-$C_6$ alkyl, $C_2$-$C_6$ alkenyl or $C_3$-$C_6$ cycloalkenyl, each unsubstituted or substituted with at least one substituent independently selected from the group consisting of halogen, $OR^{12a}$, $C_1$-$C_4$ alkyl and $C_1$-$C_4$ haloalkyl; or phenyl or a 5- or 6-membered heteroaromatic ring, each ring unsubstituted or substituted with 1 to 3 $R^4$.

Embodiment 9b

A compound or composition of Embodiment 9a wherein $R^{3e}$ is H or halogen; or $C_1$-$C_6$ alkyl or $C_2$-$C_6$ alkenyl, each unsubstituted or substituted with at least one substituent independently selected from the group consisting of halogen and $C_1$-$C_4$ haloalkyl; or a 5- or 6-membered heteroaromatic ring, each ring unsubstituted or substituted with 1 to 3 $R^4$.

Embodiment 9c

A compound or composition of Embodiment 9b wherein $R^{3e}$ is H, halogen or $C_1$-$C_6$ alkyl.

Embodiment 9c1

A compound or composition of Embodiment 9c wherein $R^{3e}$ is H.

Embodiment 9d

A compound of Formula 1, or a composition comprising a compound of Formula 1, or any one of Embodiments 1 through 8h wherein $R^{3e}$ and A can be taken together with the carbon atom to which they are attached to form a 3- to 7-membered ring containing ring members selected from carbon atoms and up to 2 heteroatoms independently selected from one oxygen atom, one sulfur atom, and up to 2 nitrogen atoms, wherein up to 2 carbon atom ring members are independently selected from C(=O) and C(=S) and the sulfur atom ring member is selected from S, S(O) or $S(O)_2$, said ring being unsubstituted or substituted with up to 4 substituents independently selected from the group consisting of halogen, cyano and $C_1$-$C_4$ alkyl.

Embodiment 10

A compound of Formula 1, or a composition comprising a compound of Formula 1, or any one of Embodiments 1 through 9d wherein $Z^1$ is phenyl substituted with 1 to 4 $R^{4a}$.

Embodiment 10a

A compound of Formula 1, or a composition comprising a compound of Formula 1, or any one of Embodiments 1 through 9d wherein $Z^1$ is a 5-membered heteroaromatic ring, unsubstituted or substituted with 1 to 3 $R^{4a}$.

Embodiment 10b

A compound or composition of Embodiment 10a wherein $Z^1$ is furanyl, thienyl, oxazolyl or thiazolyl, each unsubstituted or substituted with 1 to 3 $R^{4a}$.

Embodiment 10c

A compound of Formula 1, or a composition comprising a compound of Formula 1, or any one of Embodiments 1 through 9d wherein $Z^1$ is a 6-membered heteroaromatic ring, unsubstituted or substituted with 1 to 3 $R^{4a}$.

Embodiment 10d

A compound or composition of Embodiment 10c wherein $Z^1$ is pyridinyl or pyrimidinyl, each unsubstituted or substituted with 1 to 3 $R^{4a}$.

Embodiment 11

A compound of Formula 1, or a composition comprising a compound of Formula 1, or any one of Embodiments 1 through 9d wherein $Z^2$ is phenyl substituted with 1 to 4 $R^{4b}$.

Embodiment 11a

A compound of Formula 1, or a composition comprising a compound of Formula 1, or any one of Embodiments 1 through 9d wherein $Z^2$ is a 5-membered heteroaromatic ring, unsubstituted or substituted with 1 to 3 $R^{4b}$.

Embodiment 11b

A compound or composition of Embodiment 11a wherein $Z^2$ is furanyl, thienyl, oxazolyl or thiazolyl, each unsubstituted or substituted with 1 to 3 $R^{4b}$.

Embodiment 11c

A compound of Formula 1, or a composition comprising a compound of Formula 1, or any one of Embodiments 1 through 9d wherein $Z^2$ is a 6-membered heteroaromatic ring, unsubstituted or substituted with 1 to 3 $R^{4b}$.

Embodiment 11d

A compound or composition of Embodiment 11c wherein $Z^2$ is pyridinyl or pyrimidinyl, each unsubstituted or substituted with 1 to 3 $R^{4b}$.

Embodiment 12

A compound of Formula 1, or a composition comprising a compound of Formula 1, or any one of Embodiments 1 through 1d wherein each $R^{4a}$ and each $R^{4b}$ is independently halogen, cyano, $C_1$-$C_6$ alkyl, $C_1$-$C_6$ haloalkyl or $C_1$-$C_6$ haloalkoxy.

Embodiment 12a

A compound of Formula 1, or a composition comprising a compound of Formula 1, or any one of Embodiments 1 through 11d wherein $Z^1$ is phenyl or pyridinyl, each substituted with 1 to 3 $R^{4a}$.

Embodiment 12b

A compound or composition of Embodiment 12a wherein each $R^{4a}$ is independently halogen, $C_1$-$C_4$ alkyl or $C_1$-$C_4$ haloalkyl.

Embodiment 12c

A compound of Formula 1, or a composition comprising a compound of Formula 1, or any one of Embodiments 1 through 11d wherein $Z^2$ is phenyl substituted with 1 to 3 $R^{4b}$.

Embodiment 12d

A compound or composition of Embodiment 12c wherein each $R^{4b}$ is independently halogen, $C_1$-$C_4$ alkyl or $C_1$-$C_4$ haloalkyl.

Embodiment 12e

A compound of Formula 1, or a composition comprising a compound of Formula 1, or any one of Embodiments 1 through 11d wherein $Z^1$ is phenyl or pyridinyl, each substituted with 1 to 3 $R^{4a}$; $Z^2$ is phenyl substituted with 1 to 3 $R^4b$; and each $R^{4a}$ and each $R^{4b}$ is independently halogen, $C_1$-$C_4$ alkyl or $C_1$-$C_4$ haloalkyl.

Embodiment 13

A compound of Formula 1, or a composition comprising a compound of Formula 1, or any one of Embodiments 1 through 12e wherein X is O.

Embodiment 13a

A compound of Formula 1, or a composition comprising a compound of Formula 1, or any one of Embodiments 1 through 12e wherein X is S.

Embodiments of this invention, including Embodiments 1-13a above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-13a above as well as any other embodiments described herein, and any combination thereof, pertain to the compositions and methods of the present invention.

Combinations of Embodiments 1-13a are illustrated by:

Embodiment A

A compound of Formula 1, or a composition comprising a compound of Formula 1 wherein
$J^1$ is C($R^{3a}R^{3b}$)—;
$J^2$ is —C($R^{3c}R^{3d}$)—; and
M is —C($R^{3e}$)(A)-;
provided that when A is C(X)N$R^7R^8$ and X is O, then both $R^7$ and $R^8$ are not H.

Embodiment B

The compound or composition of Embodiment A wherein
X is O;
$R^{1a}$ is H; and
$R^{1b}$ is H.

Embodiment C

The compound or composition of Embodiment B wherein
$R^{2a}$, $R^{2b}$, $R^{2c}$ and $R^{2d}$ are H;
$R^{3e}$ is H, halogen or $C_1$-$C_6$ alkyl; and
A is cyano, C(X)$R^5$, C(O)O$R^6$, C(X)N$R^7R^8$ or N$R^9R^{10}$; or phenyl or a 5- or 6-membered heteroaromatic ring, each ring unsubstituted or substituted with 1 to 3 $R^4$.

Embodiment D

The compound or composition of Embodiment C wherein
A is cyano, C(O)O$R^{6a}$ or NHC(O)$R^{5a}$; or a 5-membered heteroaromatic ring, unsubstituted or substituted with 1 to 3 $R^4$.

Embodiment E

A compound of Formula 1, or a composition comprising a compound of Formula 1 wherein
$R^{1a}$ and $R^{1b}$ are H;
$J^1$ is C($R^{3a}R^{3b}$);
$J^2$ is a direct bond;
M is —C($R^{3e}$)(A)-;
$R^{2a}$ and $R^{2c}$ are H;

$R^{2b}$ and $R^{2d}$ are each independently H, $C_1$-$C_4$ alkyl or $C_1$-$C_4$ haloalkyl;

$R^{3a}$ and $R^{3b}$ are H;

$R^{3e}$ is H, halogen, cyano, nitro, $C(X)R^5$, $C(O)OR^6$, $C(X)NR^7R^8$, $NR^9R^{10}$, $S(O)_nR^{11}$ or $SO_2NR^9R^{10}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$; or phenyl or a 5- or 6-membered heteroaromatic ring, each ring unsubstituted or substituted with 1 to 3 $R^4$;

A is cyano, $C(X)R^5$, $C(O)OR^6$, $C(X)NR^7R^8$, $C(X)NR^{7b}R^8$, $NR^9R^{10}$, $S(O)_nR^{11}$ or $SO_2NR^9R^{10}$; or $C_1$-$C_6$ alkyl, $C_2$-$C_6$ alkenyl, $C_1$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, $C_1$-$C_4$ alkyl, $C_1$-$C_4$ haloalkyl, $C(O)R^{5a}$, $C(O)OR^{6a}$, $C(O)NR^{7a}R^{8a}$, $NR^{9a}R^{10a}$ and $S(O)_nR^{11a}$; or phenyl, a 5- or 6-membered heteroaromatic ring or a 7- to 11-membered heteroaromatic ring system, each ring or ring system unsubstituted or substituted with 1 to 3 $R^4$; provided that when A is NHC(O)CH₃ and $R^{3e}$ is H, then $Z^1$ is other than 2-fluorophenyl, 3-methylphenyl, 4-methylphenyl or 2,5-dimethylphenyl; or $R^{3e}$ and A can be taken together with the carbon atom to which they are attached to form a 3- to 7-membered ring containing ring members selected from carbon atoms and up to 2 heteroatoms independently selected from one oxygen atom, one sulfur atom, and up to 2 nitrogen atoms, wherein up to 2 carbon atom ring members are independently selected from C(=O) and C(=S) and the sulfur atom ring member is selected from S, S(O) or $S(O)_2$, said ring being unsubstituted or substituted with up to 4 substituents independently selected from the group consisting of halogen, cyano and $C_1$-$C_4$ alkyl;

provided that $R^{3e}$ and A are each other than $N(CH_3)_2$.

Embodiment F

The compound or composition of Embodiment E wherein $R^{3e}$ is H, halogen, $C(X)R^5$ or $C(O)OR^6$; or $C_1$-$C_6$ alkyl, $C_2$-$C_6$ alkenyl or $C_3$-$C_6$ cycloalkenyl, each unsubstituted or substituted with at least one substituent independently selected from the group consisting of halogen, $OR^{12a}$, $C_1$-$C_4$ alkyl and $C_1$-$C_4$ haloalkyl; or phenyl or a 5- or 6-membered heteroaromatic ring, each ring unsubstituted or substituted with 1 to 3 $R^4$.

Embodiment G

The compound or composition of Embodiment F wherein $R^{3e}$ is H or halogen; or $C_1$-$C_6$ alkyl or $C_2$-$C_6$ alkenyl, each unsubstituted or substituted with at least one substituent independently selected from the group consisting of halogen and $C_1$-$C_4$ haloalkyl; or a 5- or 6-membered heteroaromatic ring, each ring unsubstituted or substituted with 1 to 3 $R^4$.

Embodiment H

The compound or composition of Embodiment G wherein A is $NHC(O)R^{51}$; or a 5- or 6-membered heteroaromatic ring, unsubstituted or substituted with 1 to 3 $R^4$.

Embodiment I

A compound of Formula 1, or a composition comprising a compound of Formula 1 wherein $J^1$ is —$C(R^{3a}R^{3b})$— and $J^2$ is a direct bond;

M is —$C(R^{3e})(A)$-;

$R^{3e}$ is H;

A is cyano, $C(O)OR^{6a}$, $NHC(O)R^{5a}$ or $NHC(O)OR^{6a}$;

$Z^1$ is phenyl or pyridinyl, each substituted with 1 to 3 $R^{4a}$;

each $R^{4a}$ is independently halogen, $C_1$-$C_4$ alkyl or $C_1$-$C_4$ haloalkyl;

$Z^2$ is phenyl substituted with 1 to 4 $R^4b$; and each $R^{4b}$ is independently halogen, $C_1$-$C_4$ alkyl or $C_1$-$C_4$ haloalkyl.

Embodiment J

A compound of Formula 1, or a composition comprising a compound of Formula 1 wherein $J^1$ is —$C(R^{3a}R^{3b})$— and $J^2$ is —$C(R^{3c}R^{3d})$—;

M is —$C(R^{3e})(A)$-;

$R^{3e}$ is H;

A is cyano, $C(O)OR^{68}$ or $NHC(O)R^{5a}$; or a 5-membered heteroaromatic ring, unsubstituted or substituted with 1 to 3 $R^4$;

$Z^1$ is phenyl or pyridinyl, each substituted with 1 to 3 $R^{4a}$;

each $R^{4a}$ is independently halogen, $C_1$-$C_4$ alkyl or $C_1$-$C_4$ haloalkyl;

$Z^2$ is phenyl substituted with 1 to 4 $R^{4b}$; and each $R^{4b}$ is independently halogen, $C_1$-$C_4$ alkyl or $C_1$-$C_4$ haloalkyl.

Embodiment K

A compound of Formula 1, or a composition comprising a compound of Formula 1 wherein $J^1$ is —$C(R^{3a}R^{3b})$— and $J^2$ is —$C(R^{3c}R^{3d})$;

M is —O—;

$Z^1$ is phenyl or pyridinyl, each substituted with 1 to 3 $R^{4a}$;

each $R^{4a}$ is independently halogen, $C_1$-$C_4$ alkyl or $C_1$-$C_4$ haloalkyl;

$Z^2$ is phenyl substituted with 1 to 4 $R^{4b}$; and each $R^{4b}$ is independently halogen, $C_1$-$C_4$ alkyl or $C_1$-$C_4$ haloalkyl.

Specific embodiments include compounds of Formula 1 selected from the group consisting of:

methyl 1-[[3-(4-fluorophenyl)-1-[3-(trifluoromethyl)phenyl]-1H-pyrazol-4-yl]methyl]-4-piperidinecarboxylate;

1-[[3-(4-fluorophenyl)-1-[3-(trifluoromethyl)phenyl]-1H-pyrazol-4-yl]methyl]-4-piperidinecarbonitrile;

1-[[1-(3,4-dichlorophenyl)-3-(4-fluorophenyl)-1H-pyrazol-4-yl]methyl]-4-piperidinecarbonitrile;

1-[[3-(2-fluorophenyl)-1-[4-(trifluoromethoxy)phenyl]-1H-pyrazol-4-yl]methyl]-4-piperidinecarbonitrile;

1-[[3-(2,4-difluorophenyl)-1-[4-(trifluoromethoxy)phenyl]-1H-pyrazol-4-yl]methyl]-4-piperidinecarbonitrile;

1-[[1-(4-chlorophenyl)-3-(2-fluorophenyl)-1H-pyrazol-4-yl]methyl]-4-piperidinecarbonitrile;

1-[[1-(3-chloro-4-fluorophenyl)-3-(2-fluorophenyl)-1H-pyrazol-4-yl]methyl]-4-piperidinecarbonitrile;

1-[[1-(4-bromophenyl)-3-(2-fluorophenyl)-1H-pyrazol-4-yl]methyl]-4-piperidinecarbonitrile;
1-[[3-(2-fluorophenyl)-1-[4-(trifluoromethyl)phenyl]-1H-pyrazol-4-yl]methyl]-4-piperidinecarbonitrile;
1-[[3-(2-fluorophenyl)-1-[5-(trifluoromethyl)-2-pyridinyl]-1H-pyrazol-4-yl]methyl]-4-piperidinecarbonitrile;
1-[[3-(2,6-difluorophenyl)-1-[4-(trifluoromethoxy)phenyl]-1H-pyrazol-4-yl]methyl]-4-piperidinecarbonitrile;
N-[(3S)-1-[[1-(3,4-dichlorophenyl)-3-(4-fluorophenyl)-1H-pyrazol-4-yl]methyl]-3-pyrrolidinyl]cyclopropanecarboxamide;
1-[[1-(3-chloro-4-fluorophenyl)-3-(2-fluorophenyl)-1H-pyrazol-4-yl]methyl]-4-(1,3,4-oxadiazol-2-yl)piperidine;
1-[[1-(3,4-dichlorophenyl)-3-(2-fluorophenyl)-1H-pyrazol-4-yl]methyl]-4-(1,3,4-oxadiazol-2-yl)piperidine;
1-[[1-(5-chloro-2-pyridinyl)-3-(2,4,6-trifluorophenyl)-1H-pyrazol-4-yl]methyl]-4-piperidinecarbonitrile;
1-[[1-(4-chlorophenyl)-3-(2-fluorophenyl)-1H-pyrazol-4-yl]methyl]-4-(1,3,4-oxadiazol-2-yl)piperidine;
1-[[1-(3-chloro-4-fluorophenyl)-3-(2-fluorophenyl)-1H-pyrazol-4-yl]methyl]-4-piperidinecarbonitrile;
1-[[1-(4-chloro-3-fluorophenyl)-3-(2-fluorophenyl)-1H-pyrazol-4-yl]methyl]-4-piperidinecarbonitrile;
N-[(3S)-1-[[1-(3,4-dichlorophenyl)-3-(4-fluorophenyl)-1H-pyrazol-4-yl]methyl]-3-pyrrolidinyl]acetamide;
1-[[1-(4-chlorophenyl)-3-(2-fluorophenyl)-1H-pyrazol-4-yl]methyl]-4-piperidinecarbonitrile;
1-[[1-(5-chloro-2-pyridinyl)-3-(2-fluorophenyl)-1H-pyrazol-4-yl]methyl]-4-piperidinecarbonitrile;
1-[[3-(2-fluorophenyl)-1-[3-(trifluoromethyl)phenyl]-1H-pyrazol-4-yl]methyl]-4-(1,3,4-oxadiazol-2-yl)piperidine;
1-[[1-(3-bromophenyl)-3-(2-fluorophenyl)-1H-pyrazol-4-yl]methyl]-4-(1,3,4-oxadiazol-2-yl)piperidine;
1-[[1-(5-bromo-2-pyridinyl)-3-(2-fluorophenyl)-1H-pyrazol-4-yl]methyl]-4-piperidinecarbonitrile;
1-[[1-(5-chloro-2-pyridinyl)-3-(2,4-difluorophenyl)-1H-pyrazol-4-yl]methyl]-4-piperidinecarbonitrile; and
1-[[3-(2-fluorophenyl)-1-[4-(trifluoromethoxy)phenyl]-1H-pyrazol-4-yl]methyl]-4-(1,3,4-oxadiazol-2-yl)piperidine.

Of note are compounds of Embodiment I wherein when A is NHC(O)$R^{5a}$, then the carbon atom to which A and $R^3$e are attached has the (S)-stereochemistry.

Embodiments of the present invention as described in the Summary of the Invention also include those described below. In the following Embodiments Formula 1p includes stereoisomers, N-oxides, and salts thereof, and reference to "a compound of Formula 1p" includes the definitions of substituents specified in the Summary of the Invention unless further defined in the Embodiments. The group $R^2$ represents instances of $R^{2a}$, $R^{2b}$, $R^{2c}$ and $R^{2d}$. The group $R^3$ represents instances of $R^{3a}$, $R^{3b}$, $R^{3c}$ and $R^{3d}$.

Embodiment 1

A compound of Formula 1p wherein $R^{1a}$ is H, cyano, $C_1$-$C_6$ alkyl, $C_3$-$C_6$ cycloalkyl, $C_1$-$C_6$ haloalkyl, C(O)OH, C(O)$R^{5a}$, C(O)O$R^{6a}$ or C(O)N$R^{7a}R^{8a}$.

Embodiment 1a

A compound of Embodiment 1 wherein $R^{1a}$ is H, cyano or $C_1$-$C_6$ alkyl.

Embodiment 1b

A compound of Embodiment 1a wherein $R^{1a}$ is H, cyano or methyl.

Embodiment 1c

A compound of Embodiment 1b wherein $R^{1a}$ is H.

Embodiment 2

A compound of Formula 1p or any one of Embodiments 1 through 1c wherein $R^{1b}$ is H or methyl.

Embodiment 2a

A compound of Embodiment 2 wherein $R^{1b}$ is H.

Embodiment 3

A compound of Formula 1p or any one of Embodiments 1 through 2a wherein A is cyano, C(X)$R^5$, C(O)O$R^6$, C(X)N$R^7R^8$ or N$R^9R^{10}$; or $C_1$-$C_6$ alkyl, $C_3$-$C_7$ cycloalkyl or $C_4$-$C_8$ cycloalkylalkyl, each unsubstituted or substituted with at least one substituent independently selected from the group consisting of halogen, cyano, nitro, O$R^{2a}$, $C_1$-$C_4$ alkyl, $C_1$-$C_4$ haloalkyl, C(O)$R^{5a}$, C(O)O$R^{6a}$, C(O)N$R^{7a}R^{8a}$ and S(O)$R^{11a}$; or phenyl or a 5- or 6-membered heteroaromatic ring, each ring unsubstituted or substituted with 1 to 3 $R^4$.

Embodiment 3a

A compound of Embodiment 3 wherein A is cyano, C(X)$R^5$, C(O)O$R^6$ or N$R^9R^{10}$; or phenyl or a 5- or 6-membered heteroaromatic ring, each ring unsubstituted or substituted with 1 to 3 $R^4$.

Embodiment 3b

A compound of Embodiment 3a wherein A is cyano, C(X)$R^5$, C(O)O$R^6$ or N$R^9R^{10}$.

Embodiment 3c

A compound of Embodiment 3b wherein A is cyano, C(O)O$R^{6a}$, NHC(O)$R^{5a}$ or NHC(O)O$R^{6a}$.

Embodiment 4

A compound of Formula 1p or any one of Embodiments 1 through 3c wherein each $R^2$ is independently cyano, $C_1$-$C_6$ alkyl, C(O)O$R^6$.

Embodiment 5

A compound of Formula 1p or any one of Embodiments 1 through 4 wherein $R^3$ is H, halogen or $C_1$-$C_6$ alkyl.

Embodiment 5a

A compound of Embodiment 5 wherein $R^3$ is H, F, Cl, Br or methyl.

Embodiment 5b

A compound of Embodiment 5a wherein $R^3$ is H.

Embodiment 6

A compound of Formula 1p or any one of Embodiments 1 through 5b wherein $Z^1$ is phenyl substituted with 1 to 4 $R^4$.

Embodiment 6a

A compound of Formula 1p or any one of Embodiments 1 through 5b wherein $Z^1$ is a 5-membered heteroaromatic ring, unsubstituted or substituted with 1 to 3 $R^4$.

Embodiment 6b

A compound of Embodiment 6a wherein $Z^1$ is furanyl, thienyl, oxazolyl or thiazolyl, each unsubstituted or substituted with 1 to 3 $R^4$.

Embodiment 6c

A compound of Formula 1p or any one of Embodiments 1 through 5b wherein $Z^1$ is a 6-membered heteroaromatic ring, unsubstituted or substituted with 1 to 3 $R^4$.

Embodiment 6d

A compound of Embodiment 6c wherein $Z^1$ is pyridinyl or pyrimidinyl, each unsubstituted or substituted with 1 to 3 $R^4$.

Embodiment 7

A compound of Formula 1p or any one of Embodiments 1 through 5b wherein $Z^2$ is phenyl substituted with 1 to 4 $R^4$.

Embodiment 7a

A compound of Formula 1p or any one of Embodiments 1 through 5b wherein $Z^2$ is a 5-membered heteroaromatic ring, unsubstituted or substituted with 1 to 3 $R^4$.

Embodiment 7b

A compound of Embodiment 7a wherein $Z^2$ is furanyl, thienyl, oxazolyl or thiazolyl, each unsubstituted or substituted with 1 to 3 $R^4$.

Embodiment 7c

A compound of Formula 1p or any one of Embodiments 1 through 5b wherein $Z^2$ is a 6-membered heteroaromatic ring, unsubstituted or substituted with 1 to 3 $R^4$.

Embodiment 7d

A compound of Embodiment 7c wherein $Z^2$ is pyridinyl or pyrimidinyl, each unsubstituted or substituted with 1 to 3 $R^4$.

Embodiment 8

A compound of Formula 1p or any one of Embodiments 1 through 7d wherein each $R^4$ is independently halogen, cyano, $C_1$-$C_6$ alkyl, $C_1$-$C_6$ haloalkyl or $C_1$-$C_6$ haloalkoxy.

Embodiment 9

A compound of Formula 1p or any one of Embodiments 1 through 6 wherein $Z^1$ is phenyl and one $R^4$ is in the 3- or 4-position.

Embodiment 9a

A compound of Embodiment 9 wherein $R^4$ is halogen, cyano, $C_1$-$C_6$ alkyl, $C_1$-$C_6$ haloalkyl or $C_1$-$C_6$ haloalkoxy.

Embodiment 10

A compound of Formula 1p or any one of Embodiments 1 through 7 wherein $Z^2$ is phenyl and one $R^4$ is in the 2-position.

Embodiment 10a

A compound of Embodiment 10 wherein $R^4$ is halogen or methyl.

Embodiment 11

A compound of Formula 1p or any one of Embodiments 1 through 10a wherein X is O.

Embodiment 11a

A compound of Formula 1p or any one of Embodiments 1 through 10a wherein X is S.

Embodiment 12

A compound of Formula 1p or any one of Embodiments 1 through 11a wherein m is 0, 1 or 2.

Embodiment 12a

A compound of Embodiment 12 wherein m is 1 or 2.

Embodiment 12b

A compound of Embodiment 12 wherein m is 0.

Embodiments of this invention, including Embodiments 1-12b above as well as any other embodiments described herein, can be combined in any manner, and the descriptions of variables in the embodiments pertain not only to the compounds of Formula 1p but also to the starting compounds and intermediate compounds useful for preparing the compounds of Formula 1p. In addition, embodiments of this invention, including Embodiments 1-12b above as well as any other embodiments described herein, and any combination thereof, pertain to the compositions and methods of the present invention.

Combinations of Embodiments 1-12b are illustrated by:

Embodiment A

A compound of Formula 1p wherein
X is O;
$R^{1a}$ is H; and
$R^{1b}$ is H.

Embodiment B

A compound of Embodiment A wherein
$R^3$ is H, halogen or $C_1$-$C_6$ alkyl;
A is cyano, $C(X)R^5$, $C(O)OR^6$, $C(X)NR^7R^8$ or $NR^9R^{10}$; or phenyl or a 5- or 6-membered heteroaromatic ring, each ring unsubstituted or substituted with 1 to 3 $R^4$; and
each $R^2$ is independently cyano, $C_1$-$C_6$ alkyl, $NHC(O)R^{5a}$ or $NHC(O)OR^{6a}$.

Embodiment C

A compound of Embodiment B wherein
A is cyano, $C(O)OR^{6a}$, $NHC(O)R^{5a}$ or $NHC(O)OR^{6a}$.

Specific embodiments include compounds of Formula 1p selected from the group consisting of:

methyl 1-[[3-(4-fluorophenyl)-1-[3-(trifluoromethyl)phenyl]-1H-pyrazol-4-yl]methyl]-4-piperidinecarboxylate;

1-[[3-(4-fluorophenyl)-1-[3-(trifluoromethyl)phenyl]-1H-pyrazol-4-yl]methyl]-4-piperidinecarbonitrile;

1-[[1-(3,4-dichlorophenyl)-3-(4-fluorophenyl)-1H-pyrazol-4-yl]methyl]-4-piperidinecarbonitrile;

1-[[3-(2-fluorophenyl)-1-[4-(trifluoromethoxy)phenyl]-1H-pyrazol-4-yl]methyl]-4-piperidinecarbonitrile;

1-[[3-(2,4-difluorophenyl)-1-[4-(trifluoromethoxy)phenyl]-1H-pyrazol-4-yl]methyl]-4-piperidinecarbonitrile;

1-[[1-(4-chlorophenyl)-3-(2-fluorophenyl)-1H-pyrazol-4-yl]methyl]-4-piperidinecarbonitrile;

1-[[1-(3-chloro-4-fluorophenyl)-3-(2-fluorophenyl)-1H-pyrazol-4-yl]methyl]-4-piperidinecarbonitrile;

1-[[1-(4-bromophenyl)-3-(2-fluorophenyl)-1H-pyrazol-4-yl]methyl]-4-piperidinecarbonitrile;

1-[[3-(2-fluorophenyl)-1-[4-(trifluoromethyl)phenyl]-1-pyrazol-4-yl]methyl]-4-piperidinecarbonitrile;

1-[[3-(2-fluorophenyl)-1-[5-(trifluoromethyl)-2-pyridinyl]-1H-pyrazol-4-yl]methyl]-4-piperidinecarbonitrile; and 1-[[3-(2,6-difluorophenyl)-1-[4-(trifluoromethoxy)phenyl]-1H-pyrazol-4-yl]methyl]-4-piperidinecarbonitrile.

Of note is that compounds of this invention are characterized by favorable metabolic and/or soil residual patterns and exhibit activity controlling a spectrum of agronomic and nonagronomic invertebrate pests.

Of particular note, for reasons of invertebrate pest control spectrum and economic importance, protection of agronomic crops from damage or injury caused by invertebrate pests by controlling invertebrate pests are embodiments of the invention. Compounds of this invention because of their favorable translocation properties or systemicity in plants also protect foliar or other plant parts which are not directly contacted with a compound of Formula 1 or a composition comprising the compound.

Also noteworthy as embodiments of the present invention are compositions comprising a compound of any of the preceding Embodiments, as well as any other embodiments described herein, and any combinations thereof, and at least one additional component selected from the group consisting of a surfactant, a solid diluent and a liquid diluent, said compositions optionally further comprising at least one additional biologically active compound or agent.

Further noteworthy as embodiments of the present invention are compositions for controlling an invertebrate pest comprising a compound (i.e. in a biologically effective amount) of any of the preceding Embodiments, as well as any other embodiments described herein, and any combinations thereof, and at least one additional component selected from the group consisting of a surfactant, a solid diluent and a liquid diluent, said compositions optionally further comprising at least one additional biologically active compound or agent (i.e. in a biologically effective amount).

Embodiments of the invention further include methods for controlling an invertebrate pest comprising contacting the invertebrate pest or its environment with a biologically effective amount of a compound of any of the preceding Embodiments (e.g., as a composition described herein).

Embodiments of the invention also include a composition comprising a compound of any of the preceding Embodiments in the form of a soil drench liquid formulation.

Embodiments of the invention further include methods for controlling an invertebrate pest comprising contacting the soil with a liquid composition as a soil drench comprising a biologically effective amount of a compound of any of the preceding Embodiments.

Embodiments of the invention also include a spray composition for controlling an invertebrate pest comprising a compound (i.e. in a biologically effective amount) of any of the preceding Embodiments and a propellant. Embodiments of the invention further include a bait composition for controlling an invertebrate pest comprising a compound (i.e. in a biologically effective amount) of any of the preceding Embodiments, one or more food materials, optionally an attractant, and optionally a humectant. Embodiments of the invention also include a device for controlling an invertebrate pest comprising said bait composition and a housing adapted to receive said bait composition, wherein the housing has at least one opening sized to permit the invertebrate pest to pass through the opening so the invertebrate pest can gain access to said bait composition from a location outside the housing, and wherein the housing is further adapted to be placed in or near a locus of potential or known activity for the invertebrate pest.

Embodiments of the invention also include a method for protecting a seed from an invertebrate pest comprising contacting the seed with a biologically effective amount of a compound of any of the preceding Embodiments (e.g., as a composition described herein).

Embodiments of the invention also include methods for protecting an animal from an invertebrate parasitic pest comprising administering to the animal a parasiticidally effective amount of a compound of any of the preceding Embodiments.

Embodiments of the invention also include methods for controlling an invertebrate pest comprising contacting the invertebrate pest or its environment with a biologically effective amount of a compound of Formula 1, an N-oxide, or a salt thereof, (e.g., as a composition described herein), provided that the methods are not methods of medical treatment of a human or animal body by therapy.

This invention also relates to such methods wherein the invertebrate pest or its environment is contacted with a composition comprising a biologically effective amount of a compound of Formula 1, an N-oxide, or a salt thereof, and at least one additional component selected from the group consisting of surfactants, solid diluents and liquid diluents, said composition optionally further comprising a biologically effective amount of at least one additional biologically active compound or agent, provided that the methods are not methods of medical treatment of a human or animal body by therapy.

One or more of the following methods and variations as described in Schemes 1-11 can be used to prepare the compounds of Formula 1. The definitions of $R^{1a}$, $R^{1b}$, $R^{2a}$, $R^{2b}$, $R^{2c}$, $R^{2d}$, $R^{14}$, $Z^1$, $Z^2$, $J^1$, $J^2$ and M in the compounds of Formulae 1-10 below are as defined above in the Summary of the Invention unless otherwise noted. Ambient or room temperature is defined as about 20-25° C.

Compounds of Formula 1a (compounds of Formula 1 wherein $R^{1a}$ is H, alkyl, cycloalkyl or haloalkyl, and $R^{1b}$ is H) can be prepared by reductive amination of appropriately substituted carbonyl compounds of Formula 2 with optionally substituted cyclic amines of Formula 3 in the presence of reducing reagents such as sodium triacetoxyborohydride (see, for example, Li, J. et al. *Bioorganic & Medicinal Chemistry Letters* 2010, 20(16), pages 4932-4935). The reaction is typically carried out in an inert organic solvent such as dichloromethane at room temperature. This method is shown in Scheme 1 and exemplified in Step C of Synthesis Example 2.

Scheme 1

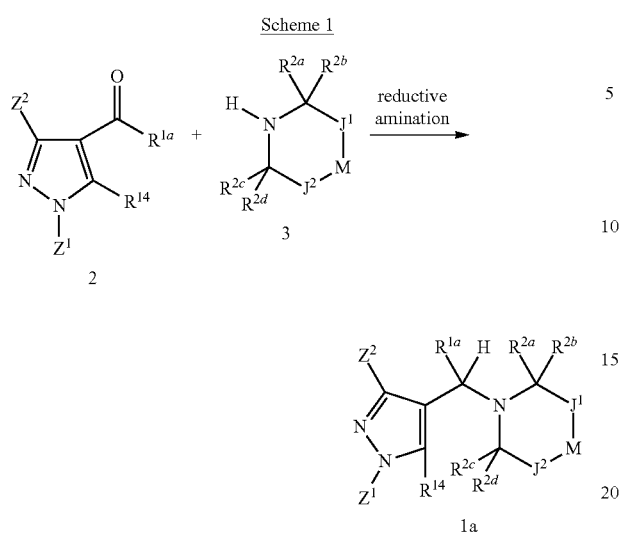

$R^{1a}$ is H, alkyl, cycloalkyl or haloalkyl

Compounds of Formula 1a can also be prepared by the method shown in Scheme 2. In this method, an appropriately substituted carbonyl compound of Formula 2 is reduced with a reducing agent such as lithium aluminum hydride in an inert solvent such as diethyl ether (see, for example, De Luca, Lidia; et al. *Synlett* 2004, 13, pages 2299-2302) to yield an intermediate alcohol of Formula 4a. The alcohol is converted to the corresponding bromide of Formula 5 by treatment with a reagent such as HBr or PBr₃ (see, for example, Toja, Emilio; et al. *European Journal of Medicinal Chemistry* 1982, 17(3), pages 223-227). Reaction of the bromide of Formula 5 with an amine of Formula 3 provides the compound of Formula 1a (see, for example, Lee, Suk Ho, et al. *Journal of Medicinal Chemistry* 2008, 51(22), pages 7216-7233). This method is exemplified in Step C of Synthesis Example 1.

Scheme 2

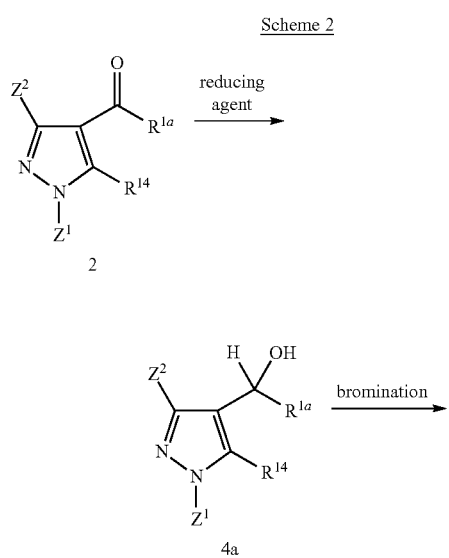

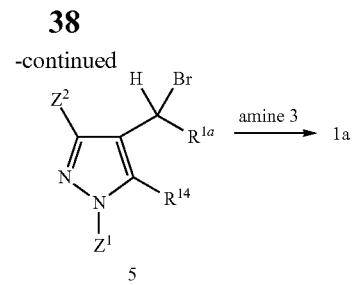

Compounds of Formula 2 wherein $R^{14}$ is H can be prepared by treating the appropriately substituted hydrazone of Formula 6 under anhydrous conditions with cyanuric chloride and N,N-dimethylformamide (see, for example, De Luca, Lidia; et al. *Synlett* 2004, 13, pages 2299-2302). This method is shown in Scheme 3 and exemplified in Step B of

Scheme 3

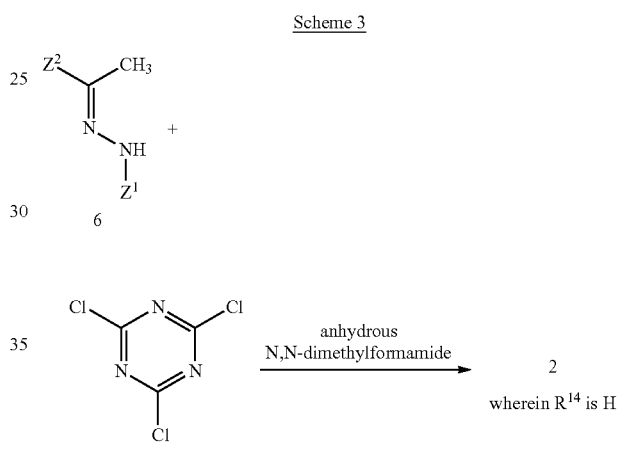

Compounds of Formula 6 can be prepared by a variety of methods known in the art, such as the condensation of an acetophenone of Formula 7 with an aryl hydrazine of Formula 8 in refluxing ethanol (see, for example, Goeker, Hakan; et al. *Journal of Heterocyclic Chemistry* 2009, 46(5), pages 936-948). This method is shown in Scheme 4 and exemplified in Step A of Synthesis Example 1 and Step A of Synthesis Example 2.

Scheme 4

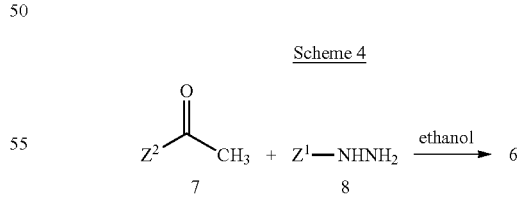

Compounds of Formulae 3, 7 and 8 are either commercially available or can be prepared by well-established methods known in the art.

Compounds of Formula 1 b (compounds of Formula 1 wherein $R^{1a}$ is H, alkyl, cycloalkyl or haloalkyl, and $R^{1b}$ is alkyl) can be prepared from compounds of Formula 2 by the method shown in Scheme 5. In this method, treatment of a compound of Formula 2 with a Grignard reagent (i.e.

R$^{1b}$MgX) under reaction conditions known in the art provides the intermediate compound of Formula 4b (see, for example, *Journal of Medicinal Chemistry* 2008, 51(22), pages 7216-7233). Conversion of the compound of Formula 4b to the compound of Formula 1 b is as described in Scheme 2.

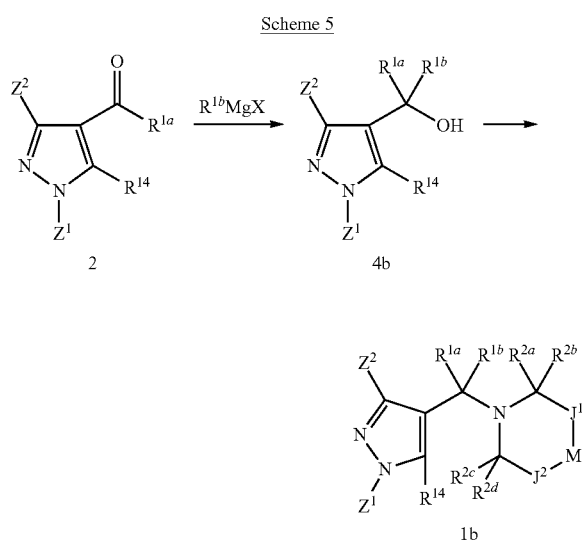

R$^{1a}$ is H, alkyl, cycloalkyl or haloalkyl
R$^{1b}$ is alkyl

Compounds of Formula 1 d (compounds of Formula 1 wherein R$^{1a}$ is CN and R$^{1b}$ is H) can be prepared from compounds of Formula 2 by the method shown in Scheme 6. In this method, treatment of a compound of Formula 2 with KCN in the presence of an amine of Formula 3 and an acid such as p-toluenesulfonic acid provides the compound of Formula 1 d.

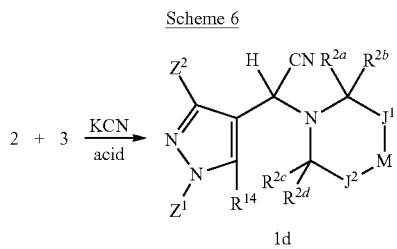

The compounds of Formula 1 d are useful in the preparation of carboxylic acid, ester and amide derivatives (see, for example, *Arzneimittels-Forschung* 1981, 31(4), pages 649-655). Scheme 7 illustrates the preparation of a carboxylic acid derivative of Formula 1e from the compound of Formula 1 d by treatment with aqueous sulfuric acid; the compound of Formula 1e can in turn be transformed into an ester of Formula 1f or an amide of Formula 1 g by methods known in the art.

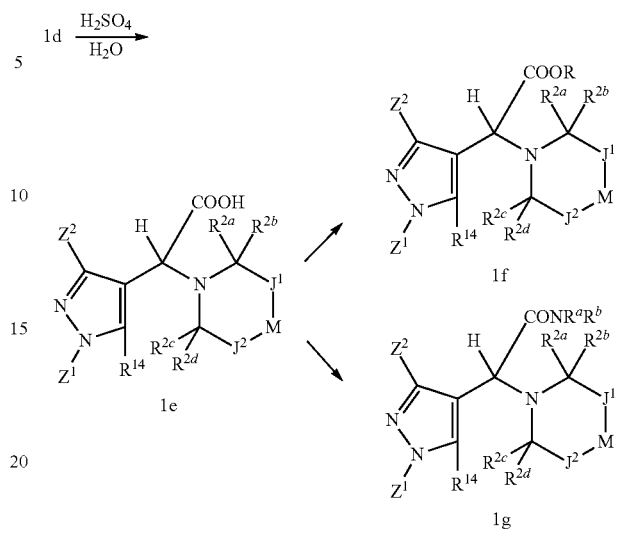

Compounds of Formula 1 wherein R$^{1a}$ is a cyano, ester or amide group and R$^{1b}$ is alkyl can be prepared by alkylation of the corresponding compounds wherein R$^{1b}$ is H by treatment with a strong base followed by an alkylating agent (see, for example, WO 2006/134459).

Compounds of Formula 1i (compounds of Formula 1 wherein R$^{14}$ is Br) can be prepared from compounds of Formula 1 h (compounds of Formula 1 wherein R$^{14}$ is H) by bromination at the R$^{14}$ position of the pyrazole as shown in Scheme 8. Typical bromination methods include reaction with bromine and sodium carbonate in dichloromethane at temperatures below 0° C. (see, for example, *Bioorganic Medicinal Chemistry Letters* 2008, 18(2), pages 509-512). The intermediate bromide of Formula ii can be further transformed to a variety of other functional groups by methods known in the art such as cross-coupling reactions (see, for example, *Journal of Medicinal Chemistry* 2005, 48(4), pages 1132-1144).

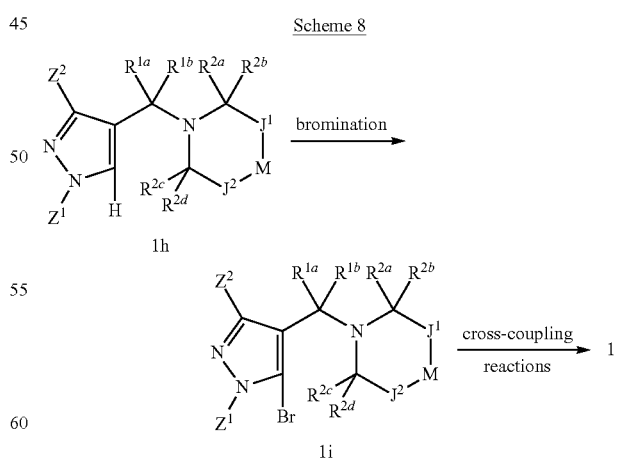

Compounds of Formula 1 j (compounds of Formula 1 wherein R$^{14}$ is halogen) can be prepared by reductive amination of compounds of Formula 2a (compounds of Formula 2 wherein R$^{14}$ is halogen) with cyclic amines of Formula 3 and reducing agents such as sodium triacetoxyborohydride (see, for example, *Bioorganic & Medicinal Chemistry Letters* 2010, 20(16), pages 4932-4935). The reaction is typically carried out at room temperature in an inert organic solvent such as dichloromethane. This method is shown in Scheme 9.

Scheme 9

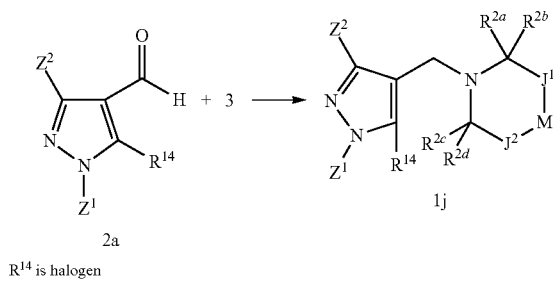

2a $R^{14}$ is halogen

Compounds of Formula 2a can be prepared from compounds of Formula 9 by the method shown in Scheme 10. In this method, treatment of a compound of Formula 9 with a phosphorus oxyhalide in the presence of N,N-dimethylformamide provides compounds of Formula 2a (see, for example, *Bulgarian Chemical Communications* 2009, 41(3), pages 241-247).

Scheme 10

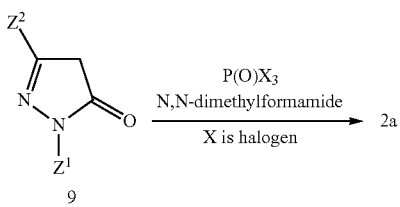

Scheme 11 illustrates the preparation of compounds of Formula 9 by cyclization of compounds of Formulae 8 and 10. This method typically consists of two steps: initial condensation typically carried out in an inert solvent such as dichloromethane and in the presence of a base such as triethylamine, followed by treatment with an acid such as acetic acid, heating, and removal of the volatile organics (see, for example, *Bioorganic & Medicinal Chemistry* 2010, 18(22), pages 7849-7854). Compounds of Formulae 8 and 10 are either commercially available or can be prepared by well-established methods known in the art.

Scheme 11

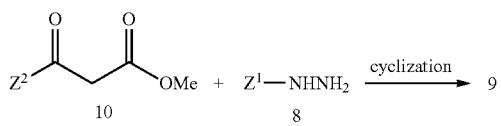

Compounds of Formula 1 containing the groups $C(X)R^5$, $C(X)R^{5a}$, $C(X)NR^7R^8$ and $C(X)NR^{7a}R^{8a}$ wherein X is S can be prepared from corresponding compounds of Formula 1 wherein X is O by general methods known in the art involving treatment with thionating reagents such as $P_4S_{10}$ or Lawessen's Reagent (2,4-bis(4-methoxyphenyl)-1,3-dithia-2,4-diphosphetane 2,4-disulfide).

Schemes 1 through 11 illustrate methods to prepare compounds of Formula 1 having a variety of substituents. Compounds of Formula 1 having substituents other than those particularly noted for Schemes 1 through 11 can be prepared by general methods known in the art of synthetic organic chemistry, including methods analogous to those described for Schemes 1 to 11.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Synthesis Examples are, therefore, to be construed as merely illustrative, and not limiting of the disclosure in any way whatsoever. Steps in the following Synthesis Examples illustrate a procedure for each step in an overall synthetic transformation, and the starting material for each step may not have necessarily been prepared by a particular preparative run whose procedure is described in other Examples or Steps. Ambient or room temperature is defined as about 20-25° C. Percentages are by weight except for chromatographic solvent mixtures or where otherwise indicated. Parts and percentages for chromatographic solvent mixtures are by volume unless otherwise indicated. MPLC refers to medium pressure liquid chromatography on silica gel. $^1$H NMR spectra are reported in ppm downfield from tetramethylsilane; "s" means singlet, "d" means doublet, "dd" means doublet of doublets, "ddd" means doublet of doublet of doublets, "t" means triplet, "m" means multiplet, and "br s" means broad singlet. Compound numbers refer to compounds in Index Tables A-E.

Synthesis Example 1

Preparation of 1-[[3-(4-fluorophenyl)-1-[3-(trifluoromethyl)phenyl]-1H-pyrazol-4-yl]methyl]-4-piperidinecarbonitrile (compound number 12)

Step A: Preparation of 1-(4-fluorophenyl)ethanone 2-[3-(trifluoromethyl)phenyl]hydrazone To a solution of 4-fluoroacetophenone (5.0 g, 36 mmol) in 200 mL of ethanol (200 mL) was added 3-(trifluoromethyl) phenyl hydrazine (6.370 g, 36.20 mmol). The reaction mixture was stirred for 18 hours, after which time the volatile materials were removed under reduced pressure, and the resulting crude reaction mixture was added to water (100 mL) and extracted with diethyl ether (3×200 mL). The combined organic extracts were dried over MgSO$_4$ and concentrated under reduced pressure. The resulting solid residue was purified by chromatography on silica gel (ethyl acetate/hexanes) to afford the title compound as a solid (4.78 g). $^1$H NMR (CDCl$_3$) δ 7.75-7.78 (dd, 2H), 7.42 (d, 2H), 7.36 (d, 1H), 7.32 (br s, NH), 7.06-7.15 (m, 3H), 2.25 (s, 3H).

Step B: Preparation of 3-(4-fluorophenyl)-1-[3-(trifluoromethyl)phenyl]-11H-pyrazole-4-carboxaldehyde Cyanuric chloride (15.0 g, 81.3 mmol) was added in one portion to anhydrous N,N-dimethylformamide (100 mL) under a nitrogen atmosphere. The reaction mixture was stirred at room temperature until the cyanuric chloride could no longer be detected by UV. After complete consumption of the cyanuric chloride, a solution of 1-(4-fluorophenyl)ethanone 2-[3-(trifluoromethyl)phenyl]hydrazone (4.78 g, 16.1 mmol) in anhydrous N,N-dimethylformamide (25 mL) was added to the reaction mixture. The reaction mixture was then stirred for 18 hours at room temperature, after which time the reaction mixture was added to aqueous sodium bicarbonate solution (200 mL) and extracted with diethyl ether (3×200 mL). The combined organic extracts were washed once with water (100 mL), dried over MgSO$_4$, and concentrated under reduced pressure. The resulting solid residue was purified by chromatography on silica gel (ethyl acetate/hexanes) to afford the title compound as a solid (1.74 g). $^1$H NMR (CDCl$_3$) δ 10.06 (s, 1H), 8.59 (s, 1H), 8.11 (s, 1H), 7.95-8.00 (m, 1H), 7.86-7.89 (m, 2H), 7.66 (d, 2H), 7.21 (t, 2H).

Step C: Preparation of 1-[[3-(4-fluorophenyl)-1-[3-(trifluoromethyl)phenyl]-1H-pyrazol-4-yl]methyl]-4-piperidinecarbonitrile To a suspension of lithium aluminum hydride (1.0 g, 26 mmol) in tetrahydrofuran (25 mL) was added a solution of 3-(4-fluorophenyl)-1-[3-(trifluoromethyl)phenyl]-1H-pyrazole-4-carboxaldehyde (1.74 g, 5.21 mmol) in tetrahydrofuran (25 mL). The reaction mixture was allowed to stir for 18 hours, after which time aqueous 50% NaOH solution (1 mL) was added, followed by water (1 mL). The reaction mixture was allowed to stir for 1 hour, magnesium sulfate was added, and the reaction mixture was filtered. The filtrate was concentrated under reduced pressure to yield the crude intermediate alcohol (1.58 g). This alcohol was dissolved in diethyl ether (100 mL) and phosphorous tribromide (1.276 g, 4.714 mmol) was added dropwise. The reaction mixture was allowed to stir for 18 hours at room temperature under nitrogen. The reaction mixture was then added to water (100 mL) and extracted with diethyl ether (3×125 mL). The combined organic extracts were dried (MgSO$_4$), concentrated under reduced pressure, and the resulting solid residue was purified by chromatography on silica gel (ethyl acetate/hexanes) to afford the intermediate bromide (632 mg). A portion of the intermediate bromide (200 mg, 0.504 mmol) and piperidine-4-carbonitrile (300 mg, 2.73 mmol) were combined in acetonitrile (20 mL) with potassium carbonate (365 mg, 2.73 mmol). The reaction mixture was stirred at room temperature for 18 hours. The reaction mixture was then added to water (100 mL) and extracted with ethyl acetate (3×100 mL). The combined organic extracts were dried (MgSO$_4$), concentrated under reduced pressure, and the resulting solid residue was purified by chromatography on silica gel (ethyl acetate/hexanes) to afford the title compound (203 mg), a compound of this invention. $^1$H NMR (CDCl$_3$) δ 8.03 (s, 1H), 7.90-7.94 (m, 4H), 7.52-7.61 (m, 2H), 7.14 (t, 2H), 3.49 (s, 2H), 2.71 (m, 3H), 2.43 (m, 2H), 1.86-1.97 (m, 4H).

Synthesis Example 2

Preparation of methyl 1-[[1-(2,4-difluorophenyl)-3-(2-fluoro-4-methylphenyl)-1H-pyrazol-4-yl]methyl]-4-piperidinecarboxylate (compound number 16)

Step A: Preparation of 1-(2-fluoro-4-methylphenyl)ethanone 2-(2,4-difluorophenyl)hydrazone To a solution of 2-fluoro-4-methylacetophenone (4.210 g, 27.70 mmol) in ethanol (200 mL) was added 2,4-difluorophenyl hydrazine HCl salt (5.0 g, 28 mmol). To this reaction mixture was added sodium acetate (2.044, 24.93 mmol) in one portion. This reaction mixture was stirred for 18 hours, after which time the volatile materials were removed under reduced pressure, and the resulting crude reaction mixture was added to water (100 mL) and extracted with diethyl ether (3×200 mL). The organic extracts were combined, dried (MgSO$_4$), evaporated under reduced pressure, and the solid residue was purified by chromatography on silica gel (ethyl acetate/hexanes) to afford the title compound as a solid (7.417 g). $^1$H NMR (CDCl$_3$) δ 7.49-7.56 (m, 2H), 7.34 (br s, NH) 6.97 (d, 1H), 6.80-6.91 (m, 3H), 2.37 (s, 3H), 2.28 (s, 3H).

Step B: Preparation of 1-(2,4-difluorophenyl)-3-(2-fluoro-4-methylphenyl)-1H-pyrazole-4-carboxaldehyde Cyanuric chloride (15.0 g, 81.3 mmol) was added in one portion to anhydrous N,N-dimethylformamide (75 mL) under a nitrogen atmosphere. The reaction mixture was allowed to stir at room temperature until the cyanuric chloride could no longer be detected by UV. After complete consumption of the cyanuric chloride, 1-(2-fluoro-4-methylphenyl) ethanone 2-(2,4-difluorophenyl)hydrazone (7.417 g, 26.68 mmol) was added in anhydrous N,N-dimethylformamide (25 mL). The reaction mixture was allowed to stir for 18 hours at room temperature, after which time the reaction mixture was added to aqueous sodium bicarbonate solution (200 mL) and extracted with diethyl ether (3×200 mL). The combined organic extracts were washed once with water (100 mL), dried (MgSO$_4$), evaporated under reduced pressure, and the solid residue was purified by chromatography on silica gel (ethyl acetate/hexanes) to afford the title compound as a solid (6.877 g). $^1$H NMR (CDCl$_3$) δ 9.85 (s, 1H), 8.49 (s, 1H), 7.89-7.96 (m, 1H), 7.49 (t, 1H), 6.99-7.06 (m, 4H), 2.39 (s, 3H).

Step C: Preparation of methyl 1-[[1-(2,4-difluorophenyl)-3-(2-fluoro-4-methylphenyl)-1H-pyrazol-4-yl]methyl]-4-piperidinecarboxylate To a solution of piperidine-4-carboxylic acid methyl ester (300 mg, 1.80 mmol) in dichloromethane (25 mL) was added 1-(2,4-difluorophenyl)-3-(2-fluoro-4-methylphenyl)-1H-pyrazole-4-carboxaldehyde (300 mg, 0.949 mmol). The reaction mixture was allowed to stir for 1 hour, and then sodium triacetoxyborohydride (358 mg, 1.90 mmol) was added in one portion. The reaction mixture was stirred for 18 hours, and was then added to 100 mL of water (100 mL) and extracted with dichloromethane (3×100 mL). The combined organic extracts were dried (MgSO$_4$), evaporated under reduced pressure, and the residue was purified by chromatography on silica gel (ethyl acetate/hexanes) to afford the title compound (144.3 mg), a compound of this invention. $^1$H NMR (CDCl$_3$) δ 7.98 (d, 1H), 7.90-7.94 (m, 1H), 7.48 (t, 1H), 6.96-7.03 (m, 4H), 3.65 (s, 3H), 3.46 (s, 2H), 2.84-2.87 (m, 2H), 2.41 (s, 3H) 2.24-2.31 (m, 1H), 1.96-2.01 (m, 2H), 1.83-1.86 (m, 2H), 1.67-1.74 (m, 2H).

Synthesis Example 3

Preparation of N-[(3S)-1-[[1-(3,4-dichlorophenyl)-3-(4-fluorophenyl)-1H-pyrazol-4-yl]methyl]-3-pyrrolidinyl]cyclopropanecarboxamide (compound number 869)

Step A: Preparation of N-[(3S)-pyrrolidinyl]cyclopropanecarboxamide

To a solution of cyclopropanecarboxylic acid (5.0 g, 58 mmol) in dichloromethane (100 mL) was added oxalyl chloride (36.918 g, 290.70 mmol), followed by the addition of 100 mg of N,N-dimethylformamide. Bubbling occurred and the reaction was allowed to stir at room temperature for 3 hours, after which time the reaction mixture was concentrated under reduced pressure to provide a white oily solid. This crude solid was dissolved in dichloromethane (100 mL), and this solution was added dropwise to a solution of (3S)-amino-1-(phenylmethyl)pyrrolidine (5.0 g, 28 mmol) in dichloromethane (100 mL) at 10° C. over the course of 15 minutes. Triethylamine (6.459 g, 63.95 mmol) was then added to the reaction mixture, the cold bath was removed, and the reaction mixture was stirred for 18 hours. The reaction mixture was then added to an aqueous saturated solution of sodium bicarbonate and extracted with dichloromethane (3×100 mL). The organic layers were combined and dried over magnesium sulfate, filtered, and concentrated under reduced pressure to yield a brown solid which was recrystallized from 1-chlorobutane to give 2.546 g of the intermediate N-[(3S)-1-(phenylmethyl)-3-pyrrolidinyl]cyclopropanecarboxamide. This intermediate (2.546 g, 10.43 mmol) was added to a nitrogen-purged solution of ethanol (100 mL) and water (3 mL), followed by the addition of 5% Pd/C (500 mg, containing 63.79% water). The reaction mixture was stirred for 1 minute, and then ammonium formate (3.100 g, 50.0 mmol) was added in one portion. The reaction mixture was then heated to reflux for 3 hours, cooled to room temperature, and filtered through Celite®. The Celite® pad was washed with dichloromethane (200 mL), and the organic filtrate was dried over magnesium sulfate, filtered, and concentrated under reduced pressure to yield the title compound as a clear oily solid (1.521 g). $^1$H NMR (CDCl$_3$): δ 6.38 (br s, 2H), 4.40-4.45 (m, 1H), 3.10-3.14 (m, 2H), 2.95-2.99 (m, 2H), 2.86-2.95 (m, 1H) 2.12-2.18 (m, 1H), 1.67-1.70 (m, 1H), 0.93-0.96 (m, 2H), 0.70-0.73 (m, 2H).

Step B: Preparation of 1-(3,4-dichlorophenyl)-3-(4-fluorophenyl)-1H-pyrazole-4-carboxaldehyde 3,4-Dichlorophenylhydrazine hydrochloride (5.86 g, 27.4 mmol) and sodium acetate (2.025 g, 24.70 mmol) were suspended in ethanol (100 mL), and the reaction mixture was stirred at room temperature for 5 minutes. 4-Fluoroacetophenone (3.79 g, 27.4 mmol) was added to the reaction mixture in one portion, and the reaction mixture was stirred at room temperature for 18 hours. The reaction mixture was then added to water (100 mL) and extracted with dichloromethane (3×200 mL). The combined organic extracts were dried over magnesium sulfate, filtered, and concentrated under reduced pressure to give the intermediate hydrazine (7.976 g). This hydrazone was added to N,N-dimethylformamide (50 mL). Seperately, cyanuric chloride (14.866 g, 80.574 mmol) was added in one portion to N,N-dimethylformamide (100 mL) and the reaction mixture stirred for 20 minutes. To this thick white suspension was added in one portion the previously prepared N,N-dimethylformamide hydrazine solution. The reaction mixture was vigorously stirred at under a nitrogen atmosphere at room temperature for 18 hours. The reaction mixture was then added to an aqueous suspension of sodium bicarbonate until the reaction mixture reached pH 8.0. The aqueous suspension was then extracted with diethyl ether (2×500 mL). The combined ether extracts were washed with water (2×200 mL), dried over magnesium sulfate, filtered, and concentrated under reduced pressure to yield a crude product, which was triturated with diethyl ether and collected by filtration to give the title compound as a white solid (8.179 g). $^1$H NMR (CDCl$_3$): δ 10.04 (s, 1H), 8.51 (s, 1H), 7.98 (s, 1H), 7.84-7.87 (m, 2H), 7.58-7.65 (m, 2H), 7.20 (t, 2H).

Step C: Preparation of N-[(3S)-1-[[1-(3,4-dichlorophenyl)-3-(4-fluorophenyl)-1H-pyrazol-4-yl]methyl]-3-pyrrolidinyl]cyclopropanecarboxamide 1-(3,4-Dichlorophenyl)-3-(4-fluorophenyl)-1H-pyrazole-4-carboxaldehyde (2.34 g, 6.99 mmol) was dissolved in dichloromethane (50 mL) and N-[(3S)-pyrrolidinyl]cyclopropanecarboxamide (1.18 g, 7.683 mmol) was added. The reaction mixture was stirred for 1 hour, and then sodium triacetoxyborohydride (4.88 g, 23.0 mmol) was added in one portion. The reaction mixture was allowed to stir for 18 hours, and was then added to water (100 mL) and extracted with dichloromethane (3×100 mL). The organic extracts were combined, dried over magnesium sulfate, concentrated under reduced pressure, and the residue was purified by chromatography on silica gel (ethyl acetate/hexane) to afford the title compound (1.841 g), a compound of this invention. $^1$H NMR (CDCl$_3$): δ 7.87-7.91 (m, 4H), 7.59 (d, 1H), 7.52 (d, 1H), 7.15 (t, 2H), 5.81 (br d, 1H), 4.46-4.48 (m, 1H), 3.45 (ab quartet, 2H), 2.91-2.95 (m, 1H), 2.56-2.66 (m, 2H), 2.28-2.34 (m, 2H), 1.60-1.65 (m, 1H), 1.21-1.26 (m, 1H), 0.92-0.95 (m, 2H), 0.69-0.73 (m, 2H).

By the procedures described herein together with methods known in the art, the following compounds of Tables 1 to 6b can be prepared. The following abbreviations are used in Tables 1 to 6b which follow: Me means methyl and Et means ethyl. $R^x$ and $R^y$ represent one or a combination of substituents.

TABLE 1

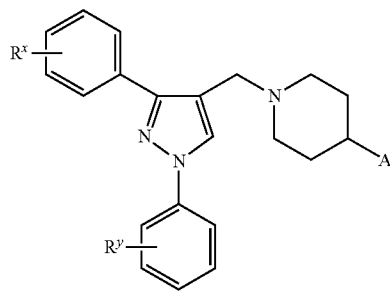

| $R^x$ | $R^y$ | $R^x$ | $R^y$ | $R^x$ | $R^y$ |
| --- | --- | --- | --- | --- | --- |
| A is cyano | | | | | |
| 2-F | 2-F | 2-F | 3-F | 2-F | 3-Cl |
| 2-Cl | 2-F | 2-Cl | 3-F | 2-Cl | 3-Cl |
| 2-Br | 2-F | 2-Br | 3-F | 2-Br | 3-Cl |
| 2-Me | 2-F | 2-Me | 3-F | 2-Me | 3-Cl |
| 2-CF$_3$ | 2-F | 2-CF3 | 3-F | 2-CF$_3$ | 3-Cl |
| 4-F | 2-F | 4-F | 3-F | 4-F | 3-Cl |
| 4-Cl | 2-F | 4-Cl | 3-F | 4-Cl | 3-Cl |
| 4-Br | 2-F | 4-Br | 3-F | 4-Br | 3-Cl |
| 2-F, 4-F | 2-F | 2-F, 4-F | 3-F | 2-F, 4-F | 3-Cl |
| 2-Cl, 4-F | 2-F | 2-Cl, 4-F | 3-F | 2-Cl, 4-F | 3-Cl |
| 2-Me, 4-F | 2-F | 2-Me, 4-F | 3-F | 2-Me, 4-F | 3-Cl |
| 2-F, 6-F | 2-F | 2-F, 6-F | 3-F | 2-F, 6-F | 3-Cl |
| 2-Cl, 6-Cl | 2-F | 2-Cl, 6-Cl | 3-F | 2-Cl, 6-Cl | 3-Cl |
| 2-Me, 6-Me | 2-F | 2-Me, 6-Me | 3-F | 2-Me, 6-Me | 3-Cl |
| 2-F, 4-F, 6-F | 2-F | 2-F, 4-F, 6-F | 3-F | 2-F, 4-F, 6-F | 3-Cl |
| 2-F | 3-Br | 2-F | 3-CF$_3$ | 2-F | 3-OCF$_3$ |
| 2-Cl | 3-Br | 2-Cl | 3-CF$_3$ | 2-Cl | 3-OCF$_3$ |
| 2-Br | 3-Br | 2-Br | 3-CF$_3$ | 2-Br | 3-OCF$_3$ |
| 2-Me | 3-Br | 2-Me | 3-CF$_3$ | 2-Me | 3-OCF$_3$ |
| 2-CF$_3$ | 3-Br | 2-CF$_3$ | 3-CF$_3$ | 2-CF$_3$ | 3-OCF$_3$ |
| 4-F | 3-Br | 4-F | 3-CF$_3$ | 4-F | 3-OCF$_3$ |
| 4-Cl | 3-Br | 4-Cl | 3-CF$_3$ | 4-Cl | 3-OCF$_3$ |
| 4-Br | 3-Br | 4-Br | 3-CF$_3$ | 4-Br | 3-OCF$_3$ |
| 2-F, 4-F | 3-Br | 2-F, 4-F | 3-CF$_3$ | 2-F, 4-F | 3-OCF$_3$ |
| 2-Cl, 4-F | 3-Br | 2-Cl, 4-F | 3-CF$_3$ | 2-Cl, 4-F | 3-OCF$_3$ |
| 2-Me, 4-F | 3-Br | 2-Me, 4-F | 3-CF$_3$ | 2-Me, 4-F | 3-OCF$_3$ |
| 2-F, 6-F | 3-Br | 2-F, 6-F | 3-CF$_3$ | 2-F, 6-F | 3-OCF$_3$ |
| 2-Cl, 6-Cl | 3-Br | 2-Cl, 6-Cl | 3-CF$_3$ | 2-Cl, 6-Cl | 3-OCF$_3$ |
| 2-Me, 6-Me | 3-Br | 2-Me, 6-Me | 3-CF$_3$ | 2-Me, 6-Me | 3-OCF$_3$ |
| 2-F, 4-F, 6-F | 3-Br | 2-F, 4-F, 6-F | 3-CF$_3$ | 2-F, 4-F, 6-F | 3-OCF$_3$ |
| 2-F | 4-F | 2-F | 4-Cl | 2-F | 4-Br |
| 2-Cl | 4-F | 2-Cl | 4-Cl | 2-Cl | 4-Br |
| 2-Br | 4-F | 2-Br | 4-Cl | 2-Br | 4-Br |
| 2-Me | 4-F | 2-Me | 4-Cl | 2-Me | 4-Br |
| 2-CF$_3$ | 4-F | 2-CF$_3$ | 4-Cl | 2-CF$_3$ | 4-Br |
| 4-F | 4-F | 4-F | 4-Cl | 4-F | 4-Br |
| 4-Cl | 4-F | 4-Cl | 4-Cl | 4-Cl | 4-Br |
| 4-Br | 4-F | 4-Br | 4-Cl | 4-Br | 4-Br |
| 2-F, 4-F | 4-F | 2-F, 4-F | 4-Cl | 2-F, 4-F | 4-Br |
| 2-Cl, 4-F | 4-F | 2-Cl, 4-F | 4-Cl | 2-Cl, 4-F | 4-Br |
| 2-Me, 4-F | 4-F | 2-Me, 4-F | 4-Cl | 2-Me, 4-F | 4-Br |
| 2-F, 6-F | 4-F | 2-F, 6-F | 4-Cl | 2-F, 6-F | 4-Br |
| 2-Cl, 6-Cl | 4-F | 2-Cl, 6-Cl | 4-Cl | 2-Cl, 6-Cl | 4-Br |
| 2-Me, 6-Me | 4-F | 2-Me, 6-Me | 4-Cl | 2-Me, 6-Me | 4-Br |
| 2-F, 4-F, 6-F | 4-F | 2-F, 4-F, 6-F | 4-Cl | 2-F, 4-F, 6-F | 4-Br |
| 2-F | 4-CF$_3$ | 2-F | 4-OCF$_3$ | 2-F | 3-F, 4-F |
| 2-Cl | 4-CF$_3$ | 2-Cl | 4-OCF$_3$ | 2-Cl | 3-F, 4-F |
| 2-Br | 4-CF$_3$ | 2-Br | 4-OCF$_3$ | 2-Br | 3-F, 4-F |
| 2-Me | 4-CF$_3$ | 2-Me | 4-OCF$_3$ | 2-Me | 3-F, 4-F |
| 2-CF$_3$ | 4-CF$_3$ | 2-CF$_3$ | 4-OCF$_3$ | 2-CF$_3$ | 3-F, 4-F |
| 4-F | 4-CF$_3$ | 4-F | 4-OCF$_3$ | 4-F | 3-F, 4-F |
| 4-Cl | 4-CF$_3$ | 4-Cl | 4-OCF$_3$ | 4-Cl | 3-F, 4-F |
| 4-Br | 4-CF$_3$ | 4-Br | 4-OCF$_3$ | 4-Br | 3-F, 4-F |
| 2-F, 4-F | 4-CF$_3$ | 2-F, 4-F | 4-OCF$_3$ | 2-F, 4-F | 3-F, 4-F |
| 2-Cl, 4-F | 4-CF$_3$ | 2-Cl, 4-F | 4-OCF$_3$ | 2-Cl, 4-F | 3-F, 4-F |
| 2-Me, 4-F | 4-CF$_3$ | 2-Me, 4-F | 4-OCF$_3$ | 2-Me, 4-F | 3-F, 4-F |
| 2-F, 6-F | 4-CF$_3$ | 2-F, 6-F | 4-OCF$_3$ | 2-F, 6-F | 3-F, 4-F |
| 2-Cl, 6-Cl | 4-CF$_3$ | 2-Cl, 6-Cl | 4-OCF$_3$ | 2-Cl, 6-Cl | 3-F, 4-F |
| 2-Me, 6-Me | 4-CF$_3$ | 2-Me, 6-Me | 4-OCF$_3$ | 2-Me, 6-Me | 3-F, 4-F |
| 2-F, 4-F, 6-F | 4-CF$_3$ | 2-F, 4-F, 6-F | 4-OCF$_3$ | 2-F, 4-F, 6-F | 3-F, 4-F |
| 2-F | 3-F, 4-Cl | 2-F | 3-F, 4-Br | 2-F | 3-F, 4-CF$_3$ |

TABLE 1-continued

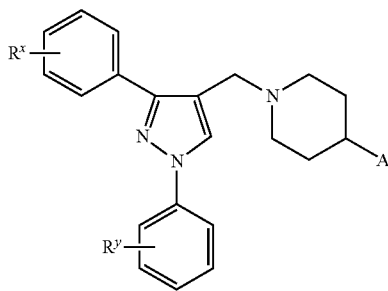

| $R^x$ | $R^y$ | $R^x$ | $R^y$ | $R^x$ | $R^y$ |
|---|---|---|---|---|---|
| 2-Cl | 3-F, 4-Cl | 2-Cl | 3-F, 4-Br | 2-Cl | 3-F,4-CF$_3$ |
| 2-Br | 3-F, 4-Cl | 2-Br | 3-F, 4-Br | 2-Br | 3-F,4-CF$_3$ |
| 2-Me | 3-F, 4-Cl | 2-Me | 3-F, 4-Br | 2-Me | 3-F, 4-CF$_3$ |
| 2-CF$_3$ | 3-F, 4-Cl | 2-CF$_3$ | 3-F, 4-Br | 2-CF$_3$ | 3-F, 4-CF$_3$ |
| 4-F | 3-F, 4-Cl | 4-F | 3-F, 4-Br | 4-F | 3-F, 4-CF$_3$ |
| 4-Cl | 3-F, 4-Cl | 4-Cl | 3-F, 4-Br | 4-Cl | 3-F, 4-CF$_3$ |
| 4-Br | 3-F, 4-Cl | 4-Br | 3-F, 4-Br | 4-Br | 3-F, 4-CF$_3$ |
| 2-F, 4-F | 3-F, 4-Cl | 2-F, 4-F | 3-F, 4-Br | 2-F, 4-F | 3-F, 4-CF$_3$ |
| 2-Cl, 4-F | 3-F, 4-Cl | 2-Cl, 4-F | 3-F, 4-Br | 2-Cl, 4-F | 3-F, 4-CF$_3$ |
| 2-Me, 4-F | 3-F, 4-Cl | 2-Me, 4-F | 3-F, 4-Br | 2-Me, 4-F | 3-F, 4-CF$_3$ |
| 2-F, 6-F | 3-F, 4-Cl | 2-F, 6-F | 3-F, 4-Br | 2-F, 6-F | 3-F, 4-CF$_3$ |
| 2-Cl, 6-Cl | 3-F, 4-Cl | 2-Cl, 6-Cl | 3-F, 4-Br | 2-Cl, 6-Cl | 3-F, 4-CF$_3$ |
| 2-Me, 6-Me | 3-F, 4-Cl | 2-Me, 6-Me | 3-F, 4-Br | 2-Me, 6-Me | 3-F, 4-CF$_3$ |
| 2-F, 4-F, 6-F | 3-F, 4-Cl | 2-F, 4-F, 6-F | 3-F, 4-Br | 2-F, 4-F, 6-F | 3-F, 4-CF$_3$ |
| 2-F | 3-F, 4-OCF$_3$ | 2-F | 3-Cl, 4-F | 2-F | 3-Cl, 4-Cl |
| 2-Cl | 3-F, 4-OCF$_3$ | 2-Cl | 3-Cl, 4-F | 2-Cl | 3-Cl, 4-Cl |
| 2-Br | 3-F, 4-OCF$_3$ | 2-Br | 3-Cl, 4-F | 2-Br | 3-Cl, 4-Cl |
| 2-Me | 3-F, 4-OCF$_3$ | 2-Me | 3-Cl, 4-F | 2-Me | 3-Cl, 4-Cl |
| 2-CF$_3$ | 3-F, 4-OCF$_3$ | 2-CF$_3$ | 3-Cl, 4-F | 2-CF$_3$ | 3-Cl, 4-Cl |
| 4-F | 3-F, 4-OCF$_3$ | 4-F | 3-Cl, 4-F | 4-F | 3-Cl, 4-Cl |
| 4-Cl | 3-F, 4-OCF$_3$ | 4-Cl | 3-Cl, 4-F | 4-Cl | 3-Cl, 4-Cl |
| 4-Br | 3-F, 4-OCF$_3$ | 4-Br | 3-Cl, 4-F | 4-Br | 3-Cl, 4-Cl |
| 2-F, 4-F | 3-F, 4-OCF$_3$ | 2-F, 4-F | 3-Cl, 4-F | 2-F, 4-F | 3-Cl, 4-Cl |
| 2-Cl, 4-F | 3-F, 4-OCF$_3$ | 2-Cl, 4-F | 3-Cl, 4-F | 2-Cl, 4-F | 3-Cl, 4-Cl |
| 2-Me, 4-F | 3-F, 4-OCF$_3$ | 2-Me, 4-F | 3-Cl, 4-F | 2-Me, 4-F | 3-Cl, 4-Cl |
| 2-F, 6-F | 3-F, 4-OCF$_3$ | 2-F, 6-F | 3-Cl, 4-F | 2-F, 6-F | 3-Cl, 4-Cl |
| 2-Cl, 6-Cl | 3-F, 4-OCF$_3$ | 2-Cl, 6-Cl | 3-Cl, 4-F | 2-Cl, 6-Cl | 3-Cl, 4-Cl |
| 2-Me, 6-Me | 3-F, 4-OCF$_3$ | 2-Me, 6-Me | 3-Cl, 4-F | 2-Me, 6-Me | 3-Cl, 4-Cl |
| 2-F, 4-F, 6-F | 3-F, 4-OCF$_3$ | 2-F, 4-F, 6-F | 3-Cl, 4-F | 2-F, 4-F, 6-F | 3-Cl, 4-Cl |
| 2-F | 3-Cl, 4-CF$_3$ | 2-F | 3-Br, 4-F | 2-F | 3-CF$_3$, 4-F |
| 2-Cl | 3-Cl, 4-CF$_3$ | 2-Cl | 3-Br, 4-F | 2-Cl | 3-CF$_3$, 4-F |
| 2-Br | 3-Cl, 4-CF$_3$ | 2-Br | 3-Br, 4-F | 2-Br | 3-CF$_3$, 4-F |
| 2-Me | 3-Cl, 4-CF$_3$ | 2-Me | 3-Br, 4-F | 2-Me | 3-CF$_3$, 4-F |
| 2-CF$_3$ | 3-Cl, 4-CF$_3$ | 2-CF$_3$ | 3-Br, 4-F | 2-CF$_3$ | 3-CF$_3$, 4-F |
| 4-F | 3-Cl, 4-CF$_3$ | 4-F | 3-Br, 4-F | 4-F | 3-CF$_3$, 4-F |
| 4-Cl | 3-Cl, 4-CF$_3$ | 4-Cl | 3-Br, 4-F | 4-Cl | 3-CF$_3$, 4-F |
| 4-Br | 3-Cl, 4-CF$_3$ | 4-Br | 3-Br, 4-F | 4-Br | 3-CF$_3$, 4-F |
| 2-F, 4-F | 3-Cl, 4-CF$_3$ | 2-F, 4-F | 3-Br, 4-F | 2-F, 4-F | 3-CF$_3$, 4-F |
| 2-Cl, 4-F | 3-Cl, 4-CF$_3$ | 2-Cl, 4-F | 3-Br, 4-F | 2-Cl, 4-F | 3-CF$_3$, 4-F |
| 2-Me, 4-F | 3-Cl, 4-CF$_3$ | 2-Me, 4-F | 3-Br, 4-F | 2-Me, 4-F | 3-CF$_3$, 4-F |
| 2-F, 6-F | 3-Cl, 4-CF$_3$ | 2-F, 6-F | 3-Br, 4-F | 2-F, 6-F | 3-CF$_3$, 4-F |
| 2-Cl, 6-Cl | 3-Cl, 4-CF$_3$ | 2-Cl, 6-Cl | 3-Br, 4-F | 2-Cl, 6-Cl | 3-CF$_3$, 4-F |
| 2-Me, 6-Me | 3-Cl, 4-CF$_3$ | 2-Me, 6-Me | 3-Br, 4-F | 2-Me, 6-Me | 3-CF$_3$, 4-F |
| 2-F, 4-F, 6-F | 3-Cl, 4-CF$_3$ | 2-F, 4-F, 6-F | 3-Br, 4-F | 2-F, 4-F, 6-F | 3-CF$_3$, 4-F |
| 2-F | 3-CF$_3$, 4-Cl | 4-F | 3-CF$_3$, 4-Cl | 2-Me, 4-F | 3-CF$_3$, 4-Cl |
| 2-Cl | 3-CF$_3$, 4-Cl | 4-Cl | 3-CF$_3$, 4-Cl | 2-F, 6-F | 3-CF$_3$, 4-Cl |
| 2-Br | 3-CF$_3$, 4-Cl | 4-Br | 3-CF$_3$, 4-Cl | 2-Cl, 6-Cl | 3-CF$_3$, 4-Cl |
| 2-Me | 3-CF$_3$, 4-Cl | 2-F, 4-F | 3-CF$_3$, 4-Cl | 2-Me, 6-Me | 3-CF$_3$, 4-Cl |
| 2-CF$_3$ | 3-CF$_3$, 4-Cl | 2-Cl, 4-F | 3-CF$_3$, 4-Cl | 2-F, 4-F, 6-F | 3-CF$_3$, 4-Cl |
| 2-F | 3,4-DFMDO* | 4-F | 3,4-DFMDO* | 2-Me, 4-F | 3,4-DFMDO* |
| 2-Cl | 3,4-DFMDO* | 4-Cl | 3,4-DFMDO* | 2-F, 6-F | 3,4-DFMDO* |
| 2-Br | 3,4-DFMDO* | 4-Br | 3,4-DFMDO* | 2-Cl, 6-Cl | 3,4-DFMDO* |
| 2-Me | 3,4-DFMDO* | 2-F, 4-F | 3,4-DFMDO* | 2-Me, 6-Me | 3,4-DFMDO* |
| 2-CF$_3$ | 3,4-DFMDO* | 2-Cl, 4-F | 3,4-DFMDO* | 2-F, 4-F, 6-F | 3,4-DFMDO* |
| | | A is CO$_2$Me | | | |
| 2-F | 2-F | 2-F | 3-F | 2-F | 3-Cl |
| 2-Cl | 2-F | 2-Cl | 3-F | 2-Cl | 3-Cl |
| 2-Br | 2-F | 2-Br | 3-F | 2-Br | 3-Cl |
| 2-Me | 2-F | 2-Me | 3-F | 2-Me | 3-Cl |
| 2-CF$_3$ | 2-F | 2-CF$_3$ | 3-F | 2-CF$_3$ | 3-Cl |
| 4-F | 2-F | 4-F | 3-F | 4-F | 3-Cl |
| 4-Cl | 2-F | 4-Cl | 3-F | 4-Cl | 3-Cl |

TABLE 1-continued

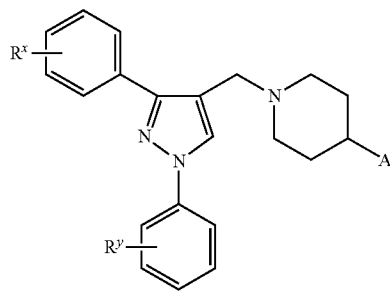

| $R^x$ | $R^y$ | $R^x$ | $R^y$ | $R^x$ | $R^y$ |
|---|---|---|---|---|---|
| 4-Br | 2-F | 4-Br | 3-F | 4-Br | 3-Cl |
| 2-F, 4-F | 2-F | 2-F, 4-F | 3-F | 2-F, 4-F | 3-Cl |
| 2-Cl, 4-F | 2-F | 2-Cl, 4-F | 3-F | 2-Cl, 4-F | 3-Cl |
| 2-Me, 4-F | 2-F | 2-Me, 4-F | 3-F | 2-Me, 4-F | 3-Cl |
| 2-F, 6-F | 2-F | 2-F, 6-F | 3-F | 2-F, 6-F | 3-Cl |
| 2-Cl, 6-Cl | 2-F | 2-Cl, 6-Cl | 3-F | 2-Cl, 6-Cl | 3-Cl |
| 2-Me, 6-Me | 2-F | 2-Me, 6-Me | 3-F | 2-Me, 6-Me | 3-Cl |
| 2-F, 4-F, 6-F | 2-F | 2-F, 4-F, 6-F | 3-F | 2-F, 4-F, 6-F | 3-Cl |
| 2-F | 3-Br | 2-F | 3-CF$_3$ | 2-F | 3-OCF$_3$ |
| 2-Cl | 3-Br | 2-Cl | 3-CF$_3$ | 2-Cl | 3-OCF$_3$ |
| 2-Br | 3-Br | 2-Br | 3-CF$_3$ | 2-Br | 3-OCF$_3$ |
| 2-Me | 3-Br | 2-Me | 3-CF$_3$ | 2-Me | 3-OCF$_3$ |
| 2-CF$_3$ | 3-Br | 2-CF$_3$ | 3-CF$_3$ | 2-CF$_3$ | 3-OCF$_3$ |
| 4-F | 3-Br | 4-F | 3-CF$_3$ | 4-F | 3-OCF$_3$ |
| 4-Cl | 3-Br | 4-Cl | 3-CF$_3$ | 4-Cl | 3-OCF$_3$ |
| 4-Br | 3-Br | 4-Br | 3-CF$_3$ | 4-Br | 3-OCF$_3$ |
| 2-F, 4-F | 3-Br | 2-F, 4-F | 3-CF$_3$ | 2-F, 4-F | 3-OCF$_3$ |
| 2-Cl, 4-F | 3-Br | 2-Cl, 4-F | 3-CF$_3$ | 2-Cl, 4-F | 3-OCF$_3$ |
| 2-Me, 4-F | 3-Br | 2-Me, 4-F | 3-CF$_3$ | 2-Me, 4-F | 3-OCF$_3$ |
| 2-F, 6-F | 3-Br | 2-F, 6-F | 3-CF$_3$ | 2-F, 6-F | 3-OCF$_3$ |
| 2-Cl, 6-Cl | 3-Br | 2-Cl, 6-Cl | 3-CF$_3$ | 2-Cl, 6-Cl | 3-OCF$_3$ |
| 2-Me, 6-Me | 3-Br | 2-Me, 6-Me | 3-CF$_3$ | 2-Me, 6-Me | 3-OCF$_3$ |
| 2-F, 4-F, 6-F | 3-Br | 2-F, 4-F, 6-F | 3-CF$_3$ | 2-F, 4-F, 6-F | 3-OCF$_3$ |
| 2-F | 4-F | 2-F | 4-Cl | 2-F | 4-Br |
| 2-Cl | 4-F | 2-Cl | 4-Cl | 2-Cl | 4-Br |
| 2-Br | 4-F | 2-Br | 4-Cl | 2-Br | 4-Br |
| 2-Me | 4-F | 2-Me | 4-Cl | 2-Me | 4-Br |
| 2-CF$_3$ | 4-F | 2-CF$_3$ | 4-Cl | 2-CF$_3$ | 4-Br |
| 4-F | 4-F | 4-F | 4-Cl | 4-F | 4-Br |
| 4-Cl | 4-F | 4-Cl | 4-Cl | 4-Cl | 4-Br |
| 4-Br | 4-F | 4-Br | 4-Cl | 4-Br | 4-Br |
| 2-F, 4-F | 4-F | 2-F, 4-F | 4-Cl | 2-F, 4-F | 4-Br |
| 2-Cl, 4-F | 4-F | 2-Cl, 4-F | 4-Cl | 2-Cl, 4-F | 4-Br |
| 2-Me, 4-F | 4-F | 2-Me, 4-F | 4-Cl | 2-Me, 4-F | 4-Br |
| 2-F, 6-F | 4-F | 2-F, 6-F | 4-Cl | 2-F, 6-F | 4-Br |
| 2-Cl, 6-Cl | 4-F | 2-Cl, 6-Cl | 4-Cl | 2-Cl, 6-Cl | 4-Br |
| 2-Me, 6-Me | 4-F | 2-Me, 6-Me | 4-Cl | 2-Me, 6-Me | 4-Br |
| 2-F, 4-F, 6-F | 4-F | 2-F, 4-F, 6-F | 4-Cl | 2-F, 4-F, 6-F | 4-Br |
| 2-F | 4-CF$_3$ | 2-F | 4-OCF$_3$ | 2-F | 3-F, 4-F |
| 2-Cl | 4-CF$_3$ | 2-Cl | 4-OCF$_3$ | 2-Cl | 3-F, 4-F |
| 2-Br | 4-CF$_3$ | 2-Br | 4-OCF$_3$ | 2-Br | 3-F, 4-F |
| 2-Me | 4-CF$_3$ | 2-Me | 4-OCF$_3$ | 2-Me | 3-F, 4-F |
| 2-CF$_3$ | 4-CF$_3$ | 2-CF$_3$ | 4-OCF$_3$ | 2-CF$_3$ | 3-F, 4-F |
| 4-F | 4-CF$_3$ | 4-F | 4-OCF$_3$ | 4-F | 3-F, 4-F |
| 4-Cl | 4-CF$_3$ | 4-Cl | 4-OCF$_3$ | 4-Cl | 3-F, 4-F |
| 4-Br | 4-CF$_3$ | 4-Br | 4-OCF$_3$ | 4-Br | 3-F, 4-F |
| 2-F, 4-F | 4-CF$_3$ | 2-F, 4-F | 4-OCF$_3$ | 2-F, 4-F | 3-F, 4-F |
| 2-Cl, 4-F | 4-CF$_3$ | 2-Cl, 4-F | 4-OCF$_3$ | 2-Cl, 4-F | 3-F, 4-F |
| 2-Me, 4-F | 4-CF$_3$ | 2-Me, 4-F | 4-OCF$_3$ | 2-Me, 4-F | 3-F, 4-F |
| 2-F, 6-F | 4-CF$_3$ | 2-F, 6-F | 4-OCF$_3$ | 2-F, 6-F | 3-F, 4-F |
| 2-Cl, 6-Cl | 4-CF$_3$ | 2-Cl, 6-Cl | 4-OCF$_3$ | 2-Cl, 6-Cl | 3-F, 4-F |
| 2-Me, 6-Me | 4-CF$_3$ | 2-Me, 6-Me | 4-OCF$_3$ | 2-Me, 6-Me | 3-F, 4-F |
| 2-F, 4-F, 6-F | 4-CF$_3$ | 2-F, 4-F, 6-F | 4-OCF$_3$ | 2-F, 4-F, 6-F | 3-F, 4-F |
| 2-F | 3-F, 4-Cl | 2-F | 3-F, 4-Br | 2-F | 3-F, 4-CF$_3$ |
| 2-Cl | 3-F, 4-Cl | 2-Cl | 3-F, 4-Br | 2-Cl | 3-F, 4-CF$_3$ |
| 2-Br | 3-F, 4-Cl | 2-Br | 3-F, 4-Br | 2-Br | 3-F, 4-CF$_3$ |
| 2-Me | 3-F, 4-Cl | 2-Me | 3-F, 4-Br | 2-Me | 3-F, 4-CF$_3$ |
| 2-CF$_3$ | 3-F, 4-Cl | 2-CF$_3$ | 3-F, 4-Br | 2-CF$_3$ | 3-F, 4-CF$_3$ |
| 4-F | 3-F, 4-Cl | 4-F | 3-F, 4-Br | 4-F | 3-F, 4-CF$_3$ |
| 4-Cl | 3-F, 4-Cl | 4-Cl | 3-F, 4-Br | 4-Cl | 3-F, 4-CF$_3$ |
| 4-Br | 3-F, 4-Cl | 4-Br | 3-F, 4-Br | 4-Br | 3-F, 4-CF$_3$ |
| 2-F, 4-F | 3-F, 4-Cl | 2-F, 4-F | 3-F, 4-Br | 2-F, 4-F | 3-F, 4-CF$_3$ |
| 2-Cl, 4-F | 3-F, 4-Cl | 2-Cl, 4-F | 3-F, 4-Br | 2-Cl, 4-F | 3-F, 4-CF$_3$ |

TABLE 1-continued

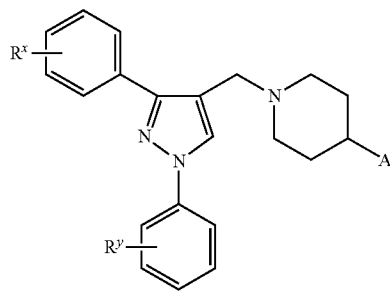

| $R^x$ | $R^y$ | $R^x$ | $R^y$ | $R^x$ | $R^y$ |
|---|---|---|---|---|---|
| 2-Me, 4-F | 3-F, 4-Cl | 2-Me, 4-F | 3-F, 4-Br | 2-Me, 4-F | 3-F, 4-CF$_3$ |
| 2-F, 6-F | 3-F, 4-Cl | 2-F, 6-F | 3-F, 4-Br | 2-F, 6-F | 3-F, 4-CF$_3$ |
| 2-Cl, 6-Cl | 3-F, 4-Cl | 2-Cl, 6-Cl | 3-F, 4-Br | 2-Cl, 6-Cl | 3-F, 4-CF$_3$ |
| 2-Me, 6-Me | 3-F, 4-Cl | 2-Me, 6-Me | 3-F, 4-Br | 2-Me, 6-Me | 3-F, 4-CF$_3$ |
| 2-F, 4-F, 6-F | 3-F, 4-Cl | 2-F, 4-F, 6-F | 3-F, 4-Br | 2-F, 4-F, 6-F | 3-F, 4-CF$_3$ |
| 2-F | 3-F, 4-OCF$_3$ | 2-F | 3-Cl, 4-F | 2-F | 3-Cl, 4-Cl |
| 2-Cl | 3-F, 4-OCF$_3$ | 2-Cl | 3-Cl, 4-F | 2-Cl | 3-Cl, 4-Cl |
| 2-Br | 3-F, 4-OCF$_3$ | 2-Br | 3-Cl, 4-F | 2-Br | 3-Cl, 4-Cl |
| 2-Me | 3-F, 4-OCF$_3$ | 2-Me | 3-Cl, 4-F | 2-Me | 3-Cl, 4-Cl |
| 2-CF$_3$ | 3-F, 4-OCF$_3$ | 2-CF$_3$ | 3-Cl, 4-F | 2-CF$_3$ | 3-Cl, 4-Cl |
| 4-F | 3-F, 4-OCF$_3$ | 4-F | 3-Cl, 4-F | 4-F | 3-Cl, 4-Cl |
| 4-Cl | 3-F, 4-OCF$_3$ | 4-Cl | 3-Cl, 4-F | 4-Cl | 3-Cl, 4-Cl |
| 4-Br | 3-F, 4-OCF$_3$ | 4-Br | 3-Cl, 4-F | 4-Br | 3-Cl, 4-Cl |
| 2-F, 4-F | 3-F, 4-OCF$_3$ | 2-F, 4-F | 3-Cl, 4-F | 2-F, 4-F | 3-Cl, 4-Cl |
| 2-Cl, 4-F | 3-F, 4-OCF$_3$ | 2-Cl, 4-F | 3-Cl, 4-F | 2-Cl, 4-F | 3-Cl, 4-Cl |
| 2-Me, 4-F | 3-F, 4-OCF$_3$ | 2-Me, 4-F | 3-Cl, 4-F | 2-Me, 4-F | 3-Cl, 4-Cl |
| 2-F, 6-F | 3-F, 4-OCF$_3$ | 2-F, 6-F | 3-Cl, 4-F | 2-F, 6-F | 3-Cl, 4-Cl |
| 2-Cl, 6-Cl | 3-F, 4-OCF$_3$ | 2-Cl, 6-Cl | 3-Cl, 4-F | 2-Cl, 6-Cl | 3-Cl, 4-Cl |
| 2-Me, 6-Me | 3-F, 4-OCF$_3$ | 2-Me, 6-Me | 3-Cl, 4-F | 2-Me, 6-Me | 3-Cl, 4-Cl |
| 2-F, 4-F, 6-F | 3-F, 4-OCF$_3$ | 2-F, 4-F, 6-F | 3-Cl, 4-F | 2-F, 4-F, 6-F | 3-Cl, 4-Cl |
| 2-F | 3-Cl, 4-CF$_3$ | 2-F | 3-Br, 4-F | 2-F | 3-CF$_3$, 4-F |
| 2-Cl | 3-Cl, 4-CF$_3$ | 2-Cl | 3-Br, 4-F | 2-Cl | 3-CF$_3$, 4-F |
| 2-Br | 3-Cl, 4-CF$_3$ | 2-Br | 3-Br, 4-F | 2-Br | 3-CF$_3$, 4-F |
| 2-Me | 3-Cl, 4-CF$_3$ | 2-Me | 3-Br, 4-F | 2-Me | 3-CF$_3$, 4-F |
| 2-CF$_3$ | 3-Cl, 4-CF$_3$ | 2-CF$_3$ | 3-Br, 4-F | 2-CF$_3$ | 3-CF$_3$, 4-F |
| 4-F | 3-Cl, 4-CF$_3$ | 4-F | 3-Br, 4-F | 4-F | 3-CF$_3$, 4-F |
| 4-Cl | 3-Cl, 4-CF$_3$ | 4-Cl | 3-Br, 4-F | 4-Cl | 3-CF$_3$, 4-F |
| 4-Br | 3-Cl, 4-CF$_3$ | 4-Br | 3-Br, 4-F | 4-Br | 3-CF$_3$, 4-F |
| 2-F, 4-F | 3-Cl, 4-CF$_3$ | 2-F, 4-F | 3-Br, 4-F | 2-F, 4-F | 3-CF$_3$, 4-F |
| 2-Cl, 4-F | 3-Cl, 4-CF$_3$ | 2-Cl, 4-F | 3-Br, 4-F | 2-Cl, 4-F | 3-CF$_3$, 4-F |
| 2-Me, 4-F | 3-Cl, 4-CF$_3$ | 2-Me, 4-F | 3-Br, 4-F | 2-Me, 4-F | 3-CF$_3$, 4-F |
| 2-F, 6-F | 3-Cl, 4-CF$_3$ | 2-F, 6-F | 3-Br, 4-F | 2-F, 6-F | 3-CF$_3$, 4-F |
| 2-Cl, 6-Cl | 3-Cl, 4-CF$_3$ | 2-Cl, 6-Cl | 3-Br, 4-F | 2-Cl, 6-Cl | 3-CF$_3$, 4-F |
| 2-Me, 6-Me | 3-Cl, 4-CF$_3$ | 2-Me, 6-Me | 3-Br, 4-F | 2-Me, 6-Me | 3-CF$_3$, 4-F |
| 2-F, 4-F, 6-F | 3-Cl, 4-CF$_3$ | 2-F, 4-F, 6-F | 3-Br, 4-F | 2-F, 4-F, 6-F | 3-CF$_3$, 4-F |
| 2-F | 3-CF$_3$, 4-Cl | 4-F | 3-CF$_3$, 4-Cl | 2-Me, 4-F | 3-CF$_3$, 4-Cl |
| 2-Cl | 3-CF$_3$, 4-Cl | 4-Cl | 3-CF$_3$, 4-Cl | 2-F, 6-F | 3-CF$_3$, 4-Cl |
| 2-Br | 3-CF$_3$, 4-Cl | 4-Br | 3-CF$_3$, 4-Cl | 2-Cl, 6-Cl | 3-CF$_3$, 4-Cl |
| 2-Me | 3-CF$_3$, 4-Cl | 2-F, 4-F | 3-CF$_3$, 4-Cl | 2-Me, 6-Me | 3-CF$_3$, 4-Cl |
| 2-CF$_3$ | 3-CF$_3$, 4-Cl | 2-Cl, 4-F | 3-CF$_3$, 4-Cl | 2-F, 4-F, 6-F | 3-CF$_3$, 4-Cl |
| 2-F | 3,4-DFMDO* | 4-F | 3,4-DFMDO* | 2-Me, 4-F | 3,4-DFMDO* |
| 2-Cl | 3,4-DFMDO* | 4-Cl | 3,4-DFMDO* | 2-F, 6-F | 3,4-DFMDO* |
| 2-Br | 3,4-DFMDO* | 4-Br | 3,4-DFMDO* | 2-Cl, 6-Cl | 3,4-DFMDO* |
| 2-Me | 3,4-DFMDO* | 2-F, 4-F | 3,4-DFMDO* | 2-Me, 6-Me | 3,4-DFMDO* |
| 2-CF$_3$ | 3,4-DFMDO* | 2-Cl, 4-F | 3,4-DFMDO* | 2-F, 4-F, 6-F | 3,4-DFMDO* |
| | | A is CO$_2$Et | | | |
| 2-F | 2-F | 2-F | 3-F | 2-F | 3-Cl |
| 2-Cl | 2-F | 2-Cl | 3-F | 2-Cl | 3-Cl |
| 2-Br | 2-F | 2-Br | 3-F | 2-Br | 3-Cl |
| 2-Me | 2-F | 2-Me | 3-F | 2-Me | 3-Cl |
| 2-CF$_3$ | 2-F | 2-CF$_3$ | 3-F | 2-CF$_3$ | 3-Cl |
| 4-F | 2-F | 4-F | 3-F | 4-F | 3-Cl |
| 4-Cl | 2-F | 4-Cl | 3-F | 4-Cl | 3-Cl |
| 4-Br | 2-F | 4-Br | 3-F | 4-Br | 3-Cl |
| 2-F, 4-F | 2-F | 2-F, 4-F | 3-F | 2-F, 4-F | 3-Cl |
| 2-Cl, 4-F | 2-F | 2-Cl, 4-F | 3-F | 2-Cl, 4-F | 3-Cl |
| 2-Me, 4-F | 2-F | 2-Me, 4-F | 3-F | 2-Me, 4-F | 3-Cl |
| 2-F, 6-F | 2-F | 2-F, 6-F | 3-F | 2-F, 6-F | 3-Cl |
| 2-Cl, 6-Cl | 2-F | 2-Cl, 6-Cl | 3-F | 2-Cl, 6-Cl | 3-Cl |
| 2-Me, 6-Me | 2-F | 2-Me, 6-Me | 3-F | 2-Me, 6-Me | 3-Cl |
| 2-F, 4-F, 6-F | 2-F | 2-F, 4-F, 6-F | 3-F | 2-F, 4-F, 6-F | 3-Cl |
| 2-F | 3-Br | 2-F | 3-CF$_3$ | 2-F | 3-OCF$_3$ |

TABLE 1-continued

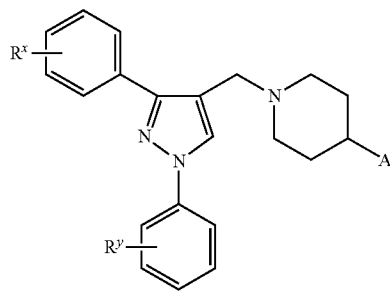

| $R^x$ | $R^y$ | $R^x$ | $R^y$ | $R^x$ | $R^y$ |
|---|---|---|---|---|---|
| 2-Cl | 3-Br | 2-Cl | 3-CF$_3$ | 2-Cl | 3-OCF$_3$ |
| 2-Br | 3-Br | 2-Br | 3-CF$_3$ | 2-Br | 3-OCF$_3$ |
| 2-Me | 3-Br | 2-Me | 3-CF$_3$ | 2-Me | 3-OCF$_3$ |
| 2-CF$_3$ | 3-Br | 2-CF$_3$ | 3-CF$_3$ | 2-CF$_3$ | 3-OCF$_3$ |
| 4-F | 3-Br | 4-F | 3-CF$_3$ | 4-F | 3-OCF$_3$ |
| 4-Cl | 3-Br | 4-Cl | 3-CF$_3$ | 4-Cl | 3-OCF$_3$ |
| 4-Br | 3-Br | 4-Br | 3-CF$_3$ | 4-Br | 3-OCF$_3$ |
| 2-F, 4-F | 3-Br | 2-F, 4-F | 3-CF$_3$ | 2-F, 4-F | 3-OCF$_3$ |
| 2-Cl, 4-F | 3-Br | 2-Cl, 4-F | 3-CF$_3$ | 2-Cl, 4-F | 3-OCF$_3$ |
| 2-Me, 4-F | 3-Br | 2-Me, 4-F | 3-CF$_3$ | 2-Me, 4-F | 3-OCF$_3$ |
| 2-F, 6-F | 3-Br | 2-F, 6-F | 3-CF$_3$ | 2-F, 6-F | 3-OCF$_3$ |
| 2-Cl, 6-Cl | 3-Br | 2-Cl, 6-Cl | 3-CF$_3$ | 2-Cl, 6-Cl | 3-OCF$_3$ |
| 2-Me, 6-Me | 3-Br | 2-Me, 6-Me | 3-CF$_3$ | 2-Me, 6-Me | 3-OCF$_3$ |
| 2-F, 4-F, 6-F | 3-Br | 2-F, 4-F, 6-F | 3-CF$_3$ | 2-F, 4-F, 6-F | 3-OCF$_3$ |
| 2-F | 4-F | 2-F | 4-Cl | 2-F | 4-Br |
| 2-Cl | 4-F | 2-Cl | 4-Cl | 2-Cl | 4-Br |
| 2-Br | 4-F | 2-Br | 4-Cl | 2-Br | 4-Br |
| 2-Me | 4-F | 2-Me | 4-Cl | 2-Me | 4-Br |
| 2-CF$_3$ | 4-F | 2-CF$_3$ | 4-Cl | 2-CF$_3$ | 4-Br |
| 4-F | 4-F | 4-F | 4-Cl | 4-F | 4-Br |
| 4-Cl | 4-F | 4-Cl | 4-Cl | 4-Cl | 4-Br |
| 4-Br | 4-F | 4-Br | 4-Cl | 4-Br | 4-Br |
| 2-F, 4-F | 4-F | 2-F, 4-F | 4-Cl | 2-F, 4-F | 4-Br |
| 2-Cl, 4-F | 4-F | 2-Cl, 4-F | 4-Cl | 2-Cl, 4-F | 4-Br |
| 2-Me, 4-F | 4-F | 2-Me, 4-F | 4-Cl | 2-Me, 4-F | 4-Br |
| 2-F, 6-F | 4-F | 2-F, 6-F | 4-Cl | 2-F, 6-F | 4-Br |
| 2-Cl, 6-Cl | 4-F | 2-Cl, 6-Cl | 4-Cl | 2-Cl, 6-Cl | 4-Br |
| 2-Me, 6-Me | 4-F | 2-Me, 6-Me | 4-Cl | 2-Me, 6-Me | 4-Br |
| 2-F, 4-F, 6-F | 4-F | 2-F, 4-F, 6-F | 4-Cl | 2-F, 4-F, 6-F | 4-Br |
| 2-F | 4-CF$_3$ | 2-F | 4-OCF$_3$ | 2-F | 3-F, 4-F |
| 2-Cl | 4-CF$_3$ | 2-Cl | 4-OCF$_3$ | 2-Cl | 3-F, 4-F |
| 2-Br | 4-CF$_3$ | 2-Br | 4-OCF$_3$ | 2-Br | 3-F, 4-F |
| 2-Me | 4-CF$_3$ | 2-Me | 4-OCF$_3$ | 2-Me | 3-F, 4-F |
| 2-CF$_3$ | 4-CF$_3$ | 2-CF$_3$ | 4-OCF$_3$ | 2-CF$_3$ | 3-F, 4-F |
| 4-F | 4-CF$_3$ | 4-F | 4-OCF$_3$ | 4-F | 3-F, 4-F |
| 4-Cl | 4-CF$_3$ | 4-Cl | 4-OCF$_3$ | 4-Cl | 3-F, 4-F |
| 4-Br | 4-CF$_3$ | 4-Br | 4-OCF$_3$ | 4-Br | 3-F, 4-F |
| 2-F, 4-F | 4-CF$_3$ | 2-F, 4-F | 4-OCF$_3$ | 2-F, 4-F | 3-F, 4-F |
| 2-Cl, 4-F | 4-CF$_3$ | 2-Cl, 4-F | 4-OCF$_3$ | 2-Cl, 4-F | 3-F, 4-F |
| 2-Me, 4-F | 4-CF$_3$ | 2-Me, 4-F | 4-OCF$_3$ | 2-Me, 4-F | 3-F, 4-F |
| 2-F, 6-F | 4-CF$_3$ | 2-F, 6-F | 4-OCF$_3$ | 2-F, 6-F | 3-F, 4-F |
| 2-Cl, 6-Cl | 4-CF$_3$ | 2-Cl, 6-Cl | 4-OCF$_3$ | 2-Cl, 6-Cl | 3-F, 4-F |
| 2-Me, 6-Me | 4-CF$_3$ | 2-Me, 6-Me | 4-OCF$_3$ | 2-Me, 6-Me | 3-F, 4-F |
| 2-F, 4-F, 6-F | 4-CF$_3$ | 2-F, 4-F, 6-F | 4-OCF$_3$ | 2-F, 4-F, 6-F | 3-F, 4-F |
| 2-F | 3-F, 4-Cl | 2-F | 3-F, 4-Br | 2-F | 3-F, 4-CF$_3$ |
| 2-Cl | 3-F, 4-Cl | 2-Cl | 3-F, 4-Br | 2-Cl | 3-F, 4-CF$_3$ |
| 2-Br | 3-F, 4-Cl | 2-Br | 3-F, 4-Br | 2-Br | 3-F, 4-CF$_3$ |
| 2-Me | 3-F, 4-Cl | 2-Me | 3-F, 4-Br | 2-Me | 3-F, 4-CF$_3$ |
| 2-CF$_3$ | 3-F, 4-Cl | 2-CF$_3$ | 3-F, 4-Br | 2-CF$_3$ | 3-F, 4-CF$_3$ |
| 4-F | 3-F, 4-Cl | 4-F | 3-F, 4-Br | 4-F | 3-F, 4-CF$_3$ |
| 4-Cl | 3-F, 4-Cl | 4-Cl | 3-F, 4-Br | 4-Cl | 3-F, 4-CF$_3$ |
| 4-Br | 3-F, 4-Cl | 4-Br | 3-F, 4-Br | 4-Br | 3-F, 4-CF$_3$ |
| 2-F, 4-F | 3-F, 4-Cl | 2-F, 4-F | 3-F, 4-Br | 2-F, 4-F | 3-F, 4-CF$_3$ |
| 2-Cl, 4-F | 3-F, 4-Cl | 2-Cl, 4-F | 3-F, 4-Br | 2-Cl, 4-F | 3-F, 4-CF$_3$ |
| 2-Me, 4-F | 3-F, 4-Cl | 2-Me, 4-F | 3-F, 4-Br | 2-Me, 4-F | 3-F, 4-CF$_3$ |
| 2-F, 6-F | 3-F, 4-Cl | 2-F, 6-F | 3-F, 4-Br | 2-F, 6-F | 3-F, 4-CF$_3$ |
| 2-Cl, 6-Cl | 3-F, 4-Cl | 2-Cl, 6-Cl | 3-F, 4-Br | 2-Cl, 6-Cl | 3-F, 4-CF$_3$ |
| 2-Me, 6-Me | 3-F, 4-Cl | 2-Me, 6-Me | 3-F, 4-Br | 2-Me, 6-Me | 3-F, 4-CF$_3$ |
| 2-F, 4-F, 6-F | 3-F, 4-Cl | 2-F, 4-F, 6-F | 3-F, 4-Br | 2-F, 4-F, 6-F | 3-F, 4-CF$_3$ |
| 2-F | 3-F, 4-OCF$_3$ | 2-F | 3-Cl, 4-F | 2-F | 3-Cl, 4-Cl |
| 2-Cl | 3-F, 4-OCF$_3$ | 2-Cl | 3-Cl, 4-F | 2-Cl | 3-Cl, 4-Cl |
| 2-Br | 3-F, 4-OCF$_3$ | 2-Br | 3-Cl, 4-F | 2-Br | 3-Cl, 4-Cl |
| 2-Me | 3-F, 4-OCF$_3$ | 2-Me | 3-Cl, 4-F | 2-Me | 3-Cl, 4-Cl |

TABLE 1-continued

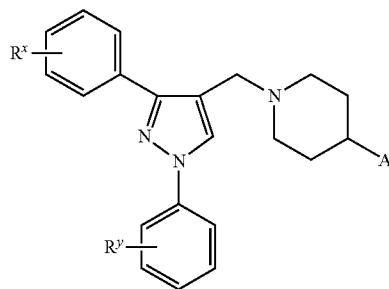

| $R^x$ | $R^y$ | $R^x$ | $R^y$ | $R^x$ | $R^y$ |
|---|---|---|---|---|---|
| 2-CF$_3$ | 3-F, 4-OCF$_3$ | 2-CF$_3$ | 3-Cl, 4-F | 2-CF$_3$ | 3-Cl, 4-Cl |
| 4-F | 3-F, 4-OCF$_3$ | 4-F | 3-Cl, 4-F | 4-F | 3-Cl, 4-Cl |
| 4-Cl | 3-F, 4-OCF$_3$ | 4-Cl | 3-Cl, 4-F | 4-Cl | 3-Cl, 4-Cl |
| 4-Br | 3-F, 4-OCF$_3$ | 4-Br | 3-Cl, 4-F | 4-Br | 3-Cl, 4-Cl |
| 2-F, 4-F | 3-F, 4-OCF$_3$ | 2-F, 4-F | 3-Cl, 4-F | 2-F, 4-F | 3-Cl, 4-Cl |
| 2-Cl, 4-F | 3-F, 4-OCF$_3$ | 2-Cl, 4-F | 3-Cl, 4-F | 2-Cl, 4-F | 3-Cl, 4-Cl |
| 2-Me, 4-F | 3-F, 4-OCF$_3$ | 2-Me, 4-F | 3-Cl, 4-F | 2-Me, 4-F | 3-Cl, 4-Cl |
| 2-F, 6-F | 3-F, 4-OCF$_3$ | 2-F, 6-F | 3-Cl, 4-F | 2-F, 6-F | 3-Cl, 4-Cl |
| 2-Cl, 6-Cl | 3-F, 4-OCF$_3$ | 2-Cl, 6-Cl | 3-Cl, 4-F | 2-Cl, 6-Cl | 3-Cl, 4-Cl |
| 2-Me, 6-Me | 3-F, 4-OCF$_3$ | 2-Me, 6-Me | 3-Cl, 4-F | 2-Me, 6-Me | 3-Cl, 4-Cl |
| 2-F, 4-F, 6-F | 3-F, 4-OCF$_3$ | 2-F, 4-F, 6-F | 3-Cl, 4-F | 2-F, 4-F, 6-F | 3-Cl, 4-Cl |
| 2-F | 3-Cl, 4-CF$_3$ | 2-F | 3-Br, 4-F | 2-F | 3-CF$_3$, 4-F |
| 2-Cl | 3-Cl, 4-CF$_3$ | 2-Cl | 3-Br, 4-F | 2-Cl | 3-CF$_3$, 4-F |
| 2-Br | 3-Cl, 4-CF$_3$ | 2-Br | 3-Br, 4-F | 2-Br | 3-CF$_3$, 4-F |
| 2-Me | 3-Cl, 4-CF$_3$ | 2-Me | 3-Br, 4-F | 2-Me | 3-CF$_3$, 4-F |
| 2-CF$_3$ | 3-Cl, 4-CF$_3$ | 2-CF$_3$ | 3-Br, 4-F | 2-CF$_3$ | 3-CF$_3$, 4-F |
| 4-F | 3-Cl, 4-CF$_3$ | 4-F | 3-Br, 4-F | 4-F | 3-CF$_3$, 4-F |
| 4-Cl | 3-Cl, 4-CF$_3$ | 4-Cl | 3-Br, 4-F | 4-Cl | 3-CF$_3$, 4-F |
| 4-Br | 3-Cl, 4-CF$_3$ | 4-Br | 3-Br, 4-F | 4-Br | 3-CF$_3$, 4-F |
| 2-F, 4-F | 3-Cl, 4-CF$_3$ | 2-F, 4-F | 3-Br, 4-F | 2-F, 4-F | 3-CF$_3$, 4-F |
| 2-Cl, 4-F | 3-Cl, 4-CF$_3$ | 2-Cl, 4-F | 3-Br, 4-F | 2-Cl, 4-F | 3-CF$_3$, 4-F |
| 2-Me, 4-F | 3-Cl, 4-CF$_3$ | 2-Me, 4-F | 3-Br, 4-F | 2-Me, 4-F | 3-CF$_3$, 4-F |
| 2-F, 6-F | 3-Cl, 4-CF$_3$ | 2-F, 6-F | 3-Br, 4-F | 2-F, 6-F | 3-CF$_3$, 4-F |
| 2-Cl, 6-Cl | 3-Cl, 4-CF$_3$ | 2-Cl, 6-Cl | 3-Br, 4-F | 2-Cl, 6-Cl | 3-CF$_3$, 4-F |
| 2-Me, 6-Me | 3-Cl, 4-CF$_3$ | 2-Me, 6-Me | 3-Br, 4-F | 2-Me, 6-Me | 3-CF$_3$, 4-F |
| 2-F, 4-F, 6-F | 3-Cl, 4-CF$_3$ | 2-F, 4-F, 6-F | 3-Br, 4-F | 2-F, 4-F, 6-F | 3-CF$_3$, 4-F |
| 2-F | 3-CF$_3$, 4-Cl | 4-F | 3-CF$_3$, 4-Cl | 2-Me, 4-F | 3-CF$_3$, 4-Cl |
| 2-Cl | 3-CF$_3$, 4-Cl | 4-Cl | 3-CF$_3$, 4-Cl | 2-F, 6-F | 3-CF$_3$, 4-Cl |
| 2-Br | 3-CF$_3$, 4-Cl | 4-Br | 3-CF$_3$, 4-Cl | 2-Cl, 6-Cl | 3-CF$_3$, 4-Cl |
| 2-Me | 3-CF$_3$, 4-Cl | 2-F, 4-F | 3-CF$_3$, 4-Cl | 2-Me, 6-Me | 3-CF$_3$, 4-Cl |
| 2-CF$_3$ | 3-CF$_3$, 4-Cl | 2-Cl, 4-F | 3-CF$_3$, 4-Cl | 2-F, 4-F, 6-F | 3-CF$_3$, 4-Cl |
| 2-F | 3,4-DFMDO* | 4-F | 3,4-DFMDO* | 2-Me, 4-F | 3,4-DFMDO* |
| 2-Cl | 3,4-DFMDO* | 4-Cl | 3,4-DFMDO* | 2-F, 6-F | 3,4-DFMDO* |
| 2-Br | 3,4-DFMDO* | 4-Br | 3,4-DFMDO* | 2-Cl, 6-Cl | 3,4-DFMDO* |
| 2-Me | 3,4-DFMDO* | 2-F, 4-F | 3,4-DFMDO* | 2-Me, 6-Me | 3,4-DFMDO* |
| 2-CF$_3$ | 3,4-DFMDO* | 2-Cl, 4-F | 3,4-DFMDO* | 2-F, 4-F, 6-F | 3,4-DFMDO* |
| A is NHC(O)Me | | | | | |
| 2-F | 2-F | 2-F | 3-F | 2-F | 3-Cl |
| 2-Cl | 2-F | 2-Cl | 3-F | 2-Cl | 3-Cl |
| 2-Br | 2-F | 2-Br | 3-F | 2-Br | 3-Cl |
| 2-Me | 2-F | 2-Me | 3-F | 2-Me | 3-Cl |
| 2-CF$_3$ | 2-F | 2-CF$_3$ | 3-F | 2-CF$_3$ | 3-Cl |
| 4-F | 2-F | 4-F | 3-F | 4-F | 3-Cl |
| 4-Cl | 2-F | 4-Cl | 3-F | 4-Cl | 3-Cl |
| 4-Br | 2-F | 4-Br | 3-F | 4-Br | 3-Cl |
| 2-F, 4-F | 2-F | 2-F, 4-F | 3-F | 2-F, 4-F | 3-Cl |
| 2-Cl, 4-F | 2-F | 2-Cl, 4-F | 3-F | 2-Cl, 4-F | 3-Cl |
| 2-Me, 4-F | 2-F | 2-Me, 4-F | 3-F | 2-Me, 4-F | 3-Cl |
| 2-F, 6-F | 2-F | 2-F, 6-F | 3-F | 2-F, 6-F | 3-Cl |
| 2-Cl, 6-Cl | 2-F | 2-Cl, 6-Cl | 3-F | 2-Cl, 6-Cl | 3-Cl |
| 2-Me, 6-Me | 2-F | 2-Me, 6-Me | 3-F | 2-Me, 6-Me | 3-Cl |
| 2-F, 4-F, 6-F | 2-F | 2-F, 4-F, 6-F | 3-F | 2-F, 4-F, 6-F | 3-Cl |
| 2-F | 3-Br | 2-F | 3-CF$_3$ | 2-F | 3-OCF$_3$ |
| 2-Cl | 3-Br | 2-Cl | 3-CF$_3$ | 2-Cl | 3-OCF$_3$ |
| 2-Br | 3-Br | 2-Br | 3-CF$_3$ | 2-Br | 3-OCF$_3$ |
| 2-Me | 3-Br | 2-Me | 3-CF$_3$ | 2-Me | 3-OCF$_3$ |
| 2-CF$_3$ | 3-Br | 2-CF$_3$ | 3-CF$_3$ | 2-CF$_3$ | 3-OCF$_3$ |
| 4-F | 3-Br | 4-F | 3-CF$_3$ | 4-F | 3-OCF$_3$ |
| 4-Cl | 3-Br | 4-Cl | 3-CF$_3$ | 4-Cl | 3-OCF$_3$ |
| 4-Br | 3-Br | 4-Br | 3-CF$_3$ | 4-Br | 3-OCF$_3$ |
| 2-F, 4-F | 3-Br | 2-F, 4-F | 3-CF$_3$ | 2-F, 4-F | 3-OCF$_3$ |
| 2-Cl, 4-F | 3-Br | 2-Cl, 4-F | 3-CF$_3$ | 2-Cl, 4-F | 3-OCF$_3$ |

TABLE 1-continued

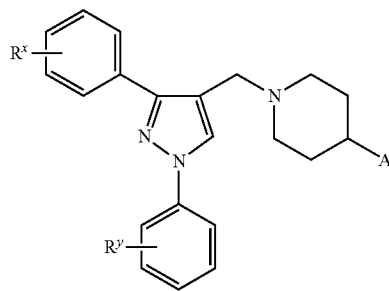

| $R^x$ | $R^y$ | $R^x$ | $R^y$ | $R^x$ | $R^y$ |
|---|---|---|---|---|---|
| 2-Me, 4-F | 3-Br | 2-Me, 4-F | 3-CF$_3$ | 2-Me, 4-F | 3-OCF$_3$ |
| 2-F, 6-F | 3-Br | 2-F, 6-F | 3-CF$_3$ | 2-F, 6-F | 3-OCF$_3$ |
| 2-Cl, 6-Cl | 3-Br | 2-Cl, 6-Cl | 3-CF$_3$ | 2-Cl, 6-Cl | 3-OCF$_3$ |
| 2-Me, 6-Me | 3-Br | 2-Me, 6-Me | 3-CF$_3$ | 2-Me, 6-Me | 3-OCF$_3$ |
| 2-F, 4-F, 6-F | 3-Br | 2-F, 4-F, 6-F | 3-CF$_3$ | 2-F, 4-F, 6-F | 3-OCF$_3$ |
| 2-F | 4-F | 2-F | 4-Cl | 2-F | 4-Br |
| 2-Cl | 4-F | 2-Cl | 4-Cl | 2-Cl | 4-Br |
| 2-Br | 4-F | 2-Br | 4-Cl | 2-Br | 4-Br |
| 2-Me | 4-F | 2-Me | 4-Cl | 2-Me | 4-Br |
| 2-CF$_3$ | 4-F | 2-CF$_3$ | 4-Cl | 2-CF$_3$ | 4-Br |
| 4-F | 4-F | 4-F | 4-Cl | 4-F | 4-Br |
| 4-Cl | 4-F | 4-Cl | 4-Cl | 4-Cl | 4-Br |
| 4-Br | 4-F | 4-Br | 4-Cl | 4-Br | 4-Br |
| 2-F, 4-F | 4-F | 2-F, 4-F | 4-Cl | 2-F, 4-F | 4-Br |
| 2-Cl, 4-F | 4-F | 2-Cl, 4-F | 4-Cl | 2-Cl, 4-F | 4-Br |
| 2-Me, 4-F | 4-F | 2-Me, 4-F | 4-Cl | 2-Me, 4-F | 4-Br |
| 2-F, 6-F | 4-F | 2-F, 6-F | 4-Cl | 2-F, 6-F | 4-Br |
| 2-Cl, 6-Cl | 4-F | 2-Cl, 6-Cl | 4-Cl | 2-Cl, 6-Cl | 4-Br |
| 2-Me, 6-Me | 4-F | 2-Me, 6-Me | 4-Cl | 2-Me, 6-Me | 4-Br |
| 2-F, 4-F, 6-F | 4-F | 2-F, 4-F, 6-F | 4-Cl | 2-F, 4-F, 6-F | 4-Br |
| 2-F | 4-CF$_3$ | 2-F | 4-OCF$_3$ | 2-F | 3-F, 4-F |
| 2-Cl | 4-CF$_3$ | 2-Cl | 4-OCF$_3$ | 2-Cl | 3-F, 4-F |
| 2-Br | 4-CF$_3$ | 2-Br | 4-OCF$_3$ | 2-Br | 3-F, 4-F |
| 2-Me | 4-CF$_3$ | 2-Me | 4-OCF$_3$ | 2-Me | 3-F, 4-F |
| 2-CF$_3$ | 4-CF$_3$ | 2-CF$_3$ | 4-OCF$_3$ | 2-CF$_3$ | 3-F, 4-F |
| 4-F | 4-CF$_3$ | 4-F | 4-OCF$_3$ | 4-F | 3-F, 4-F |
| 4-Cl | 4-CF$_3$ | 4-Cl | 4-OCF$_3$ | 4-Cl | 3-F, 4-F |
| 4-Br | 4-CF$_3$ | 4-Br | 4-OCF$_3$ | 4-Br | 3-F, 4-F |
| 2-F, 4-F | 4-CF$_3$ | 2-F, 4-F | 4-OCF$_3$ | 2-F, 4-F | 3-F, 4-F |
| 2-Cl, 4-F | 4-CF$_3$ | 2-Cl, 4-F | 4-OCF$_3$ | 2-Cl, 4-F | 3-F, 4-F |
| 2-Me, 4-F | 4-CF$_3$ | 2-Me, 4-F | 4-OCF$_3$ | 2-Me, 4-F | 3-F, 4-F |
| 2-F, 6-F | 4-CF$_3$ | 2-F, 6-F | 4-OCF$_3$ | 2-F, 6-F | 3-F, 4-F |
| 2-Cl, 6-Cl | 4-CF$_3$ | 2-Cl, 6-Cl | 4-OCF$_3$ | 2-Cl, 6-Cl | 3-F, 4-F |
| 2-Me, 6-Me | 4-CF$_3$ | 2-Me, 6-Me | 4-OCF$_3$ | 2-Me, 6-Me | 3-F, 4-F |
| 2-F, 4-F, 6-F | 4-CF$_3$ | 2-F, 4-F, 6-F | 4-OCF$_3$ | 2-F, 4-F, 6-F | 3-F, 4-F |
| 2-F | 3-F, 4-Cl | 2-F | 3-F, 4-Br | 2-F | 3-F, 4-CF$_3$ |
| 2-Cl | 3-F, 4-Cl | 2-Cl | 3-F, 4-Br | 2-Cl | 3-F, 4-CF$_3$ |
| 2-Br | 3-F, 4-Cl | 2-Br | 3-F, 4-Br | 2-Br | 3-F, 4-CF$_3$ |
| 2-Me | 3-F, 4-Cl | 2-Me | 3-F, 4-Br | 2-Me | 3-F, 4-CF$_3$ |
| 2-CF$_3$ | 3-F, 4-Cl | 2-CF$_3$ | 3-F, 4-Br | 2-CF$_3$ | 3-F, 4-CF$_3$ |
| 4-F | 3-F, 4-Cl | 4-F | 3-F, 4-Br | 4-F | 3-F, 4-CF$_3$ |
| 4-Cl | 3-F, 4-Cl | 4-Cl | 3-F, 4-Br | 4-Cl | 3-F, 4-CF$_3$ |
| 4-Br | 3-F, 4-Cl | 4-Br | 3-F, 4-Br | 4-Br | 3-F, 4-CF$_3$ |
| 2-F, 4-F | 3-F, 4-Cl | 2-F, 4-F | 3-F, 4-Br | 2-F, 4-F | 3-F, 4-CF$_3$ |
| 2-Cl, 4-F | 3-F, 4-Cl | 2-Cl, 4-F | 3-F, 4-Br | 2-Cl, 4-F | 3-F, 4-CF$_3$ |
| 2-Me, 4-F | 3-F, 4-Cl | 2-Me, 4-F | 3-F, 4-Br | 2-Me, 4-F | 3-F, 4-CF$_3$ |
| 2-F, 6-F | 3-F, 4-Cl | 2-F, 6-F | 3-F, 4-Br | 2-F, 6-F | 3-F, 4-CF$_3$ |
| 2-Cl, 6-Cl | 3-F, 4-Cl | 2-Cl, 6-Cl | 3-F, 4-Br | 2-Cl, 6-Cl | 3-F, 4-CF$_3$ |
| 2-Me, 6-Me | 3-F, 4-Cl | 2-Me, 6-Me | 3-F, 4-Br | 2-Me, 6-Me | 3-F, 4-CF$_3$ |
| 2-F, 4-F, 6-F | 3-F, 4-Cl | 2-F, 4-F, 6-F | 3-F, 4-Br | 2-F, 4-F, 6-F | 3-F, 4-CF$_3$ |
| 2-F | 3-F, 4-OCF$_3$ | 2-F | 3-Cl, 4-F | 2-F | 3-Cl, 4-Cl |
| 2-Cl | 3-F, 4-OCF$_3$ | 2-Cl | 3-Cl, 4-F | 2-Cl | 3-Cl, 4-Cl |
| 2-Br | 3-F, 4-OCF$_3$ | 2-Br | 3-Cl, 4-F | 2-Br | 3-Cl, 4-Cl |
| 2-Me | 3-F, 4-OCF$_3$ | 2-Me | 3-Cl, 4-F | 2-Me | 3-Cl, 4-Cl |
| 2-CF$_3$ | 3-F, 4-OCF$_3$ | 2-CF$_3$ | 3-Cl, 4-F | 2-CF$_3$ | 3-Cl, 4-Cl |
| 4-F | 3-F, 4-OCF$_3$ | 4-F | 3-Cl, 4-F | 4-F | 3-Cl, 4-Cl |
| 4-Cl | 3-F, 4-OCF$_3$ | 4-Cl | 3-Cl, 4-F | 4-Cl | 3-Cl, 4-Cl |
| 4-Br | 3-F, 4-OCF$_3$ | 4-Br | 3-Cl, 4-F | 4-Br | 3-Cl, 4-Cl |
| 2-F, 4-F | 3-F, 4-OCF$_3$ | 2-F, 4-F | 3-Cl, 4-F | 2-F, 4-F | 3-Cl, 4-Cl |
| 2-Cl, 4-F | 3-F, 4-OCF$_3$ | 2-Cl, 4-F | 3-Cl, 4-F | 2-Cl, 4-F | 3-Cl, 4-Cl |
| 2-Me, 4-F | 3-F, 4-OCF$_3$ | 2-Me, 4-F | 3-Cl, 4-F | 2-Me, 4-F | 3-Cl, 4-Cl |
| 2-F, 6-F | 3-F, 4-OCF$_3$ | 2-F, 6-F | 3-Cl, 4-F | 2-F, 6-F | 3-Cl, 4-Cl |
| 2-Cl, 6-Cl | 3-F, 4-OCF$_3$ | 2-Cl, 6-Cl | 3-Cl, 4-F | 2-Cl, 6-Cl | 3-Cl, 4-Cl |

TABLE 1-continued

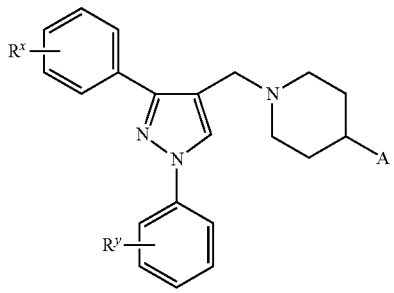

| $R^x$ | $R^y$ | $R^x$ | $R^y$ | $R^x$ | $R^y$ |
|---|---|---|---|---|---|
| 2-Me, 6-Me | 3-F, 4-OCF$_3$ | 2-Me, 6-Me | 3-Cl, 4-F | 2-Me, 6-Me | 3-Cl, 4-Cl |
| 2-F, 4-F, 6-F | 3-F, 4-OCF$_3$ | 2-F, 4-F, 6-F | 3-Cl, 4-F | 2-F, 4-F, 6-F | 3-Cl, 4-Cl |
| 2-F | 3-Cl, 4-CF$_3$ | 2-F | 3-Br, 4-F | 2-F | 3-CF$_3$, 4-F |
| 2-Cl | 3-Cl, 4-CF$_3$ | 2-Cl | 3-Br, 4-F | 2-Cl | 3-CF$_3$, 4-F |
| 2-Br | 3-Cl, 4-CF$_3$ | 2-Br | 3-Br, 4-F | 2-Br | 3-CF$_3$, 4-F |
| 2-Me | 3-Cl, 4-CF$_3$ | 2-Me | 3-Br, 4-F | 2-Me | 3-CF$_3$, 4-F |
| 2-CF$_3$ | 3-Cl, 4-CF$_3$ | 2-CF$_3$ | 3-Br, 4-F | 2-CF$_3$ | 3-CF$_3$, 4-F |
| 4-F | 3-Cl, 4-CF$_3$ | 4-F | 3-Br, 4-F | 4-F | 3-CF$_3$, 4-F |
| 4-Cl | 3-Cl, 4-CF$_3$ | 4-Cl | 3-Br, 4-F | 4-Cl | 3-CF$_3$, 4-F |
| 4-Br | 3-Cl, 4-CF$_3$ | 4-Br | 3-Br, 4-F | 4-Br | 3-CF$_3$, 4-F |
| 2-F, 4-F | 3-Cl, 4-CF$_3$ | 2-F, 4-F | 3-Br, 4-F | 2-F, 4-F | 3-CF$_3$, 4-F |
| 2-Cl, 4-F | 3-Cl, 4-CF$_3$ | 2-Cl, 4-F | 3-Br, 4-F | 2-Cl, 4-F | 3-CF$_3$, 4-F |
| 2-Me, 4-F | 3-Cl, 4-CF$_3$ | 2-Me, 4-F | 3-Br, 4-F | 2-Me, 4-F | 3-CF$_3$, 4-F |
| 2-F, 6-F | 3-Cl, 4-CF$_3$ | 2-F, 6-F | 3-Br, 4-F | 2-F, 6-F | 3-CF$_3$, 4-F |
| 2-Cl, 6-Cl | 3-Cl, 4-CF$_3$ | 2-Cl, 6-Cl | 3-Br, 4-F | 2-Cl, 6-Cl | 3-CF$_3$, 4-F |
| 2-Me, 6-Me | 3-Cl, 4-CF$_3$ | 2-Me, 6-Me | 3-Br, 4-F | 2-Me, 6-Me | 3-CF$_3$, 4-F |
| 2-F, 4-F, 6-F | 3-Cl, 4-CF$_3$ | 2-F, 4-F, 6-F | 3-Br, 4-F | 2-F, 4-F, 6-F | 3-CF$_3$, 4-F |
| 2-F | 3-CF$_3$, 4-Cl | 4-F | 3-CF$_3$, 4-Cl | 2-Me, 4-F | 3-CF$_3$, 4-Cl |
| 2-Cl | 3-CF$_3$, 4-Cl | 4-Cl | 3-CF$_3$, 4-Cl | 2-F, 6-F | 3-CF$_3$, 4-Cl |
| 2-Br | 3-CF$_3$, 4-Cl | 4-Br | 3-CF$_3$, 4-Cl | 2-Cl, 6-Cl | 3-CF$_3$, 4-Cl |
| 2-Me | 3-CF$_3$, 4-Cl | 2-F, 4-F | 3-CF$_3$, 4-Cl | 2-Me, 6-Me | 3-CF$_3$, 4-Cl |
| 2-CF$_3$ | 3-CF$_3$, 4-Cl | 2-Cl, 4-F | 3-CF$_3$, 4-Cl | 2-F, 4-F, 6-F | 3-CF$_3$, 4-Cl |
| 2-F | 3,4-DFMDO* | 4-F | 3,4-DFMDO* | 2-Me, 4-F | 3,4-DFMDO* |
| 2-Cl | 3,4-DFMDO* | 4-Cl | 3,4-DFMDO* | 2-F, 6-F | 3,4-DFMDO* |
| 2-Br | 3,4-DFMDO* | 4-Br | 3,4-DFMDO* | 2-Cl, 6-Cl | 3,4-DFMDO* |
| 2-Me | 3,4-DFMDO* | 2-F, 4-F | 3,4-DFMDO* | 2-Me, 6-Me | 3,4-DFMDO* |
| 2-CF$_3$ | 3,4-DFMDO* | 2-Cl, 4-F | 3,4-DFMDO* | 2-F, 4-F, 6-F | 3,4-DFMDO* |
| A is C(O)Me | | | | | |
| 2-F | 2-F | 2-F | 3-F | 2-F | 3-Cl |
| 2-Cl | 2-F | 2-Cl | 3-F | 2-Cl | 3-Cl |
| 2-Br | 2-F | 2-Br | 3-F | 2-Br | 3-Cl |
| 2-Me | 2-F | 2-Me | 3-F | 2-Me | 3-Cl |
| 2-CF$_3$ | 2-F | 2-CF$_3$ | 3-F | 2-CF$_3$ | 3-Cl |
| 4-F | 2-F | 4-F | 3-F | 4-F | 3-Cl |
| 4-Cl | 2-F | 4-Cl | 3-F | 4-Cl | 3-Cl |
| 4-Br | 2-F | 4-Br | 3-F | 4-Br | 3-Cl |
| 2-F, 4-F | 2-F | 2-F, 4-F | 3-F | 2-F, 4-F | 3-Cl |
| 2-Cl, 4-F | 2-F | 2-Cl, 4-F | 3-F | 2-Cl, 4-F | 3-Cl |
| 2-Me, 4-F | 2-F | 2-Me, 4-F | 3-F | 2-Me, 4-F | 3-Cl |
| 2-F, 6-F | 2-F | 2-F, 6-F | 3-F | 2-F, 6-F | 3-Cl |
| 2-Cl, 6-Cl | 2-F | 2-Cl, 6-Cl | 3-F | 2-Cl, 6-Cl | 3-Cl |
| 2-Me, 6-Me | 2-F | 2-Me, 6-Me | 3-F | 2-Me, 6-Me | 3-Cl |
| 2-F, 4-F, 6-F | 2-F | 2-F, 4-F, 6-F | 3-F | 2-F, 4-F, 6-F | 3-Cl |
| 2-F | 3-Br | 2-F | 3-CF$_3$ | 2-F | 3-OCF$_3$ |
| 2-Cl | 3-Br | 2-Cl | 3-CF$_3$ | 2-Cl | 3-OCF$_3$ |
| 2-Br | 3-Br | 2-Br | 3-CF$_3$ | 2-Br | 3-OCF$_3$ |
| 2-Me | 3-Br | 2-Me | 3-CF$_3$ | 2-Me | 3-OCF$_3$ |
| 2-CF$_3$ | 3-Br | 2-CF$_3$ | 3-CF$_3$ | 2-CF$_3$ | 3-OCF$_3$ |
| 4-F | 3-Br | 4-F | 3-CF$_3$ | 4-F | 3-OCF$_3$ |
| 4-Cl | 3-Br | 4-Cl | 3-CF$_3$ | 4-Cl | 3-OCF$_3$ |
| 4-Br | 3-Br | 4-Br | 3-CF$_3$ | 4-Br | 3-OCF$_3$ |
| 2-F, 4-F | 3-Br | 2-F, 4-F | 3-CF$_3$ | 2-F, 4-F | 3-OCF$_3$ |
| 2-Cl, 4-F | 3-Br | 2-Cl, 4-F | 3-CF$_3$ | 2-Cl, 4-F | 3-OCF$_3$ |
| 2-Me, 4-F | 3-Br | 2-Me, 4-F | 3-CF$_3$ | 2-Me, 4-F | 3-OCF$_3$ |
| 2-F, 6-F | 3-Br | 2-F, 6-F | 3-CF$_3$ | 2-F, 6-F | 3-OCF$_3$ |
| 2-Cl, 6-Cl | 3-Br | 2-Cl, 6-Cl | 3-CF$_3$ | 2-Cl, 6-Cl | 3-OCF$_3$ |
| 2-Me, 6-Me | 3-Br | 2-Me, 6-Me | 3-CF$_3$ | 2-Me, 6-Me | 3-OCF$_3$ |
| 2-F, 4-F, 6-F | 3-Br | 2-F, 4-F, 6-F | 3-CF$_3$ | 2-F, 4-F, 6-F | 3-OCF$_3$ |
| 2-F | 4-F | 2-F | 4-Cl | 2-F | 4-Br |
| 2-Cl | 4-F | 2-Cl | 4-Cl | 2-Cl | 4-Br |
| 2-Br | 4-F | 2-Br | 4-Cl | 2-Br | 4-Br |
| 2-Me | 4-F | 2-Me | 4-Cl | 2-Me | 4-Br |

TABLE 1-continued

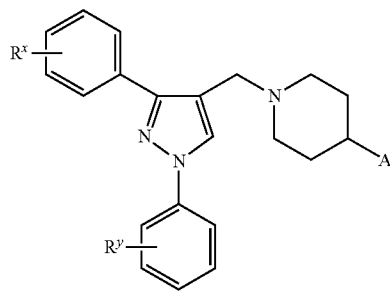

| R$^x$ | R$^y$ | R$^x$ | R$^y$ | R$^x$ | R$^y$ |
|---|---|---|---|---|---|
| 2-CF$_3$ | 4-F | 2-CF$_3$ | 4-Cl | 2-CF$_3$ | 4-Br |
| 4-F | 4-F | 4-F | 4-Cl | 4-F | 4-Br |
| 4-Cl | 4-F | 4-Cl | 4-Cl | 4-Cl | 4-Br |
| 4-Br | 4-F | 4-Br | 4-Cl | 4-Br | 4-Br |
| 2-F, 4-F | 4-F | 2-F, 4-F | 4-Cl | 2-F, 4-F | 4-Br |
| 2-Cl, 4-F | 4-F | 2-Cl, 4-F | 4-Cl | 2-Cl, 4-F | 4-Br |
| 2-Me, 4-F | 4-F | 2-Me, 4-F | 4-Cl | 2-Me, 4-F | 4-Br |
| 2-F, 6-F | 4-F | 2-F, 6-F | 4-Cl | 2-F, 6-F | 4-Br |
| 2-Cl, 6-Cl | 4-F | 2-Cl, 6-Cl | 4-Cl | 2-Cl, 6-Cl | 4-Br |
| 2-Me, 6-Me | 4-F | 2-Me, 6-Me | 4-Cl | 2-Me, 6-Me | 4-Br |
| 2-F, 4-F, 6-F | 4-F | 2-F, 4-F, 6-F | 4-Cl | 2-F, 4-F, 6-F | 4-Br |
| 2-F | 4-CF$_3$ | 2-F | 4-OCF$_3$ | 2-F | 3-F, 4-F |
| 2-Cl | 4-CF$_3$ | 2-Cl | 4-OCF$_3$ | 2-Cl | 3-F, 4-F |
| 2-Br | 4-CF$_3$ | 2-Br | 4-OCF$_3$ | 2-Br | 3-F, 4-F |
| 2-Me | 4-CF$_3$ | 2-Me | 4-OCF$_3$ | 2-Me | 3-F, 4-F |
| 2-CF$_3$ | 4-CF$_3$ | 2-CF$_3$ | 4-OCF$_3$ | 2-CF$_3$ | 3-F, 4-F |
| 4-F | 4-CF$_3$ | 4-F | 4-OCF$_3$ | 4-F | 3-F, 4-F |
| 4-Cl | 4-CF$_3$ | 4-Cl | 4-OCF$_3$ | 4-Cl | 3-F, 4-F |
| 4-Br | 4-CF$_3$ | 4-Br | 4-OCF$_3$ | 4-Br | 3-F, 4-F |
| 2-F, 4-F | 4-CF$_3$ | 2-F, 4-F | 4-OCF$_3$ | 2-F, 4-F | 3-F, 4-F |
| 2-Cl, 4-F | 4-CF$_3$ | 2-Cl, 4-F | 4-OCF$_3$ | 2-Cl, 4-F | 3-F, 4-F |
| 2-Me, 4-F | 4-CF$_3$ | 2-Me, 4-F | 4-OCF$_3$ | 2-Me, 4-F | 3-F, 4-F |
| 2-F, 6-F | 4-CF$_3$ | 2-F, 6-F | 4-OCF$_3$ | 2-F, 6-F | 3-F, 4-F |
| 2-Cl, 6-Cl | 4-CF$_3$ | 2-Cl, 6-Cl | 4-OCF$_3$ | 2-Cl, 6-Cl | 3-F, 4-F |
| 2-Me, 6-Me | 4-CF$_3$ | 2-Me, 6-Me | 4-OCF$_3$ | 2-Me, 6-Me | 3-F, 4-F |
| 2-F, 4-F, 6-F | 4-CF$_3$ | 2-F, 4-F, 6-F | 4-OCF$_3$ | 2-F, 4-F, 6-F | 3-F, 4-F |
| 2-F | 3-F, 4-Cl | 2-F | 3-F, 4-Br | 2-F | 3-F, 4-CF$_3$ |
| 2-Cl | 3-F, 4-Cl | 2-Cl | 3-F, 4-Br | 2-Cl | 3-F, 4-CF$_3$ |
| 2-Br | 3-F, 4-Cl | 2-Br | 3-F, 4-Br | 2-Br | 3-F, 4-CF$_3$ |
| 2-Me | 3-F, 4-Cl | 2-Me | 3-F, 4-Br | 2-Me | 3-F, 4-CF$_3$ |
| 2-CF$_3$ | 3-F, 4-Cl | 2-CF$_3$ | 3-F, 4-Br | 2-CF$_3$ | 3-F, 4-CF$_3$ |
| 4-F | 3-F, 4-Cl | 4-F | 3-F, 4-Br | 4-F | 3-F, 4-CF$_3$ |
| 4-Cl | 3-F, 4-Cl | 4-Cl | 3-F, 4-Br | 4-Cl | 3-F, 4-CF$_3$ |
| 4-Br | 3-F, 4-Cl | 4-Br | 3-F, 4-Br | 4-Br | 3-F, 4-CF$_3$ |
| 2-F, 4-F | 3-F, 4-Cl | 2-F, 4-F | 3-F, 4-Br | 2-F, 4-F | 3-F, 4-CF$_3$ |
| 2-Cl, 4-F | 3-F, 4-Cl | 2-Cl, 4-F | 3-F, 4-Br | 2-Cl, 4-F | 3-F, 4-CF$_3$ |
| 2-Me, 4-F | 3-F, 4-Cl | 2-Me, 4-F | 3-F, 4-Br | 2-Me, 4-F | 3-F, 4-CF$_3$ |
| 2-F, 6-F | 3-F, 4-Cl | 2-F, 6-F | 3-F, 4-Br | 2-F, 6-F | 3-F, 4-CF$_3$ |
| 2-Cl, 6-Cl | 3-F, 4-Cl | 2-Cl, 6-Cl | 3-F, 4-Br | 2-Cl, 6-Cl | 3-F, 4-CF$_3$ |
| 2-Me, 6-Me | 3-F, 4-Cl | 2-Me, 6-Me | 3-F, 4-Br | 2-Me, 6-Me | 3-F, 4-CF$_3$ |
| 2-F, 4-F, 6-F | 3-F, 4-Cl | 2-F, 4-F, 6-F | 3-F, 4-Br | 2-F, 4-F, 6-F | 3-F, 4-CF$_3$ |
| 2-F | 3-F, 4-OCF$_3$ | 2-F | 3-Cl, 4-F | 2-F | 3-Cl, 4-Cl |
| 2-Cl | 3-F, 4-OCF$_3$ | 2-Cl | 3-Cl, 4-F | 2-Cl | 3-Cl, 4-Cl |
| 2-Br | 3-F, 4-OCF$_3$ | 2-Br | 3-Cl, 4-F | 2-Br | 3-Cl, 4-Cl |
| 2-Me | 3-F, 4-OCF$_3$ | 2-Me | 3-Cl, 4-F | 2-Me | 3-Cl, 4-Cl |
| 2-CF$_3$ | 3-F, 4-OCF$_3$ | 2-CF$_3$ | 3-Cl, 4-F | 2-CF$_3$ | 3-Cl, 4-Cl |
| 4-F | 3-F, 4-OCF$_3$ | 4-F | 3-Cl, 4-F | 4-F | 3-Cl, 4-Cl |
| 4-Cl | 3-F, 4-OCF$_3$ | 4-Cl | 3-Cl, 4-F | 4-Cl | 3-Cl, 4-Cl |
| 4-Br | 3-F, 4-OCF$_3$ | 4-Br | 3-Cl, 4-F | 4-Br | 3-Cl, 4-Cl |
| 2-F, 4-F | 3-F, 4-OCF$_3$ | 2-F, 4-F | 3-Cl, 4-F | 2-F, 4-F | 3-Cl, 4-Cl |
| 2-Cl, 4-F | 3-F, 4-OCF$_3$ | 2-Cl, 4-F | 3-Cl, 4-F | 2-Cl, 4-F | 3-Cl, 4-Cl |
| 2-Me, 4-F | 3-F, 4-OCF$_3$ | 2-Me, 4-F | 3-Cl, 4-F | 2-Me, 4-F | 3-Cl, 4-Cl |
| 2-F, 6-F | 3-F, 4-OCF$_3$ | 2-F, 6-F | 3-Cl, 4-F | 2-F, 6-F | 3-Cl, 4-Cl |
| 2-Cl, 6-Cl | 3-F, 4-OCF$_3$ | 2-Cl, 6-Cl | 3-Cl, 4-F | 2-Cl, 6-Cl | 3-Cl, 4-Cl |
| 2-Me, 6-Me | 3-F, 4-OCF$_3$ | 2-Me, 6-Me | 3-Cl, 4-F | 2-Me, 6-Me | 3-Cl, 4-Cl |
| 2-F, 4-F, 6-F | 3-F, 4-OCF$_3$ | 2-F, 4-F, 6-F | 3-Cl, 4-F | 2-F, 4-F, 6-F | 3-Cl, 4-Cl |
| 2-F | 3-Cl, 4-CF$_3$ | 2-F | 3-Br, 4-F | 2-F | 3-CF$_3$, 4-F |
| 2-Cl | 3-Cl, 4-CF$_3$ | 2-Cl | 3-Br, 4-F | 2-Cl | 3-CF$_3$, 4-F |
| 2-Br | 3-Cl, 4-CF$_3$ | 2-Br | 3-Br, 4-F | 2-Br | 3-CF$_3$, 4-F |
| 2-Me | 3-Cl, 4-CF$_3$ | 2-Me | 3-Br, 4-F | 2-Me | 3-CF$_3$, 4-F |
| 2-CF$_3$ | 3-Cl, 4-CF$_3$ | 2-CF$_3$ | 3-Br, 4-F | 2-CF$_3$ | 3-CF$_3$, 4-F |
| 4-F | 3-Cl, 4-CF$_3$ | 4-F | 3-Br, 4-F | 4-F | 3-CF$_3$, 4-F |
| 4-Cl | 3-Cl, 4-CF$_3$ | 4-Cl | 3-Br, 4-F | 4-Cl | 3-CF$_3$, 4-F |

TABLE 1-continued

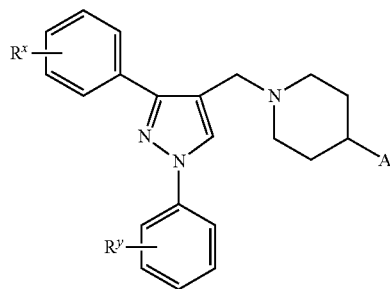

| Rx | Ry | Rx | Ry | Rx | Ry |
|---|---|---|---|---|---|
| 4-Br | 3-Cl, 4-CF3 | 4-Br | 3-Br, 4-F | 4-Br | 3-CF3, 4-F |
| 2-F, 4-F | 3-Cl, 4-CF3 | 2-F, 4-F | 3-Br, 4-F | 2-F, 4-F | 3-CF3, 4-F |
| 2-Cl, 4-F | 3-Cl, 4-CF3 | 2-Cl, 4-F | 3-Br, 4-F | 2-Cl, 4-F | 3-CF3, 4-F |
| 2-Me, 4-F | 3-Cl, 4-CF3 | 2-Me, 4-F | 3-Br, 4-F | 2-Me, 4-F | 3-CF3, 4-F |
| 2-F, 6-F | 3-Cl, 4-CF3 | 2-F, 6-F | 3-Br, 4-F | 2-F, 6-F | 3-CF3, 4-F |
| 2-Cl, 6-Cl | 3-Cl, 4-CF3 | 2-Cl, 6-Cl | 3-Br, 4-F | 2-Cl, 6-Cl | 3-CF3, 4-F |
| 2-Me, 6-Me | 3-Cl, 4-CF3 | 2-Me, 6-Me | 3-Br, 4-F | 2-Me, 6-Me | 3-CF3, 4-F |
| 2-F, 4-F, 6-F | 3-Cl, 4-CF3 | 2-F, 4-F, 6-F | 3-Br, 4-F | 2-F, 4-F, 6-F | 3-CF3, 4-F |
| 2-F | 3-CF3, 4-Cl | 4-F | 3-CF3, 4-Cl | 2-Me, 4-F | 3-CF3, 4-Cl |
| 2-Cl | 3-CF3, 4-Cl | 4-Cl | 3-CF3, 4-Cl | 2-F, 6-F | 3-CF3, 4-Cl |
| 2-Br | 3-CF3, 4-Cl | 4-Br | 3-CF3, 4-Cl | 2-Cl, 6-Cl | 3-CF3, 4-Cl |
| 2-Me | 3-CF3, 4-Cl | 2-F, 4-F | 3-CF3, 4-Cl | 2-Me, 6-Me | 3-CF3, 4-Cl |
| 2-CF3 | 3-CF3, 4-Cl | 2-Cl, 4-F | 3-CF3, 4-Cl | 2-F, 4-F, 6-F | 3-CF3, 4-Cl |
| 2-F | 3,4-DFMDO* | 4-F | 3,4-DFMDO* | 2-Me, 4-F | 3,4-DFMDO* |
| 2-Cl | 3,4-DFMDO* | 4-Cl | 3,4-DFMDO* | 2-F, 6-F | 3,4-DFMDO* |
| 2-Br | 3,4-DFMDO* | 4-Br | 3,4-DFMDO* | 2-Cl, 6-Cl | 3,4-DFMDO* |
| 2-Me | 3,4-DFMDO* | 2-F, 4-F | 3,4-DFMDO* | 2-Me, 6-Me | 3,4-DFMDO* |
| 2-CF3 | 3,4-DFMDO* | 2-Cl, 4-F | 3,4-DFMDO* | 2-F, 4-F, 6-F | 3,4-DFMDO* |
| A is NHC(O)OMe | | | | | |
| 2-F | 2-F | 2-F | 3-F | 2-F | 3-Cl |
| 2-Cl | 2-F | 2-Cl | 3-F | 2-Cl | 3-Cl |
| 2-Br | 2-F | 2-Br | 3-F | 2-Br | 3-Cl |
| 2-Me | 2-F | 2-Me | 3-F | 2-Me | 3-Cl |
| 2-CF3 | 2-F | 2-CF3 | 3-F | 2-CF3 | 3-Cl |
| 4-F | 2-F | 4-F | 3-F | 4-F | 3-Cl |
| 4-Cl | 2-F | 4-Cl | 3-F | 4-Cl | 3-Cl |
| 4-Br | 2-F | 4-Br | 3-F | 4-Br | 3-Cl |
| 2-F, 4-F | 2-F | 2-F, 4-F | 3-F | 2-F, 4-F | 3-Cl |
| 2-Cl, 4-F | 2-F | 2-Cl, 4-F | 3-F | 2-Cl, 4-F | 3-Cl |
| 2-Me, 4-F | 2-F | 2-Me, 4-F | 3-F | 2-Me, 4-F | 3-Cl |
| 2-F, 6-F | 2-F | 2-F, 6-F | 3-F | 2-F, 6-F | 3-Cl |
| 2-Cl, 6-Cl | 2-F | 2-Cl, 6-Cl | 3-F | 2-Cl, 6-Cl | 3-Cl |
| 2-Me, 6-Me | 2-F | 2-Me, 6-Me | 3-F | 2-Me, 6-Me | 3-Cl |
| 2-F, 4-F, 6-F | 2-F | 2-F, 4-F, 6-F | 3-F | 2-F, 4-F, 6-F | 3-Cl |
| 2-F | 3-Br | 2-F | 3-CF3 | 2-F | 3-OCF3 |
| 2-Cl | 3-Br | 2-Cl | 3-CF3 | 2-Cl | 3-OCF3 |
| 2-Br | 3-Br | 2-Br | 3-CF3 | 2-Br | 3-OCF3 |
| 2-Me | 3-Br | 2-Me | 3-CF3 | 2-Me | 3-OCF3 |
| 2-CF3 | 3-Br | 2-CF3 | 3-CF3 | 2-CF3 | 3-OCF3 |
| 4-F | 3-Br | 4-F | 3-CF3 | 4-F | 3-OCF3 |
| 4-Cl | 3-Br | 4-Cl | 3-CF3 | 4-Cl | 3-OCF3 |
| 4-Br | 3-Br | 4-Br | 3-CF3 | 4-Br | 3-OCF3 |
| 2-F, 4-F | 3-Br | 2-F, 4-F | 3-CF3 | 2-F, 4-F | 3-OCF3 |
| 2-Cl, 4-F | 3-Br | 2-Cl, 4-F | 3-CF3 | 2-Cl, 4-F | 3-OCF3 |
| 2-Me, 4-F | 3-Br | 2-Me, 4-F | 3-CF3 | 2-Me, 4-F | 3-OCF3 |
| 2-F, 6-F | 3-Br | 2-F, 6-F | 3-CF3 | 2-F, 6-F | 3-OCF3 |
| 2-Cl, 6-Cl | 3-Br | 2-Cl, 6-Cl | 3-CF3 | 2-Cl, 6-Cl | 3-OCF3 |
| 2-Me, 6-Me | 3-Br | 2-Me, 6-Me | 3-CF3 | 2-Me, 6-Me | 3-OCF3 |
| 2-F, 4-F, 6-F | 3-Br | 2-F, 4-F, 6-F | 3-CF3 | 2-F, 4-F, 6-F | 3-OCF3 |
| 2-F | 4-F | 2-F | 4-Cl | 2-F | 4-Br |
| 2-Cl | 4-F | 2-Cl | 4-Cl | 2-Cl | 4-Br |
| 2-Br | 4-F | 2-Br | 4-Cl | 2-Br | 4-Br |
| 2-Me | 4-F | 2-Me | 4-Cl | 2-Me | 4-Br |
| 2-CF3 | 4-F | 2-CF3 | 4-Cl | 2-CF3 | 4-Br |
| 4-F | 4-F | 4-F | 4-Cl | 4-F | 4-Br |
| 4-Cl | 4-F | 4-Cl | 4-Cl | 4-Cl | 4-Br |
| 4-Br | 4-F | 4-Br | 4-Cl | 4-Br | 4-Br |
| 2-F, 4-F | 4-F | 2-F, 4-F | 4-Cl | 2-F, 4-F | 4-Br |
| 2-Cl, 4-F | 4-F | 2-Cl, 4-F | 4-Cl | 2-Cl, 4-F | 4-Br |
| 2-Me, 4-F | 4-F | 2-Me, 4-F | 4-Cl | 2-Me, 4-F | 4-Br |
| 2-F, 6-F | 4-F | 2-F, 6-F | 4-Cl | 2-F, 6-F | 4-Br |
| 2-Cl, 6-Cl | 4-F | 2-Cl, 6-Cl | 4-Cl | 2-Cl, 6-Cl | 4-Br |

TABLE 1-continued

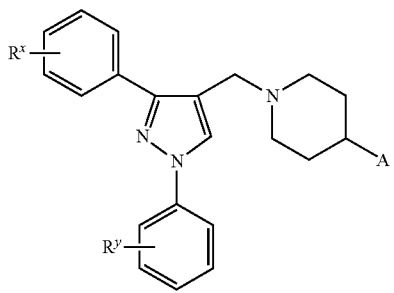

| $R^x$ | $R^y$ | $R^x$ | $R^y$ | $R^x$ | $R^y$ |
|---|---|---|---|---|---|
| 2-Me, 6-Me | 4-F | 2-Me, 6-Me | 4-Cl | 2-Me, 6-Me | 4-Br |
| 2-F, 4-F, 6-F | 4-F | 2-F, 4-F, 6-F | 4-Cl | 2-F, 4-F, 6-F | 4-Br |
| 2-F | 4-CF$_3$ | 2-F | 4-OCF$_3$ | 2-F | 3-F, 4-F |
| 2-Cl | 4-CF$_3$ | 2-Cl | 4-OCF$_3$ | 2-Cl | 3-F, 4-F |
| 2-Br | 4-CF$_3$ | 2-Br | 4-OCF$_3$ | 2-Br | 3-F, 4-F |
| 2-Me | 4-CF$_3$ | 2-Me | 4-OCF$_3$ | 2-Me | 3-F, 4-F |
| 2-CF$_3$ | 4-CF$_3$ | 2-CF$_3$ | 4-OCF$_3$ | 2-CF$_3$ | 3-F, 4-F |
| 4-F | 4-CF$_3$ | 4-F | 4-OCF$_3$ | 4-F | 3-F, 4-F |
| 4-Cl | 4-CF$_3$ | 4-Cl | 4-OCF$_3$ | 4-Cl | 3-F, 4-F |
| 4-Br | 4-CF$_3$ | 4-Br | 4-OCF$_3$ | 4-Br | 3-F, 4-F |
| 2-F, 4-F | 4-CF$_3$ | 2-F, 4-F | 4-OCF$_3$ | 2-F, 4-F | 3-F, 4-F |
| 2-Cl, 4-F | 4-CF$_3$ | 2-Cl, 4-F | 4-OCF$_3$ | 2-Cl, 4-F | 3-F, 4-F |
| 2-Me, 4-F | 4-CF$_3$ | 2-Me, 4-F | 4-OCF$_3$ | 2-Me, 4-F | 3-F, 4-F |
| 2-F, 6-F | 4-CF$_3$ | 2-F, 6-F | 4-OCF$_3$ | 2-F, 6-F | 3-F, 4-F |
| 2-Cl, 6-Cl | 4-CF$_3$ | 2-Cl, 6-Cl | 4-OCF$_3$ | 2-Cl, 6-Cl | 3-F, 4-F |
| 2-Me, 6-Me | 4-CF$_3$ | 2-Me, 6-Me | 4-OCF$_3$ | 2-Me, 6-Me | 3-F, 4-F |
| 2-F, 4-F, 6-F | 4-CF$_3$ | 2-F, 4-F, 6-F | 4-OCF$_3$ | 2-F, 4-F, 6-F | 3-F, 4-F |
| 2-F | 3-F, 4-Cl | 2-F | 3-F, 4-Br | 2-F | 3-F, 4-CF$_3$ |
| 2-Cl | 3-F, 4-Cl | 2-Cl | 3-F, 4-Br | 2-Cl | 3-F, 4-CF$_3$ |
| 2-Br | 3-F, 4-Cl | 2-Br | 3-F, 4-Br | 2-Br | 3-F, 4-CF$_3$ |
| 2-Me | 3-F, 4-Cl | 2-Me | 3-F, 4-Br | 2-Me | 3-F, 4-CF$_3$ |
| 2-CF$_3$ | 3-F, 4-Cl | 2-CF$_3$ | 3-F, 4-Br | 2-CF$_3$ | 3-F, 4-CF$_3$ |
| 4-F | 3-F, 4-Cl | 4-F | 3-F, 4-Br | 4-F | 3-F, 4-CF$_3$ |
| 4-Cl | 3-F, 4-Cl | 4-Cl | 3-F, 4-Br | 4-Cl | 3-F, 4-CF$_3$ |
| 4-Br | 3-F, 4-Cl | 4-Br | 3-F, 4-Br | 4-Br | 3-F, 4-CF$_3$ |
| 2-F, 4-F | 3-F, 4-Cl | 2-F, 4-F | 3-F, 4-Br | 2-F, 4-F | 3-F, 4-CF$_3$ |
| 2-Cl, 4-F | 3-F, 4-Cl | 2-Cl, 4-F | 3-F, 4-Br | 2-Cl, 4-F | 3-F, 4-CF$_3$ |
| 2-Me, 4-F | 3-F, 4-Cl | 2-Me, 4-F | 3-F, 4-Br | 2-Me, 4-F | 3-F, 4-CF$_3$ |
| 2-F, 6-F | 3-F, 4-Cl | 2-F, 6-F | 3-F, 4-Br | 2-F, 6-F | 3-F, 4-CF$_3$ |
| 2-Cl, 6-Cl | 3-F, 4-Cl | 2-Cl, 6-Cl | 3-F, 4-Br | 2-Cl, 6-Cl | 3-F, 4-CF$_3$ |
| 2-Me, 6-Me | 3-F, 4-Cl | 2-Me, 6-Me | 3-F, 4-Br | 2-Me, 6-Me | 3-F, 4-CF$_3$ |
| 2-F, 4-F, 6-F | 3-F, 4-Cl | 2-F, 4-F, 6-F | 3-F, 4-Br | 2-F, 4-F, 6-F | 3-F, 4-CF$_3$ |
| 2-F | 3-F, 4-OCF$_3$ | 2-F | 3-Cl, 4-F | 2-F | 3-Cl, 4-Cl |
| 2-Cl | 3-F, 4-OCF$_3$ | 2-Cl | 3-Cl, 4-F | 2-Cl | 3-Cl, 4-Cl |
| 2-Br | 3-F, 4-OCF$_3$ | 2-Br | 3-Cl, 4-F | 2-Br | 3-Cl, 4-Cl |
| 2-Me | 3-F, 4-OCF$_3$ | 2-Me | 3-Cl, 4-F | 2-Me | 3-Cl, 4-Cl |
| 2-CF$_3$ | 3-F, 4-OCF$_3$ | 2-CF$_3$ | 3-Cl, 4-F | 2-CF$_3$ | 3-Cl, 4-Cl |
| 4-F | 3-F, 4-OCF$_3$ | 4-F | 3-Cl, 4-F | 4-F | 3-Cl, 4-Cl |
| 4-Cl | 3-F, 4-OCF$_3$ | 4-Cl | 3-Cl, 4-F | 4-Cl | 3-Cl, 4-Cl |
| 4-Br | 3-F, 4-OCF$_3$ | 4-Br | 3-Cl, 4-F | 4-Br | 3-Cl, 4-Cl |
| 2-F, 4-F | 3-F, 4-OCF$_3$ | 2-F, 4-F | 3-Cl, 4-F | 2-F, 4-F | 3-Cl, 4-Cl |
| 2-Cl, 4-F | 3-F, 4-OCF$_3$ | 2-Cl, 4-F | 3-Cl, 4-F | 2-Cl, 4-F | 3-Cl, 4-Cl |
| 2-Me, 4-F | 3-F, 4-OCF$_3$ | 2-Me, 4-F | 3-Cl, 4-F | 2-Me, 4-F | 3-Cl, 4-Cl |
| 2-F, 6-F | 3-F, 4-OCF$_3$ | 2-F, 6-F | 3-Cl, 4-F | 2-F, 6-F | 3-Cl, 4-Cl |
| 2-Cl, 6-Cl | 3-F, 4-OCF$_3$ | 2-Cl, 6-Cl | 3-Cl, 4-F | 2-Cl, 6-Cl | 3-Cl, 4-Cl |
| 2-Me, 6-Me | 3-F, 4-OCF$_3$ | 2-Me, 6-Me | 3-Cl, 4-F | 2-Me, 6-Me | 3-Cl, 4-Cl |
| 2-F, 4-F, 6-F | 3-F, 4-OCF$_3$ | 2-F, 4-F, 6-F | 3-Cl, 4-F | 2-F, 4-F, 6-F | 3-Cl, 4-Cl |
| 2-F | 3-Cl, 4-CF$_3$ | 2-F | 3-Br, 4-F | 2-F | 3-CF$_3$, 4-F |
| 2-Cl | 3-Cl, 4-CF$_3$ | 2-Cl | 3-Br, 4-F | 2-Cl | 3-CF$_3$, 4-F |
| 2-Br | 3-Cl, 4-CF$_3$ | 2-Br | 3-Br, 4-F | 2-Br | 3-CF$_3$, 4-F |
| 2-Me | 3-Cl, 4-CF$_3$ | 2-Me | 3-Br, 4-F | 2-Me | 3-CF$_3$, 4-F |
| 2-CF$_3$ | 3-Cl, 4-CF$_3$ | 2-CF$_3$ | 3-Br, 4-F | 2-CF$_3$ | 3-CF$_3$, 4-F |
| 4-F | 3-Cl, 4-CF$_3$ | 4-F | 3-Br, 4-F | 4-F | 3-CF$_3$, 4-F |
| 4-Cl | 3-Cl, 4-CF$_3$ | 4-Cl | 3-Br, 4-F | 4-Cl | 3-CF$_3$, 4-F |
| 4-Br | 3-Cl, 4-CF$_3$ | 4-Br | 3-Br, 4-F | 4-Br | 3-CF$_3$, 4-F |
| 2-F, 4-F | 3-Cl, 4-CF$_3$ | 2-F, 4-F | 3-Br, 4-F | 2-F, 4-F | 3-CF$_3$, 4-F |
| 2-Cl, 4-F | 3-Cl, 4-CF$_3$ | 2-Cl, 4-F | 3-Br, 4-F | 2-Cl, 4-F | 3-CF$_3$, 4-F |
| 2-Me, 4-F | 3-Cl, 4-CF$_3$ | 2-Me, 4-F | 3-Br, 4-F | 2-Me, 4-F | 3-CF$_3$, 4-F |
| 2-F, 6-F | 3-Cl, 4-CF$_3$ | 2-F, 6-F | 3-Br, 4-F | 2-F, 6-F | 3-CF$_3$, 4-F |
| 2-Cl, 6-Cl | 3-Cl, 4-CF$_3$ | 2-Cl, 6-Cl | 3-Br, 4-F | 2-Cl, 6-Cl | 3-CF$_3$, 4-F |
| 2-Me, 6-Me | 3-Cl, 4-CF$_3$ | 2-Me, 6-Me | 3-Br, 4-F | 2-Me, 6-Me | 3-CF$_3$, 4-F |
| 2-F, 4-F, 6-F | 3-Cl, 4-CF$_3$ | 2-F, 4-F, 6-F | 3-Br, 4-F | 2-F, 4-F, 6-F | 3-CF$_3$, 4-F |
| 2-F | 3-CF$_3$, 4-Cl | 4-F | 3-CF$_3$, 4-Cl | 2-Me, 4-F | 3-CF$_3$, 4-Cl |

TABLE 1-continued

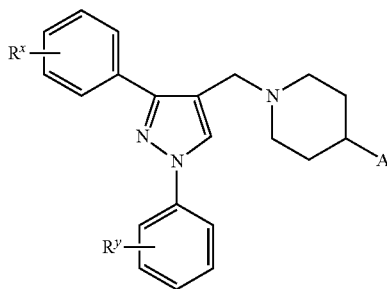

| $R^x$ | $R^y$ | $R^x$ | $R^y$ | $R^x$ | $R^y$ |
|---|---|---|---|---|---|
| 2-Cl | 3-CF$_3$, 4-Cl | 4-Cl | 3-CF$_3$, 4-Cl | 2-F, 6-F | 3-CF$_3$, 4-Cl |
| 2-Br | 3-CF$_3$, 4-Cl | 4-Br | 3-CF$_3$, 4-Cl | 2-Cl, 6-Cl | 3-CF$_3$, 4-Cl |
| 2-Me | 3-CF$_3$, 4-Cl | 2-F, 4-F | 3-CF$_3$, 4-Cl | 2-Me, 6-Me | 3-CF$_3$, 4-Cl |
| 2-CF$_3$ | 3-CF$_3$, 4-Cl | 2-Cl, 4-F | 3-CF$_3$, 4-Cl | 2-F, 4-F, 6-F | 3-CF$_3$, 4-Cl |
| 2-F | 3,4-DFMDO* | 4-F | 3,4-DFMDO* | 2-Me, 4-F | 3,4-DFMDO* |
| 2-Cl | 3,4-DFMDO* | 4-Cl | 3,4-DFMDO* | 2-F, 6-F | 3,4-DFMDO* |
| 2-Br | 3,4-DFMDO* | 4-Br | 3,4-DFMDO* | 2-Cl, 6-Cl | 3,4-DFMDO* |
| 2-Me | 3,4-DFMDO* | 2-F, 4-F | 3,4-DFMDO* | 2-Me, 6-Me | 3,4-DFMDO* |
| 2-CF$_3$ | 3,4-DFMDO* | 2-Cl, 4-F | 3,4-DFMDO* | 2-F, 4-F, 6-F | 3,4-DFMDO* |

*3,4-DMFDO is 3,4-difluoromethylenedioxy as shown below:

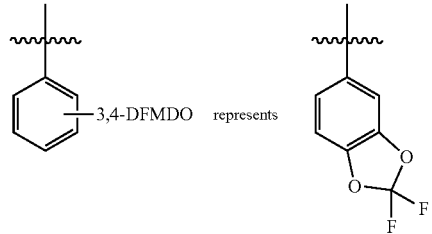

TABLE 2

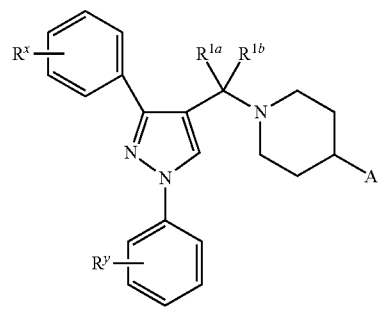 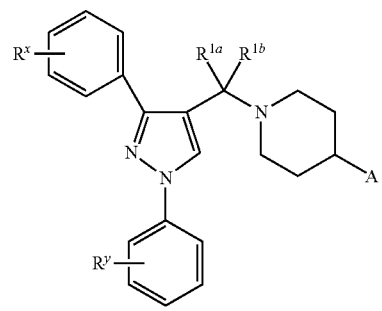

| $R^x$ | $R^y$ | $R^x$ | $R^y$ | $R^x$ | $R^y$ |
|---|---|---|---|---|---|
| \multicolumn{6}{c}{$R^{1a}$ is H, $R^{1b}$ is cyano, A is cyano} | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| \multicolumn{6}{c}{$R^{1a}$ is H, $R^{1b}$ is cyano, A is CO$_2$Me} | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |

TABLE 2-continued

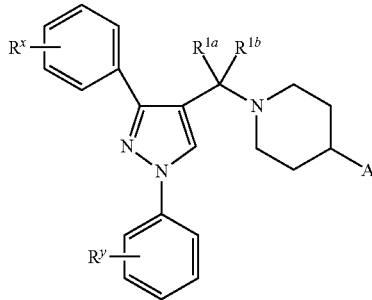

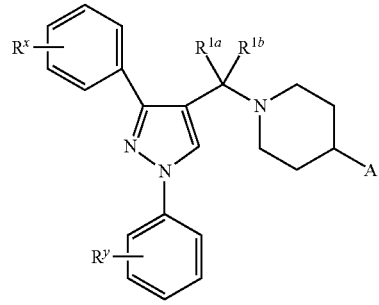

| $R^x$ | $R^y$ | $R^x$ | $R^y$ | $R^x$ | $R^y$ | | $R^x$ | $R^y$ | $R^x$ | $R^y$ | $R^x$ | $R^y$ |
|---|---|---|---|---|---|---|---|---|---|---|---|---|
| 2-F | 3-CF$_3$, 4-Cl | 2-Cl | 3-CF$_3$, 4-Cl | 2-Br | 3-CF$_3$, 4-Cl | | 2-Me | 3-CF$_3$ | 2-CF$_3$ | 3-CF$_3$ | 2-F, 4-F | 3-CF$_3$ |
| 2-F | 3-Cl, 4-F | 2-Cl | 3-Cl, 4-F | 2-Br | 3-Cl, 4-F | | 2-Me | 4-CF$_3$ | 2-CF$_3$ | 4-CF$_3$ | 2-F, 4-F | 4-CF$_3$ |
| 2-Me | 3-Cl | 2-CF$_3$ | 3-Cl | 2-F, 4-F | 3-Cl | | 2-Me | 4-OCF$_3$ | 2-CF$_3$ | 4-OCF$_3$ | 2-F, 4-F | 4-OCF$_3$ |
| 2-Me | 4-Cl | 2-CF$_3$ | 4-Cl | 2-F, 4-F | 4-Cl | | 2-Me | 3-Cl, 4-Cl | 2-CF$_3$ | 3-Cl, 4-Cl | 2-F, 4-F | 3-Cl, 4-Cl |
| 2-Me | 3-CF$_3$ | 2-CF$_3$ | 3-CF$_3$ | 2-F, 4-F | 3-CF$_3$ | | 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 4-CF$_3$ | 2-CF$_3$ | 4-CF$_3$ | 2-F, 4-F | 4-CF$_3$ | | 2-Me | 3-CF$_3$, 4-Cl | 2-CF$_3$ | 3-CF$_3$, 4-Cl | 2-F, 4-F | 3-CF$_3$, 4-Cl |
| 2-Me | 4-OCF$_3$ | 2-CF$_3$ | 4-OCF$_3$ | 2-F, 4-F | 4-OCF$_3$ | | 2-Me | 3-Cl, 4-F | 2-CF$_3$ | 3-Cl, 4-F | 2-F, 4-F | 3-Cl, 4-F |
| 2-Me | 3-Cl, 4-Cl | 2-CF$_3$ | 3-Cl, 4-Cl | 2-F, 4-F | 3-Cl, 4-Cl | | 2-F, 6-F | 3-Cl | 2-F, 4-F, 6-F | 3-Cl | 4-F | 3-Cl |
| 2-Me | 3-Cl, 4-CF$_3$ | 2-CF$_3$ | 3-Cl, 4-CF$_3$ | 2-F, 4-F | 3-Cl, 4-CF$_3$ | | 2-F, 6-F | 4-Cl | 2-F, 4-F, 6-F | 4-Cl | 4-F | 4-Cl |
| 2-Me | 3-CF$_3$, 4-Cl | 2-CF$_3$ | 3-CF$_3$, 4-Cl | 2-F, 4-F | 3-CF$_3$, 4-Cl | | 2-F, 6-F | 3-CF$_3$ | 2-F, 4-F, 6-F | 3-CF$_3$ | 4-F | 3-CF$_3$ |
| 2-Me | 3-Cl, 4-F | 2-CF$_3$ | 3-Cl, 4-F | 2-F, 4-F | 3-Cl, 4-F | | 2-F, 6-F | 4-CF$_3$ | 2-F, 4-F, 6-F | 4-CF$_3$ | 4-F | 4-CF$_3$ |
| 2-F, 6-F | 3-Cl | 2-F, 4-F, 6-F | 3-Cl | 4-F | 3-Cl | | 2-F, 6-F | 4-OCF$_3$ | 2-F, 4-F, 6-F | 4-OCF$_3$ | 4-F | 4-OCF$_3$ |
| 2-F, 6-F | 4-Cl | 2-F, 4-F, 6-F | 4-Cl | 4-F | 4-Cl | | 2-F, 6-F | 3-Cl, 4-Cl | 2-F, 4-F, 6-F | 3-Cl, 4-Cl | 4-F | 3-Cl, 4-Cl |
| 2-F, 6-F | 3-CF$_3$ | 2-F, 4-F, 6-F | 3-CF$_3$ | 4-F | 3-CF$_3$ | | 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 4-CF$_3$ | 2-F, 4-F, 6-F | 4-CF$_3$ | 4-F | 4-CF$_3$ | | 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 4-OCF$_3$ | 2-F, 4-F, 6-F | 4-OCF$_3$ | 4-F | 4-OCF$_3$ | | 2-F, 6-F | 3-Cl, 4-F | 2-F, 4-F, 6-F | 3-Cl, 4-F | 4-F | 3-Cl, 4-F |
| 2-F, 6-F | 3-Cl, 4-Cl | 2-F, 4-F, 6-F | 3-Cl, 4-Cl | 4-F | 3-Cl, 4-Cl | | colspan=6 | $R^{1a}$ is H, $R^{1b}$ is cyano, A is C(O)Me | | | | |
| 2-F, 6-F | 3-Cl, 4-CF$_3$ | 2-F, 4-F, 6-F | 3-Cl, 4-CF$_3$ | 4-F | 3-Cl, 4-CF$_3$ | | 2-F | 3-Cl | 2-Cl | 3-Cl | 2-Br | 3-Cl |
| 2-F, 6-F | 3-CF$_3$, 4-Cl | 2-F, 4-F, 6-F | 3-CF$_3$, 4-Cl | 4-F | 3-CF$_3$, 4-Cl | | 2-F | 4-Cl | 2-Cl | 4-Cl | 2-Br | 4-Cl |
| 2-F, 6-F | 3-Cl, 4-F | 2-F, 4-F, 6-F | 3-Cl, 4-F | 4-F | 3-Cl, 4-F | | 2-F | 3-CF$_3$ | 2-Cl | 3-CF$_3$ | 2-Br | 3-CF$_3$ |
| colspan=6 | $R^{1a}$ is H, $R^{1b}$ is cyano, A is CO$_2$Et | | | | | | 2-F | 4-CF$_3$ | 2-Cl | 4-CF$_3$ | 2-Br | 4-CF$_3$ |
| 2-F | 3-Cl | 2-Cl | 3-Cl | 2-Br | 3-Cl | | 2-F | 4-OCF$_3$ | 2-Cl | 4-OCF$_3$ | 2-Br | 4-OCF$_3$ |
| 2-F | 4-Cl | 2-Cl | 4-Cl | 2-Br | 4-Cl | | 2-F | 3-Cl, 4-Cl | 2-Cl | 3-Cl, 4-Cl | 2-Br | 3-Cl, 4-Cl |
| 2-F | 3-CF$_3$ | 2-Cl | 3-CF$_3$ | 2-Br | 3-CF$_3$ | | 2-F | 3-Cl, 4-CF$_3$ | 2-Cl | 3-Cl, 4-CF$_3$ | 2-Br | 3-Cl, 4-CF$_3$ |
| 2-F | 4-CF$_3$ | 2-Cl | 4-CF$_3$ | 2-Br | 4-CF$_3$ | | 2-F | 3-CF$_3$, 4-Cl | 2-Cl | 3-CF$_3$, 4-Cl | 2-Br | 3-CF$_3$, 4-Cl |
| 2-F | 4-OCF$_3$ | 2-Cl | 4-OCF$_3$ | 2-Br | 4-OCF$_3$ | | 2-F | 3-Cl, 4-F | 2-Cl | 3-Cl, 4-F | 2-Br | 3-Cl, 4-F |
| 2-F | 3-Cl, 4-Cl | 2-Cl | 3-Cl, 4-Cl | 2-Br | 3-Cl, 4-Cl | | 2-Me | 3-Cl | 2-CF$_3$ | 3-Cl | 2-F, 4-F | 3-Cl |
| 2-F | 3-Cl, 4-CF$_3$ | 2-Cl | 3-Cl, 4-CF$_3$ | 2-Br | 3-Cl, 4-CF$_3$ | | 2-Me | 4-Cl | 2-CF$_3$ | 4-Cl | 2-F, 4-F | 4-Cl |
| 2-F | 3-CF$_3$, 4-Cl | 2-Cl | 3-CF$_3$, 4-Cl | 2-Br | 3-CF$_3$, 4-Cl | | 2-Me | 3-CF$_3$ | 2-CF$_3$ | 3-CF$_3$ | 2-F, 4-F | 3-CF$_3$ |
| 2-F | 3-Cl, 4-F | 2-Cl | 3-Cl, 4-F | 2-Br | 3-Cl, 4-F | | 2-Me | 4-CF$_3$ | 2-CF$_3$ | 4-CF$_3$ | 2-F, 4-F | 4-CF$_3$ |
| 2-Me | 3-Cl | 2-CF$_3$ | 3-Cl | 2-F, 4-F | 3-Cl | | 2-Me | 4-OCF$_3$ | 2-CF$_3$ | 4-OCF$_3$ | 2-F, 4-F | 4-OCF$_3$ |
| 2-Me | 4-Cl | 2-CF$_3$ | 4-Cl | 2-F, 4-F | 4-Cl | | 2-Me | 3-Cl, 4-Cl | 2-CF$_3$ | 3-Cl, 4-Cl | 2-F, 4-F | 3-Cl, 4-Cl |
| 2-Me | 3-CF$_3$ | 2-CF$_3$ | 3-CF$_3$ | 2-F, 4-F | 3-CF$_3$ | | 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 4-CF$_3$ | 2-CF$_3$ | 4-CF$_3$ | 2-F, 4-F | 4-CF$_3$ | | 2-Me | 3-CF$_3$, 4-Cl | 2-CF$_3$ | 3-CF$_3$, 4-Cl | 2-F, 4-F | 3-CF$_3$, 4-Cl |
| 2-Me | 4-OCF$_3$ | 2-CF$_3$ | 4-OCF$_3$ | 2-F, 4-F | 4-OCF$_3$ | | 2-Me | 3-Cl, 4-F | 2-CF$_3$ | 3-Cl, 4-F | 2-F, 4-F | 3-Cl, 4-F |
| 2-Me | 3-Cl, 4-Cl | 2-CF$_3$ | 3-Cl, 4-Cl | 2-F, 4-F | 3-Cl, 4-Cl | | 2-F, 6-F | 3-Cl | 2-F, 4-F, 6-F | 3-Cl | 4-F | 3-Cl |
| 2-Me | 3-Cl, 4-CF$_3$ | 2-CF$_3$ | 3-Cl, 4-CF$_3$ | 2-F, 4-F | 3-Cl, 4-CF$_3$ | | 2-F, 6-F | 4-Cl | 2-F, 4-F, 6-F | 4-Cl | 4-F | 4-Cl |
| 2-Me | 3-CF$_3$, 4-Cl | 2-CF$_3$ | 3-CF$_3$, 4-Cl | 2-F, 4-F | 3-CF$_3$, 4-Cl | | 2-F, 6-F | 3-CF$_3$ | 2-F, 4-F, 6-F | 3-CF$_3$ | 4-F | 3-CF$_3$ |
| 2-Me | 3-Cl, 4-F | 2-CF$_3$ | 3-Cl, 4-F | 2-F, 4-F | 3-Cl, 4-F | | 2-F, 6-F | 4-CF$_3$ | 2-F, 4-F, 6-F | 4-CF$_3$ | 4-F | 4-CF$_3$ |
| 2-F, 6-F | 3-Cl | 2-F, 4-F, 6-F | 3-Cl | 4-F | 3-Cl | | 2-F, 6-F | 4-OCF$_3$ | 2-F, 4-F, 6-F | 4-OCF$_3$ | 4-F | 4-OCF$_3$ |
| 2-F, 6-F | 4-Cl | 2-F, 4-F, 6-F | 4-Cl | 4-F | 4-Cl | | 2-F, 6-F | 3-Cl, 4-Cl | 2-F, 4-F, 6-F | 3-Cl, 4-Cl | 4-F | 3-Cl, 4-Cl |
| 2-F, 6-F | 3-CF$_3$ | 2-F, 4-F, 6-F | 3-CF$_3$ | 4-F | 3-CF$_3$ | | 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 4-CF$_3$ | 2-F, 4-F, 6-F | 4-CF$_3$ | 4-F | 4-CF$_3$ | | 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 4-OCF$_3$ | 2-F, 4-F, 6-F | 4-OCF$_3$ | 4-F | 4-OCF$_3$ | | 2-F, 6-F | 3-Cl, 4-F | 2-F, 4-F, 6-F | 3-Cl, 4-F | 4-F | 3-Cl, 4-F |
| 2-F, 6-F | 3-Cl, 4-Cl | 2-F, 4-F, 6-F | 3-Cl, 4-Cl | 4-F | 3-Cl, 4-Cl | | colspan=6 | $R^{1a}$ is H, $R^{1b}$ is cyano, A is NHC(O)OMe | | | | |
| 2-F, 6-F | 3-Cl, 4-CF$_3$ | 2-F, 4-F, 6-F | 3-Cl, 4-CF$_3$ | 4-F | 3-Cl, 4-CF$_3$ | | 2-F | 3-Cl | 2-Cl | 3-Cl | 2-Br | 3-Cl |
| 2-F, 6-F | 3-CF$_3$, 4-Cl | 2-F, 4-F, 6-F | 3-CF$_3$, 4-Cl | 4-F | 3-CF$_3$, 4-Cl | | 2-F | 4-Cl | 2-Cl | 4-Cl | 2-Br | 4-Cl |
| 2-F, 6-F | 3-Cl, 4-F | 2-F, 4-F, 6-F | 3-Cl, 4-F | 4-F | 3-Cl, 4-F | | 2-F | 3-CF$_3$ | 2-Cl | 3-CF$_3$ | 2-Br | 3-CF$_3$ |
| colspan=6 | $R^{1a}$ is H, $R^{1b}$ is cyano, A is NHC(O)Me | | | | | | 2-F | 4-CF$_3$ | 2-Cl | 4-CF$_3$ | 2-Br | 4-CF$_3$ |
| 2-F | 3-Cl | 2-Cl | 3-Cl | 2-Br | 3-Cl | | 2-F | 4-OCF$_3$ | 2-Cl | 4-OCF$_3$ | 2-Br | 4-OCF$_3$ |
| 2-F | 4-Cl | 2-Cl | 4-Cl | 2-Br | 4-Cl | | 2-F | 3-Cl, 4-Cl | 2-Cl | 3-Cl, 4-Cl | 2-Br | 3-Cl, 4-Cl |
| 2-F | 3-CF$_3$ | 2-Cl | 3-CF$_3$ | 2-Br | 3-CF$_3$ | | 2-F | 3-Cl, 4-CF$_3$ | 2-Cl | 3-Cl, 4-CF$_3$ | 2-Br | 3-Cl, 4-CF$_3$ |
| 2-F | 4-CF$_3$ | 2-Cl | 4-CF$_3$ | 2-Br | 4-CF$_3$ | | 2-F | 3-CF$_3$, 4-Cl | 2-Cl | 3-CF$_3$, 4-Cl | 2-Br | 3-CF$_3$, 4-Cl |
| 2-F | 4-OCF$_3$ | 2-Cl | 4-OCF$_3$ | 2-Br | 4-OCF$_3$ | | 2-F | 3-Cl, 4-F | 2-Cl | 3-Cl, 4-F | 2-Br | 3-Cl, 4-F |
| 2-F | 3-Cl, 4-Cl | 2-Cl | 3-Cl, 4-Cl | 2-Br | 3-Cl, 4-Cl | | 2-Me | 3-Cl | 2-CF$_3$ | 3-Cl | 2-F, 4-F | 3-Cl |
| 2-F | 3-Cl, 4-CF$_3$ | 2-Cl | 3-Cl, 4-CF$_3$ | 2-Br | 3-Cl, 4-CF$_3$ | | 2-Me | 4-Cl | 2-CF$_3$ | 4-Cl | 2-F, 4-F | 4-Cl |
| 2-F | 3-CF$_3$, 4-Cl | 2-Cl | 3-CF$_3$, 4-Cl | 2-Br | 3-CF$_3$, 4-Cl | | 2-Me | 3-CF$_3$ | 2-CF$_3$ | 3-CF$_3$ | 2-F, 4-F | 3-CF$_3$ |
| 2-F | 3-Cl, 4-F | 2-Cl | 3-Cl, 4-F | 2-Br | 3-Cl, 4-F | | 2-Me | 4-CF$_3$ | 2-CF$_3$ | 4-CF$_3$ | 2-F, 4-F | 4-CF$_3$ |
| 2-Me | 3-Cl | 2-CF$_3$ | 3-Cl | 2-F, 4-F | 3-Cl | | 2-Me | 4-OCF$_3$ | 2-CF$_3$ | 4-OCF$_3$ | 2-F, 4-F | 4-OCF$_3$ |
| 2-Me | 4-Cl | 2-CF$_3$ | 4-Cl | 2-F, 4-F | 4-Cl | | 2-Me | 3-Cl, 4-Cl | 2-CF$_3$ | 3-Cl, 4-Cl | 2-F, 4-F | 3-Cl, 4-Cl |

TABLE 2-continued

| $R^x$ | $R^y$ | $R^x$ | $R^y$ | $R^x$ | $R^y$ |
|---|---|---|---|---|---|
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| $R^{1a}$ is H, $R^{1b}$ is Me, A is cyano | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| $R^{1a}$ is H, $R^{1b}$ is Me, A is CO$_2$Me | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| $R^{1a}$ is H, $R^{1b}$ is Me, A is CO$_2$Et | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| $R^{1a}$ is H, $R^{1b}$ is Me, A is NHC(O)Me | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |

TABLE 2-continued

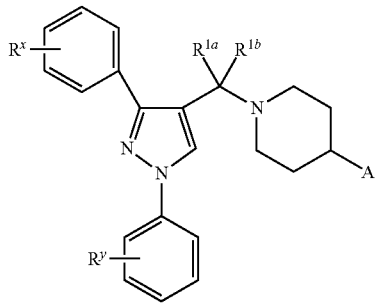

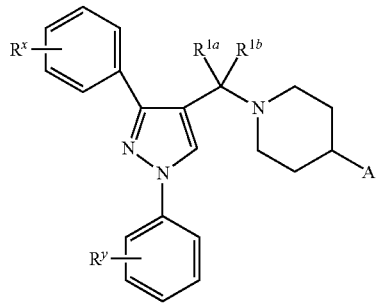

| $R^x$ | $R^y$ | $R^x$ | $R^y$ | $R^x$ | $R^y$ |
|---|---|---|---|---|---|
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{1a}$ is H, $R^{1b}$ is Me, A is C(O)Me |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{1a}$ is H, $R^{1b}$ is Me, A is NHC(O)OMe |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{1a}$ is H, $R^{1b}$ is CO$_2$Me, A is cyano |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{1a}$ is H, $R^{1b}$ is CO$_2$Me, A is CO$_2$Me |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{1a}$ is H, $R^{1b}$ is CO$_2$Me, A is CO$_2$Et |
| 2-F | 3-Cl | 2-Cl | 3-Cl | 2-Br | 3-Cl |
| 2-F | 4-Cl | 2-Cl | 4-Cl | 2-Br | 4-Cl |

TABLE 2-continued

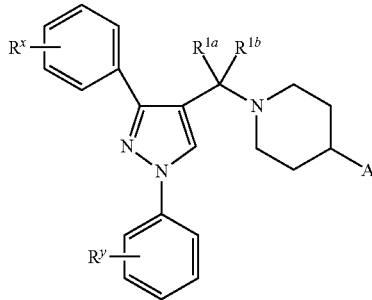

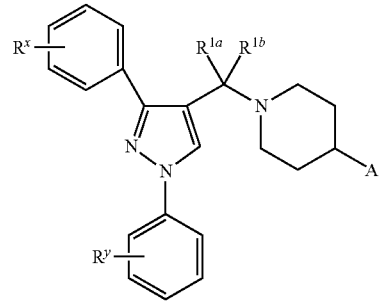

| $R^x$ | $R^y$ | $R^x$ | $R^y$ | $R^x$ | $R^y$ |
|---|---|---|---|---|---|
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{1a}$ is H, $R^{1b}$ is CO$_2$Me, A is NHC(O)Me |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{1a}$ is H, $R^{1b}$ is CO$_2$Me, A is C(O)Me |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{1a}$ is H, $R^{1b}$ is CO$_2$Me, A is NHC(O)OMe |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{1a}$ is Me, $R^{1b}$ is Me, A is cyano |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |

TABLE 2-continued

| Rˣ | Rʸ | Rˣ | Rʸ | Rˣ | Rʸ |
|---|---|---|---|---|---|
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |

R¹ᵃ is Me, R¹ᵇ is Me, A is CO₂Me

| Rˣ | Rʸ | Rˣ | Rʸ | Rˣ | Rʸ |
|---|---|---|---|---|---|
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |

R¹ᵃ is Me, R¹ᵇ is Me, A is CO₂Et

| Rˣ | Rʸ | Rˣ | Rʸ | Rˣ | Rʸ |
|---|---|---|---|---|---|
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |

R¹ᵃ is Me, R¹ᵇ is Me, A is NHC(O)Me

| Rˣ | Rʸ | Rˣ | Rʸ | Rˣ | Rʸ |
|---|---|---|---|---|---|
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |

R¹ᵃ is Me, R¹ᵇ is Me, A is C(O)Me

| Rˣ | Rʸ | Rˣ | Rʸ | Rˣ | Rʸ |
|---|---|---|---|---|---|
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |

TABLE 2-continued

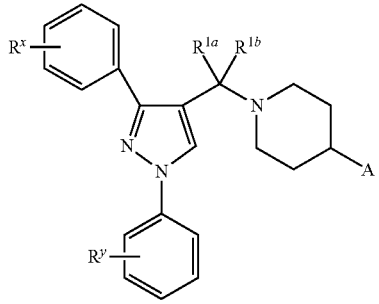

| $R^x$ | $R^y$ | $R^x$ | $R^y$ | $R^x$ | $R^y$ |
|---|---|---|---|---|---|
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{1a}$ is Me, $R^{1b}$ is Me, A is NHC(O)OMe |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |

TABLE 3

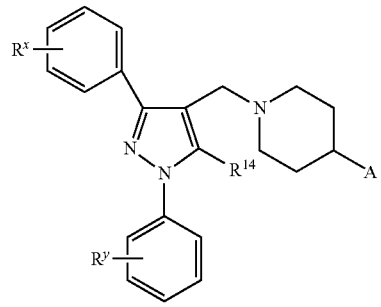

| $R^x$ | $R^y$ | $R^x$ | $R^y$ | $R^x$ | $R^y$ |
|---|---|---|---|---|---|
| | $R^{14}$ is F, A is cyano |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{14}$ is F, A is CO$_2$Me |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{14}$ is F, A is CO$_2$Et |
| 2-F | 3-Cl | 2-Cl | 3-Cl | 2-Br | 3-Cl |
| 2-F | 4-Cl | 2-Cl | 4-Cl | 2-Br | 4-Cl |

TABLE 3-continued

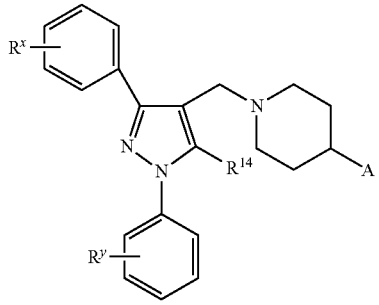
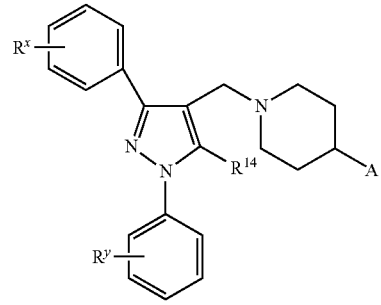

| $R^x$ | $R^y$ | $R^x$ | $R^y$ | $R^x$ | $R^y$ |
|---|---|---|---|---|---|
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{14}$ is F, A is NHC(O)Me |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{14}$ is F, A is C(O)Me |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{14}$ is F, A is NHC(O)OMe |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{14}$ is Cl, A is cyano |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |

TABLE 3-continued

| $R^x$ | $R^y$ | $R^x$ | $R^y$ | $R^x$ | $R^y$ |
|---|---|---|---|---|---|
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| $R^{14}$ is Cl, A is CO$_2$Me | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| $R^{14}$ is Cl, A is CO$_2$Et | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| $R^{14}$ is Cl, A is NHC(O)Me | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| $R^{14}$ is Cl, A is C(O)Me | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |

TABLE 3-continued

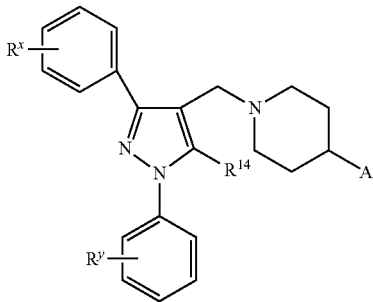

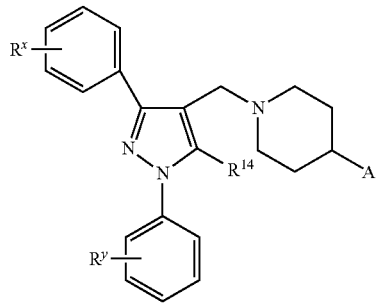

| $R^x$ | $R^y$ | $R^x$ | $R^y$ | $R^x$ | $R^y$ | $R^x$ | $R^y$ | $R^x$ | $R^y$ | $R^x$ | $R^y$ |
|---|---|---|---|---|---|---|---|---|---|---|---|
| 2-F, 6-F | 3-Cl | 2-F, 4-F, 6-F | 3-Cl | 4-F | 3-Cl | 2-F, 6-F | 4-OCF$_3$ | 2-F, 4-F, 6-F | 4-OCF$_3$ | 4-F | 4-OCF$_3$ |
| 2-F, 6-F | 4-Cl | 2-F, 4-F, 6-F | 4-Cl | 4-F | 4-Cl | 2-F, 6-F | 3-Cl, 4-Cl | 2-F, 4-F, 6-F | 3-Cl, 4-Cl | 4-F | 3-Cl, 4-Cl |
| 2-F, 6-F | 3-CF$_3$ | 2-F, 4-F, 6-F | 3-CF$_3$ | 4-F | 3-CF$_3$ | 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 4-CF$_3$ | 2-F, 4-F, 6-F | 4-CF$_3$ | 4-F | 4-CF$_3$ | 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 4-OCF$_3$ | 2-F, 4-F, 6-F | 4-OCF$_3$ | 4-F | 4-OCF$_3$ | 2-F, 6-F | 3-Cl, 4-F | 2-F, 4-F, 6-F | 3-Cl, 4-F | 4-F | 3-Cl, 4-F |
| 2-F, 6-F | 3-Cl, 4-Cl | 2-F, 4-F, 6-F | 3-Cl, 4-Cl | 4-F | 3-Cl, 4-Cl | | | $R^{14}$ is Br, A is CO$_2$Me | | | |
| 2-F, 6-F | 3-Cl, 4-CF$_3$ | 2-F, 4-F, 6-F | 3-Cl, 4-CF$_3$ | 4-F | 3-Cl, 4-CF$_3$ | 2-F | 3-Cl | 2-Cl | 3-Cl | 2-Br | 3-Cl |
| 2-F, 6-F | 3-CF$_3$, 4-Cl | 2-F, 4-F, 6-F | 3-CF$_3$, 4-Cl | 4-F | 3-CF$_3$, 4-Cl | 2-F | 4-Cl | 2-Cl | 4-Cl | 2-Br | 4-Cl |
| 2-F, 6-F | 3-Cl, 4-F | 2-F, 4-F, 6-F | 3-Cl, 4-F | 4-F | 3-Cl, 4-F | 2-F | 3-CF$_3$ | 2-Cl | 3-CF$_3$ | 2-Br | 3-CF$_3$ |
| | | $R^{14}$ is Cl, A is NHC(O)OMe | | | | 2-F | 4-CF$_3$ | 2-Cl | 4-CF$_3$ | 2-Br | 4-CF$_3$ |
| 2-F | 3-Cl | 2-Cl | 3-Cl | 2-Br | 3-Cl | 2-F | 4-OCF$_3$ | 2-Cl | 4-OCF$_3$ | 2-Br | 4-OCF$_3$ |
| 2-F | 4-Cl | 2-Cl | 4-Cl | 2-Br | 4-Cl | 2-F | 3-Cl, 4-Cl | 2-Cl | 3-Cl, 4-Cl | 2-Br | 3-Cl, 4-Cl |
| 2-F | 3-CF$_3$ | 2-Cl | 3-CF$_3$ | 2-Br | 3-CF$_3$ | 2-F | 3-Cl, 4-CF$_3$ | 2-Cl | 3-Cl, 4-CF$_3$ | 2-Br | 3-Cl, 4-CF$_3$ |
| 2-F | 4-CF$_3$ | 2-Cl | 4-CF$_3$ | 2-Br | 4-CF$_3$ | 2-F | 3-CF$_3$, 4-Cl | 2-Cl | 3-CF$_3$, 4-Cl | 2-Br | 3-CF$_3$, 4-Cl |
| 2-F | 4-OCF$_3$ | 2-Cl | 4-OCF$_3$ | 2-Br | 4-OCF$_3$ | 2-F | 3-Cl, 4-F | 2-Cl | 3-Cl, 4-F | 2-Br | 3-Cl, 4-F |
| 2-F | 3-Cl, 4-Cl | 2-Cl | 3-Cl, 4-Cl | 2-Br | 3-Cl, 4-Cl | 2-Me | 3-Cl | 2-CF$_3$ | 3-Cl | 2-F, 4-F | 3-Cl |
| 2-F | 3-Cl, 4-CF$_3$ | 2-Cl | 3-Cl, 4-CF$_3$ | 2-Br | 3-Cl, 4-CF$_3$ | 2-Me | 4-Cl | 2-CF$_3$ | 4-Cl | 2-F, 4-F | 4-Cl |
| 2-F | 3-CF$_3$, 4-Cl | 2-Cl | 3-CF$_3$, 4-Cl | 2-Br | 3-CF$_3$, 4-Cl | 2-Me | 3-CF$_3$ | 2-CF$_3$ | 3-CF$_3$ | 2-F, 4-F | 3-CF$_3$ |
| 2-F | 3-Cl, 4-F | 2-Cl | 3-Cl, 4-F | 2-Br | 3-Cl, 4-F | 2-Me | 4-CF$_3$ | 2-CF$_3$ | 4-CF$_3$ | 2-F, 4-F | 4-CF$_3$ |
| 2-Me | 3-Cl | 2-CF$_3$ | 3-Cl | 2-F, 4-F | 3-Cl | 2-Me | 4-OCF$_3$ | 2-CF$_3$ | 4-OCF$_3$ | 2-F, 4-F | 4-OCF$_3$ |
| 2-Me | 4-Cl | 2-CF$_3$ | 4-Cl | 2-F, 4-F | 4-Cl | 2-Me | 3-Cl, 4-Cl | 2-CF$_3$ | 3-Cl, 4-Cl | 2-F, 4-F | 3-Cl, 4-Cl |
| 2-Me | 3-CF$_3$ | 2-CF$_3$ | 3-CF$_3$ | 2-F, 4-F | 3-CF$_3$ | 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 4-CF$_3$ | 2-CF$_3$ | 4-CF$_3$ | 2-F, 4-F | 4-CF$_3$ | 2-Me | 3-CF$_3$, 4-Cl | 2-CF$_3$ | 3-CF$_3$, 4-Cl | 2-F, 4-F | 3-CF$_3$, 4-Cl |
| 2-Me | 4-OCF$_3$ | 2-CF$_3$ | 4-OCF$_3$ | 2-F, 4-F | 4-OCF$_3$ | 2-Me | 3-Cl, 4-F | 2-CF$_3$ | 3-Cl, 4-F | 2-F, 4-F | 3-Cl, 4-F |
| 2-Me | 3-Cl, 4-Cl | 2-CF$_3$ | 3-Cl, 4-Cl | 2-F, 4-F | 3-Cl, 4-Cl | 2-F, 6-F | 3-Cl | 2-F, 4-F, 6-F | 3-Cl | 4-F | 3-Cl |
| 2-Me | 3-Cl, 4-CF$_3$ | 2-CF$_3$ | 3-Cl, 4-CF$_3$ | 2-F, 4-F | 3-Cl, 4-CF$_3$ | 2-F, 6-F | 4-Cl | 2-F, 4-F, 6-F | 4-Cl | 4-F | 4-Cl |
| 2-Me | 3-CF$_3$, 4-Cl | 2-CF$_3$ | 3-CF$_3$, 4-Cl | 2-F, 4-F | 3-CF$_3$, 4-Cl | 2-F, 6-F | 3-CF$_3$ | 2-F, 4-F, 6-F | 3-CF$_3$ | 4-F | 3-CF$_3$ |
| 2-Me | 3-Cl, 4-F | 2-CF$_3$ | 3-Cl, 4-F | 2-F, 4-F | 3-Cl, 4-F | 2-F, 6-F | 4-CF$_3$ | 2-F, 4-F, 6-F | 4-CF$_3$ | 4-F | 4-CF$_3$ |
| 2-F, 6-F | 3-Cl | 2-F, 4-F, 6-F | 3-Cl | 4-F | 3-Cl | 2-F, 6-F | 4-OCF$_3$ | 2-F, 4-F, 6-F | 4-OCF$_3$ | 4-F | 4-OCF$_3$ |
| 2-F, 6-F | 4-Cl | 2-F, 4-F, 6-F | 4-Cl | 4-F | 4-Cl | 2-F, 6-F | 3-Cl, 4-Cl | 2-F, 4-F, 6-F | 3-Cl, 4-Cl | 4-F | 3-Cl, 4-Cl |
| 2-F, 6-F | 3-CF$_3$ | 2-F, 4-F, 6-F | 3-CF$_3$ | 4-F | 3-CF$_3$ | 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 4-CF$_3$ | 2-F, 4-F, 6-F | 4-CF$_3$ | 4-F | 4-CF$_3$ | 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 4-OCF$_3$ | 2-F, 4-F, 6-F | 4-OCF$_3$ | 4-F | 4-OCF$_3$ | 2-F, 6-F | 3-Cl, 4-F | 2-F, 4-F, 6-F | 3-Cl, 4-F | 4-F | 3-Cl, 4-F |
| 2-F, 6-F | 3-Cl, 4-Cl | 2-F, 4-F, 6-F | 3-Cl, 4-Cl | 4-F | 3-Cl, 4-Cl | | | $R^{14}$ is Br, A is CO$_2$Et | | | |
| 2-F, 6-F | 3-Cl, 4-CF$_3$ | 2-F, 4-F, 6-F | 3-Cl, 4-CF$_3$ | 4-F | 3-Cl, 4-CF$_3$ | 2-F | 3-Cl | 2-Cl | 3-Cl | 2-Br | 3-Cl |
| 2-F, 6-F | 3-CF$_3$, 4-Cl | 2-F, 4-F, 6-F | 3-CF$_3$, 4-Cl | 4-F | 3-CF$_3$, 4-Cl | 2-F | 4-Cl | 2-Cl | 4-Cl | 2-Br | 4-Cl |
| 2-F, 6-F | 3-Cl, 4-F | 2-F, 4-F, 6-F | 3-Cl, 4-F | 4-F | 3-Cl, 4-F | 2-F | 3-CF$_3$ | 2-Cl | 3-CF$_3$ | 2-Br | 3-CF$_3$ |
| | | $R^{14}$ is Br, A is cyano | | | | 2-F | 4-CF$_3$ | 2-Cl | 4-CF$_3$ | 2-Br | 4-CF$_3$ |
| 2-F | 3-Cl | 2-Cl | 3-Cl | 2-Br | 3-Cl | 2-F | 4-OCF$_3$ | 2-Cl | 4-OCF$_3$ | 2-Br | 4-OCF$_3$ |
| 2-F | 4-Cl | 2-Cl | 4-Cl | 2-Br | 4-Cl | 2-F | 3-Cl, 4-Cl | 2-Cl | 3-Cl, 4-Cl | 2-Br | 3-Cl, 4-Cl |
| 2-F | 3-CF$_3$ | 2-Cl | 3-CF$_3$ | 2-Br | 3-CF$_3$ | 2-F | 3-Cl, 4-CF$_3$ | 2-Cl | 3-Cl, 4-CF$_3$ | 2-Br | 3-Cl, 4-CF$_3$ |
| 2-F | 4-CF$_3$ | 2-Cl | 4-CF$_3$ | 2-Br | 4-CF$_3$ | 2-F | 3-CF$_3$, 4-Cl | 2-Cl | 3-CF$_3$, 4-Cl | 2-Br | 3-CF$_3$, 4-Cl |
| 2-F | 4-OCF$_3$ | 2-Cl | 4-OCF$_3$ | 2-Br | 4-OCF$_3$ | 2-F | 3-Cl, 4-F | 2-Cl | 3-Cl, 4-F | 2-Br | 3-Cl, 4-F |
| 2-F | 3-Cl, 4-Cl | 2-Cl | 3-Cl, 4-Cl | 2-Br | 3-Cl, 4-Cl | 2-Me | 3-Cl | 2-CF$_3$ | 3-Cl | 2-F, 4-F | 3-Cl |
| 2-F | 3-Cl, 4-CF$_3$ | 2-Cl | 3-Cl, 4-CF$_3$ | 2-Br | 3-Cl, 4-CF$_3$ | 2-Me | 4-Cl | 2-CF$_3$ | 4-Cl | 2-F, 4-F | 4-Cl |
| 2-F | 3-CF$_3$, 4-Cl | 2-Cl | 3-CF$_3$, 4-Cl | 2-Br | 3-CF$_3$, 4-Cl | 2-Me | 3-CF$_3$ | 2-CF$_3$ | 3-CF$_3$ | 2-F, 4-F | 3-CF$_3$ |
| 2-F | 3-Cl, 4-F | 2-Cl | 3-Cl, 4-F | 2-Br | 3-Cl, 4-F | 2-Me | 4-CF$_3$ | 2-CF$_3$ | 4-CF$_3$ | 2-F, 4-F | 4-CF$_3$ |
| 2-Me | 3-Cl | 2-CF$_3$ | 3-Cl | 2-F, 4-F | 3-Cl | 2-Me | 4-OCF$_3$ | 2-CF$_3$ | 4-OCF$_3$ | 2-F, 4-F | 4-OCF$_3$ |
| 2-Me | 4-Cl | 2-CF$_3$ | 4-Cl | 2-F, 4-F | 4-Cl | 2-Me | 3-Cl, 4-Cl | 2-CF$_3$ | 3-Cl, 4-Cl | 2-F, 4-F | 3-Cl, 4-Cl |
| 2-Me | 3-CF$_3$ | 2-CF$_3$ | 3-CF$_3$ | 2-F, 4-F | 3-CF$_3$ | 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 4-CF$_3$ | 2-CF$_3$ | 4-CF$_3$ | 2-F, 4-F | 4-CF$_3$ | 2-Me | 3-CF$_3$, 4-Cl | 2-CF$_3$ | 3-CF$_3$, 4-Cl | 2-F, 4-F | 3-CF$_3$, 4-Cl |
| 2-Me | 4-OCF$_3$ | 2-CF$_3$ | 4-OCF$_3$ | 2-F, 4-F | 4-OCF$_3$ | 2-Me | 3-Cl, 4-F | 2-CF$_3$ | 3-Cl, 4-F | 2-F, 4-F | 3-Cl, 4-F |
| 2-Me | 3-Cl, 4-Cl | 2-CF$_3$ | 3-Cl, 4-Cl | 2-F, 4-F | 3-Cl, 4-Cl | 2-F, 6-F | 3-Cl | 2-F, 4-F, 6-F | 3-Cl | 4-F | 3-Cl |
| 2-Me | 3-Cl, 4-CF$_3$ | 2-CF$_3$ | 3-Cl, 4-CF$_3$ | 2-F, 4-F | 3-Cl, 4-CF$_3$ | 2-F, 6-F | 4-Cl | 2-F, 4-F, 6-F | 4-Cl | 4-F | 4-Cl |
| 2-Me | 3-CF$_3$, 4-Cl | 2-CF$_3$ | 3-CF$_3$, 4-Cl | 2-F, 4-F | 3-CF$_3$, 4-Cl | 2-F, 6-F | 3-CF$_3$ | 2-F, 4-F, 6-F | 3-CF$_3$ | 4-F | 3-CF$_3$ |
| 2-Me | 3-Cl, 4-F | 2-CF$_3$ | 3-Cl, 4-F | 2-F, 4-F | 3-Cl, 4-F | 2-F, 6-F | 4-CF$_3$ | 2-F, 4-F, 6-F | 4-CF$_3$ | 4-F | 4-CF$_3$ |
| 2-F, 6-F | 3-Cl | 2-F, 4-F, 6-F | 3-Cl | 4-F | 3-Cl | 2-F, 6-F | 4-OCF$_3$ | 2-F, 4-F, 6-F | 4-OCF$_3$ | 4-F | 4-OCF$_3$ |
| 2-F, 6-F | 4-Cl | 2-F, 4-F, 6-F | 4-Cl | 4-F | 4-Cl | 2-F, 6-F | 3-Cl, 4-Cl | 2-F, 4-F, 6-F | 3-Cl, 4-Cl | 4-F | 3-Cl, 4-Cl |
| 2-F, 6-F | 3-CF$_3$ | 2-F, 4-F, 6-F | 3-CF$_3$ | 4-F | 3-CF$_3$ | | | | | | |
| 2-F, 6-F | 4-CF$_3$ | 2-F, 4-F, 6-F | 4-CF$_3$ | 4-F | 4-CF$_3$ | | | | | | |

TABLE 3-continued

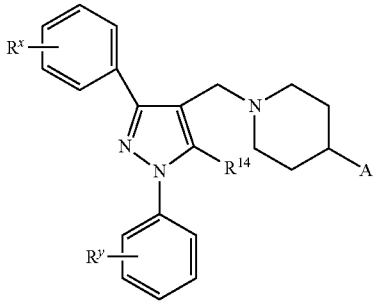

| $R^x$ | $R^y$ | $R^x$ | $R^y$ | $R^x$ | $R^y$ |
|---|---|---|---|---|---|
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{14}$ is Br, A is NHC(O)Me |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{14}$ is Br, A is C(O)Me |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |

TABLE 3-continued

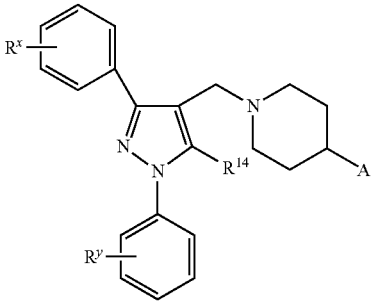

| $R^x$ | $R^y$ | $R^x$ | $R^y$ | $R^x$ | $R^y$ |
|---|---|---|---|---|---|
| | $R^{14}$ is Br, A is NHC(O)OMe |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{14}$ is Me, A is cyano |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{14}$ is Me, A is CO$_2$Me |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |

TABLE 3-continued

[Structure: pyrazole core with R^x-phenyl at 3-position, R^y-phenyl on N1, CH2-N(piperidine) with R14 and 4-A substituent]

| R^x | R^y | R^x | R^y | R^x | R^y |
|---|---|---|---|---|---|
| 2-F | 4-CF3 | 2-Cl | 4-CF3 | 2-Br | 4-CF3 |
| 2-F | 4-OCF3 | 2-Cl | 4-OCF3 | 2-Br | 4-OCF3 |
| 2-F | 3-Cl, 4-Cl | 2-Cl | 3-Cl, 4-Cl | 2-Br | 3-Cl, 4-Cl |
| 2-F | 3-Cl, 4-CF3 | 2-Cl | 3-Cl, 4-CF3 | 2-Br | 3-Cl, 4-CF3 |
| 2-F | 3-CF3, 4-Cl | 2-Cl | 3-CF3, 4-Cl | 2-Br | 3-CF3, 4-Cl |
| 2-F | 3-Cl, 4-F | 2-Cl | 3-Cl, 4-F | 2-Br | 3-Cl, 4-F |
| 2-Me | 3-Cl | 2-CF3 | 3-Cl | 2-F, 4-F | 3-Cl |
| 2-Me | 4-Cl | 2-CF3 | 4-Cl | 2-F, 4-F | 4-Cl |
| 2-Me | 3-CF3 | 2-CF3 | 3-CF3 | 2-F, 4-F | 3-CF3 |
| 2-Me | 4-CF3 | 2-CF3 | 4-CF3 | 2-F, 4-F | 4-CF3 |
| 2-Me | 4-OCF3 | 2-CF3 | 4-OCF3 | 2-F, 4-F | 4-OCF3 |
| 2-Me | 3-Cl, 4-Cl | 2-CF3 | 3-Cl, 4-Cl | 2-F, 4-F | 3-Cl, 4-Cl |
| 2-Me | 3-Cl, 4-CF3 | 2-CF3 | 3-Cl, 4-CF3 | 2-F, 4-F | 3-Cl, 4-CF3 |
| 2-Me | 3-CF3, 4-Cl | 2-CF3 | 3-CF3, 4-Cl | 2-F, 4-F | 3-CF3, 4-Cl |
| 2-Me | 3-Cl, 4-F | 2-CF3 | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF3 | 2-F, 4-F, 6-F | 3-CF3 | 4-F | 3-CF3 |
| 2-F, 6-F | 4-CF3 | 2-F, 4-F, 6-F | 4-CF3 | 4-F | 4-CF3 |
| 2-F, 6-F | 4-OCF3 | 2-F, 4-F, 6-F | 4-OCF3 | 4-F | 4-OCF3 |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF3 | 2-F, 4-F, 6-F | 3-Cl, 4-CF3 | 4-F | 3-Cl, 4-CF3 |
| 2-F, 6-F | 3-CF3, 4-Cl | 2-F, 4-F, 6-F | 3-CF3, 4-Cl | 4-F | 3-CF3, 4-Cl |
| 2-F, 6-F | 3-Cl, 4-F | 2-F, 4-F, 6-F | 3-Cl, 4-F | 4-F | 3-Cl, 4-F |

R^14 is Me, A is CO2Et

| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF3 | 2-Cl | 3-CF3 | 2-Br | 3-CF3 |
| 2-F | 4-CF3 | 2-Cl | 4-CF3 | 2-Br | 4-CF3 |
| 2-F | 4-OCF3 | 2-Cl | 4-OCF3 | 2-Br | 4-OCF3 |
| 2-F | 3-Cl, 4-Cl | 2-Cl | 3-Cl, 4-Cl | 2-Br | 3-Cl, 4-Cl |
| 2-F | 3-Cl, 4-CF3 | 2-Cl | 3-Cl, 4-CF3 | 2-Br | 3-Cl, 4-CF3 |
| 2-F | 3-CF3, 4-Cl | 2-Cl | 3-CF3, 4-Cl | 2-Br | 3-CF3, 4-Cl |
| 2-F | 3-Cl, 4-F | 2-Cl | 3-Cl, 4-F | 2-Br | 3-Cl, 4-F |
| 2-Me | 3-Cl | 2-CF3 | 3-Cl | 2-F, 4-F | 3-Cl |
| 2-Me | 4-Cl | 2-CF3 | 4-Cl | 2-F, 4-F | 4-Cl |
| 2-Me | 3-CF3 | 2-CF3 | 3-CF3 | 2-F, 4-F | 3-CF3 |
| 2-Me | 4-CF3 | 2-CF3 | 4-CF3 | 2-F, 4-F | 4-CF3 |
| 2-Me | 4-OCF3 | 2-CF3 | 4-OCF3 | 2-F, 4-F | 4-OCF3 |
| 2-Me | 3-Cl, 4-Cl | 2-CF3 | 3-Cl, 4-Cl | 2-F, 4-F | 3-Cl, 4-Cl |
| 2-Me | 3-Cl, 4-CF3 | 2-CF3 | 3-Cl, 4-CF3 | 2-F, 4-F | 3-Cl, 4-CF3 |
| 2-Me | 3-CF3, 4-Cl | 2-CF3 | 3-CF3, 4-Cl | 2-F, 4-F | 3-CF3, 4-Cl |
| 2-Me | 3-Cl, 4-F | 2-CF3 | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF3 | 2-F, 4-F, 6-F | 3-CF3 | 4-F | 3-CF3 |
| 2-F, 6-F | 4-CF3 | 2-F, 4-F, 6-F | 4-CF3 | 4-F | 4-CF3 |
| 2-F, 6-F | 4-OCF3 | 2-F, 4-F, 6-F | 4-OCF3 | 4-F | 4-OCF3 |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF3 | 2-F, 4-F, 6-F | 3-Cl, 4-CF3 | 4-F | 3-Cl, 4-CF3 |
| 2-F, 6-F | 3-CF3, 4-Cl | 2-F, 4-F, 6-F | 3-CF3, 4-Cl | 4-F | 3-CF3, 4-Cl |
| 2-F, 6-F | 3-Cl, 4-F | 2-F, 4-F, 6-F | 3-Cl, 4-F | 4-F | 3-Cl, 4-F |

R^14 is Me, A is NHC(O)Me

| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF3 | 2-Cl | 3-CF3 | 2-Br | 3-CF3 |
| 2-F | 4-CF3 | 2-Cl | 4-CF3 | 2-Br | 4-CF3 |
| 2-F | 4-OCF3 | 2-Cl | 4-OCF3 | 2-Br | 4-OCF3 |
| 2-F | 3-Cl, 4-Cl | 2-Cl | 3-Cl, 4-Cl | 2-Br | 3-Cl, 4-Cl |
| 2-F | 3-Cl, 4-CF3 | 2-Cl | 3-Cl, 4-CF3 | 2-Br | 3-Cl, 4-CF3 |
| 2-F | 3-CF3, 4-Cl | 2-Cl | 3-CF3, 4-Cl | 2-Br | 3-CF3, 4-Cl |
| 2-F | 3-Cl, 4-F | 2-Cl | 3-Cl, 4-F | 2-Br | 3-Cl, 4-F |
| 2-Me | 3-Cl | 2-CF3 | 3-Cl | 2-F, 4-F | 3-Cl |
| 2-Me | 4-Cl | 2-CF3 | 4-Cl | 2-F, 4-F | 4-Cl |
| 2-Me | 3-CF3 | 2-CF3 | 3-CF3 | 2-F, 4-F | 3-CF3 |
| 2-Me | 4-CF3 | 2-CF3 | 4-CF3 | 2-F, 4-F | 4-CF3 |
| 2-Me | 4-OCF3 | 2-CF3 | 4-OCF3 | 2-F, 4-F | 4-OCF3 |
| 2-Me | 3-Cl, 4-Cl | 2-CF3 | 3-Cl, 4-Cl | 2-F, 4-F | 3-Cl, 4-Cl |
| 2-Me | 3-Cl, 4-CF3 | 2-CF3 | 3-Cl, 4-CF3 | 2-F, 4-F | 3-Cl, 4-CF3 |
| 2-Me | 3-CF3, 4-Cl | 2-CF3 | 3-CF3, 4-Cl | 2-F, 4-F | 3-CF3, 4-Cl |
| 2-Me | 3-Cl, 4-F | 2-CF3 | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF3 | 2-F, 4-F, 6-F | 3-CF3 | 4-F | 3-CF3 |
| 2-F, 6-F | 4-CF3 | 2-F, 4-F, 6-F | 4-CF3 | 4-F | 4-CF3 |
| 2-F, 6-F | 4-OCF3 | 2-F, 4-F, 6-F | 4-OCF3 | 4-F | 4-OCF3 |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF3 | 2-F, 4-F, 6-F | 3-Cl, 4-CF3 | 4-F | 3-Cl, 4-CF3 |
| 2-F, 6-F | 3-CF3, 4-Cl | 2-F, 4-F, 6-F | 3-CF3, 4-Cl | 4-F | 3-CF3, 4-Cl |
| 2-F, 6-F | 3-Cl, 4-F | 2-F, 4-F, 6-F | 3-Cl, 4-F | 4-F | 3-Cl, 4-F |

R^14 is Me, A is C(O)Me

| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF3 | 2-Cl | 3-CF3 | 2-Br | 3-CF3 |
| 2-F | 4-CF3 | 2-Cl | 4-CF3 | 2-Br | 4-CF3 |
| 2-F | 4-OCF3 | 2-Cl | 4-OCF3 | 2-Br | 4-OCF3 |
| 2-F | 3-Cl, 4-Cl | 2-Cl | 3-Cl, 4-Cl | 2-Br | 3-Cl, 4-Cl |
| 2-F | 3-Cl, 4-CF3 | 2-Cl | 3-Cl, 4-CF3 | 2-Br | 3-Cl, 4-CF3 |
| 2-F | 3-CF3, 4-Cl | 2-Cl | 3-CF3, 4-Cl | 2-Br | 3-CF3, 4-Cl |
| 2-F | 3-Cl, 4-F | 2-Cl | 3-Cl, 4-F | 2-Br | 3-Cl, 4-F |
| 2-Me | 3-Cl | 2-CF3 | 3-Cl | 2-F, 4-F | 3-Cl |
| 2-Me | 4-Cl | 2-CF3 | 4-Cl | 2-F, 4-F | 4-Cl |
| 2-Me | 3-CF3 | 2-CF3 | 3-CF3 | 2-F, 4-F | 3-CF3 |
| 2-Me | 4-CF3 | 2-CF3 | 4-CF3 | 2-F, 4-F | 4-CF3 |
| 2-Me | 4-OCF3 | 2-CF3 | 4-OCF3 | 2-F, 4-F | 4-OCF3 |
| 2-Me | 3-Cl, 4-Cl | 2-CF3 | 3-Cl, 4-Cl | 2-F, 4-F | 3-Cl, 4-Cl |
| 2-Me | 3-Cl, 4-CF3 | 2-CF3 | 3-Cl, 4-CF3 | 2-F, 4-F | 3-Cl, 4-CF3 |
| 2-Me | 3-CF3, 4-Cl | 2-CF3 | 3-CF3, 4-Cl | 2-F, 4-F | 3-CF3, 4-Cl |
| 2-Me | 3-Cl, 4-F | 2-CF3 | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF3 | 2-F, 4-F, 6-F | 3-CF3 | 4-F | 3-CF3 |
| 2-F, 6-F | 4-CF3 | 2-F, 4-F, 6-F | 4-CF3 | 4-F | 4-CF3 |
| 2-F, 6-F | 4-OCF3 | 2-F, 4-F, 6-F | 4-OCF3 | 4-F | 4-OCF3 |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF3 | 2-F, 4-F, 6-F | 3-Cl, 4-CF3 | 4-F | 3-Cl, 4-CF3 |
| 2-F, 6-F | 3-CF3, 4-Cl | 2-F, 4-F, 6-F | 3-CF3, 4-Cl | 4-F | 3-CF3, 4-Cl |
| 2-F, 6-F | 3-Cl, 4-F | 2-F, 4-F, 6-F | 3-Cl, 4-F | 4-F | 3-Cl, 4-F |

R^14 is Me, A is NHC(O)OMe

| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF3 | 2-Cl | 3-CF3 | 2-Br | 3-CF3 |
| 2-F | 4-CF3 | 2-Cl | 4-CF3 | 2-Br | 4-CF3 |
| 2-F | 4-OCF3 | 2-Cl | 4-OCF3 | 2-Br | 4-OCF3 |
| 2-F | 3-Cl, 4-Cl | 2-Cl | 3-Cl, 4-Cl | 2-Br | 3-Cl, 4-Cl |
| 2-F | 3-Cl, 4-CF3 | 2-Cl | 3-Cl, 4-CF3 | 2-Br | 3-Cl, 4-CF3 |
| 2-F | 3-CF3, 4-Cl | 2-Cl | 3-CF3, 4-Cl | 2-Br | 3-CF3, 4-Cl |
| 2-F | 3-Cl, 4-F | 2-Cl | 3-Cl, 4-F | 2-Br | 3-Cl, 4-F |
| 2-Me | 3-Cl | 2-CF3 | 3-Cl | 2-F, 4-F | 3-Cl |
| 2-Me | 4-Cl | 2-CF3 | 4-Cl | 2-F, 4-F | 4-Cl |

TABLE 3-continued

| $R^x$ | $R^y$ | $R^x$ | $R^y$ | $R^x$ | $R^y$ |
|---|---|---|---|---|---|
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |

$R^{14}$ is NH$_2$, A is cyano

| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |

$R^{14}$ is NH$_2$, A is CO$_2$Me

| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |

$R^{14}$ is NH$_2$, A is CO$_2$Et

| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |

$R^{14}$ is NH$_2$, A is NHC(O)Me

| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |

TABLE 3-continued

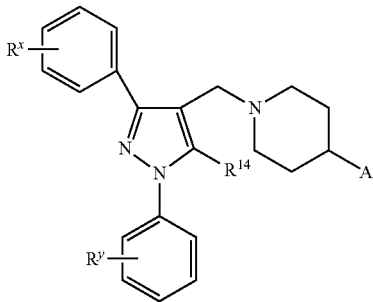

| $R^x$ | $R^y$ | $R^x$ | $R^y$ | $R^x$ | $R^y$ |
|---|---|---|---|---|---|
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |

$R^{14}$ is $NH_2$, A is C(O)Me

| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |

$R^{14}$ is $NH_2$, A is NHC(O)OMe

| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |

TABLE 3-continued

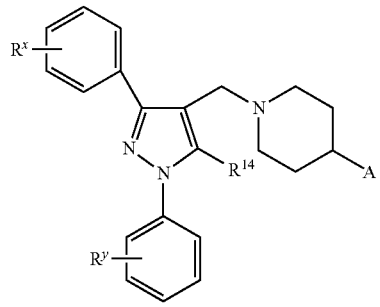

| $R^x$ | $R^y$ | $R^x$ | $R^y$ | $R^x$ | $R^y$ |
|---|---|---|---|---|---|
| 2-F, 6-F | 3-Cl, 4-F | 2-F, 4-F, 6-F | 3-Cl, 4-F | 4-F | 3-Cl, 4-F |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |

TABLE 4

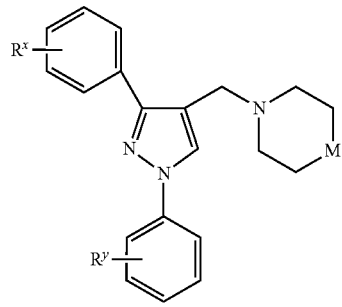

| $R^x$ | $R^y$ | $R^x$ | $R^y$ | $R^x$ | $R^y$ |
|---|---|---|---|---|---|
| M is O | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |
| M is S | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |

TABLE 4-continued

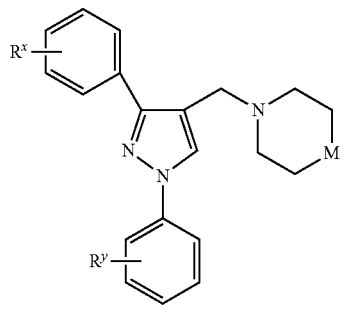

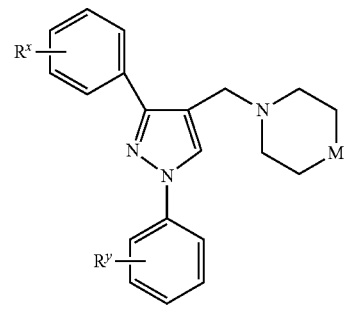

| $R^x$ | $R^y$ | $R^x$ | $R^y$ | $R^x$ | $R^y$ | | $R^x$ | $R^y$ | $R^x$ | $R^y$ | $R^x$ | $R^y$ |
|---|---|---|---|---|---|---|---|---|---|---|---|---|
| 2-F | 3-Cl, 4-Cl | 2-Cl | 3-Cl, 4-Cl | 2-Br | 3-Cl, 4-Cl | | 2-Me | 3-Cl | 2-CF$_3$ | 3-Cl | 2-F, 4-F | 3-Cl |
| 2-F | 3-Cl, 4-CF$_3$ | 2-Cl | 3-Cl, 4-CF$_3$ | 2-Br | 3-Cl, 4-CF$_3$ | | 2-Me | 4-Cl | 2-CF$_3$ | 4-Cl | 2-F, 4-F | 4-Cl |
| 2-F | 3-CF$_3$, 4-Cl | 2-Cl | 3-CF$_3$, 4-Cl | 2-Br | 3-CF$_3$, 4-Cl | | 2-Me | 3-CF$_3$ | 2-CF$_3$ | 3-CF$_3$ | 2-F, 4-F | 3-CF$_3$ |
| 2-F | 3-Cl, 4-F | 2-Cl | 3-Cl, 4-F | 2-Br | 3-Cl, 4-F | | 2-Me | 4-CF$_3$ | 2-CF$_3$ | 4-CF$_3$ | 2-F, 4-F | 4-CF$_3$ |
| 2-Me | 3-Cl | 2-CF$_3$ | 3-Cl | 2-F, 4-F | 3-Cl | | 2-Me | 4-OCF$_3$ | 2-CF$_3$ | 4-OCF$_3$ | 2-F, 4-F | 4-OCF$_3$ |
| 2-Me | 4-Cl | 2-CF$_3$ | 4-Cl | 2-F, 4-F | 4-Cl | | 2-Me | 3-Cl, 4-Cl | 2-CF$_3$ | 3-Cl, 4-Cl | 2-F, 4-F | 3-Cl, 4-Cl |
| 2-Me | 3-CF$_3$ | 2-CF$_3$ | 3-CF$_3$ | 2-F, 4-F | 3-CF$_3$ | | 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 4-CF$_3$ | 2-CF$_3$ | 4-CF$_3$ | 2-F, 4-F | 4-CF$_3$ | | 2-Me | 3-CF$_3$, 4-Cl | 2-CF$_3$ | 3-CF$_3$, 4-Cl | 2-F, 4-F | 3-CF$_3$, 4-Cl |
| 2-Me | 4-OCF$_3$ | 2-CF$_3$ | 4-OCF$_3$ | 2-F, 4-F | 4-OCF$_3$ | | 2-Me | 3-Cl, 4-F | 2-CF$_3$ | 3-Cl, 4-F | 2-F, 4-F | 3-Cl, 4-F |
| 2-Me | 3-Cl, 4-Cl | 2-CF$_3$ | 3-Cl, 4-Cl | 2-F, 4-F | 3-Cl, 4-Cl | | 2-F, 6-F | 3-Cl | 2-F, 4-F, 6-F | 3-Cl | 4-F | 3-Cl |
| 2-Me | 3-Cl, 4-CF$_3$ | 2-CF$_3$ | 3-Cl, 4-CF$_3$ | 2-F, 4-F | 3-Cl, 4-CF$_3$ | | 2-F, 6-F | 4-Cl | 2-F, 4-F, 6-F | 4-Cl | 4-F | 4-Cl |
| 2-Me | 3-CF$_3$, 4-Cl | 2-CF$_3$ | 3-CF$_3$, 4-Cl | 2-F, 4-F | 3-CF$_3$, 4-Cl | | 2-F, 6-F | 3-CF$_3$ | 2-F, 4-F, 6-F | 3-CF$_3$ | 4-F | 3-CF$_3$ |
| 2-Me | 3-Cl, 4-F | 2-CF$_3$ | 3-Cl, 4-F | 2-F, 4-F | 3-Cl, 4-F | | 2-F, 6-F | 4-CF$_3$ | 2-F, 4-F, 6-F | 4-CF$_3$ | 4-F | 4-CF$_3$ |
| 2-F, 6-F | 3-Cl | 2-F, 4-F, 6-F | 3-Cl | 4-F | 3-Cl | | 2-F, 6-F | 4-OCF$_3$ | 2-F, 4-F, 6-F | 4-OCF$_3$ | 4-F | 4-OCF$_3$ |
| 2-F, 6-F | 4-Cl | 2-F, 4-F, 6-F | 4-Cl | 4-F | 4-Cl | | 2-F, 6-F | 3-Cl, 4-Cl | 2-F, 4-F, 6-F | 3-Cl, 4-Cl | 4-F | 3-Cl, 4-Cl |
| 2-F, 6-F | 3-CF$_3$ | 2-F, 4-F, 6-F | 3-CF$_3$ | 4-F | 3-CF$_3$ | | 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 4-CF$_3$ | 2-F, 4-F, 6-F | 4-CF$_3$ | 4-F | 4-CF$_3$ | | 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 4-OCF$_3$ | 2-F, 4-F, 6-F | 4-OCF$_3$ | 4-F | 4-OCF$_3$ | | 2-F, 6-F | 3-Cl, 4-F | 2-F, 4-F, 6-F | 3-Cl, 4-F | 4-F | 3-Cl, 4-F |
| 2-F, 6-F | 3-Cl, 4-Cl | 2-F, 4-F, 6-F | 3-Cl, 4-Cl | 4-F | 3-Cl, 4-Cl | | | | M is NMe | | | |
| 2-F, 6-F | 3-Cl, 4-CF$_3$ | 2-F, 4-F, 6-F | 3-Cl, 4-CF$_3$ | 4-F | 3-Cl, 4-CF$_3$ | | 2-F | 3-Cl | 2-Cl | 3-Cl | 2-Br | 3-Cl |
| 2-F, 6-F | 3-CF$_3$, 4-Cl | 2-F, 4-F, 6-F | 3-CF$_3$, 4-Cl | 4-F | 3-CF$_3$, 4-Cl | | 2-F | 4-Cl | 2-Cl | 4-Cl | 2-Br | 4-Cl |
| 2-F, 6-F | 3-Cl, 4-F | 2-F, 4-F, 6-F | 3-Cl, 4-F | 4-F | 3-Cl, 4-F | | 2-F | 3-CF$_3$ | 2-Cl | 3-CF$_3$ | 2-Br | 3-CF$_3$ |
| | | M is S(O) | | | | | 2-F | 4-CF$_3$ | 2-Cl | 4-CF$_3$ | 2-Br | 4-CF$_3$ |
| 2-F | 3-Cl | 2-Cl | 3-Cl | 2-Br | 3-Cl | | 2-F | 4-OCF$_3$ | 2-Cl | 4-OCF$_3$ | 2-Br | 4-OCF$_3$ |
| 2-F | 4-Cl | 2-Cl | 4-Cl | 2-Br | 4-Cl | | 2-F | 3-Cl, 4-Cl | 2-Cl | 3-Cl, 4-Cl | 2-Br | 3-Cl, 4-Cl |
| 2-F | 3-CF$_3$ | 2-Cl | 3-CF$_3$ | 2-Br | 3-CF$_3$ | | 2-F | 3-Cl, 4-CF$_3$ | 2-Cl | 3-Cl, 4-CF$_3$ | 2-Br | 3-Cl, 4-CF$_3$ |
| 2-F | 4-CF$_3$ | 2-Cl | 4-CF$_3$ | 2-Br | 4-CF$_3$ | | 2-F | 3-CF$_3$, 4-Cl | 2-Cl | 3-CF$_3$, 4-Cl | 2-Br | 3-CF$_3$, 4-Cl |
| 2-F | 4-OCF$_3$ | 2-Cl | 4-OCF$_3$ | 2-Br | 4-OCF$_3$ | | 2-F | 3-Cl, 4-F | 2-Cl | 3-Cl, 4-F | 2-Br | 3-Cl, 4-F |
| 2-F | 3-Cl, 4-Cl | 2-Cl | 3-Cl, 4-Cl | 2-Br | 3-Cl, 4-Cl | | 2-Me | 3-Cl | 2-CF$_3$ | 3-Cl | 2-F, 4-F | 3-Cl |
| 2-F | 3-Cl, 4-CF$_3$ | 2-Cl | 3-Cl, 4-CF$_3$ | 2-Br | 3-Cl, 4-CF$_3$ | | 2-Me | 4-Cl | 2-CF$_3$ | 4-Cl | 2-F, 4-F | 4-Cl |
| 2-F | 3-CF$_3$, 4-Cl | 2-Cl | 3-CF$_3$, 4-Cl | 2-Br | 3-CF$_3$, 4-Cl | | 2-Me | 3-CF$_3$ | 2-CF$_3$ | 3-CF$_3$ | 2-F, 4-F | 3-CF$_3$ |
| 2-F | 3-Cl, 4-F | 2-Cl | 3-Cl, 4-F | 2-Br | 3-Cl, 4-F | | 2-Me | 4-CF$_3$ | 2-CF$_3$ | 4-CF$_3$ | 2-F, 4-F | 4-CF$_3$ |
| 2-Me | 3-Cl | 2-CF$_3$ | 3-Cl | 2-F, 4-F | 3-Cl | | 2-Me | 4-OCF$_3$ | 2-CF$_3$ | 4-OCF$_3$ | 2-F, 4-F | 4-OCF$_3$ |
| 2-Me | 4-Cl | 2-CF$_3$ | 4-Cl | 2-F, 4-F | 4-Cl | | 2-Me | 3-Cl, 4-Cl | 2-CF$_3$ | 3-Cl, 4-Cl | 2-F, 4-F | 3-Cl, 4-Cl |
| 2-Me | 3-CF$_3$ | 2-CF$_3$ | 3-CF$_3$ | 2-F, 4-F | 3-CF$_3$ | | 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 4-CF$_3$ | 2-CF$_3$ | 4-CF$_3$ | 2-F, 4-F | 4-CF$_3$ | | 2-Me | 3-CF$_3$, 4-Cl | 2-CF$_3$ | 3-CF$_3$, 4-Cl | 2-F, 4-F | 3-CF$_3$, 4-Cl |
| 2-Me | 4-OCF$_3$ | 2-CF$_3$ | 4-OCF$_3$ | 2-F, 4-F | 4-OCF$_3$ | | 2-Me | 3-Cl, 4-F | 2-CF$_3$ | 3-Cl, 4-F | 2-F, 4-F | 3-Cl, 4-F |
| 2-Me | 3-Cl, 4-Cl | 2-CF$_3$ | 3-Cl, 4-Cl | 2-F, 4-F | 3-Cl, 4-Cl | | 2-F, 6-F | 3-Cl | 2-F, 4-F, 6-F | 3-Cl | 4-F | 3-Cl |
| 2-Me | 3-Cl, 4-CF$_3$ | 2-CF$_3$ | 3-Cl, 4-CF$_3$ | 2-F, 4-F | 3-Cl, 4-CF$_3$ | | 2-F, 6-F | 4-Cl | 2-F, 4-F, 6-F | 4-Cl | 4-F | 4-Cl |
| 2-Me | 3-CF$_3$, 4-Cl | 2-CF$_3$ | 3-CF$_3$, 4-Cl | 2-F, 4-F | 3-CF$_3$, 4-Cl | | 2-F, 6-F | 3-CF$_3$ | 2-F, 4-F, 6-F | 3-CF$_3$ | 4-F | 3-CF$_3$ |
| 2-Me | 3-Cl, 4-F | 2-CF$_3$ | 3-Cl, 4-F | 2-F, 4-F | 3-Cl, 4-F | | 2-F, 6-F | 4-CF$_3$ | 2-F, 4-F, 6-F | 4-CF$_3$ | 4-F | 4-CF$_3$ |
| 2-F, 6-F | 3-Cl | 2-F, 4-F, 6-F | 3-Cl | 4-F | 3-Cl | | 2-F, 6-F | 4-OCF$_3$ | 2-F, 4-F, 6-F | 4-OCF$_3$ | 4-F | 4-OCF$_3$ |
| 2-F, 6-F | 4-Cl | 2-F, 4-F, 6-F | 4-Cl | 4-F | 4-Cl | | 2-F, 6-F | 3-Cl, 4-Cl | 2-F, 4-F, 6-F | 3-Cl, 4-Cl | 4-F | 3-Cl, 4-Cl |
| 2-F, 6-F | 3-CF$_3$ | 2-F, 4-F, 6-F | 3-CF$_3$ | 4-F | 3-CF$_3$ | | 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 4-CF$_3$ | 2-F, 4-F, 6-F | 4-CF$_3$ | 4-F | 4-CF$_3$ | | 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 4-OCF$_3$ | 2-F, 4-F, 6-F | 4-OCF$_3$ | 4-F | 4-OCF$_3$ | | 2-F, 6-F | 3-Cl, 4-F | 2-F, 4-F, 6-F | 3-Cl, 4-F | 4-F | 3-Cl, 4-F |
| 2-F, 6-F | 3-Cl, 4-Cl | 2-F, 4-F, 6-F | 3-Cl, 4-Cl | 4-F | 3-Cl, 4-Cl | | | | M is CH(phenyl) | | | |
| 2-F, 6-F | 3-Cl, 4-CF$_3$ | 2-F, 4-F, 6-F | 3-Cl, 4-CF$_3$ | 4-F | 3-Cl, 4-CF$_3$ | | 2-F | 3-Cl | 2-Cl | 3-Cl | 2-Br | 3-Cl |
| 2-F, 6-F | 3-CF$_3$, 4-Cl | 2-F, 4-F, 6-F | 3-CF$_3$, 4-Cl | 4-F | 3-CF$_3$, 4-Cl | | 2-F | 4-Cl | 2-Cl | 4-Cl | 2-Br | 4-Cl |
| 2-F, 6-F | 3-Cl, 4-F | 2-F, 4-F, 6-F | 3-Cl, 4-F | 4-F | 3-Cl, 4-F | | 2-F | 3-CF$_3$ | 2-Cl | 3-CF$_3$ | 2-Br | 3-CF$_3$ |
| | | M is S(O)$_2$ | | | | | 2-F | 4-CF$_3$ | 2-Cl | 4-CF$_3$ | 2-Br | 4-CF$_3$ |
| 2-F | 3-Cl | 2-Cl | 3-Cl | 2-Br | 3-Cl | | 2-F | 4-OCF$_3$ | 2-Cl | 4-OCF$_3$ | 2-Br | 4-OCF$_3$ |
| 2-F | 4-Cl | 2-Cl | 4-Cl | 2-Br | 4-Cl | | 2-F | 3-Cl, 4-Cl | 2-Cl | 3-Cl, 4-Cl | 2-Br | 3-Cl, 4-Cl |
| 2-F | 3-CF$_3$ | 2-Cl | 3-CF$_3$ | 2-Br | 3-CF$_3$ | | 2-F | 3-Cl, 4-CF$_3$ | 2-Cl | 3-Cl, 4-CF$_3$ | 2-Br | 3-Cl, 4-CF$_3$ |
| 2-F | 4-CF$_3$ | 2-Cl | 4-CF$_3$ | 2-Br | 4-CF$_3$ | | 2-F | 3-CF$_3$, 4-Cl | 2-Cl | 3-CF$_3$, 4-Cl | 2-Br | 3-CF$_3$, 4-Cl |
| 2-F | 4-OCF$_3$ | 2-Cl | 4-OCF$_3$ | 2-Br | 4-OCF$_3$ | | 2-F | 3-Cl, 4-F | 2-Cl | 3-Cl, 4-F | 2-Br | 3-Cl, 4-F |
| 2-F | 3-Cl, 4-Cl | 2-Cl | 3-Cl, 4-Cl | 2-Br | 3-Cl, 4-Cl | | 2-Me | 3-Cl | 2-CF$_3$ | 3-Cl | 2-F, 4-F | 3-Cl |
| 2-F | 3-Cl, 4-CF$_3$ | 2-Cl | 3-Cl, 4-CF$_3$ | 2-Br | 3-Cl, 4-CF$_3$ | | 2-Me | 4-Cl | 2-CF$_3$ | 4-Cl | 2-F, 4-F | 4-Cl |
| 2-F | 3-CF$_3$, 4-Cl | 2-Cl | 3-CF$_3$, 4-Cl | 2-Br | 3-CF$_3$, 4-Cl | | 2-Me | 3-CF$_3$ | 2-CF$_3$ | 3-CF$_3$ | 2-F, 4-F | 3-CF$_3$ |
| 2-F | 3-Cl, 4-F | 2-Cl | 3-Cl, 4-F | 2-Br | 3-Cl, 4-F | | 2-Me | 4-CF$_3$ | 2-CF$_3$ | 4-CF$_3$ | 2-F, 4-F | 4-CF$_3$ |

TABLE 4-continued

| $R^x$ | $R^y$ | $R^x$ | $R^y$ | $R^x$ | $R^y$ |
|---|---|---|---|---|---|
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |
| M is CH(Me) | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |
| M is CH(CF₃) | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |
| M is CH(OC(O)Me) | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |
| M is CH(SMe) | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |

TABLE 4-continued

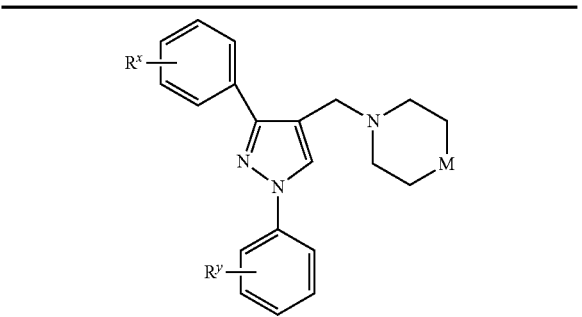
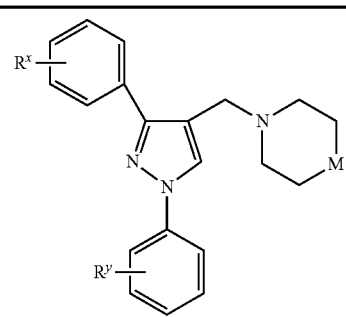

| $R^x$ | $R^y$ | $R^x$ | $R^y$ | $R^x$ | $R^y$ |
|---|---|---|---|---|---|
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |
| M is CH(S(O)Me) | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |
| M is CH(S(O)₂Me) | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |
| M is CH(OS(O)₂Me) | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |
| M is CH(C≡CH) | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |

TABLE 4-continued

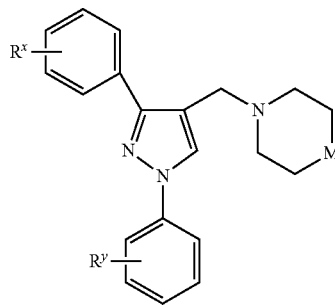

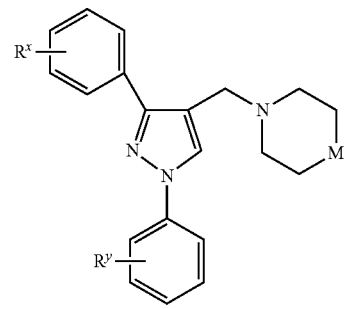

| $R^x$ | $R^y$ | $R^x$ | $R^y$ | $R^x$ | $R^y$ |
|---|---|---|---|---|---|
| M is CH(CH=CH₂) | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |
| M is CH(2-pyridinyl) | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |
| M is CH(3-pyridinyl) | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |
| M is CH(5-pyrimidinyl) | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |
| M is CH(2-imidazolyl) | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |

TABLE 4-continued

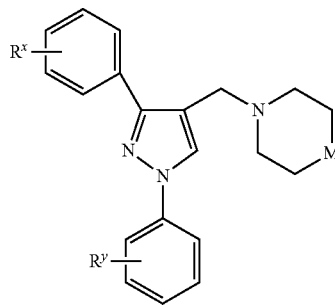

| $R^x$ | $R^y$ | $R^x$ | $R^y$ | $R^x$ | $R^y$ |
|---|---|---|---|---|---|
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |

M is CH(1-(1,2,4-triazolyl))

| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |

M is CH(2-(1,3,4-oxadiazolyl))

| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |

TABLE 4-continued

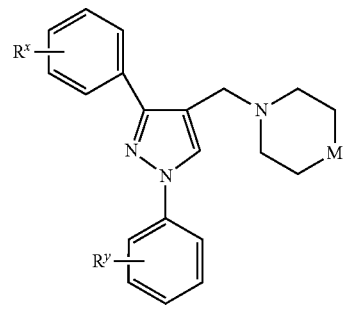

| $R^x$ | $R^y$ | $R^x$ | $R^y$ | $R^x$ | $R^y$ |
|---|---|---|---|---|---|
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |

TABLE 5a

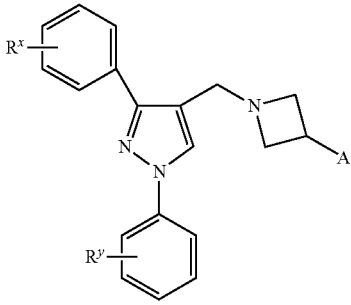

| $R^x$ | $R^y$ | $R^x$ | $R^y$ | $R^x$ | $R^y$ |
|---|---|---|---|---|---|
| A is cyano |||||| 
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |

TABLE 5a-continued

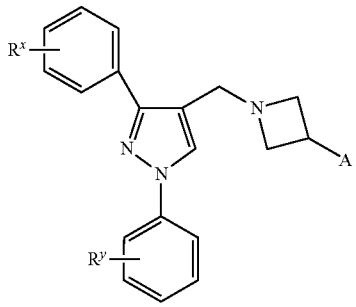

| $R^x$ | $R^y$ | $R^x$ | $R^y$ | $R^x$ | $R^y$ |
|---|---|---|---|---|---|
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |

TABLE 5a-continued

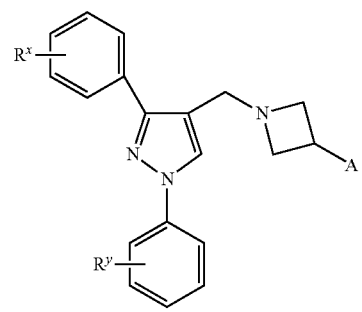

| $R^x$ | $R^y$ | $R^x$ | $R^y$ | $R^x$ | $R^y$ |
|---|---|---|---|---|---|
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |

TABLE 5b-1

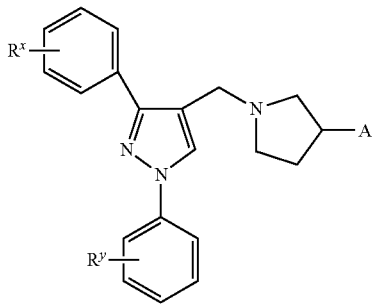

| $R^x$ | $R^y$ | $R^x$ | $R^y$ | $R^x$ | $R^y$ |
|---|---|---|---|---|---|
| | | A is NHC(O)Me | | | |
| 2-F | 2-F | 2-F | 3-F | 2-F | 3-Cl |
| 2-Cl | 2-F | 2-Cl | 3-F | 2-Cl | 3-Cl |
| 2-Br | 2-F | 2-Br | 3-F | 2-Br | 3-Cl |
| 2-Me | 2-F | 2-Me | 3-F | 2-Me | 3-Cl |
| 2-CF$_3$ | 2-F | 2-CF$_3$ | 3-F | 2-CF$_3$ | 3-Cl |
| 4-F | 2-F | 4-F | 3-F | 4-F | 3-Cl |
| 4-Cl | 2-F | 4-Cl | 3-F | 4-Cl | 3-Cl |
| 4-Br | 2-F | 4-Br | 3-F | 4-Br | 3-Cl |
| 2-F, 4-F | 2-F | 2-F, 4-F | 3-F | 2-F, 4-F | 3-Cl |
| 2-Cl, 4-F | 2-F | 2-Cl, 4-F | 3-F | 2-Cl, 4-F | 3-Cl |
| 2-Me, 4-F | 2-F | 2-Me, 4-F | 3-F | 2-Me, 4-F | 3-Cl |
| 2-F, 6-F | 2-F | 2-F, 6-F | 3-F | 2-F, 6-F | 3-Cl |
| 2-Cl, 6-Cl | 2-F | 2-Cl, 6-Cl | 3-F | 2-Cl, 6-Cl | 3-Cl |
| 2-Me, 6-Me | 2-F | 2-Me, 6-Me | 3-F | 2-Me, 6-Me | 3-Cl |
| 2-F, 4-F, 6-F | 2-F | 2-F, 4-F, 6-F | 3-F | 2-F, 4-F, 6-F | 3-Cl |
| 2-F | 3-Br | 2-F | 3-CF$_3$ | 2-F | 3-OCF$_3$ |
| 2-Cl | 3-Br | 2-Cl | 3-CF$_3$ | 2-Cl | 3-OCF$_3$ |
| 2-Br | 3-Br | 2-Br | 3-CF$_3$ | 2-Br | 3-OCF$_3$ |
| 2-Me | 3-Br | 2-Me | 3-CF$_3$ | 2-Me | 3-OCF$_3$ |
| 2-CF$_3$ | 3-Br | 2-CF$_3$ | 3-CF$_3$ | 2-CF$_3$ | 3-OCF$_3$ |
| 4-F | 3-Br | 4-F | 3-CF$_3$ | 4-F | 3-OCF$_3$ |
| 4-Cl | 3-Br | 4-Cl | 3-CF$_3$ | 4-Cl | 3-OCF$_3$ |
| 4-Br | 3-Br | 4-Br | 3-CF$_3$ | 4-Br | 3-OCF$_3$ |
| 2-F, 4-F | 3-Br | 2-F, 4-F | 3-CF$_3$ | 2-F, 4-F | 3-OCF$_3$ |
| 2-Cl, 4-F | 3-Br | 2-Cl, 4-F | 3-CF$_3$ | 2-Cl, 4-F | 3-OCF$_3$ |
| 2-Me, 4-F | 3-Br | 2-Me, 4-F | 3-CF$_3$ | 2-Me, 4-F | 3-OCF$_3$ |
| 2-F, 6-F | 3-Br | 2-F, 6-F | 3-CF$_3$ | 2-F, 6-F | 3-OCF$_3$ |
| 2-Cl, 6-Cl | 3-Br | 2-Cl, 6-Cl | 3-CF$_3$ | 2-Cl, 6-Cl | 3-OCF$_3$ |
| 2-Me, 6-Me | 3-Br | 2-Me, 6-Me | 3-CF$_3$ | 2-Me, 6-Me | 3-OCF$_3$ |
| 2-F, 4-F, 6-F | 3-Br | 2-F, 4-F, 6-F | 3-CF$_3$ | 2-F, 4-F, 6-F | 3-OCF$_3$ |
| 2-F | 4-F | 2-F | 4-Cl | 2-F | 4-Br |
| 2-Cl | 4-F | 2-Cl | 4-Cl | 2-Cl | 4-Br |
| 2-Br | 4-F | 2-Br | 4-Cl | 2-Br | 4-Br |
| 2-Me | 4-F | 2-Me | 4-Cl | 2-Me | 4-Br |
| 2-CF$_3$ | 4-F | 2-CF$_3$ | 4-Cl | 2-CF$_3$ | 4-Br |

TABLE 5b-1-continued

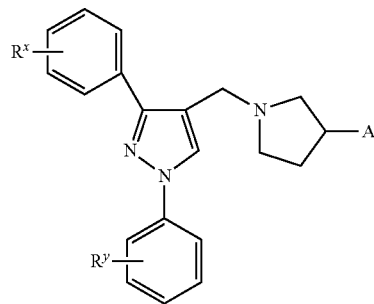

| $R^x$ | $R^y$ | $R^x$ | $R^y$ | $R^x$ | $R^y$ |
|---|---|---|---|---|---|
| 4-F | 4-F | 4-F | 4-Cl | 4-F | 4-Br |
| 4-Cl | 4-F | 4-Cl | 4-Cl | 4-Cl | 4-Br |
| 4-Br | 4-F | 4-Br | 4-Cl | 4-Br | 4-Br |
| 2-F, 4-F | 4-F | 2-F, 4-F | 4-Cl | 2-F, 4-F | 4-Br |
| 2-Cl, 4-F | 4-F | 2-Cl, 4-F | 4-Cl | 2-Cl, 4-F | 4-Br |
| 2-Me, 4-F | 4-F | 2-Me, 4-F | 4-Cl | 2-Me, 4-F | 4-Br |
| 2-F, 6-F | 4-F | 2-F, 6-F | 4-Cl | 2-F, 6-F | 4-Br |
| 2-Cl, 6-Cl | 4-F | 2-Cl, 6-Cl | 4-Cl | 2-Cl, 6-Cl | 4-Br |
| 2-Me, 6-Me | 4-F | 2-Me, 6-Me | 4-Cl | 2-Me, 6-Me | 4-Br |
| 2-F, 4-F, 6-F | 4-F | 2-F, 4-F, 6-F | 4-Cl | 2-F, 4-F, 6-F | 4-Br |
| 2-F | 4-$CF_3$ | 2-F | 4-$OCF_3$ | 2-F | 3-F, 4-F |
| 2-Cl | 4-$CF_3$ | 2-Cl | 4-$OCF_3$ | 2-Cl | 3-F, 4-F |
| 2-Br | 4-$CF_3$ | 2-Br | 4-$OCF_3$ | 2-Br | 3-F, 4-F |
| 2-Me | 4-$CF_3$ | 2-Me | 4-$OCF_3$ | 2-Me | 3-F, 4-F |
| 2-$CF_3$ | 4-$CF_3$ | 2-$CF_3$ | 4-$OCF_3$ | 2-$CF_3$ | 3-F, 4-F |
| 4-F | 4-$CF_3$ | 4-F | 4-$OCF_3$ | 4-F | 3-F, 4-F |
| 4-Cl | 4-$CF_3$ | 4-Cl | 4-$OCF_3$ | 4-Cl | 3-F, 4-F |
| 4-Br | 4-$CF_3$ | 4-Br | 4-$OCF_3$ | 4-Br | 3-F, 4-F |
| 2-F, 4-F | 4-$CF_3$ | 2-F, 4-F | 4-$OCF_3$ | 2-F, 4-F | 3-F, 4-F |
| 2-Cl, 4-F | 4-$CF_3$ | 2-Cl, 4-F | 4-$OCF_3$ | 2-Cl, 4-F | 3-F, 4-F |
| 2-Me, 4-F | 4-$CF_3$ | 2-Me, 4-F | 4-$OCF_3$ | 2-Me, 4-F | 3-F, 4-F |
| 2-F, 6-F | 4-$CF_3$ | 2-F, 6-F | 4-$OCF_3$ | 2-F, 6-F | 3-F, 4-F |
| 2-Cl, 6-Cl | 4-$CF_3$ | 2-Cl, 6-Cl | 4-$OCF_3$ | 2-Cl, 6-Cl | 3-F, 4-F |
| 2-Me, 6-Me | 4-$CF_3$ | 2-Me, 6-Me | 4-$OCF_3$ | 2-Me, 6-Me | 3-F, 4-F |
| 2-F, 4-F, 6-F | 4-$CF_3$ | 2-F, 4-F, 6-F | 4-$OCF_3$ | 2-F, 4-F, 6-F | 3-F, 4-F |
| 2-F | 3-F, 4-Cl | 2-F | 3-F, 4-Br | 2-F | 3-F, 4-$CF_3$ |
| 2-Cl | 3-F, 4-Cl | 2-Cl | 3-F, 4-Br | 2-Cl | 3-F, 4-$CF_3$ |
| 2-Br | 3-F, 4-Cl | 2-Br | 3-F, 4-Br | 2-Br | 3-F, 4-$CF_3$ |
| 2-Me | 3-F, 4-Cl | 2-Me | 3-F, 4-Br | 2-Me | 3-F, 4-$CF_3$ |
| 2-$CF_3$ | 3-F, 4-Cl | 2-$CF_3$ | 3-F, 4-Br | 2-$CF_3$ | 3-F, 4-$CF_3$ |
| 4-F | 3-F, 4-Cl | 4-F | 3-F, 4-Br | 4-F | 3-F, 4-$CF_3$ |
| 4-Cl | 3-F, 4-Cl | 4-Cl | 3-F, 4-Br | 4-Cl | 3-F, 4-$CF_3$ |
| 4-Br | 3-F, 4-Cl | 4-Br | 3-F, 4-Br | 4-Br | 3-F, 4-$CF_3$ |
| 2-F, 4-F | 3-F, 4-Cl | 2-F, 4-F | 3-F, 4-Br | 2-F, 4-F | 3-F, 4-$CF_3$ |
| 2-Cl, 4-F | 3-F, 4-Cl | 2-Cl, 4-F | 3-F, 4-Br | 2-Cl, 4-F | 3-F, 4-$CF_3$ |
| 2-Me, 4-F | 3-F, 4-Cl | 2-Me, 4-F | 3-F, 4-Br | 2-Me, 4-F | 3-F, 4-$CF_3$ |
| 2-F, 6-F | 3-F, 4-Cl | 2-F, 6-F | 3-F, 4-Br | 2-F, 6-F | 3-F, 4-$CF_3$ |
| 2-Cl, 6-Cl | 3-F, 4-Cl | 2-Cl, 6-Cl | 3-F, 4-Br | 2-Cl, 6-Cl | 3-F, 4-$CF_3$ |
| 2-Me, 6-Me | 3-F, 4-Cl | 2-Me, 6-Me | 3-F, 4-Br | 2-Me, 6-Me | 3-F, 4-$CF_3$ |
| 2-F, 4-F, 6-F | 3-F, 4-Cl | 2-F, 4-F, 6-F | 3-F, 4-Br | 2-F, 4-F, 6-F | 3-F, 4-$CF_3$ |
| 2-F | 3-F, 4-$OCF_3$ | 2-F | 3-Cl, 4-F | 2-F | 3-Cl, 4-Cl |
| 2-Cl | 3-F, 4-$OCF_3$ | 2-Cl | 3-Cl, 4-F | 2-Cl | 3-Cl, 4-Cl |
| 2-Br | 3-F, 4-$OCF_3$ | 2-Br | 3-Cl, 4-F | 2-Br | 3-Cl, 4-Cl |
| 2-Me | 3-F, 4-$OCF_3$ | 2-Me | 3-Cl, 4-F | 2-Me | 3-Cl, 4-Cl |
| 2-$CF_3$ | 3-F, 4-$OCF_3$ | 2-$CF_3$ | 3-Cl, 4-F | 2-$CF_3$ | 3-Cl, 4-Cl |
| 4-F | 3-F, 4-$OCF_3$ | 4-F | 3-Cl, 4-F | 4-F | 3-Cl, 4-Cl |
| 4-Cl | 3-F, 4-$OCF_3$ | 4-Cl | 3-Cl, 4-F | 4-Cl | 3-Cl, 4-Cl |
| 4-Br | 3-F, 4-$OCF_3$ | 4-Br | 3-Cl, 4-F | 4-Br | 3-Cl, 4-Cl |
| 2-F, 4-F | 3-F, 4-$OCF_3$ | 2-F, 4-F | 3-Cl, 4-F | 2-F, 4-F | 3-Cl, 4-Cl |
| 2-Cl, 4-F | 3-F, 4-$OCF_3$ | 2-Cl, 4-F | 3-Cl, 4-F | 2-Cl, 4-F | 3-Cl, 4-Cl |
| 2-Me, 4-F | 3-F, 4-$OCF_3$ | 2-Me, 4-F | 3-Cl, 4-F | 2-Me, 4-F | 3-Cl, 4-Cl |
| 2-F, 6-F | 3-F, 4-$OCF_3$ | 2-F, 6-F | 3-Cl, 4-F | 2-F, 6-F | 3-Cl, 4-Cl |
| 2-Cl, 6-Cl | 3-F, 4-$OCF_3$ | 2-Cl, 6-Cl | 3-Cl, 4-F | 2-Cl, 6-Cl | 3-Cl, 4-Cl |
| 2-Me, 6-Me | 3-F, 4-$OCF_3$ | 2-Me, 6-Me | 3-Cl, 4-F | 2-Me, 6-Me | 3-Cl, 4-Cl |
| 2-F, 4-F, 6-F | 3-F, 4-$OCF_3$ | 2-F, 4-F, 6-F | 3-Cl, 4-F | 2-F, 4-F, 6-F | 3-Cl, 4-Cl |
| 2-F | 3-Cl, 4-$CF_3$ | 2-F | 3-Br, 4-F | 2-F | 3-$CF_3$, 4-F |
| 2-Cl | 3-Cl, 4-$CF_3$ | 2-Cl | 3-Br, 4-F | 2-Cl | 3-$CF_3$, 4-F |
| 2-Br | 3-Cl, 4-$CF_3$ | 2-Br | 3-Br, 4-F | 2-Br | 3-$CF_3$, 4-F |
| 2-Me | 3-Cl, 4-$CF_3$ | 2-Me | 3-Br, 4-F | 2-Me | 3-$CF_3$, 4-F |
| 2-$CF_3$ | 3-Cl, 4-$CF_3$ | 2-$CF_3$ | 3-Br, 4-F | 2-$CF_3$ | 3-$CF_3$, 4-F |
| 4-F | 3-Cl, 4-$CF_3$ | 4-F | 3-Br, 4-F | 4-F | 3-$CF_3$, 4-F |
| 4-Cl | 3-Cl, 4-$CF_3$ | 4-Cl | 3-Br, 4-F | 4-Cl | 3-$CF_3$, 4-F |

TABLE 5b-1-continued

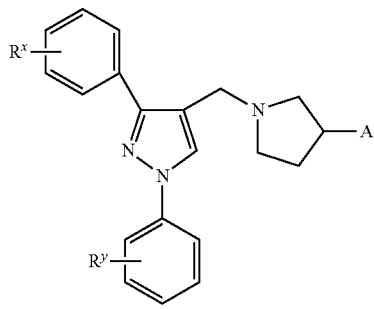

| Rx | Ry | Rx | Ry | Rx | Ry |
|---|---|---|---|---|---|
| 4-Br | 3-Cl, 4-CF3 | 4-Br | 3-Br, 4-F | 4-Br | 3-CF3, 4-F |
| 2-F, 4-F | 3-Cl, 4-CF3 | 2-F, 4-F | 3-Br, 4-F | 2-F, 4-F | 3-CF3, 4-F |
| 2-Cl, 4-F | 3-Cl, 4-CF3 | 2-Cl, 4-F | 3-Br, 4-F | 2-Cl, 4-F | 3-CF3, 4-F |
| 2-Me, 4-F | 3-Cl, 4-CF3 | 2-Me, 4-F | 3-Br, 4-F | 2-Me, 4-F | 3-CF3, 4-F |
| 2-F, 6-F | 3-Cl, 4-CF3 | 2-F, 6-F | 3-Br, 4-F | 2-F, 6-F | 3-CF3, 4-F |
| 2-Cl, 6-Cl | 3-Cl, 4-CF3 | 2-Cl, 6-Cl | 3-Br, 4-F | 2-Cl, 6-Cl | 3-CF3, 4-F |
| 2-Me, 6-Me | 3-Cl, 4-CF3 | 2-Me, 6-Me | 3-Br, 4-F | 2-Me, 6-Me | 3-CF3, 4-F |
| 2-F, 4-F, 6-F | 3-Cl, 4-CF3 | 2-F, 4-F, 6-F | 3-Br, 4-F | 2-F, 4-F, 6-F | 3-CF3, 4-F |
| 2-F | 3-CF3, 4-Cl | 4-F | 3-CF3, 4-Cl | 2-Me, 4-F | 3-CF3, 4-Cl |
| 2-Cl | 3-CF3, 4-Cl | 4-Cl | 3-CF3, 4-Cl | 2-F, 6-F | 3-CF3, 4-Cl |
| 2-Br | 3-CF3, 4-Cl | 4-Br | 3-CF3, 4-Cl | 2-Cl, 6-Cl | 3-CF3, 4-Cl |
| 2-Me | 3-CF3, 4-Cl | 2-F, 4-F | 3-CF3, 4-Cl | 2-Me, 6-Me | 3-CF3, 4-Cl |
| 2-CF3 | 3-CF3, 4-Cl | 2-Cl, 4-F | 3-CF3, 4-Cl | 2-F, 4-F, 6-F | 3-CF3, 4-Cl |
| 2-F | 3,4-DFMDO* | 4-F | 3,4-DFMDO* | 2-Me, 4-F | 3,4-DFMDO* |
| 2-Cl | 3,4-DFMDO* | 4-Cl | 3,4-DFMDO* | 2-F, 6-F | 3,4-DFMDO* |
| 2-Br | 3,4-DFMDO* | 4-Br | 3,4-DFMDO* | 2-Cl, 6-Cl | 3,4-DFMDO* |
| 2-Me | 3,4-DFMDO* | 2-F, 4-F | 3,4-DFMDO* | 2-Me, 6-Me | 3,4-DFMDO* |
| 2-CF3 | 3,4-DFMDO* | 2-Cl, 4-F | 3,4-DFMDO* | 2-F, 4-F, 6-F | 3,4-DFMDO* |
| A is NHC(O)CH(CH2)2 | | | | | |
| 2-F | 2-F | 2-F | 3-F | 2-F | 3-Cl |
| 2-Cl | 2-F | 2-Cl | 3-F | 2-Cl | 3-Cl |
| 2-Br | 2-F | 2-Br | 3-F | 2-Br | 3-Cl |
| 2-Me | 2-F | 2-Me | 3-F | 2-Me | 3-Cl |
| 2-CF3 | 2-F | 2-CF3 | 3-F | 2-CF3 | 3-Cl |
| 4-F | 2-F | 4-F | 3-F | 4-F | 3-Cl |
| 4-Cl | 2-F | 4-Cl | 3-F | 4-Cl | 3-Cl |
| 4-Br | 2-F | 4-Br | 3-F | 4-Br | 3-Cl |
| 2-F, 4-F | 2-F | 2-F, 4-F | 3-F | 2-F, 4-F | 3-Cl |
| 2-Cl, 4-F | 2-F | 2-Cl, 4-F | 3-F | 2-Cl, 4-F | 3-Cl |
| 2-Me, 4-F | 2-F | 2-Me, 4-F | 3-F | 2-Me, 4-F | 3-Cl |
| 2-F, 6-F | 2-F | 2-F, 6-F | 3-F | 2-F, 6-F | 3-Cl |
| 2-Cl, 6-Cl | 2-F | 2-Cl, 6-Cl | 3-F | 2-Cl, 6-Cl | 3-Cl |
| 2-Me, 6-Me | 2-F | 2-Me, 6-Me | 3-F | 2-Me, 6-Me | 3-Cl |
| 2-F, 4-F, 6-F | 2-F | 2-F, 4-F, 6-F | 3-F | 2-F, 4-F, 6-F | 3-Cl |
| 2-F | 3-Br | 2-F | 3-CF3 | 2-F | 3-OCF3 |
| 2-Cl | 3-Br | 2-Cl | 3-CF3 | 2-Cl | 3-OCF3 |
| 2-Br | 3-Br | 2-Br | 3-CF3 | 2-Br | 3-OCF3 |
| 2-Me | 3-Br | 2-Me | 3-CF3 | 2-Me | 3-OCF3 |
| 2-CF3 | 3-Br | 2-CF3 | 3-CF3 | 2-CF3 | 3-OCF3 |
| 4-F | 3-Br | 4-F | 3-CF3 | 4-F | 3-OCF3 |
| 4-Cl | 3-Br | 4-Cl | 3-CF3 | 4-Cl | 3-OCF3 |
| 4-Br | 3-Br | 4-Br | 3-CF3 | 4-Br | 3-OCF3 |
| 2-F, 4-F | 3-Br | 2-F, 4-F | 3-CF3 | 2-F, 4-F | 3-OCF3 |
| 2-Cl, 4-F | 3-Br | 2-Cl, 4-F | 3-CF3 | 2-Cl, 4-F | 3-OCF3 |
| 2-Me, 4-F | 3-Br | 2-Me, 4-F | 3-CF3 | 2-Me, 4-F | 3-OCF3 |
| 2-F, 6-F | 3-Br | 2-F, 6-F | 3-CF3 | 2-F, 6-F | 3-OCF3 |
| 2-Cl, 6-Cl | 3-Br | 2-Cl, 6-Cl | 3-CF3 | 2-Cl, 6-Cl | 3-OCF3 |
| 2-Me, 6-Me | 3-Br | 2-Me, 6-Me | 3-CF3 | 2-Me, 6-Me | 3-OCF3 |
| 2-F, 4-F, 6-F | 3-Br | 2-F, 4-F, 6-F | 3-CF3 | 2-F, 4-F, 6-F | 3-OCF3 |
| 2-F | 4-F | 2-F | 4-Cl | 2-F | 4-Br |
| 2-Cl | 4-F | 2-Cl | 4-Cl | 2-Cl | 4-Br |
| 2-Br | 4-F | 2-Br | 4-Cl | 2-Br | 4-Br |
| 2-Me | 4-F | 2-Me | 4-Cl | 2-Me | 4-Br |
| 2-CF3 | 4-F | 2-CF3 | 4-Cl | 2-CF3 | 4-Br |
| 4-F | 4-F | 4-F | 4-Cl | 4-F | 4-Br |
| 4-Cl | 4-F | 4-Cl | 4-Cl | 4-Cl | 4-Br |
| 4-Br | 4-F | 4-Br | 4-Cl | 4-Br | 4-Br |
| 2-F, 4-F | 4-F | 2-F, 4-F | 4-Cl | 2-F, 4-F | 4-Br |
| 2-Cl, 4-F | 4-F | 2-Cl, 4-F | 4-Cl | 2-Cl, 4-F | 4-Br |
| 2-Me, 4-F | 4-F | 2-Me, 4-F | 4-Cl | 2-Me, 4-F | 4-Br |
| 2-F, 6-F | 4-F | 2-F, 6-F | 4-Cl | 2-F, 6-F | 4-Br |

TABLE 5b-1-continued

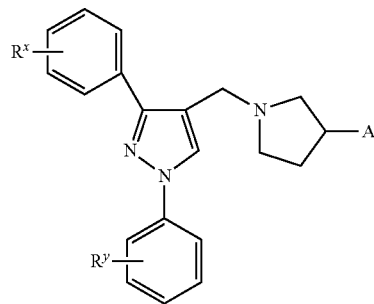

| $R^x$ | $R^y$ | $R^x$ | $R^y$ | $R^x$ | $R^y$ |
|---|---|---|---|---|---|
| 2-Cl, 6-Cl | 4-F | 2-Cl, 6-Cl | 4-Cl | 2-Cl, 6-Cl | 4-Br |
| 2-Me, 6-Me | 4-F | 2-Me, 6-Me | 4-Cl | 2-Me, 6-Me | 4-Br |
| 2-F, 4-F, 6-F | 4-F | 2-F, 4-F, 6-F | 4-Cl | 2-F, 4-F, 6-F | 4-Br |
| 2-F | 4-CF$_3$ | 2-F | 4-OCF$_3$ | 2-F | 3-F, 4-F |
| 2-Cl | 4-CF$_3$ | 2-Cl | 4-OCF$_3$ | 2-Cl | 3-F, 4-F |
| 2-Br | 4-CF$_3$ | 2-Br | 4-OCF$_3$ | 2-Br | 3-F, 4-F |
| 2-Me | 4-CF$_3$ | 2-Me | 4-OCF$_3$ | 2-Me | 3-F, 4-F |
| 2-CF$_3$ | 4-CF$_3$ | 2-CF$_3$ | 4-OCF$_3$ | 2-CF$_3$ | 3-F, 4-F |
| 4-F | 4-CF$_3$ | 4-F | 4-OCF$_3$ | 4-F | 3-F, 4-F |
| 4-Cl | 4-CF$_3$ | 4-Cl | 4-OCF$_3$ | 4-Cl | 3-F, 4-F |
| 4-Br | 4-CF$_3$ | 4-Br | 4-OCF$_3$ | 4-Br | 3-F, 4-F |
| 2-F, 4-F | 4-CF$_3$ | 2-F, 4-F | 4-OCF$_3$ | 2-F, 4-F | 3-F, 4-F |
| 2-Cl, 4-F | 4-CF$_3$ | 2-Cl, 4-F | 4-OCF$_3$ | 2-Cl, 4-F | 3-F, 4-F |
| 2-Me, 4-F | 4-CF$_3$ | 2-Me, 4-F | 4-OCF$_3$ | 2-Me, 4-F | 3-F, 4-F |
| 2-F, 6-F | 4-CF$_3$ | 2-F, 6-F | 4-OCF$_3$ | 2-F, 6-F | 3-F, 4-F |
| 2-Cl, 6-Cl | 4-CF$_3$ | 2-Cl, 6-Cl | 4-OCF$_3$ | 2-Cl, 6-Cl | 3-F, 4-F |
| 2-Me, 6-Me | 4-CF$_3$ | 2-Me, 6-Me | 4-OCF$_3$ | 2-Me, 6-Me | 3-F, 4-F |
| 2-F, 4-F, 6-F | 4-CF$_3$ | 2-F, 4-F, 6-F | 4-OCF$_3$ | 2-F, 4-F, 6-F | 3-F, 4-F |
| 2-F | 3-F, 4-Cl | 2-F | 3-F, 4-Br | 2-F | 3-F, 4-CF$_3$ |
| 2-Cl | 3-F, 4-Cl | 2-Cl | 3-F, 4-Br | 2-Cl | 3-F, 4-CF$_3$ |
| 2-Br | 3-F, 4-Cl | 2-Br | 3-F, 4-Br | 2-Br | 3-F, 4-CF$_3$ |
| 2-Me | 3-F, 4-Cl | 2-Me | 3-F, 4-Br | 2-Me | 3-F, 4-CF$_3$ |
| 2-CF$_3$ | 3-F, 4-Cl | 2-CF$_3$ | 3-F, 4-Br | 2-CF$_3$ | 3-F, 4-CF$_3$ |
| 4-F | 3-F, 4-Cl | 4-F | 3-F, 4-Br | 4-F | 3-F, 4-CF$_3$ |
| 4-Cl | 3-F, 4-Cl | 4-Cl | 3-F, 4-Br | 4-Cl | 3-F, 4-CF$_3$ |
| 4-Br | 3-F, 4-Cl | 4-Br | 3-F, 4-Br | 4-Br | 3-F, 4-CF$_3$ |
| 2-F, 4-F | 3-F, 4-Cl | 2-F, 4-F | 3-F, 4-Br | 2-F, 4-F | 3-F, 4-CF$_3$ |
| 2-Cl, 4-F | 3-F, 4-Cl | 2-Cl, 4-F | 3-F, 4-Br | 2-Cl, 4-F | 3-F, 4-CF$_3$ |
| 2-Me, 4-F | 3-F, 4-Cl | 2-Me, 4-F | 3-F, 4-Br | 2-Me, 4-F | 3-F, 4-CF$_3$ |
| 2-F, 6-F | 3-F, 4-Cl | 2-F, 6-F | 3-F, 4-Br | 2-F, 6-F | 3-F, 4-CF$_3$ |
| 2-Cl, 6-Cl | 3-F, 4-Cl | 2-Cl, 6-Cl | 3-F, 4-Br | 2-Cl, 6-Cl | 3-F, 4-CF$_3$ |
| 2-Me, 6-Me | 3-F, 4-Cl | 2-Me, 6-Me | 3-F, 4-Br | 2-Me, 6-Me | 3-F, 4-CF$_3$ |
| 2-F, 4-F, 6-F | 3-F, 4-Cl | 2-F, 4-F, 6-F | 3-F, 4-Br | 2-F, 4-F, 6-F | 3-F, 4-CF$_3$ |
| 2-F | 3-F, 4-OCF$_3$ | 2-F | 3-Cl, 4-F | 2-F | 3-Cl, 4-Cl |
| 2-Cl | 3-F, 4-OCF$_3$ | 2-Cl | 3-Cl, 4-F | 2-Cl | 3-Cl, 4-Cl |
| 2-Br | 3-F, 4-OCF$_3$ | 2-Br | 3-Cl, 4-F | 2-Br | 3-Cl, 4-Cl |
| 2-Me | 3-F, 4-OCF$_3$ | 2-Me | 3-Cl, 4-F | 2-Me | 3-Cl, 4-Cl |
| 2-CF$_3$ | 3-F, 4-OCF$_3$ | 2-CF$_3$ | 3-Cl, 4-F | 2-CF$_3$ | 3-Cl, 4-Cl |
| 4-F | 3-F, 4-OCF$_3$ | 4-F | 3-Cl, 4-F | 4-F | 3-Cl, 4-Cl |
| 4-Cl | 3-F, 4-OCF$_3$ | 4-Cl | 3-Cl, 4-F | 4-Cl | 3-Cl, 4-Cl |
| 4-Br | 3-F, 4-OCF$_3$ | 4-Br | 3-Cl, 4-F | 4-Br | 3-Cl, 4-Cl |
| 2-F, 4-F | 3-F, 4-OCF$_3$ | 2-F, 4-F | 3-Cl, 4-F | 2-F, 4-F | 3-Cl, 4-Cl |
| 2-Cl, 4-F | 3-F, 4-OCF$_3$ | 2-Cl, 4-F | 3-Cl, 4-F | 2-Cl, 4-F | 3-Cl, 4-Cl |
| 2-Me, 4-F | 3-F, 4-OCF$_3$ | 2-Me, 4-F | 3-Cl, 4-F | 2-Me, 4-F | 3-Cl, 4-Cl |
| 2-F, 6-F | 3-F, 4-OCF$_3$ | 2-F, 6-F | 3-Cl, 4-F | 2-F, 6-F | 3-Cl, 4-Cl |
| 2-Cl, 6-Cl | 3-F, 4-OCF$_3$ | 2-Cl, 6-Cl | 3-Cl, 4-F | 2-Cl, 6-Cl | 3-Cl, 4-Cl |
| 2-Me, 6-Me | 3-F, 4-OCF$_3$ | 2-Me, 6-Me | 3-Cl, 4-F | 2-Me, 6-Me | 3-Cl, 4-Cl |
| 2-F, 4-F, 6-F | 3-F, 4-OCF$_3$ | 2-F, 4-F, 6-F | 3-Cl, 4-F | 2-F, 4-F, 6-F | 3-Cl, 4-Cl |
| 2-F | 3-Cl, 4-CF$_3$ | 2-F | 3-Br, 4-F | 2-F | 3-CF$_3$, 4-F |
| 2-Cl | 3-Cl, 4-CF$_3$ | 2-Cl | 3-Br, 4-F | 2-Cl | 3-CF$_3$, 4-F |
| 2-Br | 3-Cl, 4-CF$_3$ | 2-Br | 3-Br, 4-F | 2-Br | 3-CF$_3$, 4-F |
| 2-Me | 3-Cl, 4-CF$_3$ | 2-Me | 3-Br, 4-F | 2-Me | 3-CF$_3$, 4-F |
| 2-CF$_3$ | 3-Cl, 4-CF$_3$ | 2-CF$_3$ | 3-Br, 4-F | 2-CF$_3$ | 3-CF$_3$, 4-F |
| 4-F | 3-Cl, 4-CF$_3$ | 4-F | 3-Br, 4-F | 4-F | 3-CF$_3$, 4-F |
| 4-Cl | 3-Cl, 4-CF$_3$ | 4-Cl | 3-Br, 4-F | 4-Cl | 3-CF$_3$, 4-F |
| 4-Br | 3-Cl, 4-CF$_3$ | 4-Br | 3-Br, 4-F | 4-Br | 3-CF$_3$, 4-F |
| 2-F, 4-F | 3-Cl, 4-CF$_3$ | 2-F, 4-F | 3-Br, 4-F | 2-F, 4-F | 3-CF$_3$, 4-F |
| 2-Cl, 4-F | 3-Cl, 4-CF$_3$ | 2-Cl, 4-F | 3-Br, 4-F | 2-Cl, 4-F | 3-CF$_3$, 4-F |
| 2-Me, 4-F | 3-Cl, 4-CF$_3$ | 2-Me, 4-F | 3-Br, 4-F | 2-Me, 4-F | 3-CF$_3$, 4-F |
| 2-F, 6-F | 3-Cl, 4-CF$_3$ | 2-F, 6-F | 3-Br, 4-F | 2-F, 6-F | 3-CF$_3$, 4-F |
| 2-Cl, 6-Cl | 3-Cl, 4-CF$_3$ | 2-Cl, 6-Cl | 3-Br, 4-F | 2-Cl, 6-Cl | 3-CF$_3$, 4-F |
| 2-Me, 6-Me | 3-Cl, 4-CF$_3$ | 2-Me, 6-Me | 3-Br, 4-F | 2-Me, 6-Me | 3-CF$_3$, 4-F |

TABLE 5b-1-continued

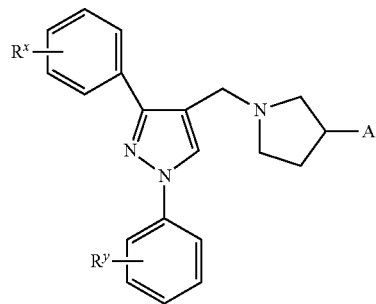

| $R^x$ | $R^y$ | $R^x$ | $R^y$ | $R^x$ | $R^y$ |
|---|---|---|---|---|---|
| 2-F, 4-F, 6-F | 3-Cl, 4-CF$_3$ | 2-F, 4-F, 6-F | 3-Br, 4-F | 2-F, 4-F, 6-F | 3-CF$_3$, 4-F |
| 2-F | 3-CF$_3$, 4-Cl | 4-F | 3-CF$_3$, 4-Cl | 2-Me, 4-F | 3-CF$_3$, 4-Cl |
| 2-Cl | 3-CF$_3$, 4-Cl | 4-Cl | 3-CF$_3$, 4-Cl | 2-F, 6-F | 3-CF$_3$, 4-Cl |
| 2-Br | 3-CF$_3$, 4-Cl | 4-Br | 3-CF$_3$, 4-Cl | 2-Cl, 6-Cl | 3-CF$_3$, 4-Cl |
| 2-Me | 3-CF$_3$, 4-Cl | 2-F, 4-F | 3-CF$_3$, 4-Cl | 2-Me, 6-Me | 3-CF$_3$, 4-Cl |
| 2-CF$_3$ | 3-CF$_3$, 4-Cl | 2-Cl, 4-F | 3-CF$_3$, 4-Cl | 2-F, 4-F, 6-F | 3-CF$_3$, 4-Cl |
| 2-F | 3,4-DFMDO* | 4-F | 3,4-DFMDO* | 2-Me, 4-F | 3,4-DFMDO* |
| 2-Cl | 3,4-DFMDO* | 4-Cl | 3,4-DFMDO* | 2-F, 6-F | 3,4-DFMDO* |
| 2-Br | 3,4-DFMDO* | 4-Br | 3,4-DFMDO* | 2-Cl, 6-Cl | 3,4-DFMDO* |
| 2-Me | 3,4-DFMDO* | 2-F, 4-F | 3,4-DFMDO* | 2-Me, 6-Me | 3,4-DFMDO* |
| 2-CF$_3$ | 3,4-DFMDO* | 2-Cl, 4-F | 3,4-DFMDO* | 2-F, 4-F, 6-F | 3,4-DFMDO* |
| A is NHC(O)N(Me)$_2$ | | | | | |
| 2-F | 2-F | 2-F | 3-F | 2-F | 3-Cl |
| 2-Cl | 2-F | 2-Cl | 3-F | 2-Cl | 3-Cl |
| 2-Br | 2-F | 2-Br | 3-F | 2-Br | 3-Cl |
| 2-Me | 2-F | 2-Me | 3-F | 2-Me | 3-Cl |
| 2-CF$_3$ | 2-F | 2-CF$_3$ | 3-F | 2-CF$_3$ | 3-Cl |
| 4-F | 2-F | 4-F | 3-F | 4-F | 3-Cl |
| 4-Cl | 2-F | 4-Cl | 3-F | 4-Cl | 3-Cl |
| 4-Br | 2-F | 4-Br | 3-F | 4-Br | 3-Cl |
| 2-F, 4-F | 2-F | 2-F, 4-F | 3-F | 2-F, 4-F | 3-Cl |
| 2-Cl, 4-F | 2-F | 2-Cl, 4-F | 3-F | 2-Cl, 4-F | 3-Cl |
| 2-Me, 4-F | 2-F | 2-Me, 4-F | 3-F | 2-Me, 4-F | 3-Cl |
| 2-F, 6-F | 2-F | 2-F, 6-F | 3-F | 2-F, 6-F | 3-Cl |
| 2-Cl, 6-Cl | 2-F | 2-Cl, 6-Cl | 3-F | 2-Cl, 6-Cl | 3-Cl |
| 2-Me, 6-Me | 2-F | 2-Me, 6-Me | 3-F | 2-Me, 6-Me | 3-Cl |
| 2-F, 4-F, 6-F | 2-F | 2-F, 4-F, 6-F | 3-F | 2-F, 4-F, 6-F | 3-Cl |
| 2-F | 3-Br | 2-F | 3-CF$_3$ | 2-F | 3-OCF$_3$ |
| 2-Cl | 3-Br | 2-Cl | 3-CF$_3$ | 2-Cl | 3-OCF$_3$ |
| 2-Br | 3-Br | 2-Br | 3-CF$_3$ | 2-Br | 3-OCF$_3$ |
| 2-Me | 3-Br | 2-Me | 3-CF$_3$ | 2-Me | 3-OCF$_3$ |
| 2-CF$_3$ | 3-Br | 2-CF$_3$ | 3-CF$_3$ | 2-CF$_3$ | 3-OCF$_3$ |
| 4-F | 3-Br | 4-F | 3-CF$_3$ | 4-F | 3-OCF$_3$ |
| 4-Cl | 3-Br | 4-Cl | 3-CF$_3$ | 4-Cl | 3-OCF$_3$ |
| 4-Br | 3-Br | 4-Br | 3-CF$_3$ | 4-Br | 3-OCF$_3$ |
| 2-F, 4-F | 3-Br | 2-F, 4-F | 3-CF$_3$ | 2-F, 4-F | 3-OCF$_3$ |
| 2-Cl, 4-F | 3-Br | 2-Cl, 4-F | 3-CF$_3$ | 2-Cl, 4-F | 3-OCF$_3$ |
| 2-Me, 4-F | 3-Br | 2-Me, 4-F | 3-CF$_3$ | 2-Me, 4-F | 3-OCF$_3$ |
| 2-F, 6-F | 3-Br | 2-F, 6-F | 3-CF$_3$ | 2-F, 6-F | 3-OCF$_3$ |
| 2-Cl, 6-Cl | 3-Br | 2-Cl, 6-Cl | 3-CF$_3$ | 2-Cl, 6-Cl | 3-OCF$_3$ |
| 2-Me, 6-Me | 3-Br | 2-Me, 6-Me | 3-CF$_3$ | 2-Me, 6-Me | 3-OCF$_3$ |
| 2-F, 4-F, 6-F | 3-Br | 2-F, 4-F, 6-F | 3-CF$_3$ | 2-F, 4-F, 6-F | 3-OCF$_3$ |
| 2-F | 4-F | 2-F | 4-Cl | 2-F | 4-Br |
| 2-Cl | 4-F | 2-Cl | 4-Cl | 2-Cl | 4-Br |
| 2-Br | 4-F | 2-Br | 4-Cl | 2-Br | 4-Br |
| 2-Me | 4-F | 2-Me | 4-Cl | 2-Me | 4-Br |
| 2-CF$_3$ | 4-F | 2-CF$_3$ | 4-Cl | 2-CF$_3$ | 4-Br |
| 4-F | 4-F | 4-F | 4-Cl | 4-F | 4-Br |
| 4-Cl | 4-F | 4-Cl | 4-Cl | 4-Cl | 4-Br |
| 4-Br | 4-F | 4-Br | 4-Cl | 4-Br | 4-Br |
| 2-F, 4-F | 4-F | 2-F, 4-F | 4-Cl | 2-F, 4-F | 4-Br |
| 2-Cl, 4-F | 4-F | 2-Cl, 4-F | 4-Cl | 2-Cl, 4-F | 4-Br |
| 2-Me, 4-F | 4-F | 2-Me, 4-F | 4-Cl | 2-Me, 4-F | 4-Br |
| 2-F, 6-F | 4-F | 2-F, 6-F | 4-Cl | 2-F, 6-F | 4-Br |
| 2-Cl, 6-Cl | 4-F | 2-Cl, 6-Cl | 4-Cl | 2-Cl, 6-Cl | 4-Br |
| 2-Me, 6-Me | 4-F | 2-Me, 6-Me | 4-Cl | 2-Me, 6-Me | 4-Br |
| 2-F, 4-F, 6-F | 4-F | 2-F, 4-F, 6-F | 4-Cl | 2-F, 4-F, 6-F | 4-Br |
| 2-F | 4-CF$_3$ | 2-F | 4-OCF$_3$ | 2-F | 3-F, 4-F |
| 2-Cl | 4-CF$_3$ | 2-Cl | 4-OCF$_3$ | 2-Cl | 3-F, 4-F |
| 2-Br | 4-CF$_3$ | 2-Br | 4-OCF$_3$ | 2-Br | 3-F, 4-F |
| 2-Me | 4-CF$_3$ | 2-Me | 4-OCF$_3$ | 2-Me | 3-F, 4-F |

TABLE 5b-1-continued

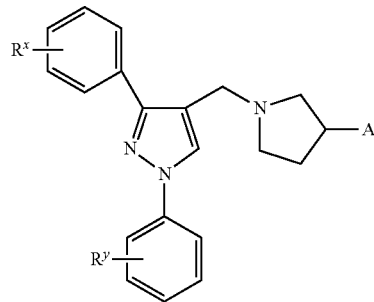

| $R^x$ | $R^y$ | $R^x$ | $R^y$ | $R^x$ | $R^y$ |
|---|---|---|---|---|---|
| 2-CF$_3$ | 4-CF$_3$ | 2-CF$_3$ | 4-OCF$_3$ | 2-CF$_3$ | 3-F, 4-F |
| 4-F | 4-CF$_3$ | 4-F | 4-OCF$_3$ | 4-F | 3-F, 4-F |
| 4-Cl | 4-CF$_3$ | 4-Cl | 4-OCF$_3$ | 4-Cl | 3-F, 4-F |
| 4-Br | 4-CF$_3$ | 4-Br | 4-OCF$_3$ | 4-Br | 3-F, 4-F |
| 2-F, 4-F | 4-CF$_3$ | 2-F, 4-F | 4-OCF$_3$ | 2-F, 4-F | 3-F, 4-F |
| 2-Cl, 4-F | 4-CF$_3$ | 2-Cl, 4-F | 4-OCF$_3$ | 2-Cl, 4-F | 3-F, 4-F |
| 2-Me, 4-F | 4-CF$_3$ | 2-Me, 4-F | 4-OCF$_3$ | 2-Me, 4-F | 3-F, 4-F |
| 2-F, 6-F | 4-CF$_3$ | 2-F, 6-F | 4-OCF$_3$ | 2-F, 6-F | 3-F, 4-F |
| 2-Cl, 6-Cl | 4-CF$_3$ | 2-Cl, 6-Cl | 4-OCF$_3$ | 2-Cl, 6-Cl | 3-F, 4-F |
| 2-Me, 6-Me | 4-CF$_3$ | 2-Me, 6-Me | 4-OCF$_3$ | 2-Me, 6-Me | 3-F, 4-F |
| 2-F, 4-F, 6-F | 4-CF$_3$ | 2-F, 4-F, 6-F | 4-OCF$_3$ | 2-F, 4-F, 6-F | 3-F, 4-F |
| 2-F | 3-F, 4-Cl | 2-F | 3-F, 4-Br | 2-F | 3-F, 4-CF$_3$ |
| 2-Cl | 3-F, 4-Cl | 2-Cl | 3-F, 4-Br | 2-Cl | 3-F, 4-CF$_3$ |
| 2-Br | 3-F, 4-Cl | 2-Br | 3-F, 4-Br | 2-Br | 3-F, 4-CF$_3$ |
| 2-Me | 3-F, 4-Cl | 2-Me | 3-F, 4-Br | 2-Me | 3-F, 4-CF$_3$ |
| 2-CF$_3$ | 3-F, 4-Cl | 2-CF$_3$ | 3-F, 4-Br | 2-CF$_3$ | 3-F, 4-CF$_3$ |
| 4-F | 3-F, 4-Cl | 4-F | 3-F, 4-Br | 4-F | 3-F, 4-CF$_3$ |
| 4-Cl | 3-F, 4-Cl | 4-Cl | 3-F, 4-Br | 4-Cl | 3-F, 4-CF$_3$ |
| 4-Br | 3-F, 4-Cl | 4-Br | 3-F, 4-Br | 4-Br | 3-F, 4-CF$_3$ |
| 2-F, 4-F | 3-F, 4-Cl | 2-F, 4-F | 3-F, 4-Br | 2-F, 4-F | 3-F, 4-CF$_3$ |
| 2-Cl, 4-F | 3-F, 4-Cl | 2-Cl, 4-F | 3-F, 4-Br | 2-Cl, 4-F | 3-F, 4-CF$_3$ |
| 2-Me, 4-F | 3-F, 4-Cl | 2-Me, 4-F | 3-F, 4-Br | 2-Me, 4-F | 3-F, 4-CF$_3$ |
| 2-F, 6-F | 3-F, 4-Cl | 2-F, 6-F | 3-F, 4-Br | 2-F, 6-F | 3-F, 4-CF$_3$ |
| 2-Cl, 6-Cl | 3-F, 4-Cl | 2-Cl, 6-Cl | 3-F, 4-Br | 2-Cl, 6-Cl | 3-F, 4-CF$_3$ |
| 2-Me, 6-Me | 3-F, 4-Cl | 2-Me, 6-Me | 3-F, 4-Br | 2-Me, 6-Me | 3-F, 4-CF$_3$ |
| 2-F, 4-F, 6-F | 3-F, 4-Cl | 2-F, 4-F, 6-F | 3-F, 4-Br | 2-F, 4-F, 6-F | 3-F, 4-CF$_3$ |
| 2-F | 3-F, 4-OCF$_3$ | 2-F | 3-Cl, 4-F | 2-F | 3-Cl, 4-Cl |
| 2-Cl | 3-F, 4-OCF$_3$ | 2-Cl | 3-Cl, 4-F | 2-Cl | 3-Cl, 4-Cl |
| 2-Br | 3-F, 4-OCF$_3$ | 2-Br | 3-Cl, 4-F | 2-Br | 3-Cl, 4-Cl |
| 2-Me | 3-F, 4-OCF$_3$ | 2-Me | 3-Cl, 4-F | 2-Me | 3-Cl, 4-Cl |
| 2-CF$_3$ | 3-F, 4-OCF$_3$ | 2-CF$_3$ | 3-Cl, 4-F | 2-CF$_3$ | 3-Cl, 4-Cl |
| 4-F | 3-F, 4-OCF$_3$ | 4-F | 3-Cl, 4-F | 4-F | 3-Cl, 4-Cl |
| 4-Cl | 3-F, 4-OCF$_3$ | 4-Cl | 3-Cl, 4-F | 4-Cl | 3-Cl, 4-Cl |
| 4-Br | 3-F, 4-OCF$_3$ | 4-Br | 3-Cl, 4-F | 4-Br | 3-Cl, 4-Cl |
| 2-F, 4-F | 3-F, 4-OCF$_3$ | 2-F, 4-F | 3-Cl, 4-F | 2-F, 4-F | 3-Cl, 4-Cl |
| 2-Cl, 4-F | 3-F, 4-OCF$_3$ | 2-Cl, 4-F | 3-Cl, 4-F | 2-Cl, 4-F | 3-Cl, 4-Cl |
| 2-Me, 4-F | 3-F, 4-OCF$_3$ | 2-Me, 4-F | 3-Cl, 4-F | 2-Me, 4-F | 3-Cl, 4-Cl |
| 2-F, 6-F | 3-F, 4-OCF$_3$ | 2-F, 6-F | 3-Cl, 4-F | 2-F, 6-F | 3-Cl, 4-Cl |
| 2-Cl, 6-Cl | 3-F, 4-OCF$_3$ | 2-Cl, 6-Cl | 3-Cl, 4-F | 2-Cl, 6-Cl | 3-Cl, 4-Cl |
| 2-Me, 6-Me | 3-F, 4-OCF$_3$ | 2-Me, 6-Me | 3-Cl, 4-F | 2-Me, 6-Me | 3-Cl, 4-Cl |
| 2-F, 4-F, 6-F | 3-F, 4-OCF$_3$ | 2-F, 4-F, 6-F | 3-Cl, 4-F | 2-F, 4-F, 6-F | 3-Cl, 4-Cl |
| 2-F | 3-Cl, 4-CF$_3$ | 2-F | 3-Br, 4-F | 2-F | 3-CF$_3$, 4-F |
| 2-Cl | 3-Cl, 4-CF$_3$ | 2-Cl | 3-Br, 4-F | 2-Cl | 3-CF$_3$, 4-F |
| 2-Br | 3-Cl, 4-CF$_3$ | 2-Br | 3-Br, 4-F | 2-Br | 3-CF$_3$, 4-F |
| 2-Me | 3-Cl, 4-CF$_3$ | 2-Me | 3-Br, 4-F | 2-Me | 3-CF$_3$, 4-F |
| 2-CF$_3$ | 3-Cl, 4-CF$_3$ | 2-CF$_3$ | 3-Br, 4-F | 2-CF$_3$ | 3-CF$_3$, 4-F |
| 4-F | 3-Cl, 4-CF$_3$ | 4-F | 3-Br, 4-F | 4-F | 3-CF$_3$, 4-F |
| 4-Cl | 3-Cl, 4-CF$_3$ | 4-Cl | 3-Br, 4-F | 4-Cl | 3-CF$_3$, 4-F |
| 4-Br | 3-Cl, 4-CF$_3$ | 4-Br | 3-Br, 4-F | 4-Br | 3-CF$_3$, 4-F |
| 2-F, 4-F | 3-Cl, 4-CF$_3$ | 2-F, 4-F | 3-Br, 4-F | 2-F, 4-F | 3-CF$_3$, 4-F |
| 2-Cl, 4-F | 3-Cl, 4-CF$_3$ | 2-Cl, 4-F | 3-Br, 4-F | 2-Cl, 4-F | 3-CF$_3$, 4-F |
| 2-Me, 4-F | 3-Cl, 4-CF$_3$ | 2-Me, 4-F | 3-Br, 4-F | 2-Me, 4-F | 3-CF$_3$, 4-F |
| 2-F, 6-F | 3-Cl, 4-CF$_3$ | 2-F, 6-F | 3-Br, 4-F | 2-F, 6-F | 3-CF$_3$, 4-F |
| 2-Cl, 6-Cl | 3-Cl, 4-CF$_3$ | 2-Cl, 6-Cl | 3-Br, 4-F | 2-Cl, 6-Cl | 3-CF$_3$, 4-F |
| 2-Me, 6-Me | 3-Cl, 4-CF$_3$ | 2-Me, 6-Me | 3-Br, 4-F | 2-Me, 6-Me | 3-CF$_3$, 4-F |
| 2-F, 4-F, 6-F | 3-Cl, 4-CF$_3$ | 2-F, 4-F, 6-F | 3-Br, 4-F | 2-F, 4-F, 6-F | 3-CF$_3$, 4-F |
| 2-F | 3-CF$_3$, 4-Cl | 4-F | 3-CF$_3$, 4-Cl | 2-Me, 4-F | 3-CF$_3$, 4-Cl |
| 2-Cl | 3-CF$_3$, 4-Cl | 4-Cl | 3-CF$_3$, 4-Cl | 2-F, 6-F | 3-CF$_3$, 4-Cl |
| 2-Br | 3-CF$_3$, 4-Cl | 4-Br | 3-CF$_3$, 4-Cl | 2-Cl, 6-Cl | 3-CF$_3$, 4-Cl |
| 2-Me | 3-CF$_3$, 4-Cl | 2-F, 4-F | 3-CF$_3$, 4-Cl | 2-Me, 6-Me | 3-CF$_3$, 4-Cl |
| 2-CF$_3$ | 3-CF$_3$, 4-Cl | 2-Cl, 4-F | 3-CF$_3$, 4-Cl | 2-F, 4-F, 6-F | 3-CF$_3$, 4-Cl |
| 2-F | 3,4-DFMDO* | 4-F | 3,4-DFMDO* | 2-Me, 4-F | 3,4-DFMDO* |

TABLE 5b-1-continued

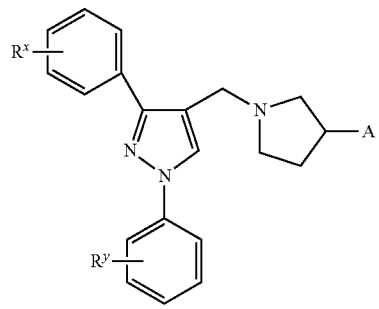

| R$^x$ | R$^y$ | R$^x$ | R$^y$ | R$^x$ | R$^y$ |
|---|---|---|---|---|---|
| 2-Cl | 3,4-DFMDO* | 4-Cl | 3,4-DFMDO* | 2-F, 6-F | 3,4-DFMDO* |
| 2-Br | 3,4-DFMDO* | 4-Br | 3,4-DFMDO* | 2-Cl, 6-Cl | 3,4-DFMDO* |
| 2-Me | 3,4-DFMDO* | 2-F, 4-F | 3,4-DFMDO* | 2-Me, 6-Me | 3,4-DFMDO* |
| 2-CF$_3$ | 3,4-DFMDO* | 2-Cl, 4-F | 3,4-DFMDO* | 2-F, 4-F, 6-F | 3,4-DFMDO* |
| A is CH$_2$C(O)N(Me)$_2$ | | | | | |
| 2-F | 2-F | 2-F | 3-F | 2-F | 3-Cl |
| 2-Cl | 2-F | 2-Cl | 3-F | 2-Cl | 3-Cl |
| 2-Br | 2-F | 2-Br | 3-F | 2-Br | 3-Cl |
| 2-Me | 2-F | 2-Me | 3-F | 2-Me | 3-Cl |
| 2-CF$_3$ | 2-F | 2-CF$_3$ | 3-F | 2-CF$_3$ | 3-Cl |
| 4-F | 2-F | 4-F | 3-F | 4-F | 3-Cl |
| 4-Cl | 2-F | 4-Cl | 3-F | 4-Cl | 3-Cl |
| 4-Br | 2-F | 4-Br | 3-F | 4-Br | 3-Cl |
| 2-F, 4-F | 2-F | 2-F, 4-F | 3-F | 2-F, 4-F | 3-Cl |
| 2-Cl, 4-F | 2-F | 2-Cl, 4-F | 3-F | 2-Cl, 4-F | 3-Cl |
| 2-Me, 4-F | 2-F | 2-Me, 4-F | 3-F | 2-Me, 4-F | 3-Cl |
| 2-F, 6-F | 2-F | 2-F, 6-F | 3-F | 2-F, 6-F | 3-Cl |
| 2-Cl, 6-Cl | 2-F | 2-Cl, 6-Cl | 3-F | 2-Cl, 6-Cl | 3-Cl |
| 2-Me, 6-Me | 2-F | 2-Me, 6-Me | 3-F | 2-Me, 6-Me | 3-Cl |
| 2-F, 4-F, 6-F | 2-F | 2-F, 4-F, 6-F | 3-F | 2-F, 4-F, 6-F | 3-Cl |
| 2-F | 3-Br | 2-F | 3-CF$_3$ | 2-F | 3-OCF$_3$ |
| 2-Cl | 3-Br | 2-Cl | 3-CF$_3$ | 2-Cl | 3-OCF$_3$ |
| 2-Br | 3-Br | 2-Br | 3-CF$_3$ | 2-Br | 3-OCF$_3$ |
| 2-Me | 3-Br | 2-Me | 3-CF$_3$ | 2-Me | 3-OCF$_3$ |
| 2-CF$_3$ | 3-Br | 2-CF$_3$ | 3-CF$_3$ | 2-CF$_3$ | 3-OCF$_3$ |
| 4-F | 3-Br | 4-F | 3-CF$_3$ | 4-F | 3-OCF$_3$ |
| 4-Cl | 3-Br | 4-Cl | 3-CF$_3$ | 4-Cl | 3-OCF$_3$ |
| 4-Br | 3-Br | 4-Br | 3-CF$_3$ | 4-Br | 3-OCF$_3$ |
| 2-F, 4-F | 3-Br | 2-F, 4-F | 3-CF$_3$ | 2-F, 4-F | 3-OCF$_3$ |
| 2-Cl, 4-F | 3-Br | 2-Cl, 4-F | 3-CF$_3$ | 2-Cl, 4-F | 3-OCF$_3$ |
| 2-Me, 4-F | 3-Br | 2-Me, 4-F | 3-CF$_3$ | 2-Me, 4-F | 3-OCF$_3$ |
| 2-F, 6-F | 3-Br | 2-F, 6-F | 3-CF$_3$ | 2-F, 6-F | 3-OCF$_3$ |
| 2-Cl, 6-Cl | 3-Br | 2-Cl, 6-Cl | 3-CF$_3$ | 2-Cl, 6-Cl | 3-OCF$_3$ |
| 2-Me, 6-Me | 3-Br | 2-Me, 6-Me | 3-CF$_3$ | 2-Me, 6-Me | 3-OCF$_3$ |
| 2-F, 4-F, 6-F | 3-Br | 2-F, 4-F, 6-F | 3-CF$_3$ | 2-F, 4-F, 6-F | 3-OCF$_3$ |
| 2-F | 4-F | 2-F | 4-Cl | 2-F | 4-Br |
| 2-Cl | 4-F | 2-Cl | 4-Cl | 2-Cl | 4-Br |
| 2-Br | 4-F | 2-Br | 4-Cl | 2-Br | 4-Br |
| 2-Me | 4-F | 2-Me | 4-Cl | 2-Me | 4-Br |
| 2-CF$_3$ | 4-F | 2-CF$_3$ | 4-Cl | 2-CF$_3$ | 4-Br |
| 4-F | 4-F | 4-F | 4-Cl | 4-F | 4-Br |
| 4-Cl | 4-F | 4-Cl | 4-Cl | 4-Cl | 4-Br |
| 4-Br | 4-F | 4-Br | 4-Cl | 4-Br | 4-Br |
| 2-F, 4-F | 4-F | 2-F, 4-F | 4-Cl | 2-F, 4-F | 4-Br |
| 2-Cl, 4-F | 4-F | 2-Cl, 4-F | 4-Cl | 2-Cl, 4-F | 4-Br |
| 2-Me, 4-F | 4-F | 2-Me, 4-F | 4-Cl | 2-Me, 4-F | 4-Br |
| 2-F, 6-F | 4-F | 2-F, 6-F | 4-Cl | 2-F, 6-F | 4-Br |
| 2-Cl, 6-Cl | 4-F | 2-Cl, 6-Cl | 4-Cl | 2-Cl, 6-Cl | 4-Br |
| 2-Me, 6-Me | 4-F | 2-Me, 6-Me | 4-Cl | 2-Me, 6-Me | 4-Br |
| 2-F, 4-F, 6-F | 4-F | 2-F, 4-F, 6-F | 4-Cl | 2-F, 4-F, 6-F | 4-Br |
| 2-F | 4-CF$_3$ | 2-F | 4-OCF$_3$ | 2-F | 3-F, 4-F |
| 2-Cl | 4-CF$_3$ | 2-Cl | 4-OCF$_3$ | 2-Cl | 3-F, 4-F |
| 2-Br | 4-CF$_3$ | 2-Br | 4-OCF$_3$ | 2-Br | 3-F, 4-F |
| 2-Me | 4-CF$_3$ | 2-Me | 4-OCF$_3$ | 2-Me | 3-F, 4-F |
| 2-CF$_3$ | 4-CF$_3$ | 2-CF$_3$ | 4-OCF$_3$ | 2-CF$_3$ | 3-F, 4-F |
| 4-F | 4-CF$_3$ | 4-F | 4-OCF$_3$ | 4-F | 3-F, 4-F |
| 4-Cl | 4-CF$_3$ | 4-Cl | 4-OCF$_3$ | 4-Cl | 3-F, 4-F |
| 4-Br | 4-CF$_3$ | 4-Br | 4-OCF$_3$ | 4-Br | 3-F, 4-F |
| 2-F, 4-F | 4-CF$_3$ | 2-F, 4-F | 4-OCF$_3$ | 2-F, 4-F | 3-F, 4-F |
| 2-Cl, 4-F | 4-CF$_3$ | 2-Cl, 4-F | 4-OCF$_3$ | 2-Cl, 4-F | 3-F, 4-F |
| 2-Me, 4-F | 4-CF$_3$ | 2-Me, 4-F | 4-OCF$_3$ | 2-Me, 4-F | 3-F, 4-F |

TABLE 5b-1-continued

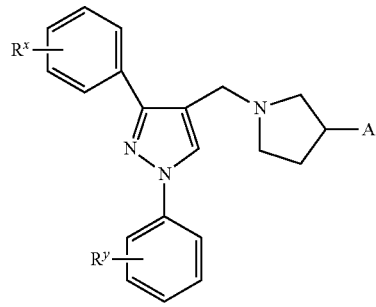

| Rˣ | Rʸ | Rˣ | Rʸ | Rˣ | Rʸ |
|---|---|---|---|---|---|
| 2-F, 6-F | 4-CF₃ | 2-F, 6-F | 4-OCF₃ | 2-F, 6-F | 3-F, 4-F |
| 2-Cl, 6-Cl | 4-CF₃ | 2-Cl, 6-Cl | 4-OCF₃ | 2-Cl, 6-Cl | 3-F, 4-F |
| 2-Me, 6-Me | 4-CF₃ | 2-Me, 6-Me | 4-OCF₃ | 2-Me, 6-Me | 3-F, 4-F |
| 2-F, 4-F, 6-F | 4-CF₃ | 2-F, 4-F, 6-F | 4-OCF₃ | 2-F, 4-F, 6-F | 3-F, 4-F |
| 2-F | 3-F, 4-Cl | 2-F | 3-F, 4-Br | 2-F | 3-F, 4-CF₃ |
| 2-Cl | 3-F, 4-Cl | 2-Cl | 3-F, 4-Br | 2-Cl | 3-F, 4-CF₃ |
| 2-Br | 3-F, 4-Cl | 2-Br | 3-F, 4-Br | 2-Br | 3-F, 4-CF₃ |
| 2-Me | 3-F, 4-Cl | 2-Me | 3-F, 4-Br | 2-Me | 3-F, 4-CF₃ |
| 2-CF₃ | 3-F, 4-Cl | 2-CF₃ | 3-F, 4-Br | 2-CF₃ | 3-F, 4-CF₃ |
| 4-F | 3-F, 4-Cl | 4-F | 3-F, 4-Br | 4-F | 3-F, 4-CF₃ |
| 4-Cl | 3-F, 4-Cl | 4-Cl | 3-F, 4-Br | 4-Cl | 3-F, 4-CF₃ |
| 4-Br | 3-F, 4-Cl | 4-Br | 3-F, 4-Br | 4-Br | 3-F, 4-CF₃ |
| 2-F, 4-F | 3-F, 4-Cl | 2-F, 4-F | 3-F, 4-Br | 2-F, 4-F | 3-F, 4-CF₃ |
| 2-Cl, 4-F | 3-F, 4-Cl | 2-Cl, 4-F | 3-F, 4-Br | 2-Cl, 4-F | 3-F, 4-CF₃ |
| 2-Me, 4-F | 3-F, 4-Cl | 2-Me, 4-F | 3-F, 4-Br | 2-Me, 4-F | 3-F, 4-CF₃ |
| 2-F, 6-F | 3-F, 4-Cl | 2-F, 6-F | 3-F, 4-Br | 2-F, 6-F | 3-F, 4-CF₃ |
| 2-Cl, 6-Cl | 3-F, 4-Cl | 2-Cl, 6-Cl | 3-F, 4-Br | 2-Cl, 6-Cl | 3-F, 4-CF₃ |
| 2-Me, 6-Me | 3-F, 4-Cl | 2-Me, 6-Me | 3-F, 4-Br | 2-Me, 6-Me | 3-F, 4-CF₃ |
| 2-F, 4-F, 6-F | 3-F, 4-Cl | 2-F, 4-F, 6-F | 3-F, 4-Br | 2-F, 4-F, 6-F | 3-F, 4-CF₃ |
| 2-F | 3-F, 4-OCF₃ | 2-F | 3-Cl, 4-F | 2-F | 3-Cl, 4-Cl |
| 2-Cl | 3-F, 4-OCF₃ | 2-Cl | 3-Cl, 4-F | 2-Cl | 3-Cl, 4-Cl |
| 2-Br | 3-F, 4-OCF₃ | 2-Br | 3-Cl, 4-F | 2-Br | 3-Cl, 4-Cl |
| 2-Me | 3-F, 4-OCF₃ | 2-Me | 3-Cl, 4-F | 2-Me | 3-Cl, 4-Cl |
| 2-CF₃ | 3-F, 4-OCF₃ | 2-CF₃ | 3-Cl, 4-F | 2-CF₃ | 3-Cl, 4-Cl |
| 4-F | 3-F, 4-OCF₃ | 4-F | 3-Cl, 4-F | 4-F | 3-Cl, 4-Cl |
| 4-Cl | 3-F, 4-OCF₃ | 4-Cl | 3-Cl, 4-F | 4-Cl | 3-Cl, 4-Cl |
| 4-Br | 3-F, 4-OCF₃ | 4-Br | 3-Cl, 4-F | 4-Br | 3-Cl, 4-Cl |
| 2-F, 4-F | 3-F, 4-OCF₃ | 2-F, 4-F | 3-Cl, 4-F | 2-F, 4-F | 3-Cl, 4-Cl |
| 2-Cl, 4-F | 3-F, 4-OCF₃ | 2-Cl, 4-F | 3-Cl, 4-F | 2-Cl, 4-F | 3-Cl, 4-Cl |
| 2-Me, 4-F | 3-F, 4-OCF₃ | 2-Me, 4-F | 3-Cl, 4-F | 2-Me, 4-F | 3-Cl, 4-Cl |
| 2-F, 6-F | 3-F, 4-OCF₃ | 2-F, 6-F | 3-Cl, 4-F | 2-F, 6-F | 3-Cl, 4-Cl |
| 2-Cl, 6-Cl | 3-F, 4-OCF₃ | 2-Cl, 6-Cl | 3-Cl, 4-F | 2-Cl, 6-Cl | 3-Cl, 4-Cl |
| 2-Me, 6-Me | 3-F, 4-OCF₃ | 2-Me, 6-Me | 3-Cl, 4-F | 2-Me, 6-Me | 3-Cl, 4-Cl |
| 2-F, 4-F, 6-F | 3-F, 4-OCF₃ | 2-F, 4-F, 6-F | 3-Cl, 4-F | 2-F, 4-F, 6-F | 3-Cl, 4-Cl |
| 2-F | 3-Cl, 4-CF₃ | 2-F | 3-Br, 4-F | 2-F | 3-CF₃, 4-F |
| 2-Cl | 3-Cl, 4-CF₃ | 2-Cl | 3-Br, 4-F | 2-Cl | 3-CF₃, 4-F |
| 2-Br | 3-Cl, 4-CF₃ | 2-Br | 3-Br, 4-F | 2-Br | 3-CF₃, 4-F |
| 2-Me | 3-Cl, 4-CF₃ | 2-Me | 3-Br, 4-F | 2-Me | 3-CF₃, 4-F |
| 2-CF₃ | 3-Cl, 4-CF₃ | 2-CF₃ | 3-Br, 4-F | 2-CF₃ | 3-CF₃, 4-F |
| 4-F | 3-Cl, 4-CF₃ | 4-F | 3-Br, 4-F | 4-F | 3-CF₃, 4-F |
| 4-Cl | 3-Cl, 4-CF₃ | 4-Cl | 3-Br, 4-F | 4-Cl | 3-CF₃, 4-F |
| 4-Br | 3-Cl, 4-CF₃ | 4-Br | 3-Br, 4-F | 4-Br | 3-CF₃, 4-F |
| 2-F, 4-F | 3-Cl, 4-CF₃ | 2-F, 4-F | 3-Br, 4-F | 2-F, 4-F | 3-CF₃, 4-F |
| 2-Cl, 4-F | 3-Cl, 4-CF₃ | 2-Cl, 4-F | 3-Br, 4-F | 2-Cl, 4-F | 3-CF₃, 4-F |
| 2-Me, 4-F | 3-Cl, 4-CF₃ | 2-Me, 4-F | 3-Br, 4-F | 2-Me, 4-F | 3-CF₃, 4-F |
| 2-F, 6-F | 3-Cl, 4-CF₃ | 2-F, 6-F | 3-Br, 4-F | 2-F, 6-F | 3-CF₃, 4-F |
| 2-Cl, 6-Cl | 3-Cl, 4-CF₃ | 2-Cl, 6-Cl | 3-Br, 4-F | 2-Cl, 6-Cl | 3-CF₃, 4-F |
| 2-Me, 6-Me | 3-Cl, 4-CF₃ | 2-Me, 6-Me | 3-Br, 4-F | 2-Me, 6-Me | 3-CF₃, 4-F |
| 2-F, 4-F, 6-F | 3-Cl, 4-CF₃ | 2-F, 4-F, 6-F | 3-Br, 4-F | 2-F, 4-F, 6-F | 3-CF₃, 4-F |
| 2-F | 3-CF₃, 4-Cl | 4-F | 3-CF₃, 4-Cl | 2-Me, 4-F | 3-CF₃, 4-Cl |
| 2-Cl | 3-CF₃, 4-Cl | 4-Cl | 3-CF₃, 4-Cl | 2-F, 6-F | 3-CF₃, 4-Cl |
| 2-Br | 3-CF₃, 4-Cl | 4-Br | 3-CF₃, 4-Cl | 2-Cl, 6-Cl | 3-CF₃, 4-Cl |
| 2-Me | 3-CF₃, 4-Cl | 2-F, 4-F | 3-CF₃, 4-Cl | 2-Me, 6-Me | 3-CF₃, 4-Cl |
| 2-CF₃ | 3-CF₃, 4-Cl | 2-Cl, 4-F | 3-CF₃, 4-Cl | 2-F, 4-F, 6-F | 3-CF₃, 4-Cl |
| 2-F | 3,4-DFMDO* | 4-F | 3,4-DFMDO* | 2-Me, 4-F | 3,4-DFMDO* |
| 2-Cl | 3,4-DFMDO* | 4-Cl | 3,4-DFMDO* | 2-F, 6-F | 3,4-DFMDO* |
| 2-Br | 3,4-DFMDO* | 4-Br | 3,4-DFMDO* | 2-Cl, 6-Cl | 3,4-DFMDO* |
| 2-Me | 3,4-DFMDO* | 2-F, 4-F | 3,4-DFMDO* | 2-Me, 6-Me | 3,4-DFMDO* |
| 2-CF₃ | 3,4-DFMDO* | 2-Cl, 4-F | 3,4-DFMDO* | 2-F, 4-F, 6-F | 3,4-DFMDO* |

TABLE 5b-1-continued

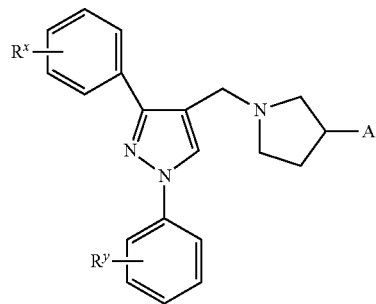

| $R^x$ | $R^y$ | $R^x$ | $R^y$ | $R^x$ | $R^y$ |
|---|---|---|---|---|---|
| A is NHC(O)CH(Me)(Et) | | | | | |
| 2-F | 2-F | 2-F | 3-F | 2-F | 3-Cl |
| 2-Cl | 2-F | 2-Cl | 3-F | 2-Cl | 3-Cl |
| 2-Br | 2-F | 2-Br | 3-F | 2-Br | 3-Cl |
| 2-Me | 2-F | 2-Me | 3-F | 2-Me | 3-Cl |
| 2-CF₃ | 2-F | 2-CF₃ | 3-F | 2-CF₃ | 3-Cl |
| 4-F | 2-F | 4-F | 3-F | 4-F | 3-Cl |
| 4-Cl | 2-F | 4-Cl | 3-F | 4-Cl | 3-Cl |
| 4-Br | 2-F | 4-Br | 3-F | 4-Br | 3-Cl |
| 2-F, 4-F | 2-F | 2-F, 4-F | 3-F | 2-F, 4-F | 3-Cl |
| 2-Cl, 4-F | 2-F | 2-Cl, 4-F | 3-F | 2-Cl, 4-F | 3-Cl |
| 2-Me, 4-F | 2-F | 2-Me, 4-F | 3-F | 2-Me, 4-F | 3-Cl |
| 2-F, 6-F | 2-F | 2-F, 6-F | 3-F | 2-F, 6-F | 3-Cl |
| 2-Cl, 6-Cl | 2-F | 2-Cl, 6-Cl | 3-F | 2-Cl, 6-Cl | 3-Cl |
| 2-Me, 6-Me | 2-F | 2-Me, 6-Me | 3-F | 2-Me, 6-Me | 3-Cl |
| 2-F, 4-F, 6-F | 2-F | 2-F, 4-F, 6-F | 3-F | 2-F, 4-F, 6-F | 3-Cl |
| 2-F | 3-Br | 2-F | 3-CF₃ | 2-F | 3-OCF₃ |
| 2-Cl | 3-Br | 2-Cl | 3-CF₃ | 2-Cl | 3-OCF₃ |
| 2-Br | 3-Br | 2-Br | 3-CF₃ | 2-Br | 3-OCF₃ |
| 2-Me | 3-Br | 2-Me | 3-CF₃ | 2-Me | 3-OCF₃ |
| 2-CF₃ | 3-Br | 2-CF₃ | 3-CF₃ | 2-CF₃ | 3-OCF₃ |
| 4-F | 3-Br | 4-F | 3-CF₃ | 4-F | 3-OCF₃ |
| 4-Cl | 3-Br | 4-Cl | 3-CF₃ | 4-Cl | 3-OCF₃ |
| 4-Br | 3-Br | 4-Br | 3-CF₃ | 4-Br | 3-OCF₃ |
| 2-F, 4-F | 3-Br | 2-F, 4-F | 3-CF₃ | 2-F, 4-F | 3-OCF₃ |
| 2-Cl, 4-F | 3-Br | 2-Cl, 4-F | 3-CF₃ | 2-Cl, 4-F | 3-OCF₃ |
| 2-Me, 4-F | 3-Br | 2-Me, 4-F | 3-CF₃ | 2-Me, 4-F | 3-OCF₃ |
| 2-F, 6-F | 3-Br | 2-F, 6-F | 3-CF₃ | 2-F, 6-F | 3-OCF₃ |
| 2-Cl, 6-Cl | 3-Br | 2-Cl, 6-Cl | 3-CF₃ | 2-Cl, 6-Cl | 3-OCF₃ |
| 2-Me, 6-Me | 3-Br | 2-Me, 6-Me | 3-CF₃ | 2-Me, 6-Me | 3-OCF₃ |
| 2-F, 4-F, 6-F | 3-Br | 2-F, 4-F, 6-F | 3-CF₃ | 2-F, 4-F, 6-F | 3-OCF₃ |
| 2-F | 4-F | 2-F | 4-Cl | 2-F | 4-Br |
| 2-Cl | 4-F | 2-Cl | 4-Cl | 2-Cl | 4-Br |
| 2-Br | 4-F | 2-Br | 4-Cl | 2-Br | 4-Br |
| 2-Me | 4-F | 2-Me | 4-Cl | 2-Me | 4-Br |
| 2-CF₃ | 4-F | 2-CF₃ | 4-Cl | 2-CF₃ | 4-Br |
| 4-F | 4-F | 4-F | 4-Cl | 4-F | 4-Br |
| 4-Cl | 4-F | 4-Cl | 4-Cl | 4-Cl | 4-Br |
| 4-Br | 4-F | 4-Br | 4-Cl | 4-Br | 4-Br |
| 2-F, 4-F | 4-F | 2-F, 4-F | 4-Cl | 2-F, 4-F | 4-Br |
| 2-Cl, 4-F | 4-F | 2-Cl, 4-F | 4-Cl | 2-Cl, 4-F | 4-Br |
| 2-Me, 4-F | 4-F | 2-Me, 4-F | 4-Cl | 2-Me, 4-F | 4-Br |
| 2-F, 6-F | 4-F | 2-F, 6-F | 4-Cl | 2-F, 6-F | 4-Br |
| 2-Cl, 6-Cl | 4-F | 2-Cl, 6-Cl | 4-Cl | 2-Cl, 6-Cl | 4-Br |
| 2-Me, 6-Me | 4-F | 2-Me, 6-Me | 4-Cl | 2-Me, 6-Me | 4-Br |
| 2-F, 4-F, 6-F | 4-F | 2-F, 4-F, 6-F | 4-Cl | 2-F, 4-F, 6-F | 4-Br |
| 2-F | 4-CF₃ | 2-F | 4-OCF₃ | 2-F | 3-F, 4-F |
| 2-Cl | 4-CF₃ | 2-Cl | 4-OCF₃ | 2-Cl | 3-F, 4-F |
| 2-Br | 4-CF₃ | 2-Br | 4-OCF₃ | 2-Br | 3-F, 4-F |
| 2-Me | 4-CF₃ | 2-Me | 4-OCF₃ | 2-Me | 3-F, 4-F |
| 2-CF₃ | 4-CF₃ | 2-CF₃ | 4-OCF₃ | 2-CF₃ | 3-F, 4-F |
| 4-F | 4-CF₃ | 4-F | 4-OCF₃ | 4-F | 3-F, 4-F |
| 4-Cl | 4-CF₃ | 4-Cl | 4-OCF₃ | 4-Cl | 3-F, 4-F |
| 4-Br | 4-CF₃ | 4-Br | 4-OCF₃ | 4-Br | 3-F, 4-F |
| 2-F, 4-F | 4-CF₃ | 2-F, 4-F | 4-OCF₃ | 2-F, 4-F | 3-F, 4-F |
| 2-Cl, 4-F | 4-CF₃ | 2-Cl, 4-F | 4-OCF₃ | 2-Cl, 4-F | 3-F, 4-F |
| 2-Me, 4-F | 4-CF₃ | 2-Me, 4-F | 4-OCF₃ | 2-Me, 4-F | 3-F, 4-F |
| 2-F, 6-F | 4-CF₃ | 2-F, 6-F | 4-OCF₃ | 2-F, 6-F | 3-F, 4-F |
| 2-Cl, 6-Cl | 4-CF₃ | 2-Cl, 6-Cl | 4-OCF₃ | 2-Cl, 6-Cl | 3-F, 4-F |
| 2-Me, 6-Me | 4-CF₃ | 2-Me, 6-Me | 4-OCF₃ | 2-Me, 6-Me | 3-F, 4-F |
| 2-F, 4-F, 6-F | 4-CF₃ | 2-F, 4-F, 6-F | 4-OCF₃ | 2-F, 4-F, 6-F | 3-F, 4-F |

TABLE 5b-1-continued

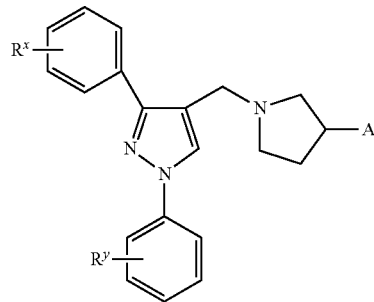

| $R^x$ | $R^y$ | $R^x$ | $R^y$ | $R^x$ | $R^y$ |
|---|---|---|---|---|---|
| 2-F | 3-F, 4-Cl | 2-F | 3-F, 4-Br | 2-F | 3-F, 4-CF$_3$ |
| 2-Cl | 3-F, 4-Cl | 2-Cl | 3-F, 4-Br | 2-Cl | 3-F, 4-CF$_3$ |
| 2-Br | 3-F, 4-Cl | 2-Br | 3-F, 4-Br | 2-Br | 3-F, 4-CF$_3$ |
| 2-Me | 3-F, 4-Cl | 2-Me | 3-F, 4-Br | 2-Me | 3-F, 4-CF$_3$ |
| 2-CF$_3$ | 3-F, 4-Cl | 2-CF$_3$ | 3-F, 4-Br | 2-CF$_3$ | 3-F, 4-CF$_3$ |
| 4-F | 3-F, 4-Cl | 4-F | 3-F, 4-Br | 4-F | 3-F, 4-CF$_3$ |
| 4-Cl | 3-F, 4-Cl | 4-Cl | 3-F, 4-Br | 4-Cl | 3-F, 4-CF$_3$ |
| 4-Br | 3-F, 4-Cl | 4-Br | 3-F, 4-Br | 4-Br | 3-F, 4-CF$_3$ |
| 2-F, 4-F | 3-F, 4-Cl | 2-F, 4-F | 3-F, 4-Br | 2-F, 4-F | 3-F, 4-CF$_3$ |
| 2-Cl, 4-F | 3-F, 4-Cl | 2-Cl, 4-F | 3-F, 4-Br | 2-Cl, 4-F | 3-F, 4-CF$_3$ |
| 2-Me, 4-F | 3-F, 4-Cl | 2-Me, 4-F | 3-F, 4-Br | 2-Me, 4-F | 3-F, 4-CF$_3$ |
| 2-F, 6-F | 3-F, 4-Cl | 2-F, 6-F | 3-F, 4-Br | 2-F, 6-F | 3-F, 4-CF$_3$ |
| 2-Cl, 6-Cl | 3-F, 4-Cl | 2-Cl, 6-Cl | 3-F, 4-Br | 2-Cl, 6-Cl | 3-F, 4-CF$_3$ |
| 2-Me, 6-Me | 3-F, 4-Cl | 2-Me, 6-Me | 3-F, 4-Br | 2-Me, 6-Me | 3-F, 4-CF$_3$ |
| 2-F, 4-F, 6-F | 3-F, 4-Cl | 2-F, 4-F, 6-F | 3-F, 4-Br | 2-F, 4-F, 6-F | 3-F, 4-CF$_3$ |
| 2-F | 3-F, 4-OCF$_3$ | 2-F | 3-Cl, 4-F | 2-F | 3-Cl, 4-Cl |
| 2-Cl | 3-F, 4-OCF$_3$ | 2-Cl | 3-Cl, 4-F | 2-Cl | 3-Cl, 4-Cl |
| 2-Br | 3-F, 4-OCF$_3$ | 2-Br | 3-Cl, 4-F | 2-Br | 3-Cl, 4-Cl |
| 2-Me | 3-F, 4-OCF$_3$ | 2-Me | 3-Cl, 4-F | 2-Me | 3-Cl, 4-Cl |
| 2-CF$_3$ | 3-F, 4-OCF$_3$ | 2-CF$_3$ | 3-Cl, 4-F | 2-CF$_3$ | 3-Cl, 4-Cl |
| 4-F | 3-F, 4-OCF$_3$ | 4-F | 3-Cl, 4-F | 4-F | 3-Cl, 4-Cl |
| 4-Cl | 3-F, 4-OCF$_3$ | 4-Cl | 3-Cl, 4-F | 4-Cl | 3-Cl, 4-Cl |
| 4-Br | 3-F, 4-OCF$_3$ | 4-Br | 3-Cl, 4-F | 4-Br | 3-Cl, 4-Cl |
| 2-F, 4-F | 3-F, 4-OCF$_3$ | 2-F, 4-F | 3-Cl, 4-F | 2-F, 4-F | 3-Cl, 4-Cl |
| 2-Cl, 4-F | 3-F, 4-OCF$_3$ | 2-Cl, 4-F | 3-Cl, 4-F | 2-Cl, 4-F | 3-Cl, 4-Cl |
| 2-Me, 4-F | 3-F, 4-OCF$_3$ | 2-Me, 4-F | 3-Cl, 4-F | 2-Me, 4-F | 3-Cl, 4-Cl |
| 2-F, 6-F | 3-F, 4-OCF$_3$ | 2-F, 6-F | 3-Cl, 4-F | 2-F, 6-F | 3-Cl, 4-Cl |
| 2-Cl, 6-Cl | 3-F, 4-OCF$_3$ | 2-Cl, 6-Cl | 3-Cl, 4-F | 2-Cl, 6-Cl | 3-Cl, 4-Cl |
| 2-Me, 6-Me | 3-F, 4-OCF$_3$ | 2-Me, 6-Me | 3-Cl, 4-F | 2-Me, 6-Me | 3-Cl, 4-Cl |
| 2-F, 4-F, 6-F | 3-F, 4-OCF$_3$ | 2-F, 4-F, 6-F | 3-Cl, 4-F | 2-F, 4-F, 6-F | 3-Cl, 4-Cl |
| 2-F | 3-Cl, 4-CF$_3$ | 2-F | 3-Br, 4-F | 2-F | 3-CF$_3$, 4-F |
| 2-Cl | 3-Cl, 4-CF$_3$ | 2-Cl | 3-Br, 4-F | 2-Cl | 3-CF$_3$, 4-F |
| 2-Br | 3-Cl, 4-CF$_3$ | 2-Br | 3-Br, 4-F | 2-Br | 3-CF$_3$, 4-F |
| 2-Me | 3-Cl, 4-CF$_3$ | 2-Me | 3-Br, 4-F | 2-Me | 3-CF$_3$, 4-F |
| 2-CF$_3$ | 3-Cl, 4-CF$_3$ | 2-CF$_3$ | 3-Br, 4-F | 2-CF$_3$ | 3-CF$_3$, 4-F |
| 4-F | 3-Cl, 4-CF$_3$ | 4-F | 3-Br, 4-F | 4-F | 3-CF$_3$, 4-F |
| 4-Cl | 3-Cl, 4-CF$_3$ | 4-Cl | 3-Br, 4-F | 4-Cl | 3-CF$_3$, 4-F |
| 4-Br | 3-Cl, 4-CF$_3$ | 4-Br | 3-Br, 4-F | 4-Br | 3-CF$_3$, 4-F |
| 2-F, 4-F | 3-Cl, 4-CF$_3$ | 2-F, 4-F | 3-Br, 4-F | 2-F, 4-F | 3-CF$_3$, 4-F |
| 2-Cl, 4-F | 3-Cl, 4-CF$_3$ | 2-Cl, 4-F | 3-Br, 4-F | 2-Cl, 4-F | 3-CF$_3$, 4-F |
| 2-Me, 4-F | 3-Cl, 4-CF$_3$ | 2-Me, 4-F | 3-Br, 4-F | 2-Me, 4-F | 3-CF$_3$, 4-F |
| 2-F, 6-F | 3-Cl, 4-CF$_3$ | 2-F, 6-F | 3-Br, 4-F | 2-F, 6-F | 3-CF$_3$, 4-F |
| 2-Cl, 6-Cl | 3-Cl, 4-CF$_3$ | 2-Cl, 6-Cl | 3-Br, 4-F | 2-Cl, 6-Cl | 3-CF$_3$, 4-F |
| 2-Me, 6-Me | 3-Cl, 4-CF$_3$ | 2-Me, 6-Me | 3-Br, 4-F | 2-Me, 6-Me | 3-CF$_3$, 4-F |
| 2-F, 4-F, 6-F | 3-Cl, 4-CF$_3$ | 2-F, 4-F, 6-F | 3-Br, 4-F | 2-F, 4-F, 6-F | 3-CF$_3$, 4-F |
| 2-F | 3-CF$_3$, 4-Cl | 4-F | 3-CF$_3$, 4-Cl | 2-Me, 4-F | 3-CF$_3$, 4-Cl |
| 2-Cl | 3-CF$_3$, 4-Cl | 4-Cl | 3-CF$_3$, 4-Cl | 2-F, 6-F | 3-CF$_3$, 4-Cl |
| 2-Br | 3-CF$_3$, 4-Cl | 4-Br | 3-CF$_3$, 4-Cl | 2-Cl, 6-Cl | 3-CF$_3$, 4-Cl |
| 2-Me | 3-CF$_3$, 4-Cl | 2-F, 4-F | 3-CF$_3$, 4-Cl | 2-Me, 6-Me | 3-CF$_3$, 4-Cl |
| 2-CF$_3$ | 3-CF$_3$, 4-Cl | 2-Cl, 4-F | 3-CF$_3$, 4-Cl | 2-F, 4-F, 6-F | 3-CF$_3$, 4-Cl |
| 2-F | 3,4-DFMDO* | 4-F | 3,4-DFMDO* | 2-Me, 4-F | 3,4-DFMDO* |
| 2-Cl | 3,4-DFMDO* | 4-Cl | 3,4-DFMDO* | 2-F, 6-F | 3,4-DFMDO* |
| 2-Br | 3,4-DFMDO* | 4-Br | 3,4-DFMDO* | 2-Cl, 6-Cl | 3,4-DFMDO* |
| 2-Me | 3,4-DFMDO* | 2-F, 4-F | 3,4-DFMDO* | 2-Me, 6-Me | 3,4-DFMDO* |
| 2-CF$_3$ | 3,4-DFMDO* | 2-Cl, 4-F | 3,4-DFMDO* | 2-F, 4-F, 6-F | 3,4-DFMDO* |
| | | A is NHC(O)OMe | | | |
| 2-F | 2-F | 2-F | 3-F | 2-F | 3-Cl |
| 2-Cl | 2-F | 2-Cl | 3-F | 2-Cl | 3-Cl |
| 2-Br | 2-F | 2-Br | 3-F | 2-Br | 3-Cl |
| 2-Me | 2-F | 2-Me | 3-F | 2-Me | 3-Cl |
| 2-CF$_3$ | 2-F | 2-CF$_3$ | 3-F | 2-CF$_3$ | 3-Cl |

TABLE 5b-1-continued

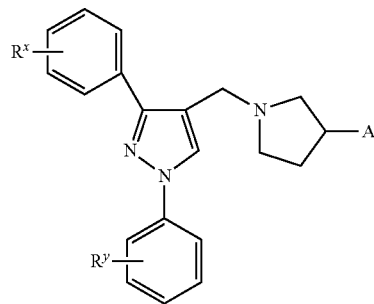

| R$^x$ | R$^y$ | R$^x$ | R$^y$ | R$^x$ | R$^y$ |
|---|---|---|---|---|---|
| 4-F | 2-F | 4-F | 3-F | 4-F | 3-Cl |
| 4-Cl | 2-F | 4-Cl | 3-F | 4-Cl | 3-Cl |
| 4-Br | 2-F | 4-Br | 3-F | 4-Br | 3-Cl |
| 2-F, 4-F | 2-F | 2-F, 4-F | 3-F | 2-F, 4-F | 3-Cl |
| 2-Cl, 4-F | 2-F | 2-Cl, 4-F | 3-F | 2-Cl, 4-F | 3-Cl |
| 2-Me, 4-F | 2-F | 2-Me, 4-F | 3-F | 2-Me, 4-F | 3-Cl |
| 2-F, 6-F | 2-F | 2-F, 6-F | 3-F | 2-F, 6-F | 3-Cl |
| 2-Cl, 6-Cl | 2-F | 2-Cl, 6-Cl | 3-F | 2-Cl, 6-Cl | 3-Cl |
| 2-Me, 6-Me | 2-F | 2-Me, 6-Me | 3-F | 2-Me, 6-Me | 3-Cl |
| 2-F, 4-F, 6-F | 2-F | 2-F, 4-F, 6-F | 3-F | 2-F, 4-F, 6-F | 3-Cl |
| 2-F | 3-Br | 2-F | 3-CF$_3$ | 2-F | 3-OCF$_3$ |
| 2-Cl | 3-Br | 2-Cl | 3-CF$_3$ | 2-Cl | 3-OCF$_3$ |
| 2-Br | 3-Br | 2-Br | 3-CF$_3$ | 2-Br | 3-OCF$_3$ |
| 2-Me | 3-Br | 2-Me | 3-CF$_3$ | 2-Me | 3-OCF$_3$ |
| 2-CF$_3$ | 3-Br | 2-CF$_3$ | 3-CF$_3$ | 2-CF$_3$ | 3-OCF$_3$ |
| 4-F | 3-Br | 4-F | 3-CF$_3$ | 4-F | 3-OCF$_3$ |
| 4-Cl | 3-Br | 4-Cl | 3-CF$_3$ | 4-Cl | 3-OCF$_3$ |
| 4-Br | 3-Br | 4-Br | 3-CF$_3$ | 4-Br | 3-OCF$_3$ |
| 2-F, 4-F | 3-Br | 2-F, 4-F | 3-CF$_3$ | 2-F, 4-F | 3-OCF$_3$ |
| 2-Cl, 4-F | 3-Br | 2-Cl, 4-F | 3-CF$_3$ | 2-Cl, 4-F | 3-OCF$_3$ |
| 2-Me, 4-F | 3-Br | 2-Me, 4-F | 3-CF$_3$ | 2-Me, 4-F | 3-OCF$_3$ |
| 2-F, 6-F | 3-Br | 2-F, 6-F | 3-CF$_3$ | 2-F, 6-F | 3-OCF$_3$ |
| 2-Cl, 6-Cl | 3-Br | 2-Cl, 6-Cl | 3-CF$_3$ | 2-Cl, 6-Cl | 3-OCF$_3$ |
| 2-Me, 6-Me | 3-Br | 2-Me, 6-Me | 3-CF$_3$ | 2-Me, 6-Me | 3-OCF$_3$ |
| 2-F, 4-F, 6-F | 3-Br | 2-F, 4-F, 6-F | 3-CF$_3$ | 2-F, 4-F, 6-F | 3-OCF$_3$ |
| 2-F | 4-F | 2-F | 4-Cl | 2-F | 4-Br |
| 2-Cl | 4-F | 2-Cl | 4-Cl | 2-Cl | 4-Br |
| 2-Br | 4-F | 2-Br | 4-Cl | 2-Br | 4-Br |
| 2-Me | 4-F | 2-Me | 4-Cl | 2-Me | 4-Br |
| 2-CF$_3$ | 4-F | 2-CF$_3$ | 4-Cl | 2-CF$_3$ | 4-Br |
| 4-F | 4-F | 4-F | 4-Cl | 4-F | 4-Br |
| 4-Cl | 4-F | 4-Cl | 4-Cl | 4-Cl | 4-Br |
| 4-Br | 4-F | 4-Br | 4-Cl | 4-Br | 4-Br |
| 2-F, 4-F | 4-F | 2-F, 4-F | 4-Cl | 2-F, 4-F | 4-Br |
| 2-Cl, 4-F | 4-F | 2-Cl, 4-F | 4-Cl | 2-Cl, 4-F | 4-Br |
| 2-Me, 4-F | 4-F | 2-Me, 4-F | 4-Cl | 2-Me, 4-F | 4-Br |
| 2-F, 6-F | 4-F | 2-F, 6-F | 4-Cl | 2-F, 6-F | 4-Br |
| 2-Cl, 6-Cl | 4-F | 2-Cl, 6-Cl | 4-Cl | 2-Cl, 6-Cl | 4-Br |
| 2-Me, 6-Me | 4-F | 2-Me, 6-Me | 4-Cl | 2-Me, 6-Me | 4-Br |
| 2-F, 4-F, 6-F | 4-F | 2-F, 4-F, 6-F | 4-Cl | 2-F, 4-F, 6-F | 4-Br |
| 2-F | 4-CF$_3$ | 2-F | 4-OCF$_3$ | 2-F | 3-F, 4-F |
| 2-Cl | 4-CF$_3$ | 2-Cl | 4-OCF$_3$ | 2-Cl | 3-F, 4-F |
| 2-Br | 4-CF$_3$ | 2-Br | 4-OCF$_3$ | 2-Br | 3-F, 4-F |
| 2-Me | 4-CF$_3$ | 2-Me | 4-OCF$_3$ | 2-Me | 3-F, 4-F |
| 2-CF$_3$ | 4-CF$_3$ | 2-CF$_3$ | 4-OCF$_3$ | 2-CF$_3$ | 3-F, 4-F |
| 4-F | 4-CF$_3$ | 4-F | 4-OCF$_3$ | 4-F | 3-F, 4-F |
| 4-Cl | 4-CF$_3$ | 4-Cl | 4-OCF$_3$ | 4-Cl | 3-F, 4-F |
| 4-Br | 4-CF$_3$ | 4-Br | 4-OCF$_3$ | 4-Br | 3-F, 4-F |
| 2-F, 4-F | 4-CF$_3$ | 2-F, 4-F | 4-OCF$_3$ | 2-F, 4-F | 3-F, 4-F |
| 2-Cl, 4-F | 4-CF$_3$ | 2-Cl, 4-F | 4-OCF$_3$ | 2-Cl, 4-F | 3-F, 4-F |
| 2-Me, 4-F | 4-CF$_3$ | 2-Me, 4-F | 4-OCF$_3$ | 2-Me, 4-F | 3-F, 4-F |
| 2-F, 6-F | 4-CF$_3$ | 2-F, 6-F | 4-OCF$_3$ | 2-F, 6-F | 3-F, 4-F |
| 2-Cl, 6-Cl | 4-CF$_3$ | 2-Cl, 6-Cl | 4-OCF$_3$ | 2-Cl, 6-Cl | 3-F, 4-F |
| 2-Me, 6-Me | 4-CF$_3$ | 2-Me, 6-Me | 4-OCF$_3$ | 2-Me, 6-Me | 3-F, 4-F |
| 2-F, 4-F, 6-F | 4-CF$_3$ | 2-F, 4-F, 6-F | 4-OCF$_3$ | 2-F, 4-F, 6-F | 3-F, 4-F |
| 2-F | 3-F, 4-Cl | 2-F | 3-F, 4-Br | 2-F | 3-F, 4-CF$_3$ |
| 2-Cl | 3-F, 4-Cl | 2-Cl | 3-F, 4-Br | 2-Cl | 3-F, 4-CF$_3$ |
| 2-Br | 3-F, 4-Cl | 2-Br | 3-F, 4-Br | 2-Br | 3-F, 4-CF$_3$ |
| 2-Me | 3-F, 4-Cl | 2-Me | 3-F, 4-Br | 2-Me | 3-F, 4-CF$_3$ |
| 2-CF$_3$ | 3-F, 4-Cl | 2-CF$_3$ | 3-F, 4-Br | 2-CF$_3$ | 3-F, 4-CF$_3$ |
| 4-F | 3-F, 4-Cl | 4-F | 3-F, 4-Br | 4-F | 3-F, 4-CF$_3$ |
| 4-Cl | 3-F, 4-Cl | 4-Cl | 3-F, 4-Br | 4-Cl | 3-F, 4-CF$_3$ |

TABLE 5b-1-continued

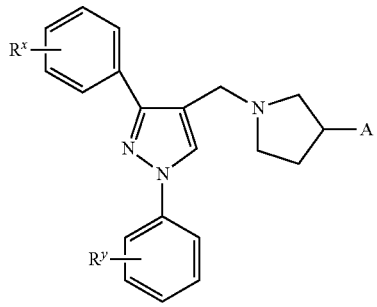

| $R^x$ | $R^y$ | $R^x$ | $R^y$ | $R^x$ | $R^y$ |
| --- | --- | --- | --- | --- | --- |
| 4-Br | 3-F, 4-Cl | 4-Br | 3-F, 4-Br | 4-Br | 3-F, 4-CF₃ |
| 2-F, 4-F | 3-F, 4-Cl | 2-F, 4-F | 3-F, 4-Br | 2-F, 4-F | 3-F, 4-CF₃ |
| 2-Cl, 4-F | 3-F, 4-Cl | 2-Cl, 4-F | 3-F, 4-Br | 2-Cl, 4-F | 3-F, 4-CF₃ |
| 2-Me, 4-F | 3-F, 4-Cl | 2-Me, 4-F | 3-F, 4-Br | 2-Me, 4-F | 3-F, 4-CF₃ |
| 2-F, 6-F | 3-F, 4-Cl | 2-F, 6-F | 3-F, 4-Br | 2-F, 6-F | 3-F, 4-CF₃ |
| 2-Cl, 6-Cl | 3-F, 4-Cl | 2-Cl, 6-Cl | 3-F, 4-Br | 2-Cl, 6-Cl | 3-F, 4-CF₃ |
| 2-Me, 6-Me | 3-F, 4-Cl | 2-Me, 6-Me | 3-F, 4-Br | 2-Me, 6-Me | 3-F, 4-CF₃ |
| 2-F, 4-F, 6-F | 3-F, 4-Cl | 2-F, 4-F, 6-F | 3-F, 4-Br | 2-F, 4-F, 6-F | 3-F, 4-CF₃ |
| 2-F | 3-F, 4-OCF₃ | 2-F | 3-Cl, 4-F | 2-F | 3-Cl, 4-Cl |
| 2-Cl | 3-F, 4-OCF₃ | 2-Cl | 3-Cl, 4-F | 2-Cl | 3-Cl, 4-Cl |
| 2-Br | 3-F, 4-OCF₃ | 2-Br | 3-Cl, 4-F | 2-Br | 3-Cl, 4-Cl |
| 2-Me | 3-F, 4-OCF₃ | 2-Me | 3-Cl, 4-F | 2-Me | 3-Cl, 4-Cl |
| 2-CF₃ | 3-F, 4-OCF₃ | 2-CF₃ | 3-Cl, 4-F | 2-CF₃ | 3-Cl, 4-Cl |
| 4-F | 3-F, 4-OCF₃ | 4-F | 3-Cl, 4-F | 4-F | 3-Cl, 4-Cl |
| 4-Cl | 3-F, 4-OCF₃ | 4-Cl | 3-Cl, 4-F | 4-Cl | 3-Cl, 4-Cl |
| 4-Br | 3-F, 4-OCF₃ | 4-Br | 3-Cl, 4-F | 4-Br | 3-Cl, 4-Cl |
| 2-F, 4-F | 3-F, 4-OCF₃ | 2-F, 4-F | 3-Cl, 4-F | 2-F, 4-F | 3-Cl, 4-Cl |
| 2-Cl, 4-F | 3-F, 4-OCF₃ | 2-Cl, 4-F | 3-Cl, 4-F | 2-Cl, 4-F | 3-Cl, 4-Cl |
| 2-Me, 4-F | 3-F, 4-OCF₃ | 2-Me, 4-F | 3-Cl, 4-F | 2-Me, 4-F | 3-Cl, 4-Cl |
| 2-F, 6-F | 3-F, 4-OCF₃ | 2-F, 6-F | 3-Cl, 4-F | 2-F, 6-F | 3-Cl, 4-Cl |
| 2-Cl, 6-Cl | 3-F, 4-OCF₃ | 2-Cl, 6-Cl | 3-Cl, 4-F | 2-Cl, 6-Cl | 3-Cl, 4-Cl |
| 2-Me, 6-Me | 3-F, 4-OCF₃ | 2-Me, 6-Me | 3-Cl, 4-F | 2-Me, 6-Me | 3-Cl, 4-Cl |
| 2-F, 4-F, 6-F | 3-F, 4-OCF₃ | 2-F, 4-F, 6-F | 3-Cl, 4-F | 2-F, 4-F, 6-F | 3-Cl, 4-Cl |
| 2-F | 3-Cl, 4-CF₃ | 2-F | 3-Br, 4-F | 2-F | 3-CF₃, 4-F |
| 2-Cl | 3-Cl, 4-CF₃ | 2-Cl | 3-Br, 4-F | 2-Cl | 3-CF₃, 4-F |
| 2-Br | 3-Cl, 4-CF₃ | 2-Br | 3-Br, 4-F | 2-Br | 3-CF₃, 4-F |
| 2-Me | 3-Cl, 4-CF₃ | 2-Me | 3-Br, 4-F | 2-Me | 3-CF₃, 4-F |
| 2-CF₃ | 3-Cl, 4-CF₃ | 2-CF₃ | 3-Br, 4-F | 2-CF₃ | 3-CF₃, 4-F |
| 4-F | 3-Cl, 4-CF₃ | 4-F | 3-Br, 4-F | 4-F | 3-CF₃, 4-F |
| 4-Cl | 3-Cl, 4-CF₃ | 4-Cl | 3-Br, 4-F | 4-Cl | 3-CF₃, 4-F |
| 4-Br | 3-Cl, 4-CF₃ | 4-Br | 3-Br, 4-F | 4-Br | 3-CF₃, 4-F |
| 2-F, 4-F | 3-Cl, 4-CF₃ | 2-F, 4-F | 3-Br, 4-F | 2-F, 4-F | 3-CF₃, 4-F |
| 2-Cl, 4-F | 3-Cl, 4-CF₃ | 2-Cl, 4-F | 3-Br, 4-F | 2-Cl, 4-F | 3-CF₃, 4-F |
| 2-Me, 4-F | 3-Cl, 4-CF₃ | 2-Me, 4-F | 3-Br, 4-F | 2-Me, 4-F | 3-CF₃, 4-F |
| 2-F, 6-F | 3-Cl, 4-CF₃ | 2-F, 6-F | 3-Br, 4-F | 2-F, 6-F | 3-CF₃, 4-F |
| 2-Cl, 6-Cl | 3-Cl, 4-CF₃ | 2-Cl, 6-Cl | 3-Br, 4-F | 2-Cl, 6-Cl | 3-CF₃, 4-F |
| 2-Me, 6-Me | 3-Cl, 4-CF₃ | 2-Me, 6-Me | 3-Br, 4-F | 2-Me, 6-Me | 3-CF₃, 4-F |
| 2-F, 4-F, 6-F | 3-Cl, 4-CF₃ | 2-F, 4-F, 6-F | 3-Br, 4-F | 2-F, 4-F, 6-F | 3-CF₃, 4-F |
| 2-F | 3-CF₃, 4-Cl | 4-F | 3-CF₃, 4-Cl | 2-Me, 4-F | 3-CF₃, 4-Cl |
| 2-Cl | 3-CF₃, 4-Cl | 4-Cl | 3-CF₃, 4-Cl | 2-F, 6-F | 3-CF₃, 4-Cl |
| 2-Br | 3-CF₃, 4-Cl | 4-Br | 3-CF₃, 4-Cl | 2-Cl, 6-Cl | 3-CF₃, 4-Cl |
| 2-Me | 3-CF₃, 4-Cl | 2-F, 4-F | 3-CF₃, 4-Cl | 2-Me, 6-Me | 3-CF₃, 4-Cl |
| 2-CF₃ | 3-CF₃, 4-Cl | 2-Cl, 4-F | 3-CF₃, 4-Cl | 2-F, 4-F, 6-F | 3-CF₃, 4-Cl |
| 2-F | 3,4-DFMDO* | 4-F | 3,4-DFMDO* | 2-Me, 4-F | 3,4-DFMDO* |
| 2-Cl | 3,4-DFMDO* | 4-Cl | 3,4-DFMDO* | 2-F, 6-F | 3,4-DFMDO* |
| 2-Br | 3,4-DFMDO* | 4-Br | 3,4-DFMDO* | 2-Cl, 6-Cl | 3,4-DFMDO* |
| 2-Me | 3,4-DFMDO* | 2-F, 4-F | 3,4-DFMDO* | 2-Me, 6-Me | 3,4-DFMDO* |
| 2-CF₃ | 3,4-DFMDO* | 2-Cl, 4-F | 3,4-DFMDO* | 2-F, 4-F, 6-F | 3,4-DFMDO* |

*3,4-DFMDO is 3,4-difluoromethylenedioxy as shown below:

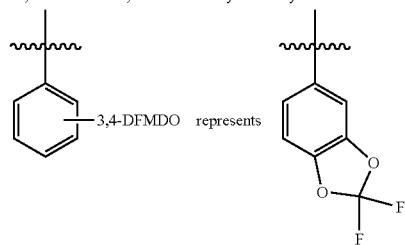

TABLE 5b-2

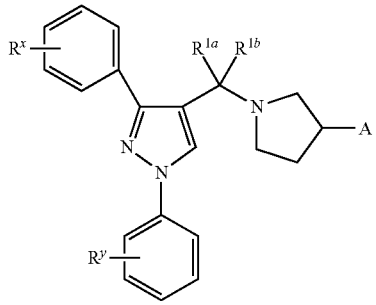

| $R^x$ | $R^y$ | $R^x$ | $R^y$ | $R^x$ | $R^y$ |
|---|---|---|---|---|---|
| $R^{1a}$ is H, $R^{1b}$ is cyano, A is NHC(O)Me | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| $R^{1a}$ is H, $R^{1b}$ is cyano, A is NHC(O)CH(CH$_2$)$_2$ | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| $R^{1a}$ is H, $R^{1b}$ is cyano, A is NHC(O)N(Me)$_2$ | | | | | |
| 2-F | 3-Cl | 2-Cl | 3-Cl | 2-Br | 3-Cl |
| 2-F | 4-Cl | 2-Cl | 4-Cl | 2-Br | 4-Cl |

TABLE 5b-2-continued

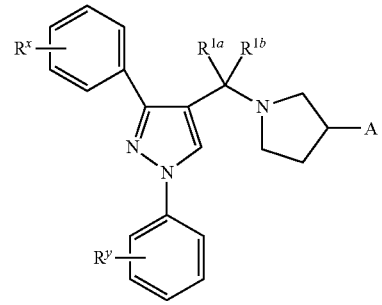

| $R^x$ | $R^y$ | $R^x$ | $R^y$ | $R^x$ | $R^y$ |
|---|---|---|---|---|---|
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| $R^{1a}$ is H, $R^{1b}$ is cyano, A is CH$_2$C(O)N(Me)$_2$ | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| $R^{1a}$ is H, $R^{1b}$ is cyano, A is NHC(O)CH(Me)(Et) | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |

TABLE 5b-2-continued

| $R^x$ | $R^y$ | $R^x$ | $R^y$ | $R^x$ | $R^y$ |
|---|---|---|---|---|---|
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| $R^{1a}$ is H, $R^{1b}$ is cyano, A is NHC(O)OMe | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| $R^{1a}$ is H, $R^{1b}$ is Me, A is NHC(O)Me | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |

TABLE 5b-2-continued

| $R^x$ | $R^y$ | $R^x$ | $R^y$ | $R^x$ | $R^y$ |
|---|---|---|---|---|---|
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| $R^{1a}$ is H, $R^{1b}$ is Me, A is NHC(O)CH(CH$_2$)$_2$ | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| $R^{1a}$ is H, $R^{1b}$ is Me, A is NHC(O)N(Me)$_2$ | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |

TABLE 5b-2-continued

| $R^x$ | $R^y$ | $R^x$ | $R^y$ | $R^x$ | $R^y$ |
|---|---|---|---|---|---|
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |
| $R^{1a}$ is H, $R^{1b}$ is Me, A is CH₂C(O)N(Me)₂ | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |
| $R^{1a}$ is H, $R^{1b}$ is Me, A is NHC(O)CH(Me)(Et) | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |
| $R^{1a}$ is H, $R^{1b}$ is Me, A is NHC(O)OMe | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |
| $R^{1a}$ is Me, $R^{1b}$ is Me, A is NHC(O)Me | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |

TABLE 5b-2-continued

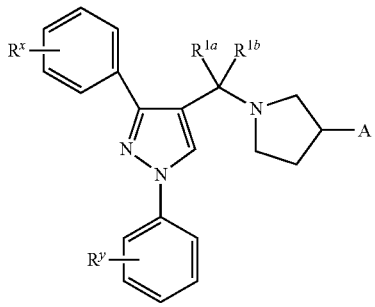

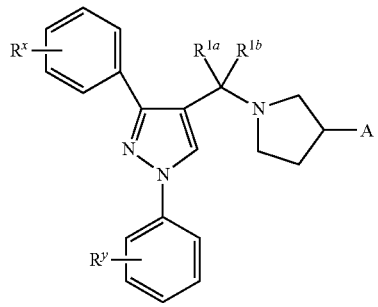

| $R^x$ | $R^y$ | $R^x$ | $R^y$ | $R^x$ | $R^y$ | $R^x$ | $R^y$ | $R^x$ | $R^y$ | $R^x$ | $R^y$ |
|---|---|---|---|---|---|---|---|---|---|---|---|
| 2-F, 6-F | 4-OCF$_3$ | 2-F, 4-F, 6-F | 4-OCF$_3$ | 4-F | 4-OCF$_3$ | 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-Cl | 2-F, 4-F, 6-F | 3-Cl, 4-Cl | 4-F | 3-Cl, 4-Cl | 2-F, 6-F | 3-Cl, 4-F | 2-F, 4-F, 6-F | 3-Cl, 4-F | 4-F | 3-Cl, 4-F |
| 2-F, 6-F | 3-Cl, 4-CF$_3$ | 2-F, 4-F, 6-F | 3-Cl, 4-CF$_3$ | 4-F | 3-Cl, 4-CF$_3$ | | | $R^{1a}$ is Me, $R^{1b}$ is Me, A is CH$_2$C(O)N(Me)$_2$ | | | | |
| 2-F, 6-F | 3-CF$_3$, 4-Cl | 2-F, 4-F, 6-F | 3-CF$_3$, 4-Cl | 4-F | 3-CF$_3$, 4-Cl | 2-F | 3-Cl | 2-Cl | 3-Cl | 2-Br | 3-Cl |
| 2-F, 6-F | 3-Cl, 4-F | 2-F, 4-F, 6-F | 3-Cl, 4-F | 4-F | 3-Cl, 4-F | 2-F | 4-Cl | 2-Cl | 4-Cl | 2-Br | 4-Cl |
| | | $R^{1a}$ is Me, $R^{1b}$ is Me, A is NHC(O)CH(CH$_2$)$_2$ | | | | 2-F | 3-CF$_3$ | 2-Cl | 3-CF$_3$ | 2-Br | 3-CF$_3$ |
| 2-F | 3-Cl | 2-Cl | 3-Cl | 2-Br | 3-Cl | 2-F | 4-CF$_3$ | 2-Cl | 4-CF$_3$ | 2-Br | 4-CF$_3$ |
| 2-F | 4-Cl | 2-Cl | 4-Cl | 2-Br | 4-Cl | 2-F | 4-OCF$_3$ | 2-Cl | 4-OCF$_3$ | 2-Br | 4-OCF$_3$ |
| 2-F | 3-CF$_3$ | 2-Cl | 3-CF$_3$ | 2-Br | 3-CF$_3$ | 2-F | 3-Cl, 4-Cl | 2-Cl | 3-Cl, 4-Cl | 2-Br | 3-Cl, 4-Cl |
| 2-F | 4-CF$_3$ | 2-Cl | 4-CF$_3$ | 2-Br | 4-CF$_3$ | 2-F | 3-Cl, 4-CF$_3$ | 2-Cl | 3-Cl, 4-CF$_3$ | 2-Br | 3-Cl, 4-CF$_3$ |
| 2-F | 4-OCF$_3$ | 2-Cl | 4-OCF$_3$ | 2-Br | 4-OCF$_3$ | 2-F | 3-CF$_3$, 4-Cl | 2-Cl | 3-CF$_3$, 4-Cl | 2-Br | 3-CF$_3$, 4-Cl |
| 2-F | 3-Cl, 4-Cl | 2-Cl | 3-Cl, 4-Cl | 2-Br | 3-Cl, 4-Cl | 2-F | 3-Cl, 4-F | 2-Cl | 3-Cl, 4-F | 2-Br | 3-Cl, 4-F |
| 2-F | 3-Cl, 4-CF$_3$ | 2-Cl | 3-Cl, 4-CF$_3$ | 2-Br | 3-Cl, 4-CF$_3$ | 2-Me | 3-Cl | 2-CF$_3$ | 3-Cl | 2-F, 4-F | 3-Cl |
| 2-F | 3-CF$_3$, 4-Cl | 2-Cl | 3-CF$_3$, 4-Cl | 2-Br | 3-CF$_3$, 4-Cl | 2-Me | 4-Cl | 2-CF$_3$ | 4-Cl | 2-F, 4-F | 4-Cl |
| 2-F | 3-Cl, 4-F | 2-Cl | 3-Cl, 4-F | 2-Br | 3-Cl, 4-F | 2-Me | 3-CF$_3$ | 2-CF$_3$ | 3-CF$_3$ | 2-F, 4-F | 3-CF$_3$ |
| 2-Me | 3-Cl | 2-CF$_3$ | 3-Cl | 2-F, 4-F | 3-Cl | 2-Me | 4-CF$_3$ | 2-CF$_3$ | 4-CF$_3$ | 2-F, 4-F | 4-CF$_3$ |
| 2-Me | 4-Cl | 2-CF$_3$ | 4-Cl | 2-F, 4-F | 4-Cl | 2-Me | 4-OCF$_3$ | 2-CF$_3$ | 4-OCF$_3$ | 2-F, 4-F | 4-OCF$_3$ |
| 2-Me | 3-CF$_3$ | 2-CF$_3$ | 3-CF$_3$ | 2-F, 4-F | 3-CF$_3$ | 2-Me | 3-Cl, 4-Cl | 2-CF$_3$ | 3-Cl, 4-Cl | 2-F, 4-F | 3-Cl, 4-Cl |
| 2-Me | 4-CF$_3$ | 2-CF$_3$ | 4-CF$_3$ | 2-F, 4-F | 4-CF$_3$ | 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 4-OCF$_3$ | 2-CF$_3$ | 4-OCF$_3$ | 2-F, 4-F | 4-OCF$_3$ | 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-Cl | 2-CF$_3$ | 3-Cl, 4-Cl | 2-F, 4-F | 3-Cl, 4-Cl | 2-Me | 3-Cl, 4-F | 2-CF$_3$ | 3-Cl, 4-F | 2-F, 4-F | 3-Cl, 4-F |
| 2-Me | 3-Cl, 4-CF$_3$ | 2-CF$_3$ | 3-Cl, 4-CF$_3$ | 2-F, 4-F | 3-Cl, 4-CF$_3$ | 2-F, 6-F | 3-Cl | 2-F, 4-F, 6-F | 3-Cl | 4-F | 3-Cl |
| 2-Me | 3-CF$_3$, 4-Cl | 2-CF$_3$ | 3-CF$_3$, 4-Cl | 2-F, 4-F | 3-CF$_3$, 4-Cl | 2-F, 6-F | 4-Cl | 2-F, 4-F, 6-F | 4-Cl | 4-F | 4-Cl |
| 2-Me | 3-Cl, 4-F | 2-CF$_3$ | 3-Cl, 4-F | 2-F, 4-F | 3-Cl, 4-F | 2-F, 6-F | 3-CF$_3$ | 2-F, 4-F, 6-F | 3-CF$_3$ | 4-F | 3-CF$_3$ |
| 2-F, 6-F | 3-Cl | 2-F, 4-F, 6-F | 3-Cl | 4-F | 3-Cl | 2-F, 6-F | 4-CF$_3$ | 2-F, 4-F, 6-F | 4-CF$_3$ | 4-F | 4-CF$_3$ |
| 2-F, 6-F | 4-Cl | 2-F, 4-F, 6-F | 4-Cl | 4-F | 4-Cl | 2-F, 6-F | 4-OCF$_3$ | 2-F, 4-F, 6-F | 4-OCF$_3$ | 4-F | 4-OCF$_3$ |
| 2-F, 6-F | 3-CF$_3$ | 2-F, 4-F, 6-F | 3-CF$_3$ | 4-F | 3-CF$_3$ | 2-F, 6-F | 3-Cl, 4-Cl | 2-F, 4-F, 6-F | 3-Cl, 4-Cl | 4-F | 3-Cl, 4-Cl |
| 2-F, 6-F | 4-CF$_3$ | 2-F, 4-F, 6-F | 4-CF$_3$ | 4-F | 4-CF$_3$ | 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 4-OCF$_3$ | 2-F, 4-F, 6-F | 4-OCF$_3$ | 4-F | 4-OCF$_3$ | 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-Cl | 2-F, 4-F, 6-F | 3-Cl, 4-Cl | 4-F | 3-Cl, 4-Cl | 2-F, 6-F | 3-Cl, 4-F | 2-F, 4-F, 6-F | 3-Cl, 4-F | 4-F | 3-Cl, 4-F |
| 2-F, 6-F | 3-Cl, 4-CF$_3$ | 2-F, 4-F, 6-F | 3-Cl, 4-CF$_3$ | 4-F | 3-Cl, 4-CF$_3$ | | | $R^{1a}$ is Me, $R^{1b}$ is Me, A is NHC(O)CH(Me)(Et) | | | | |
| 2-F, 6-F | 3-CF$_3$, 4-Cl | 2-F, 4-F, 6-F | 3-CF$_3$, 4-Cl | 4-F | 3-CF$_3$, 4-Cl | 2-F | 3-Cl | 2-Cl | 3-Cl | 2-Br | 3-Cl |
| 2-F, 6-F | 3-Cl, 4-F | 2-F, 4-F, 6-F | 3-Cl, 4-F | 4-F | 3-Cl, 4-F | 2-F | 4-Cl | 2-Cl | 4-Cl | 2-Br | 4-Cl |
| | | $R^{1a}$ is Me, $R^{1b}$ is Me, A is NHC(O)N(Me)$_2$ | | | | 2-F | 3-CF$_3$ | 2-Cl | 3-CF$_3$ | 2-Br | 3-CF$_3$ |
| 2-F | 3-Cl | 2-Cl | 3-Cl | 2-Br | 3-Cl | 2-F | 4-CF$_3$ | 2-Cl | 4-CF$_3$ | 2-Br | 4-CF$_3$ |
| 2-F | 4-Cl | 2-Cl | 4-Cl | 2-Br | 4-Cl | 2-F | 4-OCF$_3$ | 2-Cl | 4-OCF$_3$ | 2-Br | 4-OCF$_3$ |
| 2-F | 3-CF$_3$ | 2-Cl | 3-CF$_3$ | 2-Br | 3-CF$_3$ | 2-F | 3-Cl, 4-Cl | 2-Cl | 3-Cl, 4-Cl | 2-Br | 3-Cl, 4-Cl |
| 2-F | 4-CF$_3$ | 2-Cl | 4-CF$_3$ | 2-Br | 4-CF$_3$ | 2-F | 3-CF$_3$, 4-Cl | 2-Cl | 3-CF$_3$, 4-Cl | 2-Br | 3-CF$_3$, 4-Cl |
| 2-F | 4-OCF$_3$ | 2-Cl | 4-OCF$_3$ | 2-Br | 4-OCF$_3$ | 2-F | 3-Cl, 4-F | 2-Cl | 3-Cl, 4-F | 2-Br | 3-Cl, 4-F |
| 2-F | 3-Cl, 4-Cl | 2-Cl | 3-Cl, 4-Cl | 2-Br | 3-Cl, 4-Cl | 2-Me | 3-Cl | 2-CF$_3$ | 3-Cl | 2-F, 4-F | 3-Cl |
| 2-F | 3-Cl, 4-CF$_3$ | 2-Cl | 3-Cl, 4-CF$_3$ | 2-Br | 3-Cl, 4-CF$_3$ | 2-Me | 4-Cl | 2-CF$_3$ | 4-Cl | 2-F, 4-F | 4-Cl |
| 2-F | 3-CF$_3$, 4-Cl | 2-Cl | 3-CF$_3$, 4-Cl | 2-Br | 3-CF$_3$, 4-Cl | 2-Me | 3-CF$_3$ | 2-CF$_3$ | 3-CF$_3$ | 2-F, 4-F | 3-CF$_3$ |
| 2-F | 3-Cl, 4-F | 2-Cl | 3-Cl, 4-F | 2-Br | 3-Cl, 4-F | 2-Me | 4-CF$_3$ | 2-CF$_3$ | 4-CF$_3$ | 2-F, 4-F | 4-CF$_3$ |
| 2-Me | 3-Cl | 2-CF$_3$ | 3-Cl | 2-F, 4-F | 3-Cl | 2-Me | 4-OCF$_3$ | 2-CF$_3$ | 4-OCF$_3$ | 2-F, 4-F | 4-OCF$_3$ |
| 2-Me | 4-Cl | 2-CF$_3$ | 4-Cl | 2-F, 4-F | 4-Cl | 2-Me | 3-Cl, 4-Cl | 2-CF$_3$ | 3-Cl, 4-Cl | 2-F, 4-F | 3-Cl, 4-Cl |
| 2-Me | 3-CF$_3$ | 2-CF$_3$ | 3-CF$_3$ | 2-F, 4-F | 3-CF$_3$ | 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 4-CF$_3$ | 2-CF$_3$ | 4-CF$_3$ | 2-F, 4-F | 4-CF$_3$ | 2-Me | 3-CF$_3$, 4-Cl | 2-CF$_3$ | 3-CF$_3$, 4-Cl | 2-F, 4-F | 3-CF$_3$, 4-Cl |
| 2-Me | 4-OCF$_3$ | 2-CF$_3$ | 4-OCF$_3$ | 2-F, 4-F | 4-OCF$_3$ | 2-Me | 3-Cl, 4-F | 2-CF$_3$ | 3-Cl, 4-F | 2-F, 4-F | 3-Cl, 4-F |
| 2-Me | 3-Cl, 4-Cl | 2-CF$_3$ | 3-Cl, 4-Cl | 2-F, 4-F | 3-Cl, 4-Cl | 2-F, 6-F | 3-Cl | 2-F, 4-F, 6-F | 3-Cl | 4-F | 3-Cl |
| 2-Me | 3-Cl, 4-CF$_3$ | 2-CF$_3$ | 3-Cl, 4-CF$_3$ | 2-F, 4-F | 3-Cl, 4-CF$_3$ | 2-F, 6-F | 4-Cl | 2-F, 4-F, 6-F | 4-Cl | 4-F | 4-Cl |
| 2-Me | 3-CF$_3$, 4-Cl | 2-CF$_3$ | 3-CF$_3$, 4-Cl | 2-F, 4-F | 3-CF$_3$, 4-Cl | 2-F, 6-F | 3-CF$_3$ | 2-F, 4-F, 6-F | 3-CF$_3$ | 4-F | 3-CF$_3$ |
| 2-Me | 3-Cl, 4-F | 2-CF$_3$ | 3-Cl, 4-F | 2-F, 4-F | 3-Cl, 4-F | 2-F, 6-F | 4-CF$_3$ | 2-F, 4-F, 6-F | 4-CF$_3$ | 4-F | 4-CF$_3$ |
| 2-F, 6-F | 3-Cl | 2-F, 4-F, 6-F | 3-Cl | 4-F | 3-Cl | 2-F, 6-F | 4-OCF$_3$ | 2-F, 4-F, 6-F | 4-OCF$_3$ | 4-F | 4-OCF$_3$ |
| 2-F, 6-F | 4-Cl | 2-F, 4-F, 6-F | 4-Cl | 4-F | 4-Cl | 2-F, 6-F | 3-Cl, 4-Cl | 2-F, 4-F, 6-F | 3-Cl, 4-Cl | 4-F | 3-Cl, 4-Cl |
| 2-F, 6-F | 3-CF$_3$ | 2-F, 4-F, 6-F | 3-CF$_3$ | 4-F | 3-CF$_3$ | 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 4-CF$_3$ | 2-F, 4-F, 6-F | 4-CF$_3$ | 4-F | 4-CF$_3$ | 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 4-OCF$_3$ | 2-F, 4-F, 6-F | 4-OCF$_3$ | 4-F | 4-OCF$_3$ | 2-F, 6-F | 3-Cl, 4-F | 2-F, 4-F, 6-F | 3-Cl, 4-F | 4-F | 3-Cl, 4-F |
| 2-F, 6-F | 3-Cl, 4-Cl | 2-F, 4-F, 6-F | 3-Cl, 4-Cl | 4-F | 3-Cl, 4-Cl | | | | | | |
| 2-F, 6-F | 3-Cl, 4-CF$_3$ | 2-F, 4-F, 6-F | 3-Cl, 4-CF$_3$ | 4-F | 3-Cl, 4-CF$_3$ | | | | | | |

TABLE 5b-2-continued

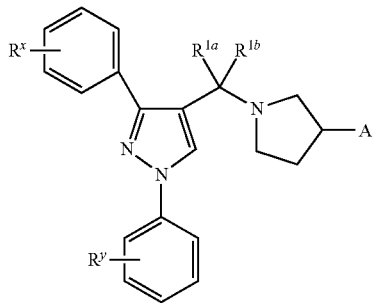

R$^{1a}$ is Me, R$^{1b}$ is Me, A is NHC(O)OMe

| R$^x$ | R$^y$ | R$^x$ | R$^y$ | R$^x$ | R$^y$ |
|---|---|---|---|---|---|
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |

TABLE 5b-3

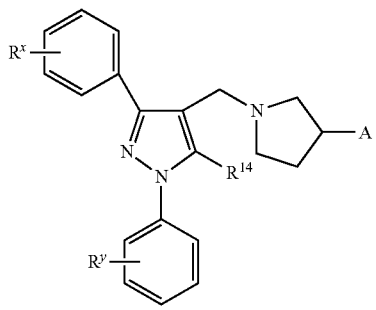

| R$^x$ | R$^y$ | R$^x$ | R$^y$ | R$^x$ | R$^y$ |
|---|---|---|---|---|---|
| R$^{14}$ is F, A is NHC(O)Me ||||||
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |

TABLE 5b-3-continued

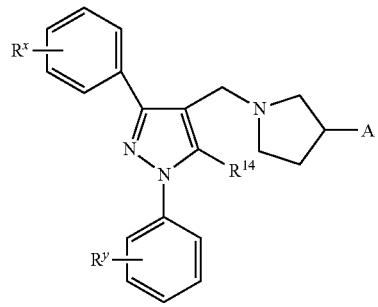

| R$^x$ | R$^y$ | R$^x$ | R$^y$ | R$^x$ | R$^y$ |
|---|---|---|---|---|---|
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| R$^{14}$ is F, A is NHC(O)CH(CH$_2$)$_2$ ||||||
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| R$^{14}$ is F, A is NHC(O)N(Me)$_2$ ||||||
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |

TABLE 5b-3-continued

| R$^x$ | R$^y$ | R$^x$ | R$^y$ | R$^x$ | R$^y$ |
|---|---|---|---|---|---|
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |

R$^{14}$ is F, A is CH$_2$C(O)N(Me)$_2$

| R$^x$ | R$^y$ | R$^x$ | R$^y$ | R$^x$ | R$^y$ |
|---|---|---|---|---|---|
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |

R$^{14}$ is F, A is NHC(O)CH(Me)(Et)

| R$^x$ | R$^y$ | R$^x$ | R$^y$ | R$^x$ | R$^y$ |
|---|---|---|---|---|---|
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |

TABLE 5b-3-continued

| R$^x$ | R$^y$ | R$^x$ | R$^y$ | R$^x$ | R$^y$ |
|---|---|---|---|---|---|
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |

R$^{14}$ is F, A is NHC(O)OMe

| R$^x$ | R$^y$ | R$^x$ | R$^y$ | R$^x$ | R$^y$ |
|---|---|---|---|---|---|
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |

R$^{14}$ is Cl, A is NHC(O)Me

| R$^x$ | R$^y$ | R$^x$ | R$^y$ | R$^x$ | R$^y$ |
|---|---|---|---|---|---|
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |

TABLE 5b-3-continued

[Structure: pyrazole with Rx-phenyl at 3-position, Ry-phenyl at N1, R14 at 5-position, and CH2-pyrrolidine-A at 4-position]

| Rx | Ry | Rx | Ry | Rx | Ry |
|---|---|---|---|---|---|
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |

R¹⁴ is Cl, A is NHC(O)CH(CH₂)₂

| Rx | Ry | Rx | Ry | Rx | Ry |
|---|---|---|---|---|---|
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |

R¹⁴ is Cl, A is NHC(O)N(Me)₂

| Rx | Ry | Rx | Ry | Rx | Ry |
|---|---|---|---|---|---|
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |

R¹⁴ is Cl, A is CH₂C(O)N(Me)₂

| Rx | Ry | Rx | Ry | Rx | Ry |
|---|---|---|---|---|---|
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |

R¹⁴ is Cl, A is NHC(O)CH(Me)(Et)

| Rx | Ry | Rx | Ry | Rx | Ry |
|---|---|---|---|---|---|
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |

TABLE 5b-3-continued

| $R^x$ | $R^y$ | $R^x$ | $R^y$ | $R^x$ | $R^y$ |
|---|---|---|---|---|---|
| $R^{14}$ is Cl, A is NHC(O)OMe | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| $R^{14}$ is Me, A is NHC(O)Me | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| $R^{14}$ is Me, A is NHC(O)CH(CH$_2$)$_2$ | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| $R^{14}$ is Me, A is NHC(O)N(Me)$_2$ | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| $R^{14}$ is Me, A is CH$_2$C(O)N(Me)$_2$ | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |

TABLE 5b-3-continued

| $R^x$ | $R^y$ | $R^x$ | $R^y$ | $R^x$ | $R^y$ |
|---|---|---|---|---|---|
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |

R¹⁴ is Me, A is NHC(O)CH(Me)(Et)

| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |

R¹⁴ is Me, A is NHC(O)OMe

| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |

TABLE 5b-3-continued

| $R^x$ | $R^y$ | $R^x$ | $R^y$ | $R^x$ | $R^y$ |
|---|---|---|---|---|---|
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |

R¹⁴ is NH₂, A is NHC(O)Me

| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |
| 2-Me | 3-Cl, 4-Cl | 2-CF₃ | 3-Cl, 4-Cl | 2-F, 4-F | 3-Cl, 4-Cl |
| 2-Me | 3-Cl, 4-CF₃ | 2-CF₃ | 3-Cl, 4-CF₃ | 2-F, 4-F | 3-Cl, 4-CF₃ |
| 2-Me | 3-CF₃, 4-Cl | 2-CF₃ | 3-CF₃, 4-Cl | 2-F, 4-F | 3-CF₃, 4-Cl |
| 2-Me | 3-Cl, 4-F | 2-CF₃ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF₃ | 2-F, 4-F, 6-F | 3-CF₃ | 4-F | 3-CF₃ |
| 2-F, 6-F | 4-CF₃ | 2-F, 4-F, 6-F | 4-CF₃ | 4-F | 4-CF₃ |
| 2-F, 6-F | 4-OCF₃ | 2-F, 4-F, 6-F | 4-OCF₃ | 4-F | 4-OCF₃ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF₃ | 2-F, 4-F, 6-F | 3-Cl, 4-CF₃ | 4-F | 3-Cl, 4-CF₃ |
| 2-F, 6-F | 3-CF₃, 4-Cl | 2-F, 4-F, 6-F | 3-CF₃, 4-Cl | 4-F | 3-CF₃, 4-Cl |
| 2-F, 6-F | 3-Cl, 4-F | 2-F, 4-F, 6-F | 3-Cl, 4-F | 4-F | 3-Cl, 4-F |

R¹⁴ is NH₂, A is NHC(O)CH(CH₂)₂

| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF₃ | 2-Cl | 3-CF₃ | 2-Br | 3-CF₃ |
| 2-F | 4-CF₃ | 2-Cl | 4-CF₃ | 2-Br | 4-CF₃ |
| 2-F | 4-OCF₃ | 2-Cl | 4-OCF₃ | 2-Br | 4-OCF₃ |
| 2-F | 3-Cl, 4-Cl | 2-Cl | 3-Cl, 4-Cl | 2-Br | 3-Cl, 4-Cl |
| 2-F | 3-Cl, 4-CF₃ | 2-Cl | 3-Cl, 4-CF₃ | 2-Br | 3-Cl, 4-CF₃ |
| 2-F | 3-CF₃, 4-Cl | 2-Cl | 3-CF₃, 4-Cl | 2-Br | 3-CF₃, 4-Cl |
| 2-F | 3-Cl, 4-F | 2-Cl | 3-Cl, 4-F | 2-Br | 3-Cl, 4-F |
| 2-Me | 3-Cl | 2-CF₃ | 3-Cl | 2-F, 4-F | 3-Cl |
| 2-Me | 4-Cl | 2-CF₃ | 4-Cl | 2-F, 4-F | 4-Cl |
| 2-Me | 3-CF₃ | 2-CF₃ | 3-CF₃ | 2-F, 4-F | 3-CF₃ |
| 2-Me | 4-CF₃ | 2-CF₃ | 4-CF₃ | 2-F, 4-F | 4-CF₃ |
| 2-Me | 4-OCF₃ | 2-CF₃ | 4-OCF₃ | 2-F, 4-F | 4-OCF₃ |

TABLE 5b-3-continued

| $R^x$ | $R^y$ | $R^x$ | $R^y$ | $R^x$ | $R^y$ |
|---|---|---|---|---|---|
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{14}$ is NH$_2$, A is NHC(O)N(Me)$_2$ |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{14}$ is NH$_2$, A is CH$_2$C(O)N(Me)$_2$ |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{14}$ is NH$_2$, A is NHC(O)CH(Me)(Et) |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| | $R^{14}$ is NH$_2$, A is NHC(O)OMe |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |

TABLE 5b-3-continued

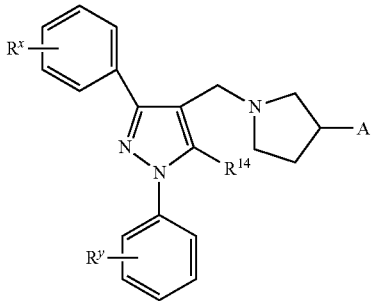

| $R^x$ | $R^y$ | $R^x$ | $R^y$ | $R^x$ | $R^y$ |
|---|---|---|---|---|---|
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |

TABLE 5b-4

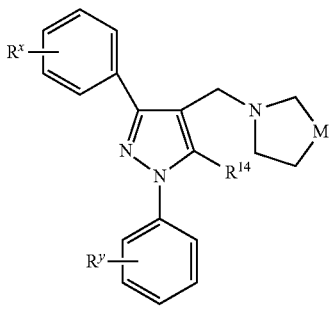

| $R^x$ | $R^y$ | $R^x$ | $R^y$ | $R^x$ | $R^y$ |
|---|---|---|---|---|---|
| M is CH(phenyl) | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| M is CH(2-pyridinyl) | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |

TABLE 5b-4-continued

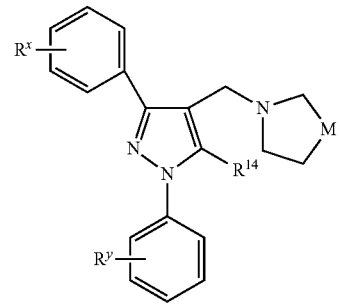

| $R^x$ | $R^y$ | $R^x$ | $R^y$ | $R^x$ | $R^y$ |
|---|---|---|---|---|---|
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| M is CH(3-pyridinyl) | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| M is CH(2-(1,3,4-oxadiazolyl)) | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |

TABLE 5b-4-continued

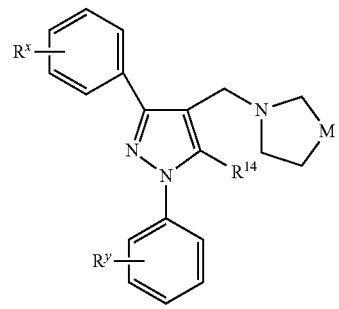

| $R^x$ | $R^y$ | $R^x$ | $R^y$ | $R^x$ | $R^y$ |
|---|---|---|---|---|---|
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |
| M is CH(1-(1,2,4-triazolyl)) | | | | | |
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-CF$_3$ | 2-Cl | 3-CF$_3$ | 2-Br | 3-CF$_3$ |
| 2-F | 4-CF$_3$ | 2-Cl | 4-CF$_3$ | 2-Br | 4-CF$_3$ |

TABLE 5b-4-continued

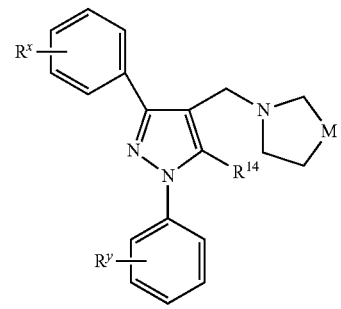

| $R^x$ | $R^y$ | $R^x$ | $R^y$ | $R^x$ | $R^y$ |
|---|---|---|---|---|---|
| 2-F | 4-OCF$_3$ | 2-Cl | 4-OCF$_3$ | 2-Br | 4-OCF$_3$ |
| 2-F | 3-Cl, 4-Cl | 2-Cl | 3-Cl, 4-Cl | 2-Br | 3-Cl, 4-Cl |
| 2-F | 3-Cl, 4-CF$_3$ | 2-Cl | 3-Cl, 4-CF$_3$ | 2-Br | 3-Cl, 4-CF$_3$ |
| 2-F | 3-CF$_3$, 4-Cl | 2-Cl | 3-CF$_3$, 4-Cl | 2-Br | 3-CF$_3$, 4-Cl |
| 2-F | 3-Cl, 4-F | 2-Cl | 3-Cl, 4-F | 2-Br | 3-Cl, 4-F |
| 2-Me | 3-Cl | 2-CF$_3$ | 3-Cl | 2-F, 4-F | 3-Cl |
| 2-Me | 4-Cl | 2-CF$_3$ | 4-Cl | 2-F, 4-F | 4-Cl |
| 2-Me | 3-CF$_3$ | 2-CF$_3$ | 3-CF$_3$ | 2-F, 4-F | 3-CF$_3$ |
| 2-Me | 4-CF$_3$ | 2-CF$_3$ | 4-CF$_3$ | 2-F, 4-F | 4-CF$_3$ |
| 2-Me | 4-OCF$_3$ | 2-CF$_3$ | 4-OCF$_3$ | 2-F, 4-F | 4-OCF$_3$ |
| 2-Me | 3-Cl, 4-Cl | 2-CF$_3$ | 3-Cl, 4-Cl | 2-F, 4-F | 3-Cl, 4-Cl |
| 2-Me | 3-Cl, 4-CF$_3$ | 2-CF$_3$ | 3-Cl, 4-CF$_3$ | 2-F, 4-F | 3-Cl, 4-CF$_3$ |
| 2-Me | 3-CF$_3$, 4-Cl | 2-CF$_3$ | 3-CF$_3$, 4-Cl | 2-F, 4-F | 3-CF$_3$, 4-Cl |
| 2-Me | 3-Cl, 4-F | 2-CF$_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-CF$_3$ | 2-F, 4-F, 6-F | 3-CF$_3$ | 4-F | 3-CF$_3$ |
| 2-F, 6-F | 4-CF$_3$ | 2-F, 4-F, 6-F | 4-CF$_3$ | 4-F | 4-CF$_3$ |
| 2-F, 6-F | 4-OCF$_3$ | 2-F, 4-F, 6-F | 4-OCF$_3$ | 4-F | 4-OCF$_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-CF$_3$ | 2-F, 4-F, 6-F | 3-Cl, 4-CF$_3$ | 4-F | 3-Cl, 4-CF$_3$ |
| 2-F, 6-F | 3-CF$_3$, 4-Cl | 2-F, 4-F, 6-F | 3-CF$_3$, 4-Cl | 4-F | 3-CF$_3$, 4-Cl |
| 2-F, 6-F | 3-Cl, 4-F | 2-F, 4-F, 6-F | 3-Cl, 4-F | 4-F | 3-Cl, 4-F |

TABLE 5b-5

| $Z^1$ | $Z^2$ | $Z^1$ | $Z^2$ |
|---|---|---|---|
| A is NHC(O)Me | | | |
| 4,5-dichloro-2-pyridinyl | 2-(OCF$_3$)-3-pyridinyl | 4,5-dichloro-2-pyridinyl | 2-(CF$_3$)-3-pyridinyl |
| 5,6-dichloro-2-pyridinyl | 2-(OCF$_3$)-3-pyridinyl | 5,6-dichloro-2-pyridinyl | 2-(CF$_3$)-3-pyridinyl |
| 4,5-dichloro-2-pyrimidinyl | 2-(OCF$_3$)-3-pyridinyl | 4,5-dichloro-2-pyrimidinyl | 2-(CF$_3$)-3-pyridinyl |
| 4-chloro-5-(CF$_3$)-2-pyridinyl | 2-(OCF$_3$)-3-pyridinyl | 4-chloro-5-(CF$_3$)-2-pyridinyl | 2-(CF$_3$)-3-pyridinyl |
| 5-chloro-6-(CF$_3$)-2-pyridinyl | 2-(OCF$_3$)-3-pyridinyl | 5-chloro-6-(CF$_3$)-2-pyridinyl | 2-(CF$_3$)-3-pyridinyl |
| 4-chloro-5-(CF$_3$)-2-pyrimidinyl | 2-(OCF$_3$)-3-pyridinyl | 4-chloro-5-(CF$_3$)-2-pyrimidinyl | 2-(CF$_3$)-3-pyridinyl |
| 4-chloro-5-(OCF$_3$)-2-pyridinyl | 2-(OCF$_3$)-3-pyridinyl | 4-chloro-5-(OCF$_3$)-2-pyridinyl | 2-(CF$_3$)-3-pyridinyl |
| 5-chloro-6-(OCF$_3$)-2-pyridinyl | 2-(OCF$_3$)-3-pyridinyl | 5-chloro-6-(OCF$_3$)-2-pyridinyl | 2-(CF$_3$)-3-pyridinyl |
| 4-chloro-5-(OCF$_3$)-2-pyrimidinyl | 2-(OCF$_3$)-3-pyridinyl | 4-chloro-5-(OCF$_3$)-2-pyrimidinyl | 2-(CF$_3$)-3-pyridinyl |
| 4-(CF$_3$)-5-chloro-2-pyridinyl | 2-(OCF$_3$)-3-pyridinyl | 4-(CF$_3$)-5-chloro-2-pyridinyl | 2-(CF$_3$)-3-pyridinyl |
| 5-(CF$_3$)-6-chloro-2-pyridinyl | 2-(OCF$_3$)-3-pyridinyl | 5-(CF$_3$)-6-chloro-2-pyridinyl | 2-(CF$_3$)-3-pyridinyl |
| 4-(CF$_3$)-5-chloro-2-pyrimidinyl | 2-(OCF$_3$)-3-pyridinyl | 4-(CF$_3$)-5-chloro-2-pyrimidinyl | 2-(CF$_3$)-3-pyridinyl |
| 4,5-bis(CF$_3$)-2-pyridinyl | 2-(OCF$_3$)-3-pyridinyl | 4,5-bis(CF$_3$)-2-pyridinyl | 2-(CF$_3$)-3-pyridinyl |
| 5,6-bis(CF$_3$)-2-pyridinyl | 2-(OCF$_3$)-3-pyridinyl | 5,6-bis(CF$_3$)-2-pyridinyl | 2-(CF$_3$)-3-pyridinyl |
| 4,5-bis(CF$_3$)-2-pyrimidinyl | 2-(OCF$_3$)-3-pyridinyl | 4,5-bis(CF$_3$)-2-pyrimidinyl | 2-(CF$_3$)-3-pyridinyl |
| 4-(OCF$_3$)-5-chloro-2-pyridinyl | 2-(OCF$_3$)-3-pyridinyl | 4-(OCF$_3$)-5-chloro-2-pyridinyl | 2-(CF$_3$)-3-pyridinyl |
| 5-(OCF$_3$)-6-chloro-2-pyridinyl | 2-(OCF$_3$)-3-pyridinyl | 5-(OCF$_3$)-6-chloro-2-pyridinyl | 2-(CF$_3$)-3-pyridinyl |
| 4-(OCF$_3$)-5-chloro-2-pyrimidinyl | 2-(OCF$_3$)-3-pyridinyl | 4-(OCF$_3$)-5-chloro-2-pyrimidinyl | 2-(CF$_3$)-3-pyridinyl |
| 4-chloro-5-fluoro-2-pyridinyl | 2-(OCF$_3$)-3-pyridinyl | 4-chloro-5-fluoro-2-pyridinyl | 2-(CF$_3$)-3-pyridinyl |
| 5-chloro-2-pyridinyl | 2-(OCF$_3$)-3-pyridinyl | 5-chloro-2-pyridinyl | 2-(CF$_3$)-3-pyridinyl |

TABLE 5b-5-continued

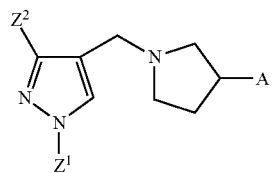

| Z¹ | Z² | Z¹ | Z² |
|---|---|---|---|
| 5-bromo-2-pyridinyl | 2-(OCF₃)-3-pyridinyl | 5-bromo-2-pyridinyl | 2-(CF₃)-3-pyridinyl |
| 5-fluoro-2-pyridinyl | 2-(OCF₃)-3-pyridinyl | 5-fluoro-2-pyridinyl | 2-(CF₃)-3-pyridinyl |
| 5-(CF₃)-2-pyridinyl | 2-(OCF₃)-3-pyridinyl | 5-(CF₃)-2-pyridinyl | 2-(CF₃)-3-pyridinyl |
| 5-(OCF₃)-2-pyridinyl | 2-(OCF₃)-3-pyridinyl | 5-(OCF₃)-2-pyridinyl | 2-(CF₃)-3-pyridinyl |
| 4-(CF₃)-2-pyridinyl | 2-(OCF₃)-3-pyridinyl | 4-(CF₃)-2-pyridinyl | 2-(CF₃)-3-pyridinyl |
| 4,5-dichloro-2-pyridinyl | 2-chloro-3-pyridinyl | 4-(CF₃)-5-chloro-2-pyridinyl | 2-chloro-3-pyridinyl |
| 5,6-dichloro-2-pyridinyl | 2-chloro-3-pyridinyl | 5-(CF₃)-6-chloro-2-pyridinyl | 2-chloro-3-pyridinyl |
| 4,5-dichloro-2-pyrimidinyl | 2-chloro-3-pyridinyl | 4-(CF₃)-5-chloro-2-pyrimidinyl | 2-chloro-3-pyridinyl |
| 4-chloro-5-(CF₃)-2-pyridinyl | 2-chloro-3-pyridinyl | 4,5-bis(CF₃)-2-pyridinyl | 2-chloro-3-pyridinyl |
| 5-chloro-6-(CF₃)-2-pyridinyl | 2-chloro-3-pyridinyl | 5,6-bis(CF₃)-2-pyridinyl | 2-chloro-3-pyridinyl |
| 4-chloro-5-(CF₃)-2-pyrimidinyl | 2-chloro-3-pyridinyl | 4,5-bis(CF₃)-2-pyrimidinyl | 2-chloro-3-pyridinyl |
| 4-chloro-5-(OCF₃)-2-pyridinyl | 2-chloro-3-pyridinyl | 4-(OCF₃)-5-chloro-2-pyridinyl | 2-chloro-3-pyridinyl |
| 5-chloro-6-(OCF₃)-2-pyridinyl | 2-chloro-3-pyridinyl | 5-(OCF₃)-6-chloro-2-pyridinyl | 2-chloro-3-pyridinyl |
| 4-chloro-5-(OCF₃)-2-pyrimidinyl | 2-chloro-3-pyridinyl | 4-(OCF₃)-5-chloro-2-pyrimidinyl | 2-chloro-3-pyridinyl |
| 5-chloro-2-pyridinyl | 2-chloro-3-pyridinyl | 5-(OCF₃)-2-pyridinyl | 2-chloro-3-pyridinyl |
| 5-bromo-2-pyridinyl | 2-chloro-3-pyridinyl | 5-(OCF₃)-2-pyridinyl | 2-chloro-3-pyridinyl |
| 5-fluoro-2-pyridinyl | 2-chloro-3-pyridinyl | 4-(CF₃)-2-pyridinyl | 2-chloro-3-pyridinyl |
| 4-chloro-5-fluoro-2-pyridinyl | 2-chloro-3-pyridinyl | 4-(CF₃)-5-chloro-2-pyridinyl | 3-fluoro-4-pyridinyl |
| 4,5-dichloro-2-pyridinyl | 3-fluoro-4-pyridinyl | 5-(CF₃)-6-chloro-2-pyridinyl | 3-fluoro-4-pyridinyl |
| 5,6-dichloro-2-pyridinyl | 3-fluoro-4-pyridinyl | 4-(CF₃)-5-chloro-2-pyrimidinyl | 3-fluoro-4-pyridinyl |
| 4,5-dichloro-2-pyrimidinyl | 3-fluoro-4-pyridinyl | 4,5-bis(CF₃)-2-pyridinyl | 3-fluoro-4-pyridinyl |
| 4-chloro-5-(CF₃)-2-pyridinyl | 3-fluoro-4-pyridinyl | 5,6-bis(CF₃)-2-pyridinyl | 3-fluoro-4-pyridinyl |
| 5-chloro-6-(CF₃)-2-pyridinyl | 3-fluoro-4-pyridinyl | 4,5-bis(CF₃)-2-pyrimidinyl | 3-fluoro-4-pyridinyl |
| 4-chloro-5-(CF₃)-2-pyrimidinyl | 3-fluoro-4-pyridinyl | 4-(OCF₃)-5-chloro-2-pyridinyl | 3-fluoro-4-pyridinyl |
| 4-chloro-5-(OCF₃)-2-pyridinyl | 3-fluoro-4-pyridinyl | 5-(OCF₃)-6-chloro-2-pyridinyl | 3-fluoro-4-pyridinyl |
| 5-chloro-6-(OCF₃)-2-pyridinyl | 3-fluoro-4-pyridinyl | 4-(OCF₃)-5-chloro-2-pyrimidinyl | 3-fluoro-4-pyridinyl |
| 4-chloro-5-(OCF₃)-2-pyrimidinyl | 3-fluoro-4-pyridinyl | 5-(CF₃)-2-pyridinyl | 3-fluoro-4-pyridinyl |
| 5-chloro-2-pyridinyl | 3-fluoro-4-pyridinyl | 5-(OCF₃)-2-pyridinyl | 3-fluoro-4-pyridinyl |
| 5-bromo-2-pyridinyl | 3-fluoro-4-pyridinyl | 4-(CF₃)-2-pyridinyl | 3-fluoro-4-pyridinyl |
| 5-fluoro-2-pyridinyl | 3-fluoro-4-pyridinyl | 4-chloro-5-fluoro-2-pyridinyl | 3-fluoro-4-pyridinyl |

A is NHC(O)CH(CH₂)₂

| 4,5-dichloro-2-pyridinyl | 2-(OCF₃)-3-pyridinyl | 4,5-dichloro-2-pyridinyl | 2-(CF₃)-3-pyridinyl |
|---|---|---|---|
| 5,6-dichloro-2-pyridinyl | 2-(OCF₃)-3-pyridinyl | 5,6-dichloro-2-pyridinyl | 2-(CF₃)-3-pyridinyl |
| 4,5-dichloro-2-pyrimidinyl | 2-(OCF₃)-3-pyridinyl | 4,5-dichloro-2-pyrimidinyl | 2-(CF₃)-3-pyridinyl |
| 4-chloro-5-(CF₃)-2-pyridinyl | 2-(OCF₃)-3-pyridinyl | 4-chloro-5-(CF₃)-2-pyridinyl | 2-(CF₃)-3-pyridinyl |
| 5-chloro-6-(CF₃)-2-pyridinyl | 2-(OCF₃)-3-pyridinyl | 5-chloro-6-(CF₃)-2-pyridinyl | 2-(CF₃)-3-pyridinyl |
| 4-chloro-5-(CF₃)-2-pyrimidinyl | 2-(OCF₃)-3-pyridinyl | 4-chloro-5-(CF₃)-2-pyrimidinyl | 2-(CF₃)-3-pyridinyl |
| 4-chloro-5-(OCF₃)-2-pyridinyl | 2-(OCF₃)-3-pyridinyl | 4-chloro-5-(OCF₃)-2-pyridinyl | 2-(CF₃)-3-pyridinyl |
| 5-chloro-6-(OCF₃)-2-pyridinyl | 2-(OCF₃)-3-pyridinyl | 5-chloro-6-(OCF₃)-2-pyridinyl | 2-(CF₃)-3-pyridinyl |
| 4-chloro-5-(OCF₃)-2-pyrimidinyl | 2-(OCF₃)-3-pyridinyl | 4-chloro-5-(OCF₃)-2-pyrimidinyl | 2-(CF₃)-3-pyridinyl |
| 4-(CF₃)-5-chloro-2-pyridinyl | 2-(OCF₃)-3-pyridinyl | 4-(CF₃)-5-chloro-2-pyridinyl | 2-(CF₃)-3-ilyridinyl |
| 5-(CF₃)-6-chloro-2-pyridinyl | 2-(OCF₃)-3-pyridinyl | 5-(CF₃)-6-chloro-2-pyridinyl | 2-(CF₃)-3-pyridinyl |
| 4-(CF₃)-5-chloro-2-pyrimidinyl | 2-(OCF₃)-3-pyridinyl | 4-(CF₃)-5-chloro-2-pyrimidinyl | 2-(CF₃)-3-pyridinyl |
| 4,5-bis(CF₃)-2-pyridinyl | 2-(OCF₃)-3-pyridinyl | 4,5-bis(CF₃)-2-pyridinyl | 2-(CF₃)-3-pyridinyl |
| 5,6-bis(CF₃)-2-pyridinyl | 2-(OCF₃)-3-pyridinyl | 5,6-bis(CF₃)-2-pyridinyl | 2-(CF₃)-3-pyridinyl |
| 4,5-bis(CF₃)-2-pyrimidinyl | 2-(OCF₃)-3-pyridinyl | 4,5-bis(CF₃)-2-pyrimidinyl | 2-(CF₃)-3-pyridinyl |
| 4-(OCF₃)-5-chloro-2-pyridinyl | 2-(OCF₃)-3-pyridinyl | 4-(OCF₃)-5-chloro-2-pyridinyl | 2-(CF₃)-3-pyridinyl |
| 5-(OCF₃)-6-chloro-2-pyridinyl | 2-(OCF₃)-3-pyridinyl | 5-(OCF₃)-6-chloro-2-pyridinyl | 2-(CF₃)-3-pyridinyl |
| 4-OCF₃)-5-chloro-2-pyrimidinyl | 2-(OCF₃)-3-pyridinyl | 4-(OCF₃)-5-chloro-2-pyrimidinyl | 2-(CF₃)-3-pyridinyl |
| 4-chloro-5-fluoro-2-pyridinyl | 2-(OCF₃)-3-pyridinyl | 4-chloro-5-fluoro-2-pyridinyl | 2-(CF₃)-3-pyridinyl |
| 5-chloro-2-pyridinyl | 2-(OCF₃)-3-pyridinyl | 5-chloro-2-pyridinyl | 2-(CF₃)-3-pyridinyl |
| 5-bromo-2-pyridinyl | 2-(OCF₃)-3-pyridinyl | 5-bromo-2-pyridinyl | 2-(CF₃)-3-pyridinyl |
| 5-fluoro-2-pyridinyl | 2-(OCF₃)-3-pyridinyl | 5-fluoro-2-pyridinyl | 2-(CF₃)-3-pyridinyl |
| 5-(CF₃)-2-pyridinyl | 2-(OCF₃)-3-pyridinyl | 5-(CF₃)-2-pyridinyl | 2-(CF₃)-3-pyridinyl |
| 5-(OCF₃)-2-pyridinyl | 2-(OCF₃)-3-pyridinyl | 5-(OCF₃)-2-pyridinyl | 2-(CF₃)-3-pyridinyl |
| 4-(CF₃)-2-pyridinyl | 2-(OCF₃)-3-pyridinyl | 4-(CF₃)-2-pyridinyl | 2-(CF₃)-3-pyridinyl |
| 4,5-dichloro-2-pyridinyl | 2-chloro-3-pyridinyl | 4-(CF₃)-5-chloro-2-pyridinyl | 2-chloro-3-pyridinyl |
| 5,6-dichloro-2-pyridinyl | 2-chloro-3-pyridinyl | 5-(CF₃)-6-chloro-2-pyridinyl | 2-chloro-3-pyridinyl |
| 4,5-dichloro-2-pyrimidinyl | 2-chloro-3-pyridinyl | 4-(CF₃)-5-chloro-2-pyrimidinyl | 2-chloro-3-pyridinyl |
| 4-chloro-5-(CF₃)-2-pyridinyl | 2-chloro-3-pyridinyl | 4,5-bis(CF₃)-2-pyridinyl | 2-chloro-3-pyridinyl |
| 5-chloro-6-(CF₃)-2-pyridinyl | 2-chloro-3-pyridinyl | 5,6-bis(CF₃)-2-pyridinyl | 2-chloro-3-pyridinyl |
| 4-chloro-5-(CF₃)-2-pyrimidinyl | 2-chloro-3-pyridinyl | 4,5-bis(CF₃)-2-pyrimidinyl | 2-chloro-3-pyridinyl |
| 4-chloro-5-(OCF₃)-2-pyridinyl | 2-chloro-3-pyridinyl | 4-(OCF₃)-5-chloro-2-pyridinyl | 2-chloro-3-pyridinyl |
| 5-chloro-6-(OCF₃)-2-pyridinyl | 2-chloro-3-pyridinyl | 5-(OCF₃)-6-chloro-2-pyridinyl | 2-chloro-3-pyridinyl |
| 4-chloro-5-(OCF₃)-2-pyrimidinyl | 2-chloro-3-pyridinyl | 4-(OCF₃)-5-chloro-2-pyrimidinyl | 2-chloro-3-pyridinyl |
| 5-chloro-2-pyridinyl | 2-chloro-3-pyridinyl | 5-(CF₃)-2-pyridinyl | 2-chloro-3-pyridinyl |
| 5-bromo-2-pyridinyl | 2-chloro-3-pyridinyl | 5-(OCF₃)-2-pyridinyl | 2-chloro-3-pyridinyl |
| 5-fluoro-2-pyridinyl | 2-chloro-3-pyridinyl | 4-(CF₃)-2-pyridinyl | 2-chloro-3-pyridinyl |

TABLE 5b-5-continued

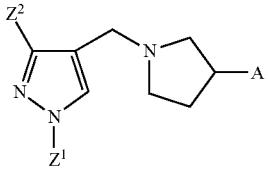

| Z¹ | Z² | Z¹ | Z² |
|---|---|---|---|
| 4-chloro-5-fluoro-2-pyridinyl | 2-chloro-3-pyridinyl | 4-(CF₃)-5-chloro-2-pyridinyl | 3-fluoro-4-pyridinyl |
| 4,5-dichloro-2-pyridinyl | 3-fluoro-4-pyridinyl | 5-(CF₃)-6-chloro-2-pyridinyl | 3-fluoro-4-pyridinyl |
| 5,6-dichloro-2-pyridinyl | 3-fluoro-4-pyridinyl | 4-(CF₃)-5-chloro-2-pyrimidinyl | 3-fluoro-4-pyridinyl |
| 4,5-dichloro-2-pyrimidinyl | 3-fluoro-4-pyridinyl | 4,5-bis(CF₃)-2-pyridinyl | 3-fluoro-4-pyridinyl |
| 4-chloro-5-(CF₃)-2-pyridinyl | 3-fluoro-4-pyridinyl | 5,6-bis(CF₃)-2-pyridinyl | 3-fluoro-4-pyridinyl |
| 5-chloro-6-(CF₃)-2-pyridinyl | 3-fluoro-4-pyridinyl | 4,5-bis(CF₃)-2-pyrimidinyl | 3-fluoro-4-pyridinyl |
| 4-chloro-5-(CF₃)-2-pyrimidinyl | 3-fluoro-4-pyridinyl | 4-(OCF₃)-5-chloro-2-pyridinyl | 3-fluoro-4-pyridinyl |
| 4-chloro-5-(OCF₃)-2-pyridinyl | 3-fluoro-4-pyridinyl | 5-(OCF₃)-6-chloro-2-pyridinyl | 3-fluoro-4-pyridinyl |
| 5-chloro-6-(OCF₃)-2-pyridinyl | 3-fluoro-4-pyridinyl | 4-(OCF₃)-5-chloro-2-pyrimidinyl | 3-fluoro-4-pyridinyl |
| 4-chloro-5-(OCF₃)-2-pyrimidinyl | 3-fluoro-4-pyridinyl | 5-(CF₃)-2-pyridinyl | 3-fluoro-4-pyridinyl |
| 5-chloro-2-pyridinyl | 3-fluoro-4-pyridinyl | 5-(OCF₃)-2-pyridinyl | 3-fluoro-4-pyridinyl |
| 5-bromo-2-pyridinyl | 3-fluoro-4-pyridinyl | 4-(CF₃)-2-pyridinyl | 3-fluoro-4-pyridinyl |
| 5-fluoro-2-pyridinyl | 3-fluoro-4-pyridinyl | 4-chloro-5-fluoro-2-pyridinyl | 3-fluoro-4-pyridinyl |

TABLE 5b-6

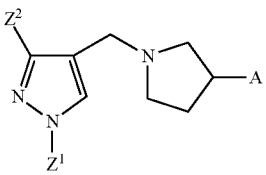

| Z¹ | Z¹ | Z¹ |
|---|---|---|
| Z² is 2-fluorophenyl, A is NHC(O)Me | | |
| 4,5-dichloro-2-pyridinyl | 4-chloro-5-(OCF₃)-2-pyridinyl | 4,5-bis(CF₃)-2-pyridinyl |
| 5,6-dichloro-2-pyridinyl | 5-chloro-6-(OCF₃)-2-pyridinyl | 5,6-bis(CF₃)-2-pyridinyl |
| 4,5-dichloro-2-pyrimidinyl | 4-chloro-5-(OCF₃)-2-pyrimidinyl | 4,5-bis(CF₃)-2-pyrimidinyl |
| 4-chloro-5-(CF₃)-2-pyridinyl | 4-(CF₃)-5-chloro-2-pyridinyl | 4-(OCF₃)-5-chloro-2-pyridinyl |
| 5-chloro-6-(CF₃)-2-pyridinyl | 5-(CF₃)-6-chloro-2-pyridinyl | 5-(OCF₃)-6-chloro-2-pyridinyl |
| 4-chloro-5-(CF₃)-2-pyrimidinyl | 4-(CF₃)-5-chloro-2-pyrimidinyl | 4-(OCF₃)-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF₃)-2-pyridinyl | 5-(OCF₃)-2-pyridinyl |
| 4-(CF₃)-2-pyridinyl | 4-chloro-5-fluoro-2-pyridinyl | |
| Z² is 2-fluorophenyl, A is NHC(O)CH(CH₂)₂ | | |
| 4,5-dichloro-2-pyridinyl | 4-chloro-5-(OCF₃)-2-pyridinyl | 4,5-bis(CF₃)-2-pyridinyl |
| 5,6-dichloro-2-pyridinyl | 5-chloro-6-(OCF₃)-2-pyridinyl | 5,6-bis(CF₃)-2-pyridinyl |
| 4,5-dichloro-2-pyrimidinyl | 4-chloro-5-(OCF₃)-2-pyrimidinyl | 4,5-bis(CF₃)-2-pyrimidinyl |
| 4-chloro-5-(CF₃)-2-pyridinyl | 4-(CF₃)-5-chloro-2-pyridinyl | 4-(OCF₃)-5-chloro-2-pyridinyl |
| 5-chloro-6-(CF₃)-2-pyridinyl | 5-(CF₃)-6-chloro-2-pyridinyl | 5-(OCF₃)-6-chloro-2-pyridinyl |
| 4-chloro-5-(CF₃)-2-pyriniddin | 4-(CF₃)-5-chloro-2-pyrimidinyl | 4-(OCF₃)-5-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF₃)-2-pyridinyl | 5-(OCF₃)-2-pyridinyl |
| 4-(CF₃)-2-pyridinyl | 4-chloro-5-fluoro-2-pyridinyl | |
| Z² is 4-fluorophenyl, A is NHC(O)Me | | |
| 4,5-dichloro-2-pyridinyl | 4-chloro-5-(OCF₃)-2-pyridinyl | 4,5-bis(CF₃)-2-pyridinyl |
| 5,6-dichloro-2-pyridinyl | 5-chloro-6-(OCF₃)-2-pyridinyl | 5,6-bis(CF₃)-2-pyridinyl |
| 4,5-dichloro-2-pyrimidinyl | 4-chloro-5-(OCF₃)-2-pyrimidinyl | 4,5-bis(CF₃)-2-pyrimidinyl |
| 4-chloro-5-(CF₃)-2-pyridinyl | 4-(CF₃)-5-chloro-2-pyridinyl | 4-(OCF₃)-5-chloro-2-pyridinyl |
| 5-chloro-6-(CF₃)-2-pyridinyl | 5-(CF₃)-6-chloro-2-pyridinyl | 5-(OCF₃)-6-chloro-2-pyridinyl |
| 4-chloro-5-(CF₃)-2-pyrimidinyl | 4-(CF₃)-5-chloro-2-pyrimidinyl | 4-(OCF₃)-5-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF₃)-2-pyridinyl | 5-(OCF₃)-2-pyridinyl |
| 4-(CF₃)-2-pyridinyl | 4-chloro-5-fluoro-2-pyridinyl | |

TABLE 5b-6-continued

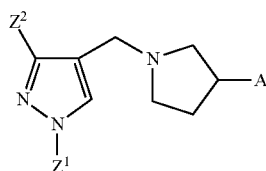

| $Z^1$ | $Z^1$ | $Z^1$ |
|---|---|---|
| $Z^2$ is 4-fluorophenyl, A is NHC(O)CH(CH$_2$)$_2$ | | |
| 4,5-dichloro-2-pyridinyl | 4-chloro-5-(OCF$_3$)-2-pyridinyl | 4,5-bis(CF$_3$)-2-pyridinyl |
| 5,6-dichloro-2-pyridinyl | 5-chloro-6-(OCF$_3$)-2-pyridinyl | 5,6-bis(CF$_3$)-2-pyridinyl |
| 4,5-dichloro-2-pyrimidinyl | 4-chloro-5-(OCF$_3$)-2-pyrimidinyl | 4,5-bis(CF$_3$)-2-pyrimidinyl |
| 4-chloro-5-(CF$_3$)-2-pyridinyl | 4-(CF$_3$)-5-chloro-2-pyridinyl | 4-(OCF$_3$)-5-chloro-2-pyridinyl |
| 5-chloro-6-(CF$_3$)-2-pyridinyl | 5-(CF$_3$)-6-chloro-2-pyridinyl | 5-(OCF$_3$)-6-chloro-2-pyridinyl |
| 4-chloro-5-(CF$_3$)-2-pyrimidinyl | 4-(CF$_3$)-5-chloro-2-pyrimidinyl | 4-(OCF$_3$)-5-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF$_3$)-2-pyridinyl | 5-(OCF$_3$)-2-pyridinyl |
| 4-(CF$_3$)-2-pyridinyl | 4-chloro-5-fluoro-2-pyridinyl | |
| $Z^2$ is 4-fluoro-2-methylphenyl, A is NHC(O)Me | | |
| 4,5-dichloro-2-pyridinyl | 4-chloro-5-(OC,F$_3$)-2-pyridinyl | 4,5-bis(CF$_3$)-2-pyridinyl |
| 5,6-dichloro-2-pyridinyl | 5-chloro-6-(OCF$_3$)-2-pyridinyl | 5,6-bis(CF$_3$)-2-pyridinyl |
| 4,5-dichloro-2-pyrimidinyl | 4-chloro-5-(OCF$_3$)-2-pyrimidinyl | 4,5-bis(CF$_3$)-2-pyrimidinyl |
| 4-chloro-5-(CF$_3$)-2-pyridinyl | 4-(CF$_3$)-5-chloro-2-pyridinyl | 4-(OCF$_3$)-5-chloro-2-pyridinyl |
| 5-chloro-6-(CF$_3$)-2-pyridinyl | 5-(CF$_3$)-6-chloro-2-pyridinyl | 5-(OCF$_3$)-6-chloro-2-pyridinyl |
| 4-chloro-5-(CF$_3$)-2-pyrimidinyl | 4-(CF$_3$)-5-chloro-2-pyrimidinyl | 4-(OCF$_3$)-5-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF$_3$)-2-pyridinyl | 5-(OCF$_3$)-2-pyridinyl |
| 4-(CF$_3$)-2-pyridinyl | 4-chloro-5-fluoro-2-pyridinyl | |
| $Z^2$ is 4-fluoro-2-methylphenyl, A is NHC(O)CH(CH$_2$)$_2$ | | |
| 4,5-dichloro-2-pyridinyl | 4-chloro-5-(OCF$_3$)-2-pyridinyl | 4,5-bis(CF$_3$)-2-pyridinyl |
| 5,6-dichloro-2-pyridinyl | 5-chloro-6-(OCF$_3$)-2-pyridinyl | 5,6-bis(CF$_3$)-2-pyridinyl |
| 4,5-dichloro-2-pyrimidinyl | 4-chloro-5-(OCF$_3$)-2-pyrimidinyl | 4,5-bis(CF$_3$)-2-pyrimidinyl |
| 4-chloro-5-(CF$_3$)-2-pyridinyl | 4-(CF$_3$)-5-chloro-2-pyridinyl | 4-(OCF$_3$)-5-chloro-2-pyridinyl |
| 5-chloro-6-(CF$_3$)-2-pyridinyl | 5-(CF$_3$)-6-chloro-2-pyridinyl | 5-(OCF$_3$)-6-chloro-2-pyridinyl |
| 4-chloro-5-(CF$_3$)-2-pyrimidinyl | 4-(CF$_3$)-5-chloro-2-pyrimidinyl | 4-(OCF$_3$)-5-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF$_3$)-2-pyridinyl | 5-(OCF$_3$)-2-pyridinyl |
| 4-(CF$_3$)-2-pyridinyl | 4-chloro-5-fluoro-2-pyridinyl | |
| $Z^2$ is 2-(trifluoromethyl)phenyl, A is NHC(O)Me | | |
| 4,5-dichloro-2-pyridinyl | 4-chloro-5-(OCF$_3$)-2-pyridinyl | 4,5-bis(CF$_3$)-2-pyridinyl |
| 5,6-dichloro-2-pyridinyl | 5-chloro-6-(OCF$_3$)-2-pyridinyl | 5,6-bis(CF$_3$)-2-pyridinyl |
| 4,5-dichloro-2-pyrimidinyl | 4-chloro-5-(OCF$_3$)-2-pyrimidinyl | 4,5-bis(CF$_3$)-2-pyrimidinyl |
| 4-chloro-5-(CF$_3$)-2-pyridinyl | 4-(CF$_3$)-5-chloro-2-pyridinyl | 4-(OCF$_3$)-5-chloro-2-pyridinyl |
| 5-chloro-6-(CF$_3$)-2-pyridinyl | 5-(CF$_3$)-6-chloro-2-pyridinyl | 5-(OCF$_3$)-6-chloro-2-pyridinyl |
| 4-chloro-5-(CF$_3$)-2-pyrimidinyl | 4-(CF$_3$)-5-chloro-2-pyrimidinyl | 4-(OCF$_3$)-5-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF$_3$)-2-pyridinyl | 5-(OCF$_3$)-2-pyridinyl |
| 4-(CF$_3$)-2-pyridinyl | 4-chloro-5-fluoro-2-pyridinyl | |
| $Z^2$ is 2-(trifluoromethyl)phenyl, A is NHC(O)CH(CH$_2$)$_2$ | | |
| 4,5-dichloro-2-pyridinyl | 4-chloro-5-(OCF$_3$)-2-pyridinyl | 4,5-bis(CF$_3$)-2-pyridinyl |
| 5,6-dichloro-2-pyridinyl | 5-chloro-6-(OCF$_3$)-2-pyridinyl | 5,6-bis(CF$_3$)-2-pyridinyl |
| 4,5-dichloro-2-pyrimidinyl | 4-chloro-5-(OCF$_3$)-2-pyrimidinyl | 4,5-bis(CF$_3$)-2-pyrimidinyl |
| 4-chloro-5-(CF$_3$)-2-pyridinyl | 4-(CF$_3$)-5-chloro-2-pyridinyl | 4-(OCF$_3$)-5-chloro-2-pyridinyl |
| 5-chloro-6-(CF$_3$)-2-pyridinyl | 5-(CF$_3$)-6-chloro-2-pyridinyl | 5-(OCF$_3$)-6-chloro-2-pyridinyl |
| 4-chloro-5-(CF$_3$)-2-pyrimidinyl | 4-(CF$_3$)-5-chloro-2-pyrimidinyl | 4-(OCF$_3$)-5-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF$_3$)-2-pyridinyl | 5-(OCF$_3$)-2-pyridinyl |
| 4-(CF$_3$)-2-pyridinyl | 4-chloro-5-fluoro-2-pyridinyl | |
| $Z^2$ is 2,4-difluorophenyl, A is NHC(O)Me | | |
| 4,5-dichloro-2-pyridinyl | 4-chloro-5-(OCF$_3$)-2-pyridinyl | 4,5-bis(CF$_3$)-2-pyridinyl |
| 5,6-dichloro-2-pyridinyl | 5-chloro-6-(OCF$_3$)-2-pyridinyl | 5,6-bis(CF$_3$)-2-pyridinyl |

TABLE 5b-6-continued

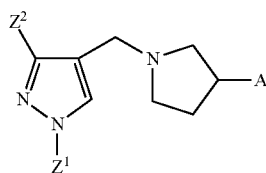

| $Z^1$ | $Z^1$ | $Z^1$ |
|---|---|---|
| 4,5-dichloro-2-pyrimidinyl | 4-chloro-5-(OCF$_3$)-2-pyrimidinyl | 4,5-bis(CF$_3$)-2-pyrimidinyl |
| 4-chloro-5-(CF$_3$)-2-pyridinyl | 4-(CF$_3$)-5-chloro-2-pyridinyl | 4-(OCF$_3$)-5-chloro-2-pyridinyl |
| 5-chloro-6-(CF$_3$)-2-pyridinyl | 5-(CF$_3$)-6-chloro-2-pyridinyl | 5-(OCF$_3$)-6-chloro-2-pyridinyl |
| 4-chloro-5-(CF$_3$)-2-pyrimidinyl | 4-(CF$_3$)-5-chloro-2-pyrimidinyl | 4-(OCF$_3$)-5-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF$_3$)-2-pyridinyl | 5-(OCF$_3$)-2-pyridinyl |
| 4-(CF$_3$)-2-pyridinyl | 4-chloro-5-fluoro-2-pyridinyl | |
| $Z^2$ is 2,4-difluorophenyl, A is NHC(O)CH(CH$_2$)$_2$ | | |
| 4,5-dichloro-2-pyrimidinyl | 4-chloro-5-(OCF$_3$)-2-pyrimidinyl | 4,5-bis(CF$_3$)-2-pyridinyl |
| 5,6-dichloro-2-pyridinyl | 5-chloro-6-(OCF$_3$)-2-pyridinyl | 5,6-bis(CF$_3$)-2-pyridinyl |
| 4,5-dichloro-2-pyrimidinyl | 4-chloro-5-(OCF$_3$)-2-pyrimidinyl | 4,5-bis(CF$_3$)-2-pyrimidinyl |
| 4-chloro-5-(CF$_3$)-2-pyridinyl | 4-(CF$_3$)-5-chloro-2-pyridinyl | 4-(OCF$_3$)-5-chloro-2-pyridinyl |
| 5-chloro-6-(CF$_3$)-2-pyridinyl | 5-(CF$_3$)-6-chloro-2-pyridinyl | 5-(OCF$_3$)-6-chloro-2-pyridinyl |
| 4-chloro-5-(CF$_3$)-2-pyrimidinyl | 4-(CF$_3$)-5-chloro-2-pyrimidinyl | 4-(OCF$_3$)-5-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF$_3$)-2-pyridinyl | 5-(OCF$_3$)-2-pyridinyl |
| 4-(CF$_3$)-2-pyridinyl | 4-chloro-5-fluoro-2-pyridinyl | |
| $Z^2$ is 2,6-difluorophenyl, A is NHC(O)Me | | |
| 4,5-dichloro-2-pyrimidinyl | 4-chloro-5-(OCF$_3$)-2-pyrimidinyl | 4,5-bis(CF$_3$)-2-pyridinyl |
| 5,6-dichloro-2-pyridinyl | 5-chloro-6-(OCF$_3$)-2-pyridinyl | 5,6-bis(CF$_3$)-2-pyridinyl |
| 4,5-dichloro-2-pyrimidinyl | 4-chloro-5-(OCF$_3$)-2-pyrimidinyl | 4,5-bis(CF$_3$)-2-pyrimidinyl |
| 4-chloro-5-(CF$_3$)-2-pyridinyl | 4-(CF$_3$)-5-chloro-2-pyridinyl | 4-(OCF$_3$)-5-chloro-2-pyridinyl |
| 5-chloro-6-(CF$_3$)-2-pyridinyl | 5-(CF$_3$)-6-chloro-2-pyridinyl | 5-(OCF$_3$)-6-chloro-2-pyridinyl |
| 4-chloro-5-(CF$_3$)-2-pyrimidinyl | 4-(CF$_3$)-5-chloro-2-pyrimidinyl | 4-(OCF$_3$)-5-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF$_3$)-2-pyridinyl | 5-(OCF$_3$)-2-pyridinyl |
| 4-(CF$_3$)-2-pyridinyl | 4-chloro-5-fluoro-2-pyridinyl | |
| $Z^2$ is 2,6-difluorophenyl, A is NHC(O)CH(CH$_2$)$_2$ | | |
| 4,5-dichloro-2-pyrimidinyl | 4-chloro-5-(OCF$_3$)-2-pyrimidinyl | 4,5-bis(CF$_3$)-2-pyridinyl |
| 5,6-dichloro-2-pyridinyl | 5-chloro-6-(OCF$_3$)-2-pyridinyl | 5,6-bis(CF$_3$)-2-pyridinyl |
| 4,5-dichloro-2-pyrimidinyl | 4-chloro-5-(OCF$_3$)-2-pyrimidinyl | 4,5-bis(CF$_3$)-2-pyrimidinyl |
| 4-chloro-5-(CF$_3$)-2-pyridinyl | 4-(CF$_3$)-5-chloro-2-pyridinyl | 4-(OCF$_3$)-5-chloro-2-pyridinyl |
| 5-chloro-6-(CF$_3$)-2-pyridinyl | 5-(CF$_3$)-6-chloro-2-pyridinyl | 5-(OCF$_3$)-6-chloro-2-pyridinyl |
| 4-chloro-5-(CF$_3$)-2-pyrimidinyl | 4-(CF$_3$)-5-chloro-2-pyrimidinyl | 4-(OCF$_3$)-5-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF$_3$)-2-pyridinyl | 5-(OCF$_3$)-2-pyridinyl |
| 4-(CF$_3$)-2-pyridinyl | 4-chloro-5-fluoro-2-pyridinyl | |
| $Z^2$ is 2,4,6-difluorophenyl, A is NHC(O)Me | | |
| 4,5-dichloro-2-pyrimidinyl | 4-chloro-5-(OCF$_3$)-2-pyrimidinyl | 4,5-bis(CF$_3$)-2-pyridinyl |
| 5,6-dichloro-2-pyridinyl | 5-chloro-6-(OCF$_3$)-2-pyridinyl | 5,6-bis(CF$_3$)-2-pyridinyl |
| 4,5-dichloro-2-pyrimidinyl | 4-chloro-5-(OCF$_3$)-2-pyrimidinyl | 4,5-bis(CF$_3$)-2-pyrimidinyl |
| 4-chloro-5-(CF$_3$)-2-pyridinyl | 4-(CF$_3$)-5-chloro-2-pyridinyl | 4-(OCF$_3$)-5-chloro-2-pyridinyl |
| 5-chloro-6-(CF$_3$)-2-pyridinyl | 5-(CF$_3$)-6-chloro-2-pyridinyl | 5-(OCF$_3$)-6-chloro-2-pyridinyl |
| 4-chloro-5-(CF$_3$)-2-pyrimidinyl | 4-(CF$_3$)-5-chloro-2-pyrimidinyl | 4-(OCF$_3$)-5-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF$_3$)-2-pyridinyl | 5-(OCF$_3$)-2-pyridinyl |
| 4-(CF$_3$)-2-pyridinyl | 4-chloro-5-fluoro-2-pyridinyl | |
| $Z^2$ is 2,4,6-difluorophenyl, A is NHC(O)CH(CH$_2$)$_2$ | | |
| 4,5-dichloro-2-pyrimidinyl | 4-chloro-5-(OCF$_3$)-2-pyrimidinyl | 4,5-bis(CF$_3$)-2-pyridinyl |
| 5,6-dichloro-2-pyridinyl | 5-chloro-6-(OCF$_3$)-2-pyridinyl | 5,6-bis(CF$_3$)-2-pyridinyl |
| 4,5-dichloro-2-pyrimidinyl | 4-chloro-5-(OCF$_3$)-2-pyrimidinyl | 4,5-bis(CF$_3$)-2-pyrimidinyl |
| 4-chloro-5-(CF$_3$)-2-pyridinyl | 4-(CF$_3$)-5-chloro-2-pyridinyl | 4-(OCF$_3$)-5-chloro-2-pyridinyl |
| 5-chloro-6-(CF$_3$)-2-pyridinyl | 5-(CF$_3$)-6-chloro-2-pyridinyl | 5-(OCF$_3$)-6-chloro-2-pyridinyl |
| 4-chloro-5-(CF$_3$)-2-pyrimidinyl | 4-(CF$_3$)-5-chloro-2-pyrimidinyl | 4-(OCF$_3$)-5-chloro-2-pyrimidinyl |

TABLE 5b-6-continued

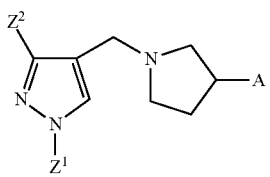

| Z¹ | Z¹ | Z¹ |
|---|---|---|
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-($CF_3$)-2-pyridinyl | 5-($OCF_3$)-2-pyridinyl |
| 4-($CF_3$)-2-pyridinyl | 4-chloro-5-fluoro-2-pyridinyl | |

TABLE 5c

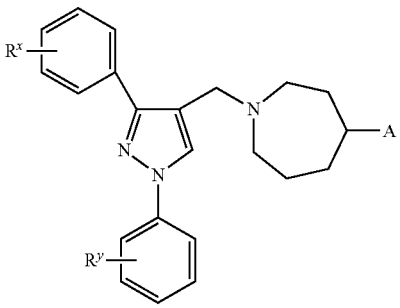

A is cyano

| $R^y$ | $R^x$ | $R^y$ | $R^x$ | $R^y$ | $R^x$ |
|---|---|---|---|---|---|
| 2-F | 3-Cl | 2-Cl | 3-Cl | 2-Br | 3-Cl |
| 2-F | 4-Cl | 2-Cl | 4-Cl | 2-Br | 4-Cl |
| 2-F | 3-$CF_3$ | 2-Cl | 3-$CF_3$ | 2-Br | 3-$CF_3$ |
| 2-F | 4-$CF_3$ | 2-Cl | 4-$CF_3$ | 2-Br | 4-$CF_3$ |
| 2-F | 4-$OCF_3$ | 2-Cl | 4-$OCF_3$ | 2-Br | 4-$OCF_3$ |
| 2-F | 3-Cl, 4-Cl | 2-Cl | 3-Cl, 4-Cl | 2-Br | 3-Cl, 4-Cl |
| 2-F | 3-Cl, 4-$CF_3$ | 2-Cl | 3-Cl, 4-$CF_3$ | 2-Br | 3-Cl, 4-$CF_3$ |
| 2-F | 3-$CF_3$, 4-Cl | 2-Cl | 3-$CF_3$, 4-Cl | 2-Br | 3-$CF_3$, 4-Cl |
| 2-F | 3-Cl, 4-F | 2-Cl | 3-Cl, 4-F | 2-Br | 3-Cl, 4-F |
| 2-Me | 3-Cl | 2-$CF_3$ | 3-Cl | 2-F, 4-F | 3-Cl |
| 2-Me | 4-Cl | 2-$CF_3$ | 4-Cl | 2-F, 4-F | 4-Cl |
| 2-Me | 3-$CF_3$ | 2-$CF_3$ | 3-$CF_3$ | 2-F, 4-F | 3-$CF_3$ |
| 2-Me | 4-$CF_3$ | 2-$CF_3$ | 4-$CF_3$ | 2-F, 4-F | 4-$CF_3$ |
| 2-Me | 4-$OCF_3$ | 2-$CF_3$ | 4-$OCF_3$ | 2-F, 4-F | 4-$OCF_3$ |

TABLE 5c-continued

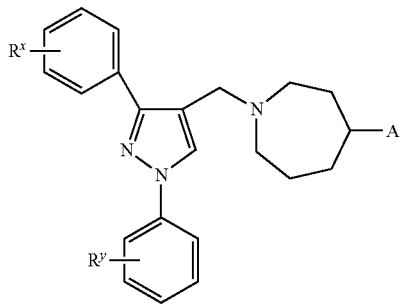

A is cyano

| $R^y$ | $R^x$ | $R^y$ | $R^x$ | $R^y$ | $R^x$ |
|---|---|---|---|---|---|
| 2-Me | 3-Cl, 4-Cl | 2-$CF_3$ | 3-Cl, 4-Cl | 2-F, 4-F | 3-Cl, 4-Cl |
| 2-Me | 3-Cl, 4-$CF_3$ | 2-$CF_3$ | 3-Cl, 4-$CF_3$ | 2-F, 4-F | 3-Cl, 4-$CF_3$ |
| 2-Me | 3-CF, 4-Cl | 2-$CF_3$ | 3-$CF_3$, 4-Cl | 2-F, 4-F | 3-$CF_3$, 4-Cl |
| 2-Me | 3-Cl, 4-F | 2-$CF_3$ | 3-Cl, 4-F | 2-F, 4-F | 3-Cl, 4-F |
| 2-F, 6-F | 3-Cl | 2-F, 4-F, 6-F | 3-Cl | 4-F | 3-Cl |
| 2-F, 6-F | 4-Cl | 2-F, 4-F, 6-F | 4-Cl | 4-F | 4-Cl |
| 2-F, 6-F | 3-$CF_3$ | 2-F, 4-F, 6-F | 3-$CF_3$ | 4-F | 3-$CF_3$ |
| 2-F, 6-F | 4-$CF_3$ | 2-F, 4-F, 6-F | 4-$CF_3$ | 4-F | 4-$CF_3$ |
| 2-F, 6-F | 4-$OCF_3$ | 2-F, 4-F, 6-F | 4-$OCF_3$ | 4-F | 4-$OCF_3$ |
| 2-F, 6-F | 3-Cl, 4-Cl | 2-F, 4-F, 6-F | 3-Cl, 4-Cl | 4-F | 3-Cl, 4-Cl |
| 2-F, 6-F | 3-Cl, 4-$CF_3$ | 2-F, 4-F, 6-F | 3-Cl, 4-$CF_3$ | 4-F | 3-Cl, 4-$CF_3$ |
| 2-F, 6-F | 3-$CF_3$, 4-Cl | 2-F, 4-F, 6-F | 3-$CF_3$, 4-Cl | 4-F | 3-$CF_3$, 4-Cl |
| 2-F, 6-F | 3-Cl, 4-F | 2-F, 4-F, 6-F | 3-Cl, 4-F | 4-F | 3-Cl, 4-F |

TABLE 6a

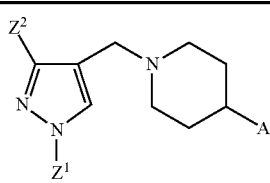

A is cyano

| Z¹ | Z² | Z¹ | Z² |
|---|---|---|---|
| 4,5-dichloro-2-pyridinyl | 2-($OCF_3$)-3-pyridinyl | 4,5-dichloro-2-pyridinyl | 2-($CF_3$)-3-pyridinyl |
| 5,6-dichloro-2-pyridinyl | 2-($OCF_3$)-3-pyridinyl | 5,6-dichloro-2-pyridinyl | 2-($CF_3$)-3-pyridinyl |
| 4,5-dichloro-2-pyrimidinyl | 2-($OCF_3$)-3-pyridinyl | 4,5-dichloro-2-pyrimidinyl | 2-($CF_3$)-3-pyridinyl |

TABLE 6a-continued

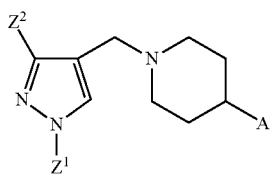

A is cyano

| Z¹ | Z² | Z¹ | Z² |
|---|---|---|---|
| 4-chloro-5-(CF₃)-2-pyridinyl | 2-(OCF₃)-3-pyridinyl | 4-chloro-5-(CF₃)-2-pyridinyl | 2-(CF₃)-3-pyridinyl |
| 5-chloro-6-(CF₃)-2-pyridinyl | 2-(OCF₃)-3-pyridinyl | 5-chloro-6-(CF₃)-2-pyridinyl | 2-(CF₃)-3-pyridinyl |
| 4-chloro-5-(CF₃)-2-pyrimidinyl | 2-(OCF₃)-3-pyridinyl | 4-chloro-5-(CF₃)-2-pyrimidinyl | 2-(CF₃)-3-pyridinyl |
| 4-chloro-5-(OCF₃)-2-pyridinyl | 2-(OCF₃)-3-pyridinyl | 4-chloro-5-(OCF₃)-2-pyridinyl | 2-(CF₃)-3-pyridinyl |
| 5-chloro-6-(OCF₃)-2-pyridinyl | 2-(OCF₃)-3-pyridinyl | 5-chloro-6-(OCF₃)-2-pyridinyl | 2-(CF₃)-3-pyridinyl |
| 4-chloro-5-(OCF₃)-2-pyrimidinyl | 2-(OCF₃)-3-pyridinyl | 4-chloro-5-(OCF₃)-2-pyrimidinyl | 2-(CF₃)-3-pyridinyl |
| 4-(CF₃)-5-chloro-2-pyridinyl | 2-(OCF₃)-3-pyridinyl | 4-(CF₃)-5-chloro-2-pyridinyl | 2-(CF₃)-3-pyridinyl |
| 5-(CF₃)-6-chloro-2-pyridinyl | 2-(OCF₃)-3-pyridinyl | 5-(CF₃)-6-chloro-2-pyridinyl | 2-(CF₃)-3-pyridinyl |
| 4-(CF₃)-5-chloro-2-pyrimiinyl | 2-(OCF₃)-3-pyridinyl | 4-(CF₃)-5-chloro-2-pyrimidinyl | 2-(CF₃)-3-pyridinyl |
| 4,5-bis(CF₃)-2-pyridinyl | 2-(OCF₃)-3-pyridinyl | 4,5-bis(CF₃)-2-pyridinyl | 2-(CF₃)-3-pyridinyl |
| 5,6-bis(CF₃)-2-pyridinyl | 2-(OCF₃)-3-pyridinyl | 5,6-bis(CF₃)-2-pyridinyl | 2-(CF₃)-3-pyridinyl |
| 4,5-bis(CF₃)-2-pyrimidinyl | 2-(OCF₃)-3-pyridinyl | 4,5-bis(CF₃)-2-pyrimidinyl | 2-(CF₃)-3-pyridinyl |
| 4-(OCF₃)-5-chloro-2-pyridinyl | 2-(OCF₃)-3-pyridinyl | 4-(OCF₃)-5-chloro-2-pyridinyl | 2-(CF₃)-3-pyridinyl |
| 5-(OCF₃)-6-chloro-2-pyridinyl | 2-(OCF₃)-3-pyridinyl | 5-(OCF₃)-6-chloro-2-pyridinyl | 2-(CF₃)-3-pyridinyl |
| 4-(OCF₃)-5-chloro-2-pyrimidinyl | 2-(OCF₃)-3-pyridinyl | 4-(OCF₃)-5-chloro-2-pyrimidinyl | 2-(CF₃)-3-pyridinyl |
| 2-naphthalenyl | 2-(OCF₃)-3-pyridinyl | 2-naphthalenyl | 2-(CF₃)-3-pyridinyl |
| 2-quinolinyl | 2-(OCF₃)-3-pyridinyl | 2-quinolinyl | 2-(CF₃)-3-pyridinyl |
| 5-chloro-2-pyridinyl | 2-(OCF₃)-3-pyridinyl | 5-chloro-2-pyridinyl | 2-(CF₃)-3-pyridinyl |
| 5-bromo-2-pyridinyl | 2-(OCF₃)-3-pyridinyl | 5-bromo-2-pyridinyl | 2-(CF₃)-3-pyridinyl |
| 5-fluoro-2-pyridinyl | 2-(OCF₃)-3-pyridinyl | 5-fluoro-2-pyridinyl | 2-(CF₃)-3-pyridinyl |
| 5-(CF₃)-2-pyridinyl | 2-(OCF₃)-3-pyridinyl | 5-(CF₃)-2-pyridinyl | 2-(CF₃)-3-pyridinyl |
| 5-(OCF₃)-2-pyridinyl | 2-(OCF₃)-3-pyridinyl | 5-(OCF₃)-2-pyridinyl | 2-(CF₃)-3-pyridinyl |
| 4-(CF₃)-2-pyridinyl | 2-(OCF₃)-3-pyridinyl | 4-(CF₃)-2-pyridinyl | 2-(CF₃)-3-pyridinyl |
| 4,5-dichloro-2-pyridinyl | 2-chloro-3-pyridinyl | 4,5-dichloro-2-pyridinyl | 3-fluoro-4-pyridinyl |
| 5,6-dichloro-2-pyridinyl | 2-chloro-3-pyridinyl | 5,6-dichloro-2-pyridinyl | 3-fluoro-4-pyridinyl |
| 4,5-dichloro-2-pyrimidinyl | 2-chloro-3-pyridinyl | 4,5-dichloro-2-pyrimidinyl | 3-fluoro-4-pyridinyl |
| 4-chloro-5-(CF₃)-2-pyridinyl | 2-chloro-3-pyridinyl | 4-chloro-5-(CF₃)-2-pyridinyl | 3-fluoro-4-pyridinyl |
| 5-chloro-6-(CF₃)-2-pyridinyl | 2-chloro-3-pyridinyl | 5-chloro-6-(CF₃)-2-pyridinyl | 3-fluoro-4-pyridinyl |
| 4-chloro-5-(CF₃)-2-pyrimidinyl | 2-chloro-3-pyridinyl | 4-chloro-5-(CF₃)-2-pyrimidinyl | 3-fluoro-4-pyridinyl |
| 4-chloro-5-(OCF₃)-2-pyridinyl | 2-chloro-3-pyridinyl | 4-chloro-5-(OCF₃)-2-pyridinyl | 3-fluoro-4-pyridinyl |
| 5-chloro-6-(OCF₃)-2-pyridinyl | 2-chloro-3-pyridinyl | 5-chloro-6-(OCF₃)-2-pyridinyl | 3-fluoro-4-pyridinyl |
| 4-chloro-5-(OCF₃)-2-pyrimidinyl | 2-chloro-3-pyridinyl | 4-chloro-5-(OCF₃)-2-pyrimidinyl | 3-fluoro-4-pyridinyl |
| 4-(CF₃)-5-chloro-2-pyridinyl | 2-chloro-3-pyridinyl | 4-(CF₃)-5-chloro-2-pyridinyl | 3-fluoro-4-pyridinyl |
| 5-(CF₃)-6-chloro-2-pyridinyl | 2-chloro-3-pyridinyl | 5-(CF₃)-6-chloro-2-pyridinyl | 3-fluoro-4-pyridinyl |
| 4-(CF₃)-5-chloro-2-pyrimidinyl | 2-chloro-3-pyridinyl | 4-(CF₃)-5-chloro-2-pyrimidinyl | 3-fluoro-4-pyridinyl |
| 4,5-bis(CF₃)-2-pyridinyl | 2-chloro-3-pyridinyl | 4,5-bis(CF₃)-2-pyridinyl | 3-fluoro-4-pyridinyl |
| 5,6-bis(CF₃)-2-pyridinyl | 2-chloro-3-pyridinyl | 5,6-bis(CF₃)-2-pyridinyl | 3-fluoro-4-pyridinyl |
| 4,5-bis(CF₃)-2-pyrimidinyl | 2-chloro-3-pyridinyl | 4,5-bis(CF₃)-2-pyrimidinyl | 3-fluoro-4-pyridinyl |
| 4-(OCF₃)-5-chloro-2-pyridinyl | 2-chloro-3-pyridinyl | 4-(OCF₃)-5-chloro-2-pyridinyl | 3-fluoro-4-pyridinyl |
| 5-(OCF₃)-6-chloro-2-pyridinyl | 2-chloro-3-pyridinyl | 5-(OCF₃)-6-chloro-2-pyridinyl | 3-fluoro-4-pyridinyl |
| 4-(OCF₃)-5-chloro-2-pyrimidinyl | 2-chloro-3-pyridinyl | 4-(OCF₃)-5-chloro-2-pyrimidinyl | 3-fluoro-4-pyridinyl |
| 2-naphthalenyl | 2-chloro-3-pyridinyl | 2-naphthalenyl | 3-fluoro-4-pyridinyl |
| 2-quinolinyl | 2-chloro-3-pyridinyl | 2-quinolinyl | 3-fluoro-4-pyridinyl |
| 5-chloro-2-pyridinyl | 2-chloro-3-pyridinyl | 5-chloro-2-pyridinyl | 3-fluoro-4-pyridinyl |
| 5-bromo-2-pyridinyl | 2-chloro-3-pyridinyl | 5-bromo-2-pyridinyl | 3-fluoro-4-pyridinyl |
| 5-fluoro-2-pyridinyl | 2-chloro-3-pyridinyl | 5-fluoro-2-pyridinyl | 3-fluoro-4-pyridinyl |
| 5-(CF₃)-2-pyridinyl | 2-chloro-3-pyridinyl | 5-(CF₃)-2-pyridinyl | 3-fluoro-4-pyridinyl |
| 5-(OCF₃)-2-pyridinyl | 2-chloro-3-pyridinyl | 5-(OCF₃)-2-pyridinyl | 3-fluoro-4-pyridinyl |
| 4-(CF₃)-2-pyridinyl | 2-chloro-3-pyridinyl | 4-(CF₃)-2-pyridinyl | 3-fluoro-4-pyridinyl |

TABLE 6b

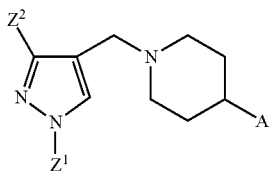

| Z¹ | Z¹ | Z¹ |
|---|---|---|
| \multicolumn{3}{c}{Z² is 2-fluorophenyl, A is cyano} |
| 4,5-dichloro-2-pyridinyl | 4-chloro-5-(OCF₃)-2-pyridinyl | 4,5-bis(CF₃)-2-pyridinyl |
| 5,6-dichloro-2-pyridinyl | 5-chloro-6-(OCF₃)-2-pyridinyl | 5,6-bis(CF₃)-2-pyridinyl |
| 4,5-dichloro-2-pyrimidinyl | 4-chloro-5-(OCF₃)-2-pyrimidinyl | 4,5-bis(CF₃)-2-pyrimidinyl |
| 4-chloro-5-(CF₃)-2-pyridinyl | 4-(CF₃)-5-chloro-2-pyridinyl | 4-(OCF₃)-5-chloro-2-pyridinyl |
| 5-chloro-6-(CF₃)-2-pyridinyl | 5-(CF₃)-6-chloro-2-pyridinyl | 5-(OCF₃)-6-chloro-2-pyridinyl |
| 4-chloro-5-(CF₃)-2-pyrimidinyl | 4-(CF₃)-5-chloro-2-pyrimidinyl | 4-(OCF₃)-5-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF₃)-2-pyridinyl | 5-(OCF₃)-2-pyridinyl |
| 4-(CF₃)-2-pyridinyl | | |
| \multicolumn{3}{c}{Z² is 4-fluorophenyl, A is cyano} |
| 4,5-dichloro-2-pyridinyl | 4-chloro-5-(OCF₃)-2-pyridinyl | 4,5-bis(CF₃)-2-pyridinyl |
| 5,6-dichloro-2-pyridinyl | 5-chloro-6-(OCF₃)-2-pyridinyl | 5,6-bis(CF₃)-2-pyridinyl |
| 4,5-dichloro-2-pyrimidinyl | 4-chloro-5-(OCF₃)-2-pyrimidinyl | 4,5-bis(CF₃)-2-pyrimidinyl |
| 4-chloro-5-(CF₃)-2-pyridinyl | 4-(CF₃)-5-chloro-2-pyridinyl | 4-(OCF₃)-5-chloro-2-pyridinyl |
| 5-chloro-6-(CF₃)-2-pyridinyl | 5-(CF₃)-6-chloro-2-pyridinyl | 5-(OCF₃)-6-chloro-2-pyridinyl |
| 4-chloro-5-(CF₃)-2-pyrimidinyl | 4-(CF₃)-5-chloro-2-pyrimidinyl | 4-(OCF₃)-5-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF₃)-2-pyridinyl | 5-(OCF₃)-2-pyridinyl |
| 4-(CF₃)-2-pyridinyl | | |
| \multicolumn{3}{c}{Z² is 2-chlorophenyl, A is cyano} |
| 4,5-dichloro-2-pyridinyl | 4-chloro-5-(OCF₃)-2-pyridinyl | 4,5-bis(CF₃)-2-pyridinyl |
| 5,6-dichloro-2-pyridinyl | 5-chloro-6-(OCF₃)-2-pyridinyl | 5,6-bis(CF₃)-2-pyridinyl |
| 4,5-dichloro-2-pyrimidinyl | 4-chloro-5-(OCF₃)-2-pyrimidinyl | 4,5-bis(CF₃)-2-pyrimidinyl |
| 4-chloro-5-(CF₃)-2-pyridinyl | 4-(CF₃)-5-chloro-2-pyridinyl | 4-(OCF₃)-5-chloro-2-pyridinyl |
| 5-chloro-6-(CF₃)-2-pyridinyl | 5-(CF₃)-6-chloro-2-pyridinyl | 5-(OCF₃)-6-chloro-2-pyridinyl |
| 4-chloro-5-(CF₃)-2-pyrimidinyl | 4-(CF₃)-5-chloro-2-pyrimidinyl | 4-(OCF₃)-5-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF₃)-2-pyridinyl | 5-(OCF₃)-2-pyridinyl |
| 4-(CF₃)-2-pyridinyl | | |
| \multicolumn{3}{c}{Z² is 2-bromophenyl, A is cyano} |
| 4,5-dichloro-2-pyridinyl | 4-chloro-5-(OCF₃)-2-pyridinyl | 4,5-bis(CF₃)-2-pyridinyl |
| 5,6-dichloro-2-pyridinyl | 5-chloro-6-(OCF₃)-2-pyridinyl | 5,6-bis(CF₃)-2-pyridinyl |
| 4,5-dichloro-2-pyrimidinyl | 4-chloro-5-(OCF₃)-2-pyrimidinyl | 4,5-bis(CF₃)-2-pyrimidinyl |
| 4-chloro-5-(CF₃)-2-pyridinyl | 4-(CF₃)-5-chloro-2-pyridinyl | 4-(OCF₃)-5-chloro-2-pyridinyl |
| 5-chloro-6-(CF₃)-2-pyridinyl | 5-(CF₃)-6-chloro-2-pyridinyl | 5-(OCF₃)-6-chloro-2-pyridinyl |
| 4-chloro-5-(CF₃)-2-pyrimidinyl | 4-(CF₃)-5-chloro-2-pyrimidinyl | 4-(OCF₃)-5-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF₃)-2-pyridinyl | 5-(OCF₃)-2-pyridinyl |
| 4-(CF₃)-2-pyridinyl | | |
| \multicolumn{3}{c}{Z² is 2-methylphenyl, A is cyano} |
| 4,5-dichloro-2-pyridinyl | 4-chloro-5-(OCF₃)-2-pyridinyl | 4,5-bis(CF₃)-2-pyridinyl |
| 5,6-dichloro-2-pyridinyl | 5-chloro-6-(OCF₃)-2-pyridinyl | 5,6-bis(CF₃)-2-pyridinyl |
| 4,5-dichloro-2-pyrimidinyl | 4-chloro-5-(OCF₃)-2-pyrimidinyl | 4,5-bis(CF₃)-2-pyrimidinyl |
| 4-chloro-5-(CF₃)-2-pyridinyl | 4-(CF₃)-5-chloro-2-pyridinyl | 4-(OCF₃)-5-chloro-2-pyridinyl |
| 5-chloro-6-(CF₃)-2-pyridinyl | 5-(CF₃)-6-chloro-2-pyridinyl | 5-(OCF₃)-6-chloro-2-pyridinyl |
| 4-chloro-5-(CF₃)-2-pyrimidinyl | 4-(CF₃)-5-chloro-2-pyrimidinyl | 4-(OCF₃)-5-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF₃)-2-pyridinyl | 5-(OCF₃)-2-pyridinyl |
| 4-(CF₃)-2-pyridinyl | | |
| \multicolumn{3}{c}{Z² is 2-(trifluoromethyl)phenyl, A is cyano} |
| 4,5-dichloro-2-pyridinyl | 4-chloro-5-(OCF₃)-2-pyridinyl | 4,5-bis(CF₃)-2-pyridinyl |
| 5,6-dichloro-2-pyridinyl | 5-chloro-6-(OCF₃)-2-pyridinyl | 5,6-bis(CF₃)-2-pyridinyl |

TABLE 6b-continued

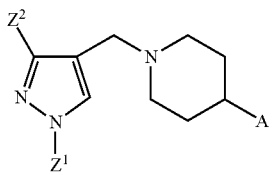

| Z¹ | Z¹ | Z¹ |
|---|---|---|
| 4,5-dichloro-2-pyrimidinyl | 4-chloro-5-(OCF₃)-2-pyrimidinyl | 4,5-bis(CF₃)-2-pyrimidinyl |
| 4-chloro-5-(CF₃)-2-pyridinyl | 4-(CF₃)-5-chloro-2-pyridinyl | 4-(OCF₃)-5-chloro-2-pyridinyl |
| 5-chloro-6-(CF₃)-2-pyridinyl | 5-(CF₃)-6-chloro-2-pyridinyl | 5-(OCF₃)-6-chloro-2-pyridinyl |
| 4-chloro-5-(CF₃)-2-pyrimidinyl | 4-(CF₃)-5-chloro-2-pyrimidinyl | 4-(OCF₃)-5-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF₃)-2-pyridinyl | 5-(OCF₃)-2-pyridinyl |
| 4-(CF₃)-2-pyridinyl | | |

Z² is 2,4-difluorophenyl, A is cyano

| Z¹ | Z¹ | Z¹ |
|---|---|---|
| 4,5-dichloro-2-pyridinyl | 4-chloro-5-(OCF₃)-2-pyridinyl | 4,5-bis(CF₃)-2-pyridinyl |
| 5,6-dichloro-2-pyridinyl | 5-chloro-6-(OCF₃)-2-pyridinyl | 5,6-bis(CF₃)-2-pyridinyl |
| 4,5-dichloro-2-pyrimidinyl | 4-chloro-5-(OCF₃)-2-pyrimidinyl | 4,5-bis(CF₃)-2-pyrimidinyl |
| 4-chloro-5-(CF₃)-2-pyridinyl | 4-(CF₃)-5-chloro-2-pyridinyl | 4-(OCF₃)-5-chloro-2-pyridinyl |
| 5-chloro-6-(CF₃)-2-pyridinyl | 5-(CF₃)-6-chloro-2-pyridinyl | 5-(OCF₃)-6-chloro-2-pyridinyl |
| 4-chloro-5-(CF₃)-2-pyrimidinyl | 4-(CF₃)-5-chloro-2-pyrimidinyl | 4-(OCF₃)-5-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF₃)-2-pyridinyl | 5-(OCF₃)-2-pyridinyl |
| 4-(CF₃)-2-pyridinyl | | |

Z² is 2,6-difluorophenyl, A is cyano

| Z¹ | Z¹ | Z¹ |
|---|---|---|
| 4,5-dichloro-2-pyridinyl | 4-chloro-5-(OCF₃)-2-pyridinyl | 4,5-bis(CF₃)-2-pyridinyl |
| 5,6-dichloro-2-pyridinyl | 5-chloro-6-(OCF₃)-2-pyridinyl | 5,6-bis(CF₃)-2-pyridinyl |
| 4,5-dichloro-2-pyrimidinyl | 4-chloro-5-(OCF₃)-2-pyrimidinyl | 4,5-bis(CF₃)-2-pyrimidinyl |
| 4-chloro-5-(CF₃)-2-pyridinyl | 4-(CF₃)-5-chloro-2-pyridinyl | 4-(OCF₃)-5-chloro-2-pyridinyl |
| 5-chloro-6-(CF₃)-2-pyridinyl | 5-(CF₃)-6-chloro-2-pyridinyl | 5-(OCF₃)-6-chloro-2-pyridinyl |
| 4-chloro-5-(CF₃)-2-pyrimidinyl | 4-(CF₃)-5-chloro-2-pyrimidinyl | 4-(OCF₃)-5-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF₃)-2-pyridinyl | 5-(OCF₃)-2-pyridinyl |
| 4-(CF₃)-2-pyridinyl | | |

Z² is 2,4,6-trifluorophenyl, A is cyano

| Z¹ | Z¹ | Z¹ |
|---|---|---|
| 4,5-dichloro-2-pyridinyl | 4-chloro-5-(OCF₃)-2-pyridinyl | 4,5-bis(CF₃)-2-pyridinyl |
| 5,6-dichloro-2-pyridinyl | 5-chloro-6-(OCF₃)-2-pyridinyl | 5,6-bis(CF₃)-2-pyridinyl |
| 4,5-dichloro-2-pyrimidinyl | 4-chloro-5-(OCF₃)-2-pyrimidinyl | 4,5-bis(CF₃)-2-pyrimidinyl |
| 4-chloro-5-(CF₃)-2-pyridinyl | 4-(CF₃)-5-chloro-2-pyridinyl | 4-(OCF₃)-5-chloro-2-pyridinyl |
| 5-chloro-6-(CF₃)-2-pyridinyl | 5-(CF₃)-6-chloro-2-pyridinyl | 5-(OCF₃)-6-chloro-2-pyridinyl |
| 4-chloro-5-(CF₃)-2-pyrimidinyl | 4-(CF₃)-5-chloro-2-pyrimidinyl | 4-(OCF₃)-5-chloro-2-pyrimidinyl |
| 5,6-dichloro-3-pyridinyl | 6-chloro-3-pyridinyl | 2-chloro-4-pyridinyl |
| 4,5-dichloro-2-furanyl | 4,5-dichloro-2-thienyl | 2-naphthalenyl |
| 2-quinolinyl | 5-chloro-2-pyridinyl | 5-bromo-2-pyridinyl |
| 5-fluoro-2-pyridinyl | 5-(CF₃)-2-pyridinyl | 5-(OCF₃)-2-pyridinyl |
| 4-(CF₃)-2-pyridinyl | | |

Z² is 2-chloro-3-pyridinyl, A is cyano

| | | |
|---|---|---|
| 2-fluorophenyl | 2-chlorophenyl | 2-bromophenyl |
| 2-methylphenyl | 2-(trifluoromethyl)phenyl | 2,4-difluorophenyl |
| 2,6-difluorophenyl | | |

Z² is 2-(trifluoromethyl)-3-pyridinyl, A is cyano

| | | |
|---|---|---|
| 2-fluorophenyl | 2-chlorophenyl | 2-bromophenyl |
| 2-methylphenyl | 2-(trifluoromethyl)phenyl | 2,4-difluorophenyl |
| 2,6-difluorophenyl | | |

Z² is 2-(trifluoromethoxy)-3-pyridinyl, A is cyano

| | | |
|---|---|---|
| 2-fluorophenyl | 2-chlorophenyl | 2-bromophenyl |
| 2-methylphenyl | 2-(trichloromethyl)phenyl | 2,4-difluorophenyl |
| 2,6-difluorophenyl | | |

A compound of this invention will generally be used as an invertebrate pest control active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g, oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids can be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which are branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention can also contain formulation auxiliaries and additives, known to those skilled in the art as formulation aids (some of which can be considered to also function as solid diluents, liquid diluents or surfactants). Such formulation auxiliaries and additives can control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172, 714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all formulations are prepared in conventional ways. Compound numbers refer to compounds in Index Tables A-D. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

High Strength Concentrate

| | |
|---|---|
| compound 41 | 98.5% |
| silica aerogel | 0.5% |
| synthetic amorphous fine silica | 1.0% |

Example B

Wettable Powder

| | |
|---|---|
| compound 77 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

Granule

| | |
|---|---|
| compound 546 | 10.0% |
| attapulgite granules (low volatile matter, 0.71/0.30 mm; U.S.S. No. 25-50 sieves) | 90.0% |

Example D

Extruded Pellet

| | |
|---|---|
| compound 613 | 25.0% |
| anhydrous sodium sulfate | 10.0% |
| crude calcium ligninsulfonate | 5.0% |
| sodium alkyinaphthalenesulfonate | 1.0% |
| calcium/magnesium bentonite | 59.0% |

Example E

Emulsifiable Concentrate

| | |
|---|---|
| compound 869 | 10.0% |
| polyoxyethylene sorbitol hexoleate | 20.0% |
| $C_6$—$C_{10}$ fatty acid methyl ester | 70.0% |

Example F

Microemulsion

| | |
|---|---|
| compound 805 | 5.0% |
| polyvinylpyrrolidone-vinyl acetate copolymer | 30.0% |

Microemulsion -continued

| | |
|---|---|
| alkylpolyglycoside | 30.0% |
| glyceryl monooleate | 15.0% |
| water | 20.0% |

Example G

Seed Treatment

| | |
|---|---|
| compound 800 | 20.00% |
| polyvinylpyrrolidone-vinyl acetate copolymer | 5.00% |
| montan acid wax | 5.00% |
| calcium ligninsulfonate | 1.00% |
| polyoxyethylerte/polyoxypropylene block copolymers | 1.00% |
| stearyl alcohol (POE 20) | 2.00% |
| polyorganosilane | 0.20% |
| colorant red dye | 0.05% |
| water | 65.75% |

Example H

Fertilizer Stick

| | |
|---|---|
| compound 720 | 2.50% |
| pyrrolidone-styrene copolymer | 4.80% |
| tristyrylphenyl 16-ethoxylate | 2.30% |
| talc | 0.80% |
| corn starch | 5.00% |
| slow-release fertilizer | 36.00% |
| kaolin | 38.00% |
| water | 10.60% |

Example I

Suspension Concentrate

| | |
|---|---|
| compound 802 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example J

Emulsion in Water

| | |
|---|---|
| compound 801 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |

-continued

Emulsion in Water

| | |
|---|---|
| 1,2-benzisothiazolin-3-one | 0.1% |
| aromatic petroleum based hydrocarbon | 20.0% |
| water | 58.7% |

Example K

Oil Dispersion

| | |
|---|---|
| compound 807 | 25% |
| polyoxyethylene sorbitol hexaoleate | 15% |
| organically modified bentonite clay | 2.5% |
| fatty acid methyl ester | 57.5% |

Example L

Suspoemulsion

| | |
|---|---|
| compound 806 | 10.0% |
| imidacloprid | 5.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0% |
| water | 53.7% |

Compounds of this invention exhibit activity against a wide spectrum of invertebrate pests. These pests include invertebrates inhabiting a variety of environments such as, for example, plant foliage, roots, soil, harvested crops or other foodstuffs, building structures or animal integuments. These pests include, for example, invertebrates feeding on foliage (including leaves, stems, flowers and fruits), seeds, wood, textile fibers or animal blood or tissues, and thereby causing injury or damage to, for example, growing or stored agronomic crops, forests, greenhouse crops, ornamentals, nursery crops, stored foodstuffs or fiber products, or houses or other structures or their contents, or being harmful to animal health or public health. Those skilled in the art will appreciate that not all compounds are equally effective against all growth stages of all pests.

These present compounds and compositions are thus useful agronomically for protecting field crops from phytophagous invertebrate pests, and also nonagronomically for protecting other horticultural crops and plants from phytophagous invertebrate pests. This utility includes protecting crops and other plants (i.e. both agronomic and nonagronomic) that contain genetic material introduced by genetic engineering (i.e. transgenic) or modified by mutagenesis to provide advantageous traits. Examples of such traits include tolerance to herbicides, resistance to phytophagous pests (e.g., insects, mites, aphids, spiders, nematodes, snails, plant-pathogenic fungi, bacteria and viruses), improved plant growth, increased tolerance of adverse growing conditions such as high or low temperatures, low or high soil moisture, and high salinity, increased flowering or fruiting, greater harvest yields, more rapid maturation, higher quality and/or nutritional value of the harvested product, or improved storage or process properties of the harvested products. Transgenic plants can be modified to express multiple traits. Examples of plants containing traits provided by genetic engineering or mutagenesis include varieties of corn, cotton, soybean and potato expressing an insecticidal *Bacillus thuringiensis* toxin such as YIELD GARD®, KNOCKOUT®, STARLINK®, BOLLGARD®, NuCOTN® and NEWLEAF®, and herbicide-tolerant varieties of corn, cotton, soybean and rapeseed such as ROUNDUP READY®, LIBERTY LINK®, IMI®, STS® and CLEARFIELD®, as well as crops expressing N-acetyltransferase (GAT) to provide resistance to glyphosate herbicide, or crops containing the HRA gene providing resistance to herbicides inhibiting acetolactate synthase (ALS). The present compounds and compositions may interact synergistically with traits introduced by genetic engineering or modified by mutagenesis, thus enhancing phenotypic expression or effectiveness of the traits or increasing the invertebrate pest control effectiveness of the present compounds and compositions. In particular, the present compounds and compositions may interact synergistically with the phenotypic expression of proteins or other natural products toxic to invertebrate pests to provide greater-than-additive control of these pests.

Compositions of this invention can also optionally comprise plant nutrients, e.g., a fertilizer composition comprising at least one plant nutrient selected from nitrogen, phosphorus, potassium, sulfur, calcium, magnesium, iron, copper, boron, manganese, zinc, and molybdenum. Of note are compositions comprising at least one fertilizer composition comprising at least one plant nutrient selected from nitrogen, phosphorus, potassium, sulfur, calcium and magnesium. Compositions of the present invention which further comprise at least one plant nutrient can be in the form of liquids or solids. Of note are solid formulations in the form of granules, small sticks or tablets. Solid formulations comprising a fertilizer composition can be prepared by mixing the compound or composition of the present invention with the fertilizer composition together with formulating ingredients and then preparing the formulation by methods such as granulation or extrusion. Alternatively solid formulations can be prepared by spraying a solution or suspension of a compound or composition of the present invention in a volatile solvent onto a previous prepared fertilizer composition in the form of dimensionally stable mixtures, e.g., granules, small sticks or tablets, and then evaporating the solvent.

Examples of agronomic or nonagronomic invertebrate pests include eggs, larvae and adults of the order Lepidoptera, such as armyworms, cutworms, loopers, and heliothines in the family Noctuidae (e.g., pink stem borer (*Sesamia inferens* Walker), corn stalk borer (*Sesamia nonagrioides* Lefebvre), southern armyworm (*Spodoptera eridania* Cramer), fall armyworm (*Spodoptera fugiperda* J. E. Smith), beet armyworm (*Spodoptera exigua* Hübner), cotton leafworm (*Spodoptera litoralis* Boisduval), yellowstriped armyworm (*Spodoptera ornithogalli* Guenée), black cutworm (*Agrotis ipsilon* Hufnagel), velvetbean caterpillar (*Anticarsia gemmalalis* Hübner), green fruitworm (*Lithophane antennata* Walker), cabbage armyworm (*Barathra brassicae* Linnaeus), soybean looper (*Pseudoplusia includens* Walker), cabbage looper (*Trichophlsia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworms (Pyralidae: Crambinae) such as sod worm (*Herpetogramma licarsisalis Walker), sugarcane stem borer (*Chilo infuscatellus* Snellen), tomato small borer (*Neoleucinodes elegantalis* Guenée), green leafroller (*Cnaphalocerus medinalis*), grape leaffolder (*fDesmia funeralis* Hübner), melon worm (*Diaphania nitidalis* Stoll), cabbage center grub (*Helluala hydralis* Guenée), yellow stem borer (*Scirpophaga incertulas* Walker), early shoot borer (*Scirpophaga infiscatellus* Snellen), white stem borer (*Scirpophaga innotata* Walker), top shoot borer (*Scirpophaga nivella* Fabricius), dark-headed rice borer (*Chilo polychrysus* Meyrick), cabbage cluster caterpillar (*Crocidolomia binotalis* English)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck), citrus false codling moth (*Cryptophlebia leucotreta* Meyrick), citrus borer (*Ecdyiolopha aurantiana* Lima), redbanded leafroller (*Argyrotaenia velhttinana* Walker), obliquebanded leafroller (*Choristoneura rosaceana* Harris), light brown apple moth (*Epiphyas postvittana* Walker), European grape berry moth (*Eupoecilia ambiguella* Hlbner), apple bud moth (*Pandemis pyrusana* Kearfott), omnivorous leafroller (*Platynota stultana* Walsingham), barred fruit-tree tortrix (*Pandemis cerasana* Hübner), apple brown tortrix (*Pandemis heparana* Denis & Schiffermaller)); and many other economically important lepidoptera (e.g., diamondback moth (*Plutella xylostella* Linnacus), pink bollworm (*Pectinophora gossypiella* Saunders), gypsy moth (*Lymantria dispar* Linnaeus), peach fruit borer (*Carposina niponensis* Walsingham), peach twig borer (*Anarsia lineatella* Zeller), potato tuberworm (*Phthorimaea operculella* Zeller), spotted teniform leafminer (*Lithocolletis blancardella* Fabricius), Asiatic apple leafminer (*Lithocolletis ringoniella* Matsumura), rice leaffolder (*Lerodea eufala* Edwards), apple leafininer (*Leucoptera scitella* Zeller)); eggs, nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella germanica* Linnaeus), brownbanded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius)), smoky brown cockroach (*Periplaneta fuliginosa* Service), Australian Cockroach (*Periplaneta australasiae* Fabr.), lobster cockroach (*Naupho-eta cinerea* Olivier) and smooth cockroach (*Symploce pallens* Stephens)); eggs, foliar feeding, fruit feeding, root feeding, seed feeding and vesicular tissue feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Silophilus granarius* Linnaeus), rice weevil (*Silophilus oryzae* Linnaeus)), annual bluegrass weevil (*Listronotus maculicollis* Dietz), bluegrass billbug (*Sphenophorus parvulus* Gyllenhal), hunting billbug (*Sphenophorus venatus* vestitus), Denver billbug (*Sphenophorus cicatristriatus* Fahraeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scarabaeidae (e.g., Japanese beetle (*Popillia japonica* Newman), oriental beetle (*Anomala orientalis* Waterhouse, *Exomala orientalis* (Waterhouse) Baraud), northern masked chafer (*Cyclocephala borealis* Arrow), southern masked chafer (*Cyclocephala immaculata* Olivier or *C. lurida* Bland), dung beetle and white grub (*Aphodius* spp.), black turfgrass ataenius (*Ataenius spretulus* Haldeman), green June beetle (*Cotinis nitida* Linnaeus), Asiatic garden beetle (*Maladera castanea* Arrow), May/June beetles (*Phyllophaga* spp.) and European chafer (*Rhizotrogus majalis* Razoumowsky)); carpet beetles from the family Dermestidae; wireworms from the family Elateridae; bark beetles from the family Scolytidae and flour beetles from the family Tenebrionidae.

In addition, agronomic and nonagronomic pests include: eggs, adults and larvae of the order Dermaptera including earwigs from the family Forficulidae (e.g., European earwig (*Forficula auricularia* Linnaeus), black earwig (*Chelisoches morio* Fabricius)); eggs, immatures, adults and nymphs of the orders Hemiptera and Homoptera such as, plant bugs from the family Miridae, cicadas from the family Cicadidae, leafhoppers (e.g. *Empoasca* spp.) from the family Cicadellidae, bed bugs (e.g., *Cimex lectularius* Linnaeus) from the family Cimicidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, chinch bugs (e.g., hairy chinch bug (*Blissus leucopterus hirtus* Montandon) and southern chinch bug (*Blissus insularis* Barber)) and other seed bugs from the family Lygacidae, spittlebugs from the family Cercopidae squash bugs from the family Coreidae, and red bugs and cotton stainers from the family Pyrrhocoridae.

Agronomic and nonagronomic pests also include: eggs, larvae, nymphs and adults of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)); flat mites in the family Tenuipalpidae (e.g., citrus flat mite (*Brevipalpus lewisi* McGregor)); rust and bud mites in the family Eriophyidae and other foliar feeding mites and mites important in human and animal health, i.e. dust mites in the family Epidermoptidae, follicle mites in the family Demodicidae, grain mites in the family Glycyphagidae; ticks in the family Ixodidae, commonly known as hard ticks (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus)) and ticks in the family Argasidae, commonly known as soft ticks (e.g., relapsing fever tick (*Ornithodoros turicata*), common fowl tick (*Argas radiatus*)); scab and itch mites in the families Psoroptidae, Pyemotidae, and Sarcoptidae; eggs, adults and immatures of the order Orthoptera including grasshoppers, locusts and crickets (e.g., migratory grasshoppers (e.g., *Melanoplus sanguinipes* Fabricius, *M. dfferentialis* Thomas), American grasshoppers (e.g., *Schistocerca americana* Drury), desert locust (*Schistocerca gregaria* Forskal), migratory locust (*Locusta migratoria* Linnaeus), bush locust (*Zonocerus* spp.), house cricket (*Acheta domesticus* Linnaeus), mole crickets (e.g., tawny mole cricket (*Scapteriscus vicinus* Scudder) and southern mole cricket (*Scapteriscus borellii* Giglio-Tos)); eggs, adults and immatures of the order Diptera including leafminers (e.g., *Liriomyza* spp. such as serpentine vegetable leafminer (*Liriomyza sativae* Blanchard)), midges, fruit flies (Tephritidae), frit flies (e.g., *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chlysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; eggs, adults and immatures of the order Thysanoptera including onion thrips (*Thrips tabaci* Lindeman), flower thrips (*Frankliniella* spp.), and other foliar feeding thrips; insect pests of the order Hymenoptera including ants of the Family Formicidae including the Florida carpenter ant (*Camponotus floridanus* Buckley), red carpenter ant (*Camponotus ferrugineus* Fabricius), black carpenter ant (*Camponotus pennsylvanicus* De Geer), white-footed ant (*Technomyrmex albipes* fr. Smith), big headed ants (*Pheidole* sp.), ghost ant (*Tapinoma melanocephalum* Fabricius); Pharaoh ant (*Monomorium pharaonis* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster) and odorous house ant (*Tapinoma sessile* Say). Other Hymenoptera including bees (including carpenter bees), hornets, yellow jackets, wasps, and sawflies (*Neodiprion* spp.; *Cephus* spp.); insect pests of the order lsoptera including termites in the Termitidae (e.g., *Macrotermes* sp., *Odontotermes obesus* Rambur), Kalotermitidae (e.g., *Cryptotermes* sp.), and Rhinotermitidae (e.g., *Reticulitermes* sp., *Coptotelmes* sp., *Heterotermes tenuis* Hagen) families, the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder), powder post termite (*Cryptotermes brevis* Walker), drywood termite (*Incisitermes snyderi* Light), southeastern subterranean termite (*Reticulitermes virginicus* Banks), western drywood termite (*Incisitermes minor* Hagen), arboreal termites such as *Nasutitermes* sp. and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus* Linnaeus), chicken body louse (*Menacanthus stramineus* Nitszch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsvlla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus).

Examples of invertebrate pests of stored grain include larger grain borer (*Prostephanus truncatus*), lesser grain borer (*Rhyzopertha dominica*), rice weevil (*Stiophilus oryzae*), maize weevil (*Stiophilus zeamais*), cowpea weevil (*Callosobruchus maculatus*), red flour beetle (*Tribolium castaneum*), granary weevil (*Sliophihts granarius*), Indian meal moth (*Plodia inteipunctella*), Mediterranean flour beetle (*Ephestia kuhniella*) and flat or rusty grain beetle (*Cyptolestis ferrugineus*).

Compounds of the invention show particularly high activity against pests in the order Lepidoptera (e.g., *Alabama argillacea* Hübner (cotton leaf worm), *Archips argyrospila* Walker (fruit tree leaf roller), *A. rosana* Linnaeus (European leaf roller) and other *Archips* species, *Chilo suppressalis* Walker (rice stem borer), *Cnaphalocrosis medinalis* Guenée (rice leaf roller), *Crambus caliginosellus* Clemens (corn root webworm), *Crambus tetelrellus* Zincken (bluegrass webworm), *Cydia pomonella* Linnaeus (codling moth), *Earias insulana* Boisduval (spiny bollworm), *Earias vittella* Fabricius (spotted bollworm), *Helicoverpa armigera* Hübner (American bollworm), *Helicoverpa zea* Boddie (corn earworm), *Heliothis virescens* Fabricius (tobacco budworm), *Herpetogramma licarsisalis* Walker (sod webworm), *Lobesia botrana* Denis & Schiffermilller (grape berry moth), *Pectinophora gossypiella* Saunders (pink bollworm), *Phyllocnistis citrella* Stainton (citrus leafminer), *Pieris brassicae* Linnaeus (large white butterfly), *Pieris rapae* Linnaeus (small white butterfly), *Plutella xyostella* Linnaeus (diamondback moth), *Spodoptera exigla* Hübner (beet armyworm), *Spodoptera litura* Fabricius (tobacco cutworm, cluster caterpillar), *Spodoptera frugiperda* J. E. Smith (fall armyworm), *Trichophlsia ni* Hübner (cabbage looper) and *Tuta absoluta* Meyrick (tomato leafminer)).

Compounds of the invention also have activity on members from the order Homoptera including: *Acyrthosiphon pisum* Harris (pea aphid), *Aphis craccivora* Koch (cowpea aphid), *Aphis fabae* Scopoli (black bean aphid), *Aphis gossypii* Glover (cotton aphid, melon aphid), *Aphis pomi* De Geer (apple aphid), *Aphis spiraecola* Patch (spirea aphid), *Aulacorthum solani* Kaltenbach (foxglove aphid), *Chaetosiphon fragaefolii* Cockerell (strawberry aphid), *Diuraphis noxia* Kurdjumov/Mordvilko (Russian wheat aphid), *Dysaphis planlaginea* Paaserini (rosy apple aphid), *Eriosoma lanigerum* Hausmann (woolly apple aphid), *Hlyalopterus pruni* Geoffroy (mealy plum aphid), *Lipaphis elysimi* Kaltenbach (turnip aphid), *Metopolophium dirrhodum* Walker (cereal aphid), *Macrosiphum euphorbiae* Thomas (potato aphid), *Myzus persicae* Sulzer (peach-potato aphid, green peach aphid), *Nasonovia ribisnigri* Mosley (lettuce aphid), *Pemphigus* spp. (root aphids and gall aphids), *Rhopalosiphum maidis* Fitch (corn leaf aphid), *Rhopalosiphum padi* Linnaeus (bird cherry-oat aphid), *Schizaphis graminum* Rondani (greenbug), *Sitobion avenae* Fabricius (English grain aphid), *Therioaphis maculata* Buckton (spotted alfalfa aphid), *Toxoptera aurantii* Boyer de Fonscolombe (black citrus aphid), and *Toxoptera citricida* Kirkaldy (brown citrus aphid); *Adelges* spp. (adelgids); *Phylloxera devastatrix* Pergande (pecan phylloxera); *Bemisia labaci* Gennadius (tobacco whitefly, sweetpotato whitefly), *Bemisia argentiflii* Bellows & Perring (silverleaf whitefly), *Dialeurodes citri* Ashmead (citrus whitefly) and *Trialeurodes vaporariorum* Westwood (greenhouse whitefly); *Empoasca fabae* Harris (potato leafhopper), *Laodelphax striatelus* Fallen (smaller brown planthopper), *Macrolestes quadrilineatus* Forbes (aster leafhopper), *Nephotettix cinticeps* Uhler (green leafhopper), *Nephoteltix nigropiclus* Stål (rice leafhopper), *Nilaparvata hlgens* Stål (brown planthopper), *Peregrinus maidis* Ashmead (corn planthopper), *Sogatella furcifera* Horvath (white-backed planthopper), *Sogatodes orizicola* Muir (rice delphacid), *Typhlocyba pomaria* McAtee white apple leafhopper, *Erylhroneoura* spp. (grape leafhoppers); *Magicidada septen-*

*decim* Linnaeus (periodical cicada); *Icerya purchasi* Maskell (cottony cushion scale), *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla), *Trioza diospyri* Ashmead (persimmon psylla).

Compounds of this invention may also have activity on members from the order Hemiptera including: *Acrosternum hilare* Say (green stink bug), *Anasa tristis* De Geer (squash bug), *Blissus leucopterus leucopterus* Say (chinch bug), *Cimex lectularius* Linnaeus (bed bug) *Corythuca gossypii* Fabricius (cotton lace bug), *Cyrtopeltis modesta* Distant (tomato bug), *Dysdercus suturellus* Herrich-Schäffer (cotton stainer), *Euchistus servus* Say (brown stink bug), *Euchistus variolarius* Palisot de Beauvois (one-spotted stink bug), *Graptosthetus* spp. (complex of seed bugs), *Leptoglossus corculus* Say (leaf-footed pine seed bug), *Lygus lineolaris* Palisot de Beauvois (tarnished plant bug), *Nezara viridula* Linnaeus (southern green stink bug), *Oebalus pugnar* Fabricius (rice stink bug), *Oncopeltus fasciatus* Dallas (large milkweed bug), *Pseudomoscelis seriatus* Reuter (cotton fleahopper). Other insect orders controlled by compounds of the invention include Thysanoptera (e.g., *Frankliniella occidentalis* Pergande (western flower thrips), *Scirthothrips citri* Moulton (citrus thrips), *Sericothrips variabilis* Beach (soybean thrips), and *Thrips tabaci* Lindeman (onion thrips); and the order Coleoptera (e.g., *Leptinotarsa decemlineata* Say (Colorado potato beetle), *Epilachna varivestis* Mulsant (Mexican bean beetle) and wireworms of the genera *Agriotes, Athous* or *Limonius*).

Note that some contemporary classification systems place Homoptera as a suborder within the order Hemiptera.

Of note is use of compounds of this invention for controlling diamondback moth (*Plutella xylostella*). Of note is use of compounds of this invention for controlling fall armyworm (*Spodoptera frugiperda*).

Compounds of this invention can also be mixed with one or more other biologically active compounds or agents including insecticides, fungicides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agronomic and nonagronomic utility. Thus the present invention also pertains to a composition comprising a biologically effective amount of a compound of Formula 1, an N-oxide, or salt thereof, at least one additional component selected from the group consisting of surfactants, solid diluents and liquid diluents, and at least one additional biologically active compound or agent. For mixtures of the present invention, the other biologically active compounds or agents can be formulated together with the present compounds, including the compounds of Formula 1, to form a premix, or the other biologically active compounds or agents can be formulated separately from the present compounds, including the compounds of Formula 1, and the two formulations combined together before application (e.g., in a spray tank) or, alternatively, applied in succession.

Examples of such biologically active compounds or agents with which compounds of this invention can be formulated are insecticides such as abamectin, acephate, acequinocyl, acetamiprid, acrinathrin, amidoflumet, amitraz, avermectin, azadirachtin, azinphos-methyl, benfuracarb, bensultap, bifenthrin, bifenazate, bistrifluoron, borate, buprofezin, cadusafos, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyantraniliprole, cycloprothrin, cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenitrothion, fenothiocarb, fenoxycarb, fenpropathrin, fenvalerate, fipronil, flonicamid, flubendiamide, flucythrinate, flufenerim, flufenoxuron, fluvalinate, tau-fluvalinate, fonophos, formetanate, fosthiazate, halofenozide, hexaflumuron, hexythiazox, hydramethylnon, imidacloprid, indoxacarb, insecticidal soaps, isofenphos, lufenuron, malathion, meperfluthrin, metaflumizone, metaldehyde, methamidophos, methidathion, methiodicarb, methomyl, methoprene, methoxychlor, metofluthrin, monocrotophos, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, silafluofen, spinetoram, spinosad, spirodiclofen, spiromesifen, spirotetramat, sulprofos, sulfoxaflor, tebufenozide, tebufenpyrad, teflubenzuron, tefluthrin, terbufos, tetrachlorvinphos, tetramethrin, tetramethylfluthrin, thiacloprid, thiamethoxam, thiodicarb, thiosultap-sodium, tolfenpyrad, tralomethrin, triazamate, trichlorfon, triflumuron, *Bacillus thuringiensis* delta-endotoxins, entomopathogenic bacteria, entomopathogenic viruses and entomopathogenic fungi.

Of note are insecticides such as abamectin, acetamiprid, acrinathrin, amitraz, avermectin, azadirachtin, bensultap, bifenthrin, buprofezin, cadusafos, carbaryl, cartap, chlorantraniliprole, chlorfenapyr, chlorpyrifos, clothianidin, cyantraniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiodicarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, sulfoxaflor, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of Nucleo polyhydrosis viruses.

One embodiment of biological agents for mixing with compounds of this invention include entomopathogenic bacteria such as *Bacillus thuringiensis*, and the encapsulated delta-endotoxins of *Bacillus thuringiensis* such as MVP® and MVPII® bioinsecticides prepared by the CellCap® process (CellCap®, MVP® and MVPII® are trademarks of Mycogen Corporation, Indianapolis, Ind., USA); entomopathogenic fungi such as green muscardine fungus; and entomopathogenic (both naturally occurring and genetically modified) viruses including baculovirus, nucleopolyhedro virus (NPV) such as *Helicoverpa zea* nucleopolyhedrovirus (HzNPV), *Anagrapha falcifera* nucleopolyhedrovirus (AfNPV); and granulosis virus (GV) such as *Cydia pomonella* granulosis virus (CpGV).

Of particular note is such a combination where the other invertebrate pest control active ingredient belongs to a different chemical class or has a different site of action than the compound of Formula 1. In certain instances, a combination with at least one other invertebrate pest control active ingredient having a similar spectrum of control but a different site of action will be particularly advantageous for resistance management. Thus, a composition of the present invention can further comprise a biologically effective amount of at least one additional invertebrate pest control active ingredient having a similar spectrum of control but belonging to a different chemical class or having a different site of action. These additional biologically active compounds or agents include, but are not limited to, sodium channel modulators such as bifenthrin, cypermethrin, cyhalothrin, lambda-cyhalothrin, cyfluthrin, beta-cyfluthrin, deltamethrin, dimefluthrin, esfenvalerate, fenvalerate, indoxacarb, metofluthrin, profluthrin, pyrethrin and tralomethrin: cholinesterase inhibitors such as chlorpyrifos, methomyl, oxamyl, thiodicarb and triazamate: neonicotinoids such as acetamiprid, clothianidin, dinotefuran, imidacloprid, nitenpyram, nithiazine, thiacloprid and thiamethoxam; insecticidal macrocyclic lactones such as spinetoram, spinosad, abamectin, avermectin and emamectin; GABA (γ-aminobutyric acid)-gated chloride channel antagonists such as avermectin or blockers such as ethiprole and fipronil; chitin synthesis inhibitors such as buprofezin, cyromazine, flufenoxuron, hexaflumuron, lufenuron, novaluron, noviflumuron and triflumuron; juvenile hormone mimics such as diofenolan, fenoxycarb, methoprene and pyriproxyfen; octopamine receptor ligands such as amitraz; molting inhibitors and ecdysone agonists such as azadirachtin, methoxyfenozide and tebufenozide; ryanodine receptor ligands such as ryanodine, anthranilic diamides such as chlorantraniliprole, cyantraniliprole and flubendiamide; nereistoxin analogs such as cartap; mitochondrial electron transport inhibitors such as chlorfenapyr, hydramethylnon and pyridaben; lipid biosynthesis inhibitors such as spirodiclofen and spiromesifen; cyclodiene insecticides such as dieldrin or endosulfan; pyrethroids; carbamates; insecticidal ureas; and biological agents including nucleopolyhedro viruses (NPV), members of *Bacillus thuringiensis*, encapsulated delta-endotoxins of *Bacillus thuringiensis*, and other naturally occurring or genetically modified insecticidal viruses.

Further examples of biologically active compounds or agents with which compounds of this invention can be formulated are: fungicides such as 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, fluxapyroxad, folpet, fosetyl-aluminum, fthalide, fuberidazole, furalaxyl, furametpyr, hexaconazole, hymexazole, guazatine, imazalil, imibenconazole, iminoctadine, iodicarb, ipconazole, iprobenfos, iprodione, iprovalicarb, isoconazole, isoprothiolane, isotianil, kasugamycin, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penflufen, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pyrametostrobin, pyraoxystrobin, pyrazophos, pyrifenox, pyrimethanil, pyrifenox, pyriofenone, pyrolnitrine, pyroquilon, quinconazole, quinoxyfen, quintozene, silthiofam, simeconazole, spiroxamine, streptomycin, sulfur, tebuconazole, tebufloquin, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimorphamide, tricyclazole, trifloxystrobin, triflumizole, triforine, triticonazole, uniconazole, validamycin, valifenalate, vinclozolin, zineb, ziram, and zoxamide; nematocides such as aldicarb, imicyafos, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad.

Of note are fungicides and compositions comprising fungicides such as 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, azoxystrobin, copper hydroxide, cymoxanil, cyproconazole, difenoconazole, famoxadone, fenoxanil, ferimzone, flusilazole, flutolanil, fthalide, furametpyr, hexaconazole, isoprothiolane, isotianil, kasugamycin, mancozeb, metominostrobin, orysastrobin, pencycuron, penthiopyrad, picoxystrobin, probenazole, propiconazole, proquinazid, pyroquilon, simeconazole, tiadinil, tricyclazole, trifloxystrobin and validamycin.

In certain instances, combinations of a compound of this invention with other biologically active (particularly invertebrate pest control) compounds or agents (i.e. active ingredients) can result in a greater-than-additive (i.e. synergistic) effect. Reducing the quantity of active ingredients released in the environment while ensuring effective pest control is always desirable. When synergism of invertebrate pest control active ingredients occurs at application rates giving agronomically satisfactory levels of invertebrate pest control, such combinations can be advantageous for reducing crop production cost and decreasing environmental load.

Compounds of this invention and compositions thereof can be applied to plants genetically transformed to express proteins toxic to invertebrate pests (such as *Bacillus thuringiensis* delta-endotoxins). Such an application may provide a broader spectrum of plant protection and be advantageous for resistance management. The effect of the exogenously applied invertebrate pest control compounds of this invention may be synergistic with the expressed toxin proteins.

General references for these agricultural protectants (i.e. insecticides, fungicides, nematocides, acaricides, herbicides and biological agents) include *The Pesticide Manual. 13th Edition*, C. D. S. Tomlin, Ed., British Crop Protection Council, Farnham, Surrey, U.K., 2003 and *The BioPesticide Manual, 2nd Edition*, L. G. Copping, Ed., British Crop Protection Council, Farnham, Surrey, U.K., 2001.

For embodiments where one or more of these various mixing partners are used, the weight ratio of these various mixing partners (in total) to the compound of Formula 1, an N-oxide, or salt thereof, is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components can expand the spectrum of invertebrate pests controlled beyond the spectrum controlled by the compound of Formula 1 alone.

Table A lists specific combinations of a compound of Formula 1 with other invertebrate pest control agents illustrative of the mixtures, compositions and methods of the present invention. The first column of Table A lists the specific invertebrate pest control agents (e.g., "Abamectin" in the first line). The second column of Table A lists the mode of action (if known) or chemical class of the invertebrate pest control agents. The third column of Table A lists embodiment(s) of ranges of weight ratios for rates at which a compound of Formula 1 can be applied relative to an invertebrate pest control agent (e.g., "50:1 to 1:50" of a compound of Formula 1 relative to abamectin by weight). Thus, for example, the first line of Table A specifically discloses the combination of a compound of Formula 1 with abamectin can be applied in a weight ratio between 50:1 to 1:50. The remaining lines of Table A are to be construed similarly. Of further note Table A lists specific combinations of a compound of Formula 1 with other invertebrate pest control agents illustrative of the mixtures, compositions and methods of the present invention and includes additional embodiments of weight ratio ranges for application rates.

TABLE A

| Invertebrate Pest Control Agent | Mode of Action or Chemical Class | Typical Weight Ratio |
|---|---|---|
| Abamectin | macrocyclic lactones | 50:1 to 1:50 |
| Acetamiprid | neonicotinoids | 150:1 to 1:200 |
| Amitraz | octopamine receptor ligands | 200:1 to 1:100 |
| Avermectin | macrocyclic lactones | 50:1 to 1:50 |
| Azadirachtin | ecdysone agonists | 100:1 to 1:120 |
| Beta-cyfluthrin | sodium channel modulators | 150:1 to 1:200 |
| Bifenthrin | sodium channel modulators | 100:1 to 1:10 |
| Buprofezin | chitin synthesis inhibitors | 500:1 to 1:50 |
| Cartap | nereistoxin analogs | 100:1 to 1:200 |
| Chlorantraniliprole | ryanodine receptor ligands | 100:1 to 1:120 |
| Chlorfenapyr | mitochondrial electron transport inhibitors | 300:1 to 1:200 |
| Chlorpyrifos | cholinesterase inhibitors | 500:1 to 1:200 |
| Clothianidin | neonicotinoids | 100:1 to 1:400 |
| Cyantraniliprole | ryanodine receptor ligands | 100:1 to 1:120 |
| Cyfluthrin | sodium channel modulators | 150:1 to 1:200 |
| Cyhalothrin | sodium channel modulators | 150:1 to 1:200 |
| Cypermethrin | sodium channel modulators | 150:1 to 1:200 |
| Cyromazine | chitin synthesis inhibitors | 400:1 to 1:50 |
| Deltamethrin | sodium channel modulators | 50:1 to 1:400 |
| Dieldrin | cyclodiene insecticides | 200:1 to 1:100 |
| Dinotefuran | neonicotinoids | 150:1 to 1:200 |

TABLE A-continued

| Invertebrate Pest Control Agent | Mode of Action or Chemical Class | Typical Weight Ratio |
|---|---|---|
| Diofenolan | molting inhibitor | 150:1 to 1:200 |
| Emamectin | macrocyclic lactones | 50:1 to 1:10 |
| Endosulfan | cyclodiene insecticides | 200:1 to 1:100 |
| Esfenvalerate | sodium channel modulators | 100:1 to 1:400 |
| Ethiprole | GABA-regulated chloride channel blockers | 200:1 to 1:100 |
| Fenothiocarb | | 150:1 to 1:200 |
| Fenoxycarb | juvenile hormone mimics | 500:1 to 1:100 |
| Fenvalerate | sodium channel modulators | 150:1 to 1:200 |
| Fipronil | GABA-regulated chloride channel blockers | 150:1 to 1:100 |
| Flonicamid | | 200:1 to 1:100 |
| Flubendiamide | ryanodine receptor ligands | 100:1 to 1:120 |
| Flufenoxuron | chitin synthesis inhibitors | 200:1 to 1:100 |
| Hexaflumuron | chitin synthesis inhibitors | 300:1 to 1:50 |
| Hydramethylnon | mitochondrial electron transport inhibitors | 150:1 to 1:250 |
| Imidacloprid | neonicotinoids | 1000:1 to 1:1000 |
| Indoxacarb | sodium channel modulators | 200:1 to 1:50 |
| Lambda-cyhalothrin | sodium channel modulators | 50:1 to 1:250 |
| Lufenuron | chitin synthesis inhibitors | 500:1 to 1:250 |
| Metaflumizone | | 200:1 to 1:200 |
| Methomyl | cholinesterase inhibitors | 500:1 to 1:100 |
| Methoprene | juvenile hormone mimics | 500:1 to 1:100 |
| Methoxyfenozide | ecdysone agonists | 50:1 to 1:50 |
| Nitenpyram | neonicotinoids | 150:1 to 1:200 |
| Nithiazine | neonicotinoids | 150:1 to 1:200 |
| Novaluron | chitin synthesis inhibitors | 500:1 to 1:150 |
| Oxamyl | cholinesterase inhibitors | 200:1 to 1:200 |
| Pymetrozine | | 200:1 to 1:100 |
| Pyrethrin | sodium channel modulators | 100:1 to 1:10 |
| Pyridaben | mitochondrial electron transport inhibitors | 200:1 to 1:100 |
| Pyridalyl | | 200:1 to 1:100 |
| Pyriproxyfen | juvenile hormone mimics | 500:1 to 1:100 |
| Ryanodine | ryanodine receptor ligands | 100:1 to 1:120 |
| Spinetoram | macrocyclic lactones | 150:1 to 1:100 |
| Spinosad | macrocyclic lactones | 500:1 to 1:10 |
| Spirodiclofen | lipid biosynthesis inhibitors | 200:1 to 1:200 |
| Spiromesifen | lipid biosynthesis inhibitors | 200:1 to 1:200 |
| Tebufenozide | ecdysone agonists | 500:1 to 1:250 |
| Thiacloprid | neonicotinoids | 100:1 to 1:200 |
| Thiamethoxam | neonicotinoids | 1250:1 to 1:1000 |
| Thiodicarb | cholinesterase inhibitors | 500:1 to 1:400 |
| Thiosultap-sodium | | 150:1 to 1:100 |
| Tralomethrin | sodium channel modulators | 150:1 to 1:200 |
| Triazamate | cholinesterase inhibitors | 250:1 to 1:100 |
| Triflumuron | chitin synthesis inhibitors | 200:1 to 1:100 |
| *Bacillus thuringiensis* | biological agents | 50:1 to 1:10 |
| *Bacillus thuringiensis* delta-endotoxin | biological agents | 50:1 to 1:10 |
| NPV (e.g., Gemstar) | biological agents | 50:1 to 1:10 |

Of note is the composition of the present invention wherein the at least one additional biologically active compound or agent is selected from the Invertebrate Pest Control Agents listed in Table A above.

The weight ratios of a compound, including a compound of Formula 1, an N-oxide, or salt thereof, to the additional invertebrate pest control agent typically are between 1000:1 and 1:1000, with one embodiment being between 500:1 and 1:500, another embodiment being between 250:1 and 1:200 and another embodiment being between 100:1 and 1:50.

Listed below in Tables B1 to B15 are embodiments of specific compositions comprising a compound of Formula 1 (compound numbers (Cmpd. No.) refer to compounds in Index Table A) and an additional invertebrate pest control agent.

TABLE B1

| Mixture No. | Cmpd. No. | and | Invertebrate Pest Control Agent |
|---|---|---|---|
| B1-1 | 41 | and | Abamectin |
| B1-2 | 41 | and | Acetamiprid |
| B1-3 | 41 | and | Amitraz |
| B1-4 | 41 | and | Avermectin |
| B1-5 | 41 | and | Azadirachtin |
| B1-5a | 41 | and | Bensultap |
| B1-6 | 41 | and | Beta-cyfluthrin |
| B1-7 | 41 | and | Bifenthrin |
| B1-8 | 41 | and | Buprofezin |
| B1-9 | 41 | and | Cartap |
| B1-10 | 41 | and | Chlorantraniliprole |
| B1-11 | 41 | and | Chlorfenapyr |
| B1-12 | 41 | and | Chlorpyrifos |
| B1-13 | 41 | and | Clothianidin |
| B1-14 | 41 | and | Cyantraniliprole |
| B1-15 | 41 | and | Cyfluthrin |
| B1-16 | 41 | and | Cyhalothrin |
| B1-17 | 41 | and | Cypermethrin |
| B1-18 | 41 | and | Cyromazine |
| B1-19 | 41 | and | Deltamethrin |
| B1-20 | 41 | and | Dieldrin |
| B1-21 | 41 | and | Dinotefuran |
| B1-22 | 41 | and | Diofenolan |
| B1-23 | 41 | and | Emamectin |
| B1-24 | 41 | and | Endosulfan |
| B1-25 | 41 | and | Esfenvalerate |
| B1-26 | 41 | and | Ethiprole |
| B1-27 | 41 | and | Fenothiocarb |
| B1-28 | 41 | and | Fenoxycarb |
| B1-29 | 41 | and | Fenvalerate |
| B1-30 | 41 | and | Fipronil |
| B1-31 | 41 | and | Flonicamid |
| B1-32 | 41 | and | Flubendiamide |
| B1-33 | 41 | and | Flufenoxuron |
| B1-34 | 41 | and | Hexaflumuron |
| B1-35 | 41 | and | Hydramethylnon |
| B1-36 | 41 | and | Imidacloprid |
| B1-37 | 41 | and | Indoxacarb |
| B1-38 | 41 | and | Lambda-cyhalothrin |
| B1-39 | 41 | and | Lufenuron |
| B1-40 | 41 | and | Metaflumizone |
| B1-41 | 41 | and | Methomyl |
| B1-42 | 41 | and | Methoprene |
| B1-43 | 41 | and | Methoxyfenozide |
| B1-44 | 41 | and | Nitenpyram |
| B1-45 | 41 | and | Nithiazine |
| B1-46 | 41 | and | Novaluron |
| B1-47 | 41 | and | Oxamyl |
| B1-48 | 41 | and | Phosmet |
| B1-49 | 41 | and | Pymetrozine |
| B1-50 | 41 | and | Pyrethrin |
| B1-51 | 41 | and | Pyridaben |
| B1-52 | 41 | and | Pyridalyl |
| B1-53 | 41 | and | Pyriproxyfen |
| B1-54 | 41 | and | Ryanodine |
| B1-55 | 41 | and | Spinetoram |
| B1-56 | 41 | and | Spinosad |
| B1-57 | 41 | and | Spirodiclofen |
| B1-58 | 41 | and | Spiromesifen |
| B1-59 | 41 | and | Spirotetramat |
| B1-59a | 41 | and | Sulfoxaflor |
| B1-60 | 41 | and | Tebufenozide |
| B1-61 | 41 | and | Thiacloprid |
| B1-62 | 41 | and | Thiamethoxam |
| B1-63 | 41 | and | Thiodicarb |
| B1-64 | 41 | and | Thiosultap-sodium |
| B1-65 | 41 | and | Tolfenpyrad |
| B1-66 | 41 | and | Tralomethrin |
| B1-67 | 41 | and | Triazamate |
| B1-68 | 41 | and | Triflumuron |
| B1-69 | 41 | and | *Bacillus thuringiensis* |
| B1-70 | 41 | and | *Bacillus thuringiensis* delta-endotoxin |
| B1-71 | 41 | and | NPV (e.g., Gemstar) |

Table B2

Table B2 is identical to Table B1, except that each reference to compound 41 in the column headed "Cmpd. No." is replaced by a reference to compound 77. For example, the first mixture in Table B2 is designated B2-1 and is a mixture of compound 77 and the additional invertebrate pest control agent abamectin.

Table B3

Table B3 is identical to Table B1, except that each reference to compound 41 in the column headed "Cmpd. No." is replaced by a reference to compound 546. For example, the first mixture in Table B3 is designated B3-1 and is a mixture of compound 546 and the additional invertebrate pest control agent abamectin.

Table B4

Table B4 is identical to Table B1, except that each reference to compound 41 in the column headed "Cmpd. No." is replaced by a reference to compound 613. For example, the first mixture in Table B4 is designated B4-1 and is a mixture of compound 613 and the additional invertebrate pest control agent abamectin.

Table B5

Table B5 is identical to Table B, except that each reference to compound 41 in the column headed "Cmpd. No." is replaced by a reference to compound 652. For example, the first mixture in Table B5 is designated B5-1 and is a mixture of compound 652 and the additional invertebrate pest control agent abamectin.

Table B6

Table B6 is identical to Table B1, except that each reference to compound 41 in the column headed "Cmpd. No." is replaced by a reference to compound 720. For example, the first mixture in Table B6 is designated B6-1 and is a mixture of compound 720 and the additional invertebrate pest control agent abamectin.

Table B7

Table B7 is identical to Table B1, except that each reference to compound 41 in the column headed "Cmpd. No." is replaced by a reference to compound 800. For example, the first mixture in Table B7 is designated B7-1 and is a mixture of compound 800 and the additional invertebrate pest control agent abamectin.

Table B8

Table B8 is identical to Table B1, except that each reference to compound 41 in the column headed "Cmpd. No." is replaced by a reference to compound 801. For example, the first mixture in Table B8 is designated B8-1 and is a mixture of compound 801 and the additional invertebrate pest control agent abamectin.

Table B9

Table B9 is identical to Table B1, except that each reference to compound 41 in the column headed "Cmpd. No." is replaced by a reference to compound 802. For example, the first mixture in Table B9 is designated B9-1 and is a mixture of compound 802 and the additional invertebrate pest control agent abamectin.

Table B10

Table B10 is identical to Table B1, except that each reference to compound 41 in the column headed "Cmpd. No." is replaced by a reference to compound 804. For example, the first mixture in Table B10 is designated B10-1 and is a mixture of compound 804 and the additional invertebrate pest control agent abamectin.

Table B11

Table B11 is identical to Table B1, except that each reference to compound 41 in the column headed "Cmpd. No." is replaced by a reference to compound 805. For example, the first mixture in Table B11 is designated B11-1 and is a mixture of compound 805 and the additional invertebrate pest control agent abamectin.

Table B12

Table B12 is identical to Table B1, except that each reference to compound 41 in the column headed "Cmpd. No." is replaced by a reference to compound 806. For example, the first mixture in Table B12 is designated B 2-1 and is a mixture of compound 806 and the additional invertebrate pest control agent abamectin.

Table B13

Table B13 is identical to Table B1, except that each reference to compound 41 in the column headed "Cmpd. No." is replaced by a reference to compound 807. For example, the first mixture in Table B13 is designated B 3-1 and is a mixture of compound 807 and the additional invertebrate pest control agent abamectin.

Table B14

Table B14 is identical to Table B1, except that each reference to compound 41 in the column headed "Cmpd. No." is replaced by a reference to compound 820. For example, the first mixture in Table B14 is designated B14-1 and is a mixture of compound 820 and the additional invertebrate pest control agent abamectin.

Table B15

Table B15 is identical to Table B1, except that each reference to compound 41 in the column headed "Cmpd. No." is replaced by a reference to compound 869. For example, the first mixture in Table B15 is designated B15-1 and is a mixture of compound 869 and the additional invertebrate pest control agent abamectin.

The specific mixtures listed in Tables B to B15 typically combine a compound of Formula 1 with the other invertebrate pest agent in the ratios specified in Table A.

Listed below in Tables C1 to C15 are embodiments of specific compositions comprising a compound of Formula 1 (compound numbers (Cmpd. No.) refer to compounds in Index Tables A-E) and an additional fungicide.

TABLE C1

| Mixture No. | Cmpd. No. | and | Fungicide |
|---|---|---|---|
| C1-1 | 41 | and | Probenazole |
| C1-2 | 41 | and | Tiadinil |
| C1-3 | 41 | and | Isotianil |
| C1-4 | 41 | and | Pyroquilon |
| C1-5 | 41 | and | Metominostrobin |
| C1-6 | 41 | and | Flutolanil |
| C1-7 | 41 | and | Validamycin |
| C1-8 | 41 | and | Furametpyr |
| C1-9 | 41 | and | Pencycuron |
| C1-10 | 41 | and | Simeconazole |
| C1-11 | 41 | and | Orysastrobin |
| C1-12 | 41 | and | Trifloxystrobin |
| C1-13 | 41 | and | Isoprothiolane |
| C1-14 | 41 | and | Azoxystrobin |
| C1-15 | 41 | and | Tricyclazole |
| C1-16 | 41 | and | Hexaconazole |
| C1-17 | 41 | and | Difenoconazole |
| C1-18 | 41 | and | Cyproconazole |
| C1-19 | 41 | and | Propiconazole |
| C1-20 | 41 | and | Fenoxanil |
| C1-21 | 41 | and | Ferimzone |
| C1-22 | 41 | and | Fthalide |
| C1-23 | 41 | and | Kasugamycin |
| C1-24 | 41 | and | Picoxystrobin |
| C1-25 | 41 | and | Penthiopyrad |
| C1-26 | 41 | and | Famoxadone |
| C1-27 | 41 | and | Cymoxanil |
| C1-28 | 41 | and | Proquinazid |
| C1-29 | 41 | and | Flusilazole |
| C1-30 | 41 | and | Mancozeb |
| C1-31 | 41 | and | Copper hydroxide |
| C1-32 | 41 | and | (a) |

(a) 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone Table C2

Table C2 is identical to Table C1, except that each reference to compound 41 in the column headed "Cmpd. No." is replaced by a reference to compound 77. For example, the first mixture in Table C2 is designated C2-1 and is a mixture of compound 77 and the additional fungicide probenazole.

Table C3

Table C3 is identical to Table C1, except that each reference to compound 41 in the column headed "Cmpd. No." is replaced by a reference to compound 546. For example, the first mixture in Table C3 is designated C3-1 and is a mixture of compound 546 and the additional fungicide probenazole.

Table C4

Table C4 is identical to Table C1, except that each reference to compound 41 in the column headed "Cmpd. No." is replaced by a reference to compound 613. For example, the first mixture in Table C4 is designated C4-1 and is a mixture of compound 613 and the additional fungicide probenazole.

Table C5

Table C5 is identical to Table C1, except that each reference to compound 41 in the column headed "Cmpd. No." is replaced by a reference to compound 652. For example, the first mixture in Table C5 is designated C5-1 and is a mixture of compound 652 and the additional fungicide probenazole.

Table C6

Table C6 is identical to Table C1, except that each reference to compound 41 in the column headed "Cmpd. No." is replaced by a reference to compound 720 For example, the first mixture in Table C6 is designated C6-1 and is a mixture of compound 720 and the additional fungicide probenazole.

Table C7

Table C7 is identical to Table C1, except that each reference to compound 41 in the column headed "Cmpd. No." is replaced by a reference to compound 800. For example, the first mixture in Table C7 is designated C7-1 and is a mixture of compound 800 and the additional fungicide probenazole.

Table C8

Table C8 is identical to Table C1, except that each reference to compound 41 in the column headed "Cmpd. No." is replaced by a reference to compound 801. For example, the first mixture in Table C8 is designated C8-1 and is a mixture of compound 801 and the additional fungicide probenazole.

Table C9

Table C9 is identical to Table C1, except that each reference to compound 41 in the column headed "Cmpd. No." is replaced by a reference to compound 802. For example, the first mixture in Table C9 is designated C9-1 and is a mixture of compound 802 and the additional fungicide probenazole.

Table C10

Table C10 is identical to Table C1, except that each reference to compound 41 in the column headed "Cmpd. No." is replaced by a reference to compound 804. For example, the first mixture in Table C10 is designated C10-1 and is a mixture of compound 804 and the additional fungicide probenazole.

Table C11

Table C11 is identical to Table C1, except that each reference to compound 41 in the column headed "Cmpd. No." is replaced by a reference to compound 805. For example, the first mixture in Table C11 is designated C11-1 and is a mixture of compound 805 and the additional fungicide probenazole.

Table C12

Table C12 is identical to Table C1, except that each reference to compound 41 in the column headed "Cmpd. No." is replaced by a reference to compound 806. For example, the first mixture in Table C12 is designated C12-1 and is a mixture of compound 806 and the additional fungicide probenazole.

Table C13

Table C13 is identical to Table C1, except that each reference to compound 41 in the column headed "Cmpd. No." is replaced by a reference to compound 807. For example, the first mixture in Table C13 is designated C13-1 and is a mixture of compound 807 and the additional fungicide probenazole.

Table C14

Table C14 is identical to Table C1, except that each reference to compound 41 in the column headed "Cmpd. No." is replaced by a reference to compound 820. For example, the first mixture in Table C14 is designated C14-1 and is a mixture of compound 820 and the additional fungicide probenazole.

Table C15

Table C15 is identical to Table C1, except that each reference to compound 41 in the column headed "Cmpd. No." is replaced by a reference to compound 869. For example, the first mixture in Table C15 is designated C15-1 and is a mixture of compound 869 and the additional fungicide probenazole.

Invertebrate pests are controlled in agronomic and nonagronomic applications by applying one or more compounds of this invention, typically in the form of a composition, in a biologically effective amount, to the environment of the pests, including the agronomic and/or nonagronomic locus of infestation, to the area to be protected, or directly on the pests to be controlled.

Thus the present invention comprises a method for controlling an invertebrate pest in agronomic and/or nonagronomic applications, comprising contacting the invertebrate pest or its environment with a biologically effective amount of one or more of the compounds of the invention, or with a composition comprising at least one such compound or a composition comprising at least one such compound and a biologically effective amount of at least one additional biologically active compound or agent. Examples of suitable compositions comprising a compound of the invention and a biologically effective amount of at least one additional biologically active compound or agent include granular compositions wherein the additional active compound is present on the same granule as the compound of the invention or on granules separate from those of the compound of the invention.

Embodiments of the method of this invention include contacting the environment. Of note is the method wherein the environment is a plant. Also of note is the method wherein the environment is an animal. Also of note is the method wherein the environment is a seed.

To achieve contact with a compound or composition of the invention to protect a field crop from invertebrate pests, the compound or composition is typically applied to the seed of the crop before planting, to the foliage (e.g., leaves, stems, flowers, fruits) of crop plants, or to the soil or other growth medium before or after the crop is planted.

One embodiment of a method of contact is by spraying. Alternatively, a granular composition comprising a compound of the invention can be applied to the plant foliage or the soil. Compounds of this invention can also be effectively delivered through plant uptake by contacting the plant with a composition comprising a compound of this invention applied as a soil drench of a liquid formulation, a granular formulation to the soil, a nursery box treatment or a dip of transplants. Of note is a composition of the present invention in the form of a soil drench liquid formulation. Also of note is a method for controlling an invertebrate pest comprising contacting the invertebrate pest or its environment with a biologically effective amount of a compound of the present invention or with a composition comprising a biologically effective amount of a compound of the present invention. Of further note is this method wherein the environment is soil and the composition is applied to the soil as a soil drench formulation. Of further note is that compounds of this invention are also effective by localized application to the locus of infestation. Other methods of contact include application of a compound or a composition of the invention by direct and residual sprays, aerial sprays, gels, seed coatings, microencapsulations, systemic uptake, baits, ear tags, boluses, foggers, fumigants, aerosols, dusts and many others. One embodiment of a method of contact is a dimensionally stable fertilizer granule, stick or tablet comprising a compound or composition of the invention. The compounds of this invention can also be impregnated into materials for fabricating invertebrate control devices (e.g., insect netting).

Compounds of this invention are also useful in seed treatments for protecting seeds from invertebrate pests. In the context of the present disclosure and claims, treating a seed means contacting the seed with a biologically effective amount of a compound of this invention, which is typically formulated as a composition of the invention. This seed treatment protects the seed from invertebrate soil pests and generally can also protect roots and other plant parts in contact with the soil of the seedling developing from the germinating seed. The seed treatment may also provide protection of foliage by translocation of the compound of this invention or a second active ingredient within the developing plant. Seed treatments can be applied to all types of seeds, including those from which plants genetically transformed to express specialized traits will germinate. Representative examples include those expressing proteins toxic to invertebrate pests, such as Bacillus thuringiensis toxin or those expressing herbicide resistance such as glyphosate acetyltransferase, which provides resistance to glyphosate.

One method of seed treatment is by spraying or dusting the seed with a compound of the invention (i.e. as a formulated composition) before sowing the seeds. Compositions formulated for seed treatment generally comprise a film former or adhesive agent. Therefore typically a seed coating composition of the present invention comprises a biologically effective amount of a compound of Formula 1, an N-oxide, or salt thereof, and a film former or adhesive agent. Seed can be coated by spraying a flowable suspension concentrate directly into a tumbling bed of seeds and then drying the seeds. Alternatively, other formulation types such as wetted powders, solutions, suspoemulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., Seed Treatment Progress and Prospects, 1994 BCPC Monograph No. 57, and references listed therein.

The treated seed typically comprises a compound of the present invention in an amount from about 0.1 g to 1 kg per 100 kg of seed (i.e. from about 0.0001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

The compounds of this invention can be incorporated into a bait composition that is consumed by an invertebrate pest or used within a device such as a trap, bait station, and the like. Such a bait composition can be in the form of granules which comprise (a) active ingredients, namely a biologically effective amount of a compound of Formula 1 an N-oxide, or salt thereof (b) one or more food materials; optionally (c) an attractant, and optionally (d) one or more humectants. Of note are granules or bait compositions which comprise between about 0.001-5% active ingredients, about 40-99% food material and/or attractant; and optionally about 0.05-10% humectants, which are effective in controlling soil invertebrate pests at very low application rates, particularly at doses of active ingredient that are lethal by ingestion rather than by direct contact. Some food materials can function both as a food source and an attractant. Food materials include carbohydrates, proteins and lipids. Examples of food materials are vegetable flour, sugar, starches, animal fat, vegetable oil, yeast extracts and milk solids. Examples of attractants are odorants and flavorants, such as fruit or plant extracts, perfume, or other animal or plant component, pheromones or other agents known to attract a target invertebrate pest. Examples of humectants, i.e. moisture retaining agents, are glycols and other polyols, glycerine and sorbitol. Of note is a bait composition (and a method utilizing such a bait composition) used to control at least one invertebrate pest selected from the group consisting of ants, termites and cockroaches. A device for controlling an invertebrate pest can comprise the present bait composition and a housing adapted to receive the bait composition, wherein the housing has at least one opening sized to permit the invertebrate pest to pass through the opening so the invertebrate pest can gain access to the bait composition from a location outside the housing, and wherein the housing is further adapted to be placed in or near a locus of potential or known activity for the invertebrate pest.

The compounds of this invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of a compound of the present invention. Combinations with spray oils, spray oil concentrations, spreader stickers, adjuvants, other solvents, and synergists such as piperonyl butoxide often enhance compound efficacy. For nonagronomic uses such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as needed for application. Of note is a spray composition comprising a biologically effective amount of a compound or a composition of the present invention and a carrier. One embodiment of such a spray composition comprises a biologically effective amount of a compound or a composition of the present invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one invertebrate pest selected from the group consisting of mosquitoes, black flies, stable flies, deer flies, horse flies, wasps, yellow jackets, hornets, ticks, spiders, ants, gnats, and the like, including individually or in combinations.

Nonagronomic uses refer to invertebrate pest control in the areas other than fields of crop plants. Nonagronomic uses of the present compounds and compositions include control of invertebrate pests in stored grains, beans and other foodstuffs, and in textiles such as clothing and carpets. Nonagronomic uses of the present compounds and compositions also include invertebrate pest control in ornamental plants, forests, in yards, along roadsides and railroad rights of way, and on turf such as lawns, golf courses and pastures. Nonagronomic uses of the present compounds and compositions also include invertebrate pest control in houses and other buildings which may be occupied by humans and/or companion, farm, ranch, zoo or other animals. Nonagronomic uses of the present compounds and compositions also include the control of pests such as termites that can damage wood or other structural materials used in buildings.

For agronomic applications, the rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like.

Under normal circumstances, application rates of about 0.01 to 2 kg of active ingredients per hectare are sufficient to control pests in agronomic ecosystems, but as little as 0.0001 kg/hectare may be sufficient or as much as 8 kg-hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

Representative compounds of this invention prepared by the methods described herein are shown in Index Tables A-E. See Index Table F for $^1$H NMR data. The column titled "m.p. (° C.) or AP+ (M+1)" contains either mass spectral data as a single numerical entry (e.g., 348), or melting point data as a numerical range (e.g., 122-124° C.). For mass spectral data (AP+ (M+1)), the numerical value reported is the molecular weight of the parent molecular ion (M) formed by addition of H$^+$ (molecular weight of 1) to the molecule to give a M+1 peak observed by mass spectrometry using atmospheric pressure chemical ionization (AP$^+$). The alternate molecular ion peaks (e.g., M+2 or M+4) that occur with compounds containing multiple halogens are not reported.

In Index Table B, entries in the column titled "X" represent definitions of the variable M of Formula 1. When M is —C(R$^{3e}$)(A)- and R$^{3e}$ and A are taken together to form a ring, the ring is represented in the form "C(-ring members-)" with the first and last ring members being bonded to the carbon atom of —C(R$^{3e}$)(A). For example, when X is defined as "C[—CH$_2$N(C(O)OC(Me)$_3$)CH$_2$—]", the structure of the piperidine ring containing X would be as shown below.

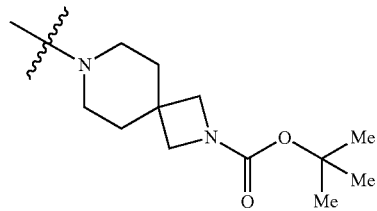 [SMILES: *N1CCC2(CC1)CN(C(=O)OC(C)(C)C)C2]

The following abbreviations are used in the Index Tables which follow: Cmpd means Compound, Me is methyl, Et is ethyl, c-Pr is cyclopropyl, Ph is phenyl, CHO is formyl and CN is cyano.

INDEX TABLE A $R^{1a}$, $R^{1b}$ and $R^{14}$ are H

| Cmpd | $Z^1$ | $Z^2$ | A | $R^{3e}$ | m.p. (° C.) or AP+ (M + 1) |
|---|---|---|---|---|---|
| 1 | 2-chlorophenyl | 4-fluorophenyl | phenyl | H | |
| 2 | 3-methylphenyl | 3-fluorophenyl | CO$_2$Me | H | 408.5 |
| 3 | 2,4-difluorophenyl | 2-methylphenyl | CO$_2$Me | H | 426.5 |
| 4 | 4-methylphenyl | 4-fluorophenyl | CO$_2$Me | H | 408.5 |
| 5 | 3-methylphenyl | 3-fluorophenyl | CH$_2$OCH$_3$ | H | 394.5 |
| 6 | 2-methylphenyl | 3-fluoro-4-methoxyphenyl | CO$_2$Et | H | |
| 7 | 4-methylphenyl | 4-fluorophenyl | CH$_2$OCH$_3$ | H | |
| 8 | 4-methylphenyl | 4-fluorophenyl | C(O)NEt$_2$ | H | |
| 9 | 2,4-difluorophenyl | 4-fluorophenyl | CO$_2$Me | H | 91-92° C. |
| 10 | 4-(trifluoromethoxy)phenyl | 4-fluorophenyl | CO$_2$Me | H | 478.4 |
| 11 | 3-(trifluoromethyl)phenyl | 4-fluorophenyl | CO$_2$Me | H | 462.5 |
| 12 | 3-(trifluoromethyl)phenyl | 4-fluorophenyl | cyano | H | 429.4 |
| 13 | 4-chlorophenyl | 4-fluorophenyl | CO$_2$Me | H | 428.4 |
| 14 | 4-chlorophenyl | 4-fluorophenyl | cyano | H | 395.4 |
| 15 | 2,4-difluorophenyl | 3-(trifluoromethyl)phenyl | CO$_2$Me | H | 480.4 |
| 16 | 2,4-difluorophenyl | 2-fluoro-4-methylphenyl | CO$_2$Me | H | 444.5 |
| 17 | 2,4-difluorophenyl | 4-chlorophenyl | CO$_2$Me | H | 446.4 |
| 18 | 2,6-dichloro-4-(trifluoromethyl)phenyl | 4-chlorophenyl | CO$_2$Me | H | 546.3 |
| 19 | 3-chlorophenyl | 2-fluorophenyl | CO$_2$Me | H | 442.5 |
| 20 | 3-chlorophenyl | 3-fluorophenyl | CO$_2$Et | H | 442.4 |
| 21 | 3-chlorophenyl | 4-fluorophenyl | CO$_2$Et | H | 442.4 |

INDEX TABLE A-continued

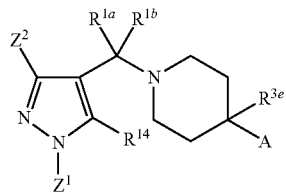

$R^{1a}$, $R^{1b}$ and $R^{14}$ are H

| Cmpd | $Z^1$ | $Z^2$ | A | $R^{3e}$ | m.p. (° C.) or AP+ (M + 1) |
|---|---|---|---|---|---|
| 22 | 3,4-dichlorophenyl | 2-fluorophenyl | $CO_2Et$ | H | 476.4 |
| 23 | 3,4-dichlorophenyl | 3-fluorophenyl | $CO_2Et$ | H | 476.4 |
| 24 | 3,4-dichlorophenyl | 4-fluorophenyl | $CO_2Et$ | H | 476.4 |
| 25 | 3-chlorophenyl | 3-fluorophenyl | $CF_3$ | H | 438.4 |
| 26 | 3-chlorophenyl | 2-fluorophenyl | NHC(O)OEt | H | 457.5 |
| 27 | 3-chlorophenyl | 3-fluorophenyl | NHC(O)OEt | H | 457.5 |
| 28 | 3-chlorophenyl | 4-fluorophenyl | NHC(O)OEt | H | 457.5 |
| 29 | 3,4-dichlorophenyl | 2-fluorophenyl | C(O)Me | H | 446.4 |
| 30 | 3,4-dichlorophenyl | 3-fluorophenyl | C(O)Me | H | 446.4 |
| 31 | 3,4-dichlorophenyl | 4-fluorophenyl | C(O)Me | H | 446.4 |
| 32 | 3,4-dichlorophenyl | 4-fluorophenyl | $CO_2Me$ | H | 462.4 |
| 33 | 3,4-dichlorophenyl | 4-fluorophenyl | cyano | H | 429.4 |
| 34 | 3,5-bis(trifluoromethyl)phenyl | 4-fluorophenyl | $CO_2Me$ | H | 530.5 |
| 35 | 3,5-dichlorophenyl | 4-fluorophenyl | $CO_2Et$ | H | 476.4 |
| 36 | 3,5-dichlorophenyl | 4-fluorophenyl | cyano | H | 429.4 |
| 37 | 3-chloro-2-pyridinyl | 4-fluorophenyl | cyano | H | 396.5 |
| 38 | 3,5-bis(trifluoromethyl)phenyl | 4-fluorophenyl | cyano | H | 497.4 |
| 39 | 2-fluorophenyl | 2-fluorophenyl | cyano | H | 379.5 |
| 40 | 3-fluorophenyl | 2-fluorophenyl | cyano | H | 379.5 |
| 41 | 3-chloro-4-fluorophenyl | 2-fluorophenyl | cyano | H | 413.4 |
| 42 | 4-cyanophenyl | 4-fluorophenyl | cyano | H | 386.5 |
| 43 | 2-fluorophenyl | 2-fluorophenyl | $CO_2Me$ | H | 412.5 |
| 44 | 3-fluorophenyl | 2-fluorophenyl | $CO_2Me$ | H | 412.5 |
| 45 | 3-chloro-4-fluorophenyl | 2-fluorophenyl | $CO_2Me$ | H | 446.4 |
| 46 | 4-(trifluoromethyl)-2-pyrimidinyl | 2-fluorophenyl | cyano | H | 431.5 |
| 47 | 4-(trifluoromethyl)-2-pyrimidinyl | 2-fluorophenyl | $CO_5Me$ | H | 464.5 |
| 48 | 4-(trifluoromethyl)phenyl | 2-fluorophenyl | cyano | H | 429.4 |
| 49 | 4-(trifluoromethyl)phenyl | 2-fluorophenyl | NHC(O)OEt | H | 491.5 |
| 50 | 4-(trifluoromethyl)phenyl | 2-fluorophenyl | $CO_2Me$ | H | 462.5 |
| 51 | 4-bromophenyl | 2-fluorophenyl | cyano | H | 440.4 |
| 52 | 4-bromophenyl | 2-fluorophenyl | $CO_2Me$ | H | 472.4 |
| 53 | 4-chloro-3-fluorophenyl | 2-fluorophenyl | cyano | H | 393.5 |
| 54 | 4-chloro-3-fluorophenyl | 2-fluorophenyl | NHC(O)OEt | H | 455.5 |
| 55 | 4-chloro-3-fluorophenyl | 2-fluorophenyl | $CO_2Me$ | H | 426.5 |
| 56 | 3,4-dichlorophenyl | 2-fluorophenyl | cyano | H | 429.4 |
| 57 | 3,4-dichlorophenyl | 2-fluorophenyl | NHC(O)OEt | H | 491.4 |
| 58 | 4-(trifluoromethyl)phenyl | 2-fluorophenyl | cyano | Ph | 505.5 |
| 59 | 4-(trifluoromethyl)phenyl | 2-fluorophenyl | NHC(O)Me | H | 461.5 |
| 60 | 4-bromophenyl | 2-fluorophenyl | NHPh | H | 505.4 |
| 61 | 4-chloro-3-fluorophenyl | 2-fluorophenyl | NHC(O)Me | H | 425.5 |
| 62 | 3,4-dichlorophenyl | 2-fluorophenyl | NHC(O)Me | H | 461.4 |
| 63 | 4-(trifluoromethoxy)phenyl | 2-fluorophenyl | cyano | H | 445.5 |
| 64 | 4-(trifluoromethoxy)phenyl | 2-fluorophenyl | $CO_2Me$ | H | 478.5 |
| 65 | 4-(trifluoromethoxy)phenyl | 2-fluorophenyl | NHC(O)Me | H | 477.4 |
| 66 | 4-(trifluoromethoxy)phenyl | 2,4-difluorophenyl | cyano | H | 463.4 |
| 67 | 4-(trifluoromethoxy)phenyl | 2,4-difluorophenyl | $CO_2Me$ | H | 496.4 |
| 68 | 4-(trifluoromethoxy)phenyl | 2,4-difluorophenyl | NHC(O)Me | H | 495.5 |
| 69 | 4-(trifluoromethoxy)phenyl | 2-fluorophenyl | cyano | Ph | 521.5 |
| 70 | 4-(trifluoromethoxy)phenyl | 2,4-difluorophenyl | cyano | Ph | 539.5 |
| 71 | 3-(trifluoromethyl)phenyl | 2-fluorophenyl | cyano | H | 429.4 |
| 72 | 3-(trifluoromethyl)phenyl | 2-fluorophenyl | $CO_2Me$ | H | 461.5 |
| 73 | 3-(trifluoromethyl)phenyl | 2-fluorophenyl | cyano | Ph | 505.5 |
| 74 | 3-(trifluoromethyl)phenyl | 2-fluorophenyl | NHC(O)Me | H | 461.5 |
| 75 | 4-chlorophenyl | 2-fluorophenyl | $CO_2Me$ | H | 428.4 |
| 76 | 4-chlorophenyl | 2-fluorophenyl | NHC(O)Me | H | 427.5 |
| 77 | 4-chlorophenyl | 2-fluorophenyl | cyano | H | 395.4 |
| 78 | 5-(trifluoromethyl)-2-pyridinyl | 2-fluorophenyl | cyano | H | # |
| 79 | 4-(trifluoromethoxy)phenyl | 2,6-difluorophenyl | cyano | H | 463.4 |
| 80 | 4-(trifluoromethoxy)phenyl | 2,6-difluorophenyl | $CO_2Me$ | H | 496.5 |

INDEX TABLE A-continued

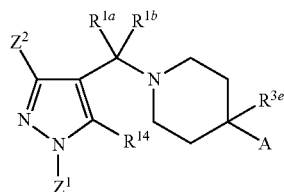

R$^{1a}$, R$^{1b}$ and R$^{14}$ are H

| Cmpd | Z$^1$ | Z$^2$ | A | R$^{3e}$ | m.p. (° C.) or AP+ (M + 1) |
|---|---|---|---|---|---|
| 81 | 5-(trifluoromethyl)-2-pyridinyl | 2-fluorophenyl | CO$_2$Me | H | 463.4 |
| 82 | 4-(trifluoromethoxy)phenyl | 2-fluorophenyl | 1-BZT* | H | 537.6 |
| 83 | 3,4-dichlorophenyl | 2-chlorophenyl | cyano | H | 445.4 |
| 84 | 3,4-dichlorophenyl | 2-chlorophenyl | CO$_2$Me | H | 478.4 |
| 85 | 3-chloro-4-cyanophenyl | 2-fluorophenyl | cyano | H | 420 |
| 86 | 3,4-dichlorophenyl | 2-methylphenyl | cyano | H | 425 |
| 87 | 3-chlorophenyl | 2-fluorophenyl | cyano | H | 395 |
| 88 | 3-chlorophenyl | 2-fluorophenyl | CO$_2$Me | H | 428 |
| 89 | 4-(methylsulfonyl)phenyl | 2-fluorophenyl | cyano | H | 439 |
| 90 | 4-(methylsulfonyl)phenyl | 2-fluorophenyl | CO$_2$Me | H | 472 |
| 91 | 4-(trifluoromethyl)phenyl | 2-furanyl | cyano | H | 401.5 |
| 92 | 4-(trifluoromethyl)phenyl | 2-finallyl | CO$_2$Me | H | 434 |
| 94 | 3,4-difluorophenyl | 2-fluorophenyl | cyano | H | 397 |
| 95 | 3,4-difluorophenyl | 2-fluorophenyl | CO$_2$Me | H | 430 |
| 96 | 3-chloro-4-methylphenyl | 2-fluorophenyl | cyano | H | 409 |
| 97 | 3-chloro-4-methylphenyl | 2-fluorophenyl | CO$_2$Me | H | 442.5 |
| 98 | 3,4-dichlorophenyl | 3-pyridinyl | cyano | H | 412.4 |
| 99 | 4-cyano-3-(trifluoromethyl)phenyl | 2-fluorophenyl | cyano | H | 454 |
| 100 | 4-cyano-3-(trifluoromethyl)phenyl | 2-fluorophenyl | CO$_2$Me | H | 487 |
| 101 | 4-cyano-3-(trifluoromethyl)phenyl | 2-fluorophenyl | CO/Et | H | 501 |
| 102 | 3,4-dichlorophenyl | 2-fluorophenyl | CO$_2$Me | H | 463 |
| 103 | 4-chlorophenyl | 2-fluorophenyl | CHO | H | 398 |
| 104 | 4-(trifluoromethyl)-2-pyrimidinyl | 2-fluorophenyl | NHC(O)Me | H | 463.5 |
| 105 | 4-(trifluoromethoxy)phenyl | 2,6-difluorophenyl | NHC(O)Me | H | 495.5 |
| 106 | 5-(trifluoromethyl)-2-pyridinyl | 2-fluorophenyl | NHC(O)Me | H | 462.5 |
| 107 | 3,4-dichlorophenyl | 2-chlorophenyl | NHC(O)Me | H | 477 |
| 108 | 3,4-dichlorophenyl | 2-methylphenyl | NHC(O)Me | H | 457.4 |
| 109 | 3-chlorophenyl | 2-fluorophenyl | NHC(O)Me | H | 427.5 |
| 110 | 4-(methylsulfonyl)phenyl | 2-fluorophenyl | NHC(O)Me | H | 471.5 |
| 111 | 4-(trifluoromethyl)phenyl | 2-furanyl | NHC(O)Me | H | 433.4 |
| 112 | 3,4-difluorophenyl | 2-fluorophenyl | NHC(O)Me | H | 429.5 |
| 113 | 3-chloro-4-methylphenyl | 2-fluorophenyl | NHC(O)Me | H | 441.5 |
| 114 | 3,4-dichlorophenyl | 2-fluorophenyl | NHC(O)OC(Me)$_3$ | H | 519.4 |
| 115 | 3,4-dichlorophenyl | 2-(trifluoromethyl)phenyl | cyano | H | 479.4 |
| 116 | 3,4-dichlorophenyl | 2-(trifluoromethyl)phenyl | CO$_2$Me | H | 512.4 |
| 117 | 3,4-dichlorophenyl | 2-(trifluoromethyl)phenyl | NHC(O)Me | H | 511.4 |
| 118 | 3,4-dichlorophenyl | 2-thienyl | cyano | H | 417.4 |
| 119 | 3,4-dichlorophenyl | 2-thienyl | NHC(O)Me | H | 201-202° C. |
| 120 | 3,4-dichlorophenyl | 2-fluorophenyl | NH$_2$ | H | 419.5 |
| 121 | 3,4-dichlorophenyl | 2-fluorophenyl | NHC(O)CF$_3$ | H | 515 |
| 122 | 3,4-difluorophenyl | 2-fluorophenyl | CH$_2$NHC(O)Me | H | 443.5 |
| 123 | 3,4-dichlorophenyl | 2-(trifluoromethyl)phenyl | CH$_2$NHC(O)Me | H | 525.4 |
| 124 | 3,4-dichlorophenyl | 2-chlorophenyl | CH$_2$NHC(O)Me | H | 492.4 |
| 125 | 3-(trifluoromethyl)phenyl | 2-fluorophenyl | CH$_2$NHC(O)Me | H | 475.5 |
| 126 | 4-(trifluoromethoxy)phenyl | 2-fluorophenyl | CH$_2$NHC(O)Me | H | 491.5 |
| 127 | 3-chloro-4-methylphenyl | 2-fluorophenyl | CH$_2$NHC(O)Me | H | 455.5 |
| 128 | 3,4-dichlorophenyl | 5-chloro-2-thienyl | cyano | H | 451 |
| 129 | 5-(trifluoromethyl)-3-pyridinyl | 2-fluorophenyl | cyano | H | 430.5 |
| 130 | 3,4-dimethylphenyl | 2-fluorophenyl | CO$_2$Me | H | 422.5 |
| 131 | 3,4-dimethylphenyl | 2-fluorophenyl | cyano | H | 389.5 |
| 132 | 3-bromophenyl | 2-fluorophenyl | CO$_2$Me | H | 472.4 |
| 133 | 3-bromophenyl | 2-fluorophenyl | cyano | H | 439.4 |
| 134 | 4-fluorophenyl | 2-methylphenyl | cyano | H | 375.5 |

INDEX TABLE A-continued

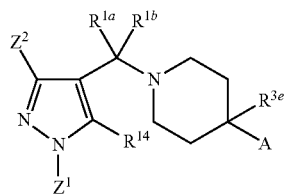

$R^{1a}$, $R^{1b}$ and $R^{14}$ are H

| Cmpd | $Z^1$ | $Z^2$ | A | $R^{3e}$ | m.p. (° C.) or AP+ (M + 1) |
|---|---|---|---|---|---|
| 135 | 3-bromophenyl | 2-fluorophenyl | C(O)NHMe | H | 471.4 |
| 136 | 3,4-difluorophenyl | 2-fluorophenyl | C(O)NHMe | H | 429.5 |
| 137 | 3-chloro-4-methylphenyl | 2-fluorophenyl | C(O)NHMe | H | 441.5 |
| 138 | 3,4-dichlorophenyl | 2-(trifluoromethyl)phenyl | C(O)NHMe | H | 511.5 |
| 500 | 4-methylphenyl | 4-fluorophenyl | C(O)N(—(CH$_2$)$_4$—) | H | |
| 505 | 2,5-dimethylphenyl | phenyl | CO$_2$Me | H | |
| 506 | 4-methylphenyl | 3-methylphenyl | OMe | H | |
| 510 | 4-chlorophenyl | 2-fluorophenyl | CH$_2$OH | H | 400 |
| 511 | 3,4-dichlorophenyl | 2-fluorophenyl | NHC(O)OC(Me)$_3$ | H | 519.4 |
| 512 | 4-fluorophenyl | 2-methylphenyl | CO$_2$Me | H | 408.4 |
| 516 | 3,4-dichlorophenyl | 5-chloropyridin-2-yl | cyano | H | 448 |
| 517 | 3-methylphenyl | 2-methylphenyl | cyano | H | 371.5 |
| 519 | 3,4-dichlorophenyl | 5-methylthiophen-2-yl | cyano | H | 431 |
| 520 | 3,4-dichlorophenyl | thiophen-2-yl | cyano | H | 417 |
| 530 | 3,4-difluorophenyl | 2-chlorophenyl | cyano | H | 413.5 |
| 531 | 3,4-difluorophenyl | 2-chlorophenyl | CO$_2$Me | H | 446.4 |
| 534 | 3,4-difluorophenyl | 2-bromophenyl | cyano | H | 457.4 |
| 535 | 3,4-difluorophenyl | 2-bromophenyl | CO$_2$Me | H | 490.4 |
| 538 | 3,4-difluorophenyl | 2-(trifluoromethyl)phenyl | cyano | H | 447.5 |
| 539 | 3,4-difluorophenyl | 2-(trifluoromethyl)phenyl | CO$_2$Me | H | 480.4 |
| 542 | 3,4-dichlorophenyl | 2,5-dichlorothiophen-3-yl | cyano | H | 487 |
| 543 | 3,4-dichlorophenyl | 2,5-dimethylthiophen-3-yl | cyano | H | 445 |
| 544 | 3,4-dichlorophenyl | 3-methylthiophen-2-yl | cyano | H | 431 |
| 546 | 4-chloro-3-fluorophenyl | 2-fluorophenyl | cyano | H | 413.5 |
| 547 | 4-chloro-3-fluorophenyl | 2-fluorophenyl | CO$_2$Me | H | 446.4 |
| 549 | 4-chloro-3-fluorophenyl | 2-fluorophenyl | NHC(O)Me | H | 445.5 |
| 550 | 4-chloro-3-fluorophenyl | 2-chlorophenyl | cyano | H | 429.4 |
| 551 | 4-chloro-3-fluorophenyl | 2-chlorophenyl | CO$_2$Me | H | 462.4 |
| 553 | 4-chloro-3-fluorophenyl | 2-fluorophenyl | NHC(O)Me | H | 461.5 |
| 556 | 4-(trifluoromethoxy)phenyl | 2-chlorophenyl | cyano | H | 461.5 |
| 557 | 4-(trifluoromethoxy)phenyl | 2-chlorophenyl | NHC(O)Me | H | 493.5 |
| 559 | 4-(trifluoromethoxy)phenyl | 2-methylphenyl | cyano | H | 441.5 |
| 560 | 4-(trifluoromethoxy)phenyl | 2-methylphenyl | NHC(O)Me | H | 473.5 |
| 562 | 4-(trifluoromethoxy)phenyl | 2-methylphenyl | CO$_2$Me | H | 474.5 |
| 563 | 4-(trifluoromethoxy)phenyl | 2-(trifluoromethyl)phenyl | cyano | H | 495.5 |
| 565 | 2-thienyl | 2-fluorophenyl | CO$_2$Me | H | 400.2 |
| 566 | 3,4-dichlorophenyl | 2-fluoropyridin-3-yl | cyano | H | 430 |
| 567 | 4-methylphenyl | 2-fluorophenyl | cyano | H | 375.5 |
| 568 | 4-methylphenyl | 2-fluorophenyl | NHC(O)Me | H | 407.6 |
| 570 | 4-methylphenyl | 2-fluorophenyl | CO$_2$Me | H | 408.5 |
| 571 | 4-methylphenyl | 2-methylphenyl | cyano | H | 371.6 |
| 572 | 4-fluorophenyl | 2-fluorophenyl | cyano | H | 379.5 |
| 573 | 4-fluorophenyl | 2-fluorophenyl | NHC(O)Me | H | 411.5 |
| 575 | 4-fluorophenyl | 2-fluorophenyl | CO$_2$Me | H | 412.5 |
| 576 | 3,4-difluorophenyl | 2-fluorophenyl | OH | H | 388.5 |
| 577 | 3-chloro-4-fluorophenyl | 4-fluorophenyl | cyano | H | 413.4 |
| 579 | 3-chloro-4-fluorophenyl | 4-chlorophenyl | cyano | H | 429.4 |
| 581 | 3-chloro-4-fluorophenyl | 2,6-difluorophenyl | cyano | H | 431.4 |
| 583 | 3-chloro-4-fluorophenyl | 2,4-difluorophenyl | cyano | H | 431.4 |
| 585 | 3-chloro-4-fluorophenyl | 2-fluorophenyl | Cl | H | 422.4 |
| 586 | 3-chloro-4-fluorophenyl | 2-fluorophenyl | F | H | 406.4 |
| 587 | 4-chloro-2-fluorophenyl | 2-fluorophenyl | cyano | H | 390.4 |
| 591 | 3-chloro-2-fluorophenyl | 2-fluorophenyl | cyano | H | 413.4 |
| 594 | 3-chloro4-fluorophenyl | 2-fluorophenyl | C(S)NH$_2$ | H | 447.4 |
| 597 | 3-chloro-4-fluorophenyl | 2-fluorophenyl | OH | H | 404.4 |
| 602 | 4-chlorophenyl | 2,4,6-trifluorophenyl | cyano | H | 431.4 |
| 604 | 4-chlorophenyl | 2-chloro-4-fluorophenyl | cyano | H | 429.4 |
| 606 | 4-chlorophenyl | 3-chloro-5-fluorophenyl | cyano | H | 429.4 |

INDEX TABLE A-continued

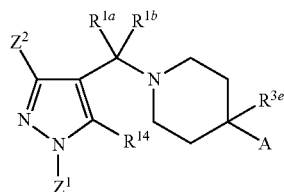

$R^{1a}$, $R^{1b}$ and $R^{14}$ are H

| Cmpd | $Z^1$ | $Z^2$ | A | $R^{3e}$ | m.p. (° C.) or AP+ (M + 1) |
|---|---|---|---|---|---|
| 609 | 5-bromopyrinidin-2-yl | 2-fluorophenyl | cyano | H | 443.1 |
| 610 | 2-thiophen-2-yl | 2-fluorophenyl | cyano | H | 367.1 |
| 613 | 5-bromopyridin-2-yl | 2-fluorophenyl | cyano | H | 440.4 |
| 615 | 4-chloro-2-methylphenyl | 2-fluorophenyl | cyano | H | 409.5 |
| 617 | 3-chloro-4-fluorophenyl | 2,4-difluorophenyl | cyano | $CO_2Me$ | 489.4 |
| 618 | 4-chloro-3-fluorophenyl | 2-fluorophenyl | cyano | $CO_2Me$ | 471.4 |
| 626 | 4-chlorophenyl | 2-fluorophenyl | NHC(O)Me | $C(O)NHC(Me)_3$ | 526.5 |
| 627 | 4-chlorophenyl | 2-fluorophenyl | NHC(O)Me | $C(O)NH_2$ | 470.5 |
| 629 | 4-chlorophenyl | 2,4-difluorophenyl | cyano | H | 413.5 |
| 632 | 4-chloro-3-(trifluoromethyl)phenyl | 2-fluorophenyl | cyano | H | 463.4 |
| 633 | 4-chlorophenyl | 2,4-difluorophenyl | N(Me)C(O)Me | H | 459.5 |
| 634 | 4-chlorophenyl | 2-fluorophenyl | N(Me)C(O)Me | H | 441.5 |
| 641 | 4-chlorophenyl | 2-fluorophenyl | $SO_2CH_3$ | H | 448 |
| 643 | 4-chlorophenyl | 2,4-difluorophenyl | cyano | NHC(O)Me | 470.4 |
| 644 | 4-chlorophenyl | 2,4-difluorophenyl | NHC(O)Me | $C(O)NH_2$ | 488.4 |
| 645 | 4-chlorophenyl | 2-fluorophenyl | cyano | NHC(O)Me | 452.4 |
| 646 | 3-chloro-4-fluorophenyl | 2,4-difluorophenyl | NHC(O)Me | $C(O)NH_2$ | 506.4 |
| 647 | 3-chloro-4-fluorophenyl | 2,4-difluorophenyl | cyano | NHC(O)Me | 488.4 |
| 648 | 4-(trifluoromethoxy)phenyl | 2,4-difluorophenyl | cyano | NHC(O)Me | 520.4 |
| 649 | 4-(trifluoromethoxy)phenyl | 2,4-difluorophenyl | NHC(O)Me | $C(O)NH_2$ | 538.5 |
| 650 | 2,4-difluorophenyl | 2,4-difluorophenyl | cyano | H | 415.4 |
| 652 | 5-chloromidin-2-yl | 2,4-difluorophenyl | cyano | H | 414.4 |
| 654 | 5-(trifluoromethyl)pyridine-2-yl | 2-fluorophenyl | cyano | H | 430.5 |
| 663 | 4-chlorophenyl | 2,4-difluorophenyl | 1H-imidazol-2-yl | H | 454.4 |
| 664 | 5-chloropyridin-2-yl | 2,4-difluorophenyl | 1H-imidazol-2-yl | H | 455.4 |
| 667 | 4-chlorophenyl | 2-fluorophenyl | 1H-imidazol-2-yl | H | 436.5 |
| 674 | 2-benzotriazolyl | 2-fluorophenyl | NHC(O)Me | H | 450.4 |
| 676 | 2-benzotriazolyl | 2-fluorophenyl | cyano | H | 418.4 |
| 677 | 4-chlorophenyl | 2-fluorophenyl | OH | H | 386.4 |
| 678 | 4-chlorophenyl | 2-fluorophenyl | OC(O)Me | H | 428.4 |
| 679 | 4-chlorophenyl | 2-fluorophenyl | COOH | H | 414 |
| 680 | 4-chlorophenyl | 2-fluorophenyl | C(O)NHNHC(O)Me | H | 470 |
| 681 | 4-chlorophenyl | 2-fluorophenyl | C(O)NHNHC(O)OEt | H | 500 |
| 686 | 4-(trifluoromethoxy)phenyl | 2-fluorophenyl | $NHC(O)OC(Me)_3$ | H | 535.1 |
| 690 | 4-(trifluoromethoxy)phenyl | 2-fluorophenyl | $NHSO_2Me$ | H | 513 |
| 691 | 4-(trifluoromethoxy)phenyl | 2-fluorophenyl | $NHC(O)CF_3$ | H | 531 |
| 692 | 4-(trifluoromethoxy)phenyl | 2-fluorophenyl | NHCHO | H | 463.1 |
| 693 | 4-bromophenyl | 2-fluorophenyl | $CH(OH)CH_3$ | H | 414 |
| 694 | 3-chloro-4-fluorophenyl | 2-fluorophenyl | 1,2,4-triazol-1-yl | H | 455.4 |
| 695 | 4-chlorophenyl | 2-fluorophenyl | 1,2,4-triazol-1-yl | H | 437.4 |
| 696 | 4-(trifluoromethoxy)phenyl | 2,4-difluorophenyl | 1,2,4-triazol-1-yl | H | 505.4 |
| 697 | 3-chloro-4-fluorophenyl | 2-fluorophenyl | imidazol-1-yl | H | 454.4 |
| 698 | 4-chlorophenyl | 2-fluorophenyl | imidazol-1-yl | H | 436.4 |
| 699 | 3,4-difluorophenyl | 2-chlorophenyl | imidazol-1-yl | H | 454.4 |
| 700 | 3-chloro-4-fluorophenyl | 2-fluorophenyl | $CH_2N(Me)_2$ | H | 445.2 |
| 702 | 3-chloro-4-fluorophenyl | 2-fluorophenyl | $N(Me)_2$ | H | 431.31 |
| 704 | 3-chloro-4-fluorophenyl | 2-fluorophenyl | $NHC(O)NH_2$ | H | 196-198° C. |
| 706 | 3,4-dichlorophenyl | 2-fluorophenyl | $NHC(O)NH_2$ | H | 214-216° C. |
| 707 | 3,4-dichlorophenyl | 2-fluorophenyl | $CH_2N(Me)_2$ | H | 460.97 |
| 708 | 3,4-dichlorophenyl | 2-fluorophenyl | $N(Me)_2$ | H | 447.1 |
| 710 | 3-chloro-4-fluorophenyl | 2-fluorophenyl | cyano | cyano | 438.3 |
| 717 | 4-chlorophenyl | 2-fluorophenyl | $CH_2Br$ | H | 463 |
| 718 | 4-chlorophenyl | 2-fluorophenyl | $CH_2OCH_3$ | H | 415 |
| 719 | 4-chlorophenyl | 2-fluorophenyl | $C(O)NHNH_2$ | H | 428.4 |
| 720 | 4-chlorophenyl | 2-fluorophenyl | 1,3,4-oxadiazol-2-yl | H | 438.3 |
| 721 | 4-chlorophenyl | 2-fluorophenyl | 5-methyl-1,3,4-oxadiazol-2-yl | H | 452.4 |
| 727 | 4-chlorophenyl | 2-fluorophenyl | 5-$CF_3$-pyrazol-1-yl | H | 518 |
| 729 | 2,3,4-trifluorophenyl | 2-fluorophenyl | NHC(O)Me | H | 505.2 |
| 730 | 2,3,4-trifluorophenyl | 2-fluorophenyl | cyano | H | 415.3 |
| 736 | 4-(trifluoromethoxy)phenyl | 2,4-difluorophenyl | 1,2,4-triazol-4-yl | H | 505.3 |
| 737 | 3-chloro-4-fluorophenyl | 2-fluorophenyl | 1,2,4-triazol-4-yl | H | 455.3 |

INDEX TABLE A-continued

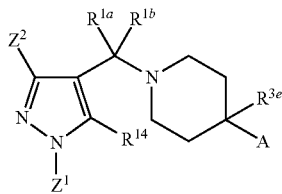

$R^{1a}$, $R^{1b}$ and $R^{14}$ are H

| Cmpd | $Z^1$ | $Z^2$ | A | $R^{3e}$ | m.p. (° C.) or AP+ (M + 1) |
|---|---|---|---|---|---|
| 738 | 4-chlorophenyl | 2,4,6-trifluorophenyl | 1,2,4-triazol-4-yl | H | 473.3 |
| 742 | 4-chlorophenyl | 2-fluorophenyl | 3-CH$_3$-1,2,4-oxadiazol-5-yl | H | 452.4 |
| 743 | 4-chlorophenyl | 2-fluorophenyl | 2-oxo-1,3-oxazolidin-3-yl | H | 455.3 |
| 744 | 3-chloro-4-fluorophenyl | 2-fluorophenyl | 2-oxo-1,3-oxazolidin-3-yl | H | 473.4 |
| 745 | 4-chlorophenyl | 2,4,6-trifluorophenyl | 2-oxo-1,3-oxazolidin-3-yl | H | 491.4 |
| 746 | 4-chlorophenyl | 2-fluorophenyl | pyridin-4-yl | H | 446.7 |
| 747 | 3-chloro-4-fluorophenyl | 2-fluorophenyl | pyridin-4-yl | H | 464.6 |
| 748 | 4-chlorophenyl | 2,4,6-trifluorophenyl | pyridin-4-yl | H | 483 |
| 755 | 4-chlorophenyl | phenyl | cyano | H | 377.3 |
| 765 | 4-chlorophenyl | 2-cyanophenyl | cyano | H | 402.4 |
| 767 | 4-bromophenyl | 2-fluorophenyl | C(O)NH$_2$ | H | 474.3 |
| 768 | 4-bromophenyl | 2-fluorophenyl | 1,3,4-oxadiazol-2-yl | H | 484.3 |
| 769 | 4-bromophenyl | 2-fluorophenyl | 5-methyl-1,3,4-oxadiazol-2-yl | H | 498.3 |
| 770 | 4-bromophenyl | 2,4,6-trifluorophenyl | cyano | H | 475.2 |
| 771 | 4-bromophenyl | 2,4-difluorophenyl | cyano | H | 457.2 |
| 772 | 4-chlorophenyl | phenyl | CO$_2$Me | H | 410.4 |
| 773 | 4-bromophenyl | 2,4-difluorophenyl | CO$_2$Me | H | 490.2 |
| 774 | 4-bromophenyl | 2,4,6-triffuorophenyl | CO$_2$Me | H | 508.3 |
| 778 | 2'-fluoro[1,1'-biphenyl]-4-yl | 2,4,6-trifluorophenyl | cyano | H | 491.4 |
| 779 | 3'-fluoro[1,1'-biphenyl]-4-yl | 2,4,6-trifluorophenyl | cyano | H | 491.3 |
| 780 | 4'-fluoro[1,1'-biphenyl]-4-yl | 2,4,6-trifluorophenyl | cyano | H | 491.3 |
| 784 | 2'-fluoro[1,1'-biphenyl]-4-yl | 2,4-difluorophenyl | cyano | H | 473.4 |
| 785 | 3'-fluoro[1,1'-biphenyl]-4-yl | 2,4-difluorophenyl | cyano | H | 473.4 |
| 786 | 4'-fluoro[1,1'-biphenyl]-4-yl | 2,4-difluorophenyl | cyano | H | 473.4 |
| 787 | 4-chlorophenyl | phenyl | C(O)NHNH$_2$ | H | 410.4 |
| 788 | 4-bromophenyl | 2,4-difluorophenyl | C(O)NHNH$_2$ | H | 492.2 |
| 789 | 3-chloro-4-fluorophenyl | 2-fluorophenyl | C(O)NHNH$_2$ | H | 446.3 |
| 790 | 4-(trifluoromethoxy)phenyl | 2-fluorophenyl | C(O)NHNH$_2$ | H | 478.3 |
| 791 | 3,4-dichlorophenyl | 2-fluorophenyl | C(O)NHNH$_2$ | H | 462.3 |
| 792 | 4-chlorophenyl | phenyl | 5-oxo-1,3,4-oxadiazol-2-yl | H | 436.3 |
| 793 | 4-chlorophenyl | 2,4,6-trifluorophenyl | 5-oxo-1,3,4-oxadiazol-2-yl | H | 490.2 |
| 794 | 5-chloropyridin-2-yl | 2,4-difluorophenyl | 5-oxo-1,3,4-oxadiazol-2-yl | H | 473.3 |
| 795 | 4-chlorophenyl | 2-fluorophenyl | 5-oxo-1,3,4-oxadiazol-2-yl | H | 454.3 |
| 798 | 4-chlorophenyl | phenyl | 1,3,4-oxadiazol-2-yl | H | 420.3 |
| 799 | 4-bromophenyl | 2,4-difluorophenyl | 1,3,4-oxadiazol-2-yl | H | 502.3 |
| 800 | 3-chloro-fluorophenyl | 2-fluorophenyl | 1,3,4-oxadiazol-2-yl | H | 456.3 |
| 801 | 4-(trifluoromethoxy)phenyl | 2-fluorophenyl | 1,3,4-oxadiazol-2-yl | H | 488.3 |
| 802 | 3,4-dichlorophenyl | 2-fluorophenyl | 1,3,4-oxadiazol-2-yl | H | 472.3 |
| 803 | 4-(trifluoromethoxy)phenyl | 2,6-difluorophenyl | 1,3,4-oxadiazol-2-yl | H | 506.4 |
| 804 | 3-bromophenyl | 2-fluorophenyl | 1,3,4-oxadiazol-2-yl | H | 484.2 |
| 805 | 3-(triflyuoromethyl)phenyl | 2-fluorophenyl | 1,3,4-oxadiazol-2-yl | H | 472.4 |
| 806 | 5-chloropyridin-2-yl | 2,4,6-trifluorophenyl | cyano | H | 432.2 |
| 807 | 5-chloropyridin-2-yl | 2-fluorophenyl | cyano | H | 396.4 |
| 808 | 4-isopropylphenyl | 2-fluorophenyl | cyano | H | 403.5 |
| 809 | 4-chlorophenyl | phenyl | cyano | H | 376.4 |
| 810 | 4-chlorophenyl | 2,4,6-trifluorophenyl | cyano | H | 430.3 |
| 811 | 4-bromophenyl | 2,4,6-trifluorophenyl | cyano | H | 474.2 |
| 812 | 4-chlorophenyl | pyridin-2-yl | cyano | H | 378.4 |
| 814 | 4-chlorophenyl | pyridin-2-yl | NHC(O)Me | H | 410.4 |
| 815 | quinolin-2-yl | 2-fluorophenyl | cyano | H | 412.4 |
| 816 | quinolin-2-yl | 2,4-difluorophenyl | cyano | H | 430.4 |
| 817 | 3'-(trifluoromethyl)[1,1'-biphenyl]-3-yl | 2-fluorophenyl | cyano | H | 505.8 |
| 818 | 2'-(trifluoromethyl)[1,1'-biphenyl]-3-yl | 2-fluorophenyl | cyano | H | 505.3 |

INDEX TABLE A-continued

*Structure: pyrazole ring with Z² at 3-position, Z¹ on N1, R¹⁴ at 5-position, connected via C(R¹ᵃ)(R¹ᵇ) to N of piperidine bearing R³ᵉ and A at 4-position*

R¹ᵃ, R¹ᵇ and R¹⁴ are H

| Cmpd | Z¹ | Z² | A | R³ᵉ | m.p. (° C.) or AP+ (M + 1) |
|---|---|---|---|---|---|
| 819 | 4'-(trifluoromethyl)[1,1'-biphenyl]-3-yl | 2-fluorophenyl | cyano | H | 505.2 |
| 822 | 4-chlorophenyl | 2-fluorophenyl | 1,3-oxazol-5-yl | H | 437.4 |
| 823 | 4-chlorophenyl | 2-fluorophenyl | 4,5-dihydro-1,3-oxazol-2-yl | H | 439.4 |
| 824 | 3,5-difluorophenyl | 2,4,6-trifluorophenyl | cyano | H | 433.3 |
| 825 | 4-chlorophenyl | 2,4-difluorophenyl | CO₂Me | Me | 460.4 |
| 826 | 5-chloropyridin-2-yl | 2,4-difluorophenyl | CO₂Me | Me | 461.4 |
| 827 | 4-chlorophenyl | pyridin-2-yl | 1,2,4-oxadiazol-3-yl | H | 421.4 |
| 828 | 4-bromophenyl | 2,4,6-trifluorophenyl | 1,2,4-oxadiazol-3-yl | H | 518.4 |
| 829 | 5-chloropyridin-2-yl | 2-fluorophenyl | 1,2,4-oxadiazol-3-yl |  | 439.4 |
| 830 | 4-chlorophenyl | 2-fluorophenyl | 1,2,4-oxadiazol-3-yl |  | 438.4 |
| 831 | 4-chlorophenyl | 2-fluorophenyl | 1,2,4-triazol-3-yl | H | 437.4 |
| 832 | 4-chlorophenyl | 2-fluorophenyl | C(O)CH₃ | H | 412.4 |
| 834 | 4-chlorophenyl | 2-fluorophenyl | 4-methyl-4H-1,2,4-triazol-3-yl | H | 451.4 |
| 835 | 5-chloropyridin-2-yl | 2,4-difluorophenyl | 4-methyl-4H-1,2,4-triazol-3-yl | H | 470.4 |
| 836 | 4-bromophenyl | 2,4,6-trifluorophenyl | 4-methyl-4H-1,2,4-triazol-3-yl | H | 531.3 |
| 837 | 3-chloro-4-fluorophenyl | 2,6-difluorophenyl | 4-methyl-4H-1,2,4-triazol-3-yl | H | 487.3 |
| 838 | 4-chlorophenyl | 2-fluorophenyl | 1H-tetrazol-5-yl | H | 438.3 |
| 839 | 5-chloromidin-2-yl | 2,4-difluorophenyl | 1H-tetrazol-5-yl | H | 457.4 |
| 840 | 4-bromophenyl | 2,4,6-trifluorophenyl | 1H-tetrazol-5-yl | H | 518.3 |
| 841 | 3-chloro-4-fluorophenyl | 2,6-difluorophenyl | 1H-tetrazol-5-yl | H | 474.3 |
| 846 | 4-chlorophenyl | 2,3,4,5,6-tetrafluorophenyl | cyano | H | 467.3 |
| 847 | 4-chlorophenyl | 2-bromo-4-fluorophenyl | cyano | H | 473.2 |
| 848 | 4-chlorophenyl | 2,3-difluorophenyl | cyano | H | 413.3 |
| 849 | 4-chlorophenyl | 2,4,5-trifluorophenyl | cyano | H | 431.3 |
| 850 | 4-chlorophenyl | 5-chloro-2-methoxyphenyl | cyano | H | 441.3 |
| 851 | 4-chlorophenyl | 2-chloro-6-fluorophenyl | cyano | H | 429.3 |
| 852 | 4-chlorophenyl | 5-fluoro-2-methoxyphenyl | cyano | H | 425.4 |
| 851 | 4-chlorophenyl | 2,5-difluorophenyl | cyano | H | 413.3 |
| 854 | 4-chlorophenyl | 2,6-difluoro-3-methylphenyl | cyano | H | 427.3 |
| 855 | 4-chlorophenyl | 2,3,6-trifluorophenyl | cyano | H | 431.3 |
| 856 | 4-chlorophenyl | 4-fluoro-2-methoxyphenyl | cyano | H | 425.4 |
| 857 | quinoxalin-2-yl | 2-fluorophenyl | cyano | H | 413.4 |
| 858 | quinolin-6-yl | 2-fluorophenyl | cyano | H | 412.4 |
| 860 | 4-chlorophenyl | 2-fluorophenyl | thiazol-2-yl | H | 453 |
| 861 | 4-chlorophenyl | 2-fluorophenyl | isoxazol-5-yl | H | 437.4 |
| 862 | 3,4-dichlorophenyl | 2-fluorophenyl | isoxazol-5-yl | H | 471.3 |
| 863 | 3,5-dichloropyridin-2-yl | 4-fluorophenyl | cyano | H | 430.3 |
| 864 | 2,3-dibromopyridin-5-yl | 4-fluorophenyl | cyano | H | 520.2 |
| 865 | 4-phenoxyphenyl | 2-fluorophenyl | cyano | H | 453.5 |
| 866 | 4-(4-chlorophenoxy)phenyl | 2-fluorophenyl | cyano | H | 487.4 |
| 867 | 5-chloro-3-fluoropyridin-2-yl | 2-fluorophenyl | cyano | H | 414.4 |
| 868 | 5-chloropyridin-2-yl | 2-fluorophenyl | 1,3,4-oxadiazol-2-yl | H | 439.4 |
| 877 | 4-(2,2,2-trifluoroethoxy)phenyl | 2-fluorophenyl | cyano | H | 459.4 |
| 878 | 6-chloropyridin-2-yl | 2-fluorophenyl | cyano | H | 396.4 |
| 879 | 5-chloropyridin-2-yl | 2,4,6-trifluorophenyl | pyrimidin-2-yl | H | 485.4 |
| 880 | 4-chlorophenyl | 2,4,6-trifluorophenyl | pyrimidin-2-yl | H | 484.4 |
| 881 | 5-bromopyridin-2-yl | 2-fluorophenyl | pyrimidin-2-yl | H | 493.4 |
| 882 | 5-chloro-6-fluoropyridin-2-yl | 2-fluorophenyl | cyano | H | 414.4 |
| 883 | 5-bromo-6-fluoropyridin-2-yl | 2,4,6-trifluorophenyl | cyano | H | 494.3 |
| 884 | 1,3-benzodioxol-5-yl | 2-fluorophenyl | cyano | H | 405.2 |
| 885 | 4-chlorophenyl | 2-fluorophenyl | pyrimidin-5-yl | H | 448.5 |

INDEX TABLE A-continued

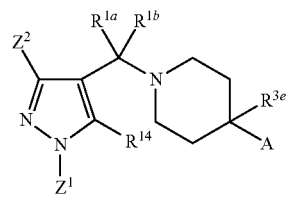

$R^{1a}$, $R^{1b}$ and $R^{14}$ are H

| Cmpd | $Z^1$ | $Z^2$ | A | $R^{3e}$ | m.p. (° C.) or AP+ (M + 1) |
|---|---|---|---|---|---|
| 886 | 4-chlorophenyl | 2-methoxyphenyl | cyano | H | 407.3 |
| 887 | 2-chloropyridin-4-yl | 2,4,6-trifluoronhenyl | cyano | H | 432.4 |
| 888 | 4-chlorophenyl | 2-fluoro-4-methoxyphenyl | cyano | H | 425.4 |
| 889 | 4-chlorophenyl | 2,6-difluoro-4-methoxyphenyl | cyano | H | 443.4 |
| 890 | 4-chlorophenyl | 4-methoxyphenyl | cyano | H | 407.2 |
| 891 | 5-chloropyridin-2-yl | 2,6-difluorophenyl | cyano | H | 414 |
| 893 | 5-bromopyridin-2-yl | 2,6-difluorophenyl | cyano | H | 458.4 |
| 895 | 5-chloropyridin-2-yl | 4-fluorophenyl | cyano | H | 396.2 |
| 897 | 5-bromopyridin-2-yl | 4-fluorophenyl | cyano | H | 440.4 |
| 899 | 5-bromopyridin-2-yl | 2,4,6-trifluorophenyl | cyano | H | 476.4 |
| 904 | 3,4-dichlorophenyl | phenyl | cyano | H | 411.4 |
| 905 | 5-fluoropyridin-2-yl | 4-fluorophenyl | cyano | H | 380.3 |
| 907 | 3,4-dichlorophenyl | 4-fluorophenyl | NHC(O)Me | H | 461.5 |
| 908 | 3,4-dichlorophenyl | phenyl | NHC(O)Me | H | 443.4 |
| 909 | 5-chloropyridin-2-yl | 4-fluorophenyl | NHC(O)Me | H | 428.5 |
| 924 | 3-chloro-4-fluorophenyl | 2,4,6-trifluorophenyl | cyano | H | 449.5 |
| 927 | 4-(trifluoromethyl)pyridin-2-yl | 4-fluorophenyl | cyano | H | 430.5 |
| 928 | 4-(trifluoromethyl)pyridin-2-yl | 4-fluorophenyl | NHC(O)Me | H | 462.5 |
| 930 | 6-(trifluoromethyl)pyridin-2-yl | 4-fluorophenyl | cyano | H | 430.4 |
| 932 | 3-(chloro-4-fluorophenyl | 2,4,6-trifluorophenyl | $CO_2Me$ | H | 482.5 |
| 933 | 3,4-dichlorophenyl | 1H-1,2,3-triazol-4-yl | cyano | H | 402.1 |
| 937 | 3-chloro-4-fluorophenyl | 2,4,6-trifluorophenyl | 1,3,4-oxadiazol-2-yl | H | 492.5 |
| 938 | 3,4-dichlorophenyl | 4-fluorophenyl | 1,3,4-oxadiazol-2-yl | H | 472.5 |
| 939 | 6-chloropyridin-2-yl | 4-fluorophenyl | cyano | H | 396.5 |
| 941 | 6-chloropyridin-2-yl | 4-fluorophenyl | NHC(O)Me | H | 438.5 |

\# See Index Table F for $^1$H NMR data.
*1-BZT means 1-benzotriazole

INDEX TABLE A

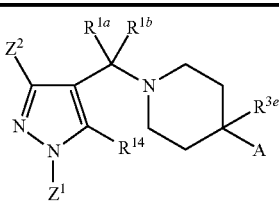

$R^{1a}$ and $R^{14}$ are H

| Cmpd | $Z^1$ | $Z^2$ | $R^{1b}$ | A | $R^{3e}$ | m.p. (° C.) or AP+ (M + 1) |
|---|---|---|---|---|---|---|
| 545 | 3-(trifluoromethyl)phenyl | 2-fluorophenyl | cyano | NHC(O)Me | H | 193-195° C. |
| 590 | 3-(trifluoromethyl)phenyl | 4-fluorophenyl | cyano | CN | H | 127-429° C. |
| 635 | 3-(trifluoromethyl)phenyl | 4-fluorophenyl | Me | NHC(O)Me | H | 185-187° C. |
| 636 | 3-(trifluoromethyl)phenyl | 2-fluorophenyl | Me | $CO_2Me$ | H | 124-125° C. |
| 655 | 3-(trifluoromethyl)phenyl | 2-fluorophenyl | Me | CN | H | 95-97° C. |
| 656 | 3-(trifluoromethyl)phenyl | 4-fluorophenyl | Me | $CO_2Me$ | H | 165-166° C. |
| 658 | 3-(trifluoromethyl)phenyl | 4-fluorophenyl | Me | CN | H | 157-160° C. |
| 659 | 3-(trifluoromethyl)phenyl | 2-fluorophenyl | Me | NHC(O)Me | H | 110-113 ° C. |
| 701 | 3-chloro-4-fluorophenyl | 2-fluorophenyl | Me | CN | H | 264-268 ° C. |
| 703 | 3-chloro-4-fluorophenyl | 2-fluorophenyl | Me | NHC(O)Me | H | 459.2 |
| 709 | 3-chloro-4-fluorophenyl | 2-fluorophenyl | Me | $CO_2Me$ | H | 460.2 |

INDEX TABLE A2

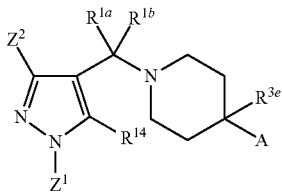

$R^{1a}$ and $R^{1b}$ are H

| Cmpd | $Z^1$ | $Z^2$ | $R^{14}$ | A | $R^{3e}$ | AP+ (M + 1) |
|---|---|---|---|---|---|---|
| 739 | 4-chlorophenyl | 2-fluorophenyl | Cl | $CO_2Me$ | H | 462.3 |
| 740 | 4-chlorophenyl | 2-fluorophenyl | Cl | cyano | H | 429.3 |
| 741 | 4-chlorophenyl | 2-fluorophenyl | Cl | NHC(O)Me | H | 461.3 |
| 759 | 4-chlorophenyl | 2-fluorophenyl | F | $CO_2Me$ | H | 446.3 |
| 760 | 4-chlorophenyl | 2-fluorophenyl | F | cyano | H | 413.3 |

INDEX TABLE A2-continued

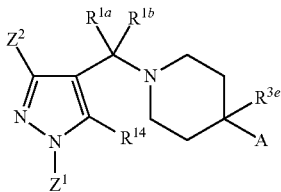

$R^{1a}$ and $R^{1b}$ are H

| Cmpd | $Z^1$ | $Z^2$ | $R^{14}$ | A | $R^{3e}$ | AP+ (M + 1) |
|---|---|---|---|---|---|---|
| 761 | 4-chlorophenyl | 2-fluorophenyl | F | NHC(O)Me | H | 445.3 |
| 762 | 4-chlorophenyl | 2-fluorophenyl | OMe | $CO_2Me$ | H | 458.3 |
| 763 | 4-chlorophenyl | 2-fluorophenyl | OMe | cyano | H | 425.3 |
| 764 | 4-chlorophenyl | 2-fluorophenyl | OMe | NHC(O)Me | H | 457.3 |

INDEX TABLE B

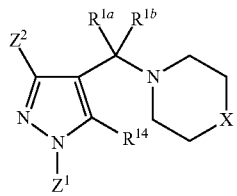

$R^{1a}$, $R^{1b}$ and $R^{14}$ are H

| Cmpd | $Z^1$ | $Z^2$ | X | AP+ (M + 1) |
|---|---|---|---|---|
| 201 | 3-methylphenyl | 3-fluorophenyl | $NCH_2C(O)NMe2$ | |
| 202 | 3-chlorophenyl | 2-fluorophenyl | $NCO_2Et$ | 443.5 |
| 203 | 3,4-dichlorophenyl | 2-fluorophenyl | $NCO_2Et$ | 477.4 |
| 204 | 3,4-dichlorophenyl | 3-fluorophenyl | $NCO_2Et$ | 477.4 |
| 205 | 3,5-bis(trifluoromethyl)phenyl | 4-fluorophenyl | $NCO_2Et$ | 545.5 |
| 206 | 3,5-dichlorophenyl | 4-fluorophenyl | $NCO_2Et$ | 477.4 |
| 207 | 2-fluorophenyl | 2-fluorophenyl | $NCO_2Et$ | 427.5 |
| 208 | 3-fluorophenyl | 2-fluorophenyl | $NCO_2Et$ | 427.5 |
| 209 | 3-chloro-4-fluorophenyl | 2-fluorophenyl | $NCO_2Et$ | 461.4 |
| 210 | 4-(trifluoromethoxy)phenyl | 2-fluorophenyl | N(2-pyrimidinyl) | 499.5 |
| 211 | 4-(trifluoromethoxy)phenyl | 2-fluorophenyl | O | 422.5 |
| 212 | 2,4-difluorophenyl | 2-methylphenyl | $CHC(O)NH_2$ | 411.5 |
| 213 | 4-cyano-3-(trifluoromethyl)phenyl | 2-fluorophenyl | $NCO_2Et$ | 502.5 |
| 214 | 4-cyano-3-(trifluoromethyl)phenyl | 2-fluorophenyl | $SO_2$ | 479 |
| 215 | 3,4-dichlorophenyl | 2-(trifluoromethyl)phenyl | NC(O)Me | 497.4 |
| 216 | 3,4-dimethylphenyl | 2-fluorophenyl | O | 366.5 |
| 217 | 3-bromophenyl | 2-fluorophenyl | O | 416.4 |
| 218 | 4-fluorophenyl | 2-methylphenyl | O | 352.5 |
| 219 | 3-(trifluoromethyl)phenyl | 2-fluorophenyl | O | 406.4 |
| 220 | 3,4-dichlorophenyl | 2-fluorophenyl | NC(O)Me | 447.4 |
| 501 | 3-chlorophenyl | 2-fluorophenyl | $C(—OCH_2CH_2O—)$ | 429.7 |
| 502 | 3-chlorophenyl | 3-fluorophenyl | $C(—OCH_2CH_2O—)$ | 429.7 |
| 503 | 3-chlorophenyl | 4-fluorophenyl | $C(—OCH_2CH_2O—)$ | 428.7 |
| 504 | 4-(trifluoromethoxy)phenyl | 2-fluorophenyl | $C(—OC(O)NHCH_2—)$ | 492.2 |
| 525 | 3,4-dichlorophenyl | 2-fluorophenyl | O | 406.4 |
| 526 | 3,4-dichlorophenyl | 2-chlorophenyl | O | 422.3 |
| 527 | 3,4-dichlorophenyl | 2-methylphenyl | O | 402.4 |
| 528 | 3,4-dichlorophenyl | 2-(trifluoromethyl)phenyl | O | 456.4 |
| 532 | 3,4-difluororophenyl | 2-chlorophenyl | O | 390.4 |
| 533 | 3,4-difluororophenyl | 2-chlorophenyl | S | 406.4 |
| 536 | 3,4-difluororophenyl | 2-bromophenyl | O | 434.4 |
| 537 | 3,4-difluororophenyl | 2-bromophenyl | S | 450.4 |
| 540 | 3,4-difluororophenyl | 2-(trifluoromethyl)phenyl | O | 424.5 |
| 541 | 3,4-difluororophenyl | 2-(trifluoromethyl)phenyl | S | 440.5 |
| 548 | 4-chloro-3-fluorophenyl | 2-fluorophenyl | O | 390.4 |
| 552 | 4-chloro-3-fluorophenyl | 2-chlorophenyl | O | 406.4 |
| 554 | 4-chloro-3-fluorophenyl | 2-chlorophenyl | NC(O)Me | 447.4 |
| 555 | 3-chloro-4-fluorophenyl | 2-fluorophenyl | O | 390.1 |
| 558 | 4-(trifluoromethoxy)phenyl | 2-chlorophenyl | O | 438.4 |
| 561 | 4-(trifluoromethoxy)phenyl | 2-methylphenyl | O | 418.5 |
| 569 | 4-methylphenyl | 2-fluorophenyl | O | 352.5 |

INDEX TABLE B-continued

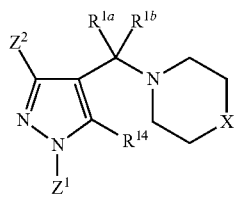

$R^{1a}$, $R^{1b}$ and $R^{14}$ are H

| Cmpd | $Z^1$ | $Z^2$ | X | AP+ (M + 1) |
|---|---|---|---|---|
| 574 | 4-fluorophenyl | 2-fluorophenyl | O | 356.5 |
| 578 | 3-chloro-4-fluorophenyl | 4-fluorophenyl | O | 390.4 |
| 580 | 3-chloro-4-fluorophenyl | 4-chlorophenyl | O | 406.4 |
| 582 | 3-chloro-4-fluorophenyl | 2,6-difluorophenyl | O | 408.4 |
| 584 | 3-chloro-4-fluorophenyl | 2,4-difluorophenyl | O | 408.4 |
| 588 | 4-chloro-2-fluorophenyl | 2-fluorophenyl | O | 390.4 |
| 593 | 3-chloro-2-fluorophenyl | 2-fluorophenyl | O | 390.4 |
| 595 | 3-chloro-4-fluorophenyl | 2-fluorophenyl | NC(O)OC(Me)$_3$ | 489.5 |
| 596 | 3-chloro-4-fluorophenyl | 2-fluorophenyl | NCN | 414.4 |
| 598 | 4-chlorophenyl | 2-fluorophenyl | C(—OC(O)CH$_2$CH$_2$—) | 440 |
| 599 | 3,4-dichlorophenyl | 2-fluorophenyl | C(—OC(O)NHCH$_2$—) | 476 |
| 600 | 3,4-dichlorophenyl | 2-fluorophenyl | C(—CH$_2$C(O)NHCH$_2$—) | 474 |
| 601 | 3,4-dichlorophenyl | 2-fluorophenyl | C(—OC(O)CH$_2$CH$_2$—) | 475 |
| 603 | 4-chlorophenyl | 2,4,6-trifluorophenyl | O | 408.4 |
| 605 | 4-chlorophenyl | 2-chloro-4-fluorophenyl | O | 406.4 |
| 607 | 4-chlorophenyl | 4-chloro-2-fluorophenyl | O | 406.1 |
| 611 | 4-chlorophenyl | 2-fluorophenyl | C(—CH$_2$C(O)NHCH$_2$—) | 439 |
| 612 | 4-chlorophenyl | 2-fluorophenyl | C(—OC(O)NHCH$_2$—) | 441 |
| 614 | 5-bromomidin-2-yl | 2-fluorophenyl | O | 417.4 |
| 616 | 4-chloro-2-methylphenyl | 2-fluorophenyl | O | 386.5 |
| 622 | 4-chlorophenyl | 2-fluorophenyl | C(—CH$_2$CH(CN))CH$_2$—) | 435 |
| 623 | 4-chlorophenyl | 2-fluorophenyl | C(—OCH$_2$CH$_2$CH$_2$—) | 426 |
| 624 | 4-chlorophenyl | 2-fluorophenyl | C(—CH$_2$OCH$_2$—) | 412 |
| 630 | 4-chlorophenyl | 2,4-difluorophenyl | O | 390.4 |
| 631 | 4-chlorophenyl | 2-fluorophenyl | O | 372.4 |
| 651 | 2,4-difluorophenyl | 2,4-difluorophenyl | O | 392.4 |
| 653 | 5-chloropyrimidin-2-yl | 2,4-difluorophenyl | O | 391.4 |
| 668 | 4-chlorophenyl | 2-fluorophenyl | NCH$_2$CN | 410.5 |
| 669 | 4-chlorophenyl | 2,4-difluorophenyl | NCH$_2$CN | 428.4 |
| 670 | 3-chloro-4-fluorophenyl | 2,6-difluorophenyl | NCH$_2$CN | 446.4 |
| 675 | benzothiazol-2-yl | 2-fluorophenyl | O | 395.4 |
| 683 | 4-chlorophenyl | 2-fluorophenyl | C(—C(O)NHC(O)NH—) | 454.3 |
| 684 | 4-(trifluoromethoxy)phenyl | 2,4-difluorophenyl | C(—C(O)NHC(O)NH—) | 522.3 |
| 685 | 3-chloro-4-fluorophenyl | 2,6-difluorophenyl | C(—C(O)NHC(O)NH—) | 490.3 |
| 688 | 3,4-dichlorophenyl | 2-fluorophenyl | S(O) | 438.3 |
| 705 | 4-chlorophenyl | 2-fluorophenyl | C(—C(O)OCH$_2$CH$_2$—) | 440 |
| 711 | 3-chloro-4-fluorophenyl | 2-fluorophenyl | C[—CH$_2$N(C(O)OC(Me)$_3$)CH$_2$—] | 529.4 |
| 712 | 4-chlorophenyl | 2-fluorophenyl | C[—CH$_2$N(C(O)OC(Me)$_3$)CH$_2$—] | 511.4 |
| 713 | 3,4-difluororophenyl | 2-chlorophenyl | C[—CH$_2$N(C(O)OC(Me)$_3$)CH$_2$—] | 529.4 |
| 731 | 2,3,4-trifluorophenyl | 2-fluorophenyl | O | 391.8 |
| 756 | 4-chlorophenyl | phenyl | O | 354.3 |
| 757 | 3-chloro-4-fluorophenyl | 2-fluorophenyl | NCH$_2$(c-Pr) | 443.4 |
| 758 | 5-chloropyridin-2-yl | 2,4-difluorophenyl | NCH$_2$(c-Pr) | 444.3 |
| 766 | 4-chlorophenyl | 2-cyanophenyl | O | 379.4 |
| 775 | 4-chlorophenyl | phenyl | C(—CH$_2$CH$_2$C(O)NH—) | 421.4 |
| 776 | 3-chloro-4-fluorophenyl | 2-fluorophenyl | C(—CH$_2$CH$_2$C(O)NH—) | 457.3 |
| 777 | 4-chlorophenyl | 2,4,6-trifluorophenyl | C(—CH$_2$CH$_2$C(O)NH—) | 475.3 |
| 813 | 4-chlorophenyl | pyridin-2-yl | O | 355.4 |
| 926 | 3-chloro-4-fluorophenyl | 2,4,6-trifluorophenyl | O | 427.2 |
| 940 | 6-chloropyridin-2-yl | 4-fluorophenyl | O | 373.4 |

INDEX TABLE B1

$R^{1a}$ and $R^{14}$ are H

| Cmpd | $Z^1$ | $Z^2$ | $R^{1b}$ | X | m.p. (° C.) |
|---|---|---|---|---|---|
| 592 | 3-(trifluoromethyl)phenyl | 2-fluorophenyl | cyano | O | 110-113° C. |
| 657 | 3-(trifluoromethyl)phenyl | 2-fluorophenyl | CH₃ | O | 135-137° C. |

INDEX TABLE C $R^{1a}$, $R^{1b}$ and $R^{14}$ are H

| Cmpd | $Z^1$ | $Z^2$ | X | AP+ (M + 1) |
|---|---|---|---|---|
| 301 | 4-bromophenyl | 2-fluorophenyl | CO₂Et | 486.4 |
| 302 | 4-chloro-3-fluorophenyl | 2-fluorophenyl | CO₂Et | 440.6 |
| 303 | 3-(trifluoromethyl)phenyl | 2-fluorophenyl | CO₂Et | 476.5 |
| 304 | 3,4-dichlorophenyl | 2-methylphenyl | CO₂Et | 472 |
| 305 | 3-chlorophenyl | 2-fluorophenyl | CO₂Et | 442 |
| 306 | 4-(methylsulfonyl)phenyl | 2-fluorophenyl | CO₂Et | 486 |
| 307 | 4-(trifluoromethyl)phenyl | 2-furanyl | CO₂Et | 448 |
| 308 | 4-methylphenyl | 4-fluorophenyl | CH₂OMe | 394.5 |
| 309 | 3,4-difluorophenyl | 2-fluorophenyl | CO₂Et | 444.5 |
| 310 | 4-chlorophenyl | 2-fluorophenyl | CHO | 398 |
| 311 | 4-cyano-3-(trifluoromethyl)phenyl | 2-fluorophenyl | NHC(O)Me | 486 |
| 312 | 4-cyano-3-(trifluoromethyl)phenyl | 2-fluorophenyl | CO₂Et | 501 |
| 313 | 3,4-dichlorophenyl | 2-fluorophenyl | NHC(O)Me | 462 |
| 314 | 3,4-dichlorophenyl | 2-fluorophenyl | CO₂Me | 462.4 |
| 315 | 3,4-dichlorophenyl | 2-(trifluoromethyl)phenyl | NHC(O)Me | 511.4 |
| 316 | 3,4-dichlorophenyl | 2-(trifluoromethyl)phenyl | CO₂Me | 512.4 |
| 507 | 3-chloro-4-methylphenyl | 2-fluorophenyl | CO₂Et | 456.4 |
| 508 | 4-chlorophenyl | 2-fluorophenyl | CH₂OH | 400 |
| 521 | 3,4-dichlorophenyl | 2-fluorophenyl | cyano | 429.4 |
| 522 | 3,4-dichlorophenyl | 2-chlorophenyl | cyano | 445.3 |
| 523 | 3,4-dichlorophenyl | 2-methylphenyl | cyano | 425.4 |
| 524 | 3,4-dichlorophenyl | 2-(trifluoromethyl)phenyl | cyano | 479.4 |
| 608 | 3-chloro-4-fluorophenyl | 2,4-difluorophenyl | cyano | 431.4 |
| 620 | 3-chloro-4-fluorophenyl | 2,4-difluorophenyl | NHC(O)Me | 463.5 |
| 621 | 4-chlorofluorophenyl | 2,4,6-trifluorophenyl | NHC(O)Me | 463.5 |
| 726 | 3,4-dichlorophenyl | 2-fluorophenyl | NHC(O)OC(Me)₃ | 519.07 |

INDEX TABLE D

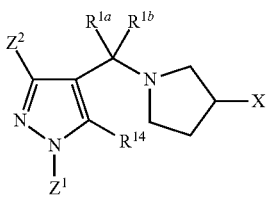

$R^{1a}$, $R^{1b}$ and $R^{14}$ are H

| Cmpd | $Z^1$ | $Z^2$ | X | AP+ (M + 1) |
|---|---|---|---|---|
| 402 | 4-(trifluoromethoxy)phenyl | 2-fluorophenyl | CO₂Me | 464 |
| 403 | 3-chloro-4-fluorophenyl | 2-fluorophenyl | CO₂Me | 432 |
| 404 | 3-(trifluoromethyl)phenyl | 4-fluorophenyl | CO₂Me | 448 |
| 408 | 3-(trifluoromethyl)phenyl | 4-fluorophenyl | NHC(O)Me | 447.1 |
| 513 | 3,4-dichlorophenyl | 2-fluorophenyl | CO₂Me | 448 |
| 514 | 3,4-dichlorophenyl | 2-fluorophenyl | CO₂H | 434 |
| 515 | 3,4-dichlorophenyl | 2-fluorophenyl | C(O)NH₂ | 433 |
| 518 | 3,4-dichlorophenyl | 2-fluorophenyl | cyano | 415 |
| 637 | 3-(trifluoromethyl)phenyl | 4-fluorophenyl | (R)-NHC(O)OC(Me)₃ | 505.2 |
| 638 | 3-(trifluoromethyl)phenyl | 4-fluorophenyl | (S)-NHC(O)OC(Me)₃ | 505.2 |
| 639 | 3-(trifluoromethyl)phenyl | 4-fluorophenyl | (R)-NH₂-TFA** | 405.1 |
| 640 | 3-(trifluoromethyl)phenyl | 4-fluorophenyl | (R)-NHC(O)Me | 447.1 |
| 642 | 3-(trifluoromethyl)phenyl | 4-fluorophenyl | (S)-NH₂-TFA** | # |
| 660 | 3-(trifluoromethyl)phenyl | 4-fluorophenyl | (S)-NHC(O)Me | 447.2 |
| 661 | 3-(trifluoromethyl)phenyl | 4-fluorophenyl | (R)-NHSO₂Me | 483.2 |
| 662 | 3-(trifluoromethyl)phenyl | 4-fluorophenyl | (S)-NHSO₂Me | 483.1 |
| 665 | 3-(trifluoromethyl)phenyl | 4-fluorophenyl | (R)-NHCHO | 433.2 |
| 666 | 3-(trifluoromethyl)phenyl | 4-fluorophenyl | (S)-NHCHO | # |
| 749 | 3-chloro-4-fluorophenyl | 2-fluorophenyl | (S)-NHC(O)Me | 431 |
| 750 | 3-(trifluoromethyl)phenyl | 4-fluorophenyl | (S)-NHC(O)C(Me)₃ | 489 |
| 751 | 4-chlorophenyl | 2-fluorophenyl | (S)-NHC(O)Me | 413 |
| 752 | 4-chlorophenyl | 2,4,6-trifluorophenyl | (S)-NHC(O)Me | 449.3 |
| 753 | 3,4-dichlorophenyl | 2-fluorophenyl | (S)-NHC(O)Me | 447 |
| 781 | 3,4-dichlorophenyl | 2-fluorophenyl | (S)-NHC(O)C(Me)₃ | 490 |
| 782 | 3,4-dichlorophenyl | 2-fluorophenyl | (S)-NHC(O)—c-Pr | 473 |
| 783 | 3,4-dichlorophenyl | 2-fluorophenyl | (S)-NHC(O)CF₃ | 500.9 |
| 820 | 3,4-dichlorophenyl | 4-fluorophenyl | (S)-NHC(O)Me | 447 |
| 821 | 3,4-dichlorophenyl | 3-thienyl | (S)-NHC(O)Me | |
| 833 | 5-bromo-2-pyridinyl | 2-fluorophenyl | (S)-NHC(O)Me | 460.1 |
| 842 | 3,4-dichlorophenyl | 2,4,6-trifluorophenyl | (S)-NHC(O)Me | 483.1 |
| 843 | 3,4-dichlorophenyl | 2,4,6-trifluorophenyl | (S)-NHC(O)—c-Pr | 509 |
| 844 | 3-(trifluoromethyl)phenyl | 2-fluorophenyl | (S)-NHC(O)Me | 447.1 |
| 845 | 3-(trifluoromethyl)phenyl | 2-fluorophenyl | (S)-NHC(O)—c-Pr | 473.1 |
| 859 | 3-(trifluoromethyl)phenyl | 4-fluorophenyl | (S)-NHC(O)C(Me)₃ | 489.1 |
| 869 | 3,4-dichlorophenyl | 4-fluorophenyl | (S)-NHC(O)—c-Pr | 473.1 |
| 870 | 3,4-dichlorophenyl | 3-fluorophenyl | (S)-NHC(O)—c-Pr | 473.1 |
| 871 | 3-chloro-4-fluorophenyl | 4-fluorophenyl | (S)-NHC(O)—c-Pr | 457.1 |
| 872 | 3-chloro-4-fluorophenyl | 4-chlorophenyl | (S)-NHC(O)—c-Pr | 473.1 |
| 873 | 3,4-dichlorophenyl | 2-methylphenyl | (S)-NHC(O)—c-Pr | 469.1 |
| 874 | 3,4-dichlorophenyl | 4-fluorophenyl | (S)-NHC(O)CF₃ | 501 |
| 892 | 5-chloro-2-pyridinyl | 2,6-difluorophenyl | (S)-NHC(O)Me | 432 |
| 894 | 5-bromo-2-pyridinyl | 2,6-difluorophenyl | (S)-NHC(O)Me | 476.4 |
| 896 | 5-chloro-2-pyridinyl | 4-fluorophenyl | (S)-NHC(O)Me | 414 |
| 898 | 5-bromo-2-pyridinyl | 4-fluorophenyl | (S)-NHC(O)Me | 458.4 |
| 900 | 5-bromo-2-pyridinyl | 2,4,6-trifluorophenyl | (S)-NHC(O)Me | 495.4 |
| 901 | 3,4-dichlorophenyl | 4-fluorophenyl | (S)-NHC(O)CH(—CH₂CF₂—) | 509.1 |
| 902 | 3,4-dichlorophenyl | 4-fluorophenyl | (S)-NHC(O)CH(—CH₂CCl₂—) | 541.1 |
| 903 | 3,4-dichlorophenyl | 4-fluorophenyl | (S)-NHC(O)C(CF₃)(—CH₂CH₂—) | 591.1 |
| 906 | 5-fluoro-2-pyridinyl | 4-fluorophenyl | (S)-NHC(O)Me | 398.3 |
| 910 | 3,4-dichlorophenyl | 4-fluorophenyl | (S)-1-imidazolyl | 456.4 |
| 911 | 4-chlorophenyl | 2-fluorophenyl | (S)-1-imidazolyl | 422.5 |
| 912 | 3,4-dichlorophenyl | 4-fluorophenyl | 3-pyridinyl | 467.5 |
| 913 | 4-chlorophenyl | 2-fluorophenyl | 3-pyridinyl | 433.5 |
| 914 | 3,4-dichlorophenyl | 4-fluorophenyl | 4-pyridinyl | 467.5 |
| 915 | 4-chlorophenyl | 2-fluorophenyl | 4-pyridinyl | 433.5 |
| 916 | 3,4-dichlorophenyl | 4-fluorophenyl | 2-pyridinyl | 467.5 |
| 917 | 4-chlorophenyl | 2-fluorophenyl | 2-pyridinyl | 433.5 |
| 918 | 3-chlorophenyl | 2-fluorophenyl | (S)-NHC(O)Me | 413.2 |
| 919 | 3,4-dichlorophenyl | 4-fluorophenyl | (S)-OC(O)Me | 448.1 |
| 920 | 3,4-dichlorophenyl | 4-fluorophenyl | (S)-OC(O)—c-Pr | 474.1 |
| 921 | 3,4-dichlorophenyl | 4-fluorophenyl | (S)-N(Me)C(O)OC(Me)₃ | 519.5 |
| 922 | 3,4-dichlorophenyl | 4-fluorophenyl | (S)-N(Me)C(O)—c-Pr | 487.6 |
| 923 | 3,4-dichlorophenyl | 4-fluorophenyl | (S)-N(Me)C(O)Me | 461.5 |
| 925 | 3-chloro-4-fluorophenyl | 2,4,6-trifluorophenyl | (S)-NHC(O)Me | 467.5 |
| 929 | 4-(trifluoromethyl)-2-pyridinyl | 4-fluorophenyl | (S)-NHC(O)Me | 448.5 |
| 931 | 6-(trifluoromethyl)-2-pyridinyl | 4-fluorophenyl | (S)-NHC(O)Me | 448.5 |

INDEX TABLE D-continued

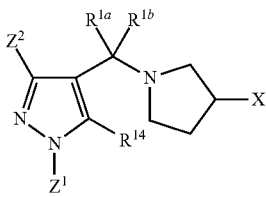

$R^{1a}$, $R^{1b}$ and $R^{14}$ are H

| Cmpd | $Z^1$ | $Z^2$ | X | AP+ (M + 1) |
|---|---|---|---|---|
| 934 | 3,4-dichlorophenyl | 4-fluorophenyl | (S)-1-pyrrolidinone | 473.5 |
| 935 | 6-(trifluoromethyl)-2-pyridinyl | 4-fluorophenyl | (S)-1-pyrrolidinone | 474.6 |
| 936 | 4-(trifluoromethyl)-2-pyridinyl | 4-fluorophenyl | (S)-1-pyrrolidinone | 474.6 |
| 942 | 6-chloro-2-pyridinyl | 4-fluorophenyl | (S)-NHC(O)Me | 414.5 |
| 943 | 3,4-dichlorophenyl | 2-fluorophenyl | (S)-NHC(O)OC(Me)$_3$ | 505.3 |
| 944 | 3,4-dichlorophenyl | 2-fluorophenyl | (S)-NHCH(Me)$_2$ | 447.2 |
| 945 | 3,4-dichlorophenyl | 2-fluorophenyl | (S)-NHC(O)—c-Pn | 501.18 |
| 946 | 3,4-dichlorophenyl | 2-fluorophenyl | (R)-NHC(O)OC(Me)$_3$ | 505.2 |
| 947 | 3,4-dichlorophenyl | 2-fluorophenyl | (S)-NH$_2$ | 405.14 |
| 948 | 3,4-dichlorophenyl | 2-fluorophenyl | (S)-NH$_2$ | 405.1 |
| 949 | 3,4-dichlorophenyl | phenyl | (S)-NHC(O)Me | 429.2 |

See Index Table F for $^1$H NMR data.

**TFA is trifluoracetic acid

INDEX TABLE E

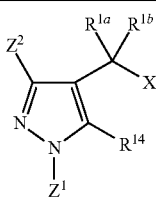

$R^{1a}$, $R^{1b}$ and $R^{14}$ are H

| Cmpd | $Z^1$ | $Z^2$ | X | m.p. (° C.) or AP+ (M + 1) |
|---|---|---|---|---|
| 401 | 4-(trifluoromethoxy)phenyl | 2-fluorophenyl | ![N-piperazine-CO2C(CH3)3] | 535.6 |
| 405 | 4-fluorophenyl | 2-fluorophenyl | ![azetidine-CN] | 351.4 |
| 406 | 4-chlorophenyl | 2-fluorophenyl | ![azetidine-CN] | 367.5 |
| 407 | 4-chlorophenyl | 2-fluorophenyl | ![azetidine-CO2Me] | 400.5 |

INDEX TABLE E-continued

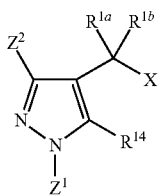

$R^{1a}$, $R^{1b}$ and $R^{14}$ are H

| Cmpd | $Z^1$ | $Z^2$ | X | m.p. (° C.) or AP+ (M + 1) |
|---|---|---|---|---|
| 529 | 3,4-dichlorophenyl | 2-fluorophenyl | 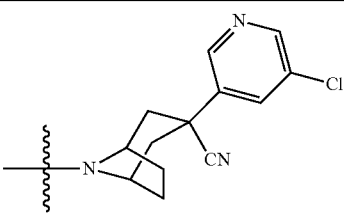 | 566.4 |
| 564 | 3-(trifluoromethyl)phenyl | 2-fluorophenyl | 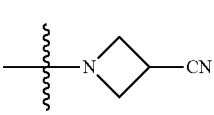 [SMILES: *N1CC(C#N)C1] | 74-76° C. |
| 589 | 3-(trifluoromethyl)phenyl | 2-fluorophenyl | 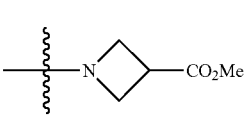 [SMILES: *N1CC(C(=O)OC)C1] | 434 |
| 619 | 4-fluorophenyl | 2-fluorophenyl | 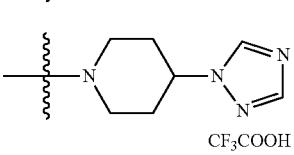 CF$_3$COOH | 421.5 |
| 625 | 4-chlorophenyl | 2-fluorophenyl | 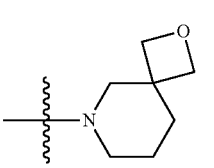 [SMILES: *N1CCCC2(COC2)C1] | 412 |
| 671 | 4-chlorophenyl | 2-fluorophenyl | 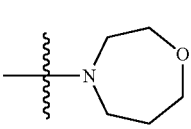 [SMILES: *N1CCCOCC1] | 386.4 |
| 672 | 3-(trifluoromethyl)phenyl | 4-fluorophenyl | 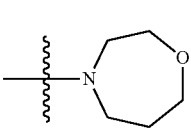 [SMILES: *N1CCCOCC1] | 420.4 |
| 673 | 3,4-difluorophenyl | 2-chlorophenyl | 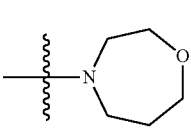 [SMILES: *N1CCCOCC1] | 404.3 |
| 682 | 4-chlorophenyl | 2-fluorophenyl | 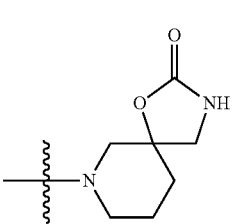 [SMILES: *N1CCCC2(CNC(=O)O2)C1] | 441 |

INDEX TABLE E-continued $R^{1a}$, $R^{1b}$ and $R^{14}$ are H

| Cmpd | $Z^1$ | $Z^2$ | X | m.p. (° C.) or AP+ (M + 1) |
|---|---|---|---|---|
| 687 | 4-(trifluoromethoxy)phenyl | 2-fluorophenyl | —NH₂·CF₃COOH | 435.4 |
| 689 | 4-chlorophenyl | 2-fluorophenyl | bicyclic N with CN | 421.4 |
| 714 | 3-chloro-4-fluorophenyl | 2-fluorophenyl | spiro azetidine-oxetane | 402.4 |
| 715 | 2-chlorophenyl | 2-fluorophenyl | spiro azetidine-oxetane | 384.3 |
| 716 | 3,4-difluorophenyl | 2-chlorophenyl | spiro azetidine-oxetane | 402.4 |
| 722 | 3-chloro-4-fluorophenyl | 2-fluorophenyl | bicyclic N with O | 416.4 |
| 723 | 4-chlorophenyl | 2-fluorophenyl | bicyclic N with O | 398.4 |
| 724 | 3-chloro-4-fluorophenyl | 2-fluorophenyl | morpholine-CO₂Me | 448.4 |
| 725 | 3,4-dichlorophenyl | 2-chlorophenyl | morpholine-CO₂Me | 482.3 |
| 728 | 4-chlorophenyl | 2-fluorophenyl | azetidine-OC(O)OMe | 416 |
| 732 | 4-chlorophenyl | 2,4,6-trifluorophenyl | spiro azetidine-piperidine-N—C(O)OC(Me)₃ | 547.4 |

INDEX TABLE E-continued

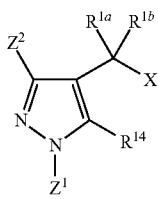

$R^{1a}$, $R^{1b}$ and $R^{14}$ are H

| Cmpd | $Z^1$ | $Z^2$ | X | m.p. (° C.) or AP+ (M + 1) |
|---|---|---|---|---|
| 733 | 4-chlorophenyl | 2,4,6-trifluorophenyl | (3-methylmorpholin-4-yl) | 422.3 |
| 734 | 4-chlorophenyl | 2,4,6-trifluorophenyl | (2-azaspiro[3.5]... N—C(O)Me) | 489.3 |
| 796 | 4-chlorophenyl | 2-fluorophenyl | (4-(oxazol-5-yl)piperidin-1-yl) CF₃COOH | 505.3 |

INDEX TABLE F

| Cmpd No. | $^1$H NMR Data[a] |
|---|---|
| 78 | δ 8.66 (s, 1 H), 8.58 (s, 1 H), 8.15 (d, 1 H), 8.02 (dd, 1 H), 7.61 (dt, 1 H), 7.42 (dq, 1 H), 7.24 (t, 1 H), 7.17 (t, 1 H), 3.50 (s, 2 H), 2.63 (m, 2 H), 2.56 (m, 1 H), 2.28 (m, 2 H), 1.80-1.84 (m, 2 H), 1.70-1.76 (m, 2 H). |
| 642 | δ 8.45 (br s, 1 H), 8.03 (br s, 1 H), 7.92-7.90 (m, 1 H), 7.64 (d, 2 H), 7.51-7.57 (m, 2 H), 7.21 (t, 2 H), 5.43 (br s, 2 H), 4.51 (d, 1 H), 4.23-4.41 (m, 2 H), 3.92 (d, 1 H), 3.62 (br s, 1 H), 3.31 (br s, 1 H), 2.74 (br s, 1 H), 2.61 (br s, 1 H), 2.16-2.23 (m, 1 H). |
| 666 | δ 8.04 (s, 1 H), 8.02 (s. 1 H), 7.84-7.96 (m, 4 ), 7.59 (t, 1 H), 7.54 (d, 1 H), 7.15 (t, 2 H), 5.72 (d, 1 H), 4.57-4.51 (m, 1 H), 3.69 (d, 1 H), 3.62 (d, 1 H), 2.87-2.97 (m, 1 H), 2.27-2.43 (m, 2 H) 2.56-2.70 (m, 2 H), 1.65-1.69 (m, 1 H). |

[a] $^1$H NMR data are in ppm downfield from tetramethylsilane. CDCl₃ solution unless indicated otherwise. Couplings are designated by (s)-singlet, (d)-doublet, (t)-triplet, (m)-multiplet, (dd)-doublet of doublets, (dt)-doublet of triplets, (dq)-doublet of quartets, (br s)-broad singlet.

The following Tests demonstrate the control efficacy of compounds of this invention on specific pests. "Control efficacy" represents inhibition of invertebrate pest development (including mortality) that causes significantly reduced feeding. The pest control protection afforded by the compounds is not limited, however, to these species. Compound numbers refer to compounds in Index Tables A-E.

Biological Examples of the Invention

Test A

For evaluating control of diamondback moth (*Plutella xylostella*) the test unit consisted of a small open container with a 12-14-day-old radish plant inside. This was pre-infested with ~50 neonate larvae that were dispensed into the test unit via corn cob grits using a bazooka inoculator. The larvae moved onto the test plant after being dispensed into the test unit.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and isopropanol (Loveland Industries, Inc. Greeley, Colo., USA). The formulated compounds were applied in 1 mL of liquid through a SUJ2 atomizer nozzle with 1/8 JJ custom body (Spraying Systems Co., Wheaton, Ill., USA) positioned 1.27 cm (0.5 inches) above the top of each test unit. Test compounds were sprayed at 250 ppm and/or 50 ppm, and replicated three times. After spraying of the formulated test compound, each test unit was allowed to dry for 1 h and then a black, screened cap was placed on top. The test units were held for 6 days in a growth chamber at 25° C. and 70% relative humidity. Plant feeding damage was then visually assessed based on foliage consumed.

Of the compounds of Formula 1 tested at 250 ppm, the following provided very good to excellent levels of control efficacy (40% or less feeding damage and/or 100% mortality): 3, 4, 7, 9, 10, 11, 12, 13, 14, 16, 17, 19, 20, 21, 22, 24, 25, 26, 27, 28, 29, 30, 31, 32, 33, 34, 39, 40, 41, 42, 43, 44, 45, 46, 47, 48, 49, 50, 51, 52, 53, 54, 55, 56, 57, 58, 59, 62, 63, 64, 65, 66, 67, 68, 69, 70, 71, 72, 73, 74, 75, 76, 77, 79, 80, 81, 82, 83, 84, 85, 86, 103, 202, 203, 207, 208, 209, 210, 211, 301, 302, 303, 310, 401, 403.404, 508 and 510.

Of the compounds of Formula 1 tested at 50 ppm, the following provided very good to excellent levels of control efficacy (40% or less feeding damage and/or 100% mortality): 4, 9, 10, 11, 12, 13, 14, 19, 22, 24, 26, 28, 29, 30, 31, 32, 33, 39, 40, 41, 42, 43, 44, 45, 46, 47, 48, 49, 50, 51, 52, 53, 54, 55, 56, 57, 58, 59, 62, 63, 64, 65, 66, 67, 68, 69, 71, 72, 74, 75, 76, 77, 78, 79, 80, 81, 82, 83, 84, 86, 87, 88, 91, 94, 95, 96, 97, 98, 99, 102, 105, 106, 107, 108, 109, 112, 114, 116, 117, 118, 121, 124, 129, 130, 131, 132, 133, 134, 135, 203, 207, 209, 211, 216, 217, 218, 219, 220, 301, 309, 315, 404, 408, 508, 510, 511, 512, 513, 515, 516, 517, 518, 519, 520, 521, 522, 523, 525, 526, 527, 528, 530, 531, 532, 534, 535, 536, 539, 546, 547, 548, 549, 550, 551, 553, 555, 556, 558, 560, 562, 566, 572, 581, 583, 596, 602, 629, 630, 631, 632, 633, 634, 640, 648, 649, 650, 651, 652, 653, 654, 660, 661, 662, 665, 666, 768, 769, 770, 771, 772, 773, 774, 775, 776, 777, 778, 780, 781, 782, 783, 784, 785, 786, 792, 793, 794, 795, 796, 798, 799, 800, 801, 802, 803, 804, 805, 806, 807, 808, 809, 810, 811, 812, 813, 815, 816, 820, 821, 822, 824, 825, 826, 827, 829, 830, 831, 832, 833, 835, 839, 842, 843, 844, 845, 847, 848, 849, 851, 852, 854, 855, 856, 857, 858, 860, 861, 862, 863, 867, 868, 869, 870, 871, 872, 873, 874, 875, 876, 877, 878, 879, 880, 881, 884, 885, 886, 887, 889, 891, 892, 893, 894, 895, 896, 897, 898, 899, 900, 901, 902 and 903.

Test B

For evaluating control of fall armyworm (*Spodoptera frugiperda*) the test unit consisted of a small open container with a 4-5-day-old maize (corn) plant inside. This was pre-infested (using a core sampler) with 10-15 1-day-old larvae on a piece of insect diet.

Test compounds were formulated and sprayed at 250 ppm and/or 50 ppm as described for Test A. The applications were replicated three times. After spraying, the test units were maintained in a growth chamber at 25° C. and 70% relative humidity and then visually rated as described for Test A.

Of the compounds of Formula 1 tested at 250 ppm, the following provided very good to excellent levels of control efficacy (40% or less feeding damage and/or 100% mortality): 4, 13, 14, 57, 82, 83, 84, 85, 86, 203, 211, 404, 559, 561, 563, 567, 569, 571, 574, 577, 578, 579, 582, 584, 585, 586, 587, 588, 591, 594, 601, 603, 604, 605, 606, 607, 608, 609, 613, 614, 619, 620, 621, 622, 624, 675, 676, 691, 694, 695, 696, 705, 720, 721, 726, 727, 730, 731, 733, 740, 742, 745, 746, 747, 748, 749, 750, 752, 753, 754, 755, 756, 757, 758, 759, 760, 768, 769, 770, 771, 773, 774, 776, 778, 780, 781, 782 and 796.

Of the compounds of Formula 1 tested at 50 ppm, the following provided very good to excellent levels of control efficacy (40% or less feeding damage and/or 100% mortality): 10, 12, 14, 33, 40, 41, 42, 48, 49, 51, 53, 56, 57, 63, 65, 66, 71, 77, 78, 79, 83, 86, 87, 91, 94, 115, 118, 121, 129, 131, 133, 134, 209, 211, 216, 217, 218, 219, 220, 408, 517, 520, 521, 523, 525, 526, 527, 530, 532, 534, 536, 544, 546, 548, 550, 552, 555, 556, 559, 563, 566, 567, 569, 571, 572, 574, 577, 578, 581, 582, 583, 584, 587, 588, 594, 602, 603, 604, 605, 606, 607, 608, 613, 614, 629, 630, 632, 633, 637, 650, 651, 652, 653, 654, 660, 676, 705, 720, 721, 733, 742, 748, 750, 753, 754, 755, 760, 768, 769, 770, 771, 777, 778, 780, 781, 782, 783, 784, 785, 786, 794, 798, 799, 800, 801, 802, 803, 804, 805, 806, 807, 809, 810, 811, 815, 820, 821, 822, 824, 825, 826, 829, 842, 843, 845, 847, 848, 849, 851, 854, 855, 857, 858, 860, 861, 862, 868, 869, 870, 871, 872, 873, 874, 875, 876, 878, 879, 880, 884, 885, 886, 888, 889, 891, 893, 895, 897, 899, 900, 901, 902 and 903.

Test C

For evaluating control of green peach aphid (*Myzus persicae*) through contact and/or systemic means, the test unit consisted of a small open container with a 12-15-day-old radish plant inside. This was pre-infested by placing on a leaf of the test plant 30-40 aphids on a piece of leaf excised from a culture plant (cut-leaf method). The aphids moved onto the test plant as the leaf piece desiccated. After pre-infestation, the soil of the test unit was covered with a layer of sand.

Test compounds were formulated and sprayed at 250 ppm and/or 50 ppm as described for Test A. The applications were replicated three times. After spraying of the formulated test compound, each test unit was allowed to dry for 1 h and then a black, screened cap was placed on top. The test units were held for 6 days in a growth chamber at 19-21° C. and 50-70% relative humidity. Each test unit was then visually assessed for insect mortality.

Of the compounds of Formula 1 tested at 250 ppm, the following resulted in at least 80% mortality: 3, 41, 63, 77, 79, 86, 88, 94, 131, 132, 512, 521, 522, 523, 525, 529, 531, 546, 556, 567, 581, 587, 602, 603, 613, 625, 629, 650, 720, 733, 748, 770, 784, 806, 807, 810, 825, 826, 830, 861 and 880.

Of the compounds of Formula 1 tested at 50 ppm, the following resulted in at least 80% mortality: 806.

Test D

For evaluating control of cotton melon aphid (*Aphis gossypii*) through contact and/or systemic means, the test unit consisted of a small open container with a 6-7-day-old cotton plant inside. This was pre-infested with 30-40 insects on a piece of leaf according to the cut-leaf method described for Test C, and the soil of the test unit was covered with a layer of sand.

Test compounds were formulated and sprayed at 250 ppm as described for Test C. The applications were replicated three times. After spraying, the test units were maintained in a growth chamber and then visually rated as described for Test C.

Of the compounds of Formula 1 tested at 250 ppm, the following resulted in at least 80% mortality: 529 and 806.

Test E

For evaluating control of corn planthopper (*Peregrinus maidis*) through contact and/or systemic means, the test unit consisted of a small open container with a 3-4-day-old maize plant (spike) inside. White sand was added to the top of the soil prior to application. Test compounds were formulated and sprayed at 250 ppm, and replicated three times as described for Test A. After spraying, the test units were allowed to dry for 1 h before they were post-infested with ~15-20 nymphs (18 to 21 day old) by sprinkling them onto the sand with a salt shaker. A black, screened cap was placed on the top of each test unit, and the test units were held for 6 days in a growth chamber at 22-24° C. and 50-70% relative humidity. Each test unit was then visually assessed for insect mortality.

Of the compounds of Formula 1 tested at 250 ppm the following provided very good to excellent levels of control efficacy (80% or more mortality): 64, 66, 742, 863, 880 and 881.

Test F

For evaluating control of potato leafhopper (*Empoasca fabae*) through contact and/or systemic means, the test unit consisted of a small open container with a 5-6-day-old Soleil bean plant (primary leaves emerged) inside. White sand was added to the top of the soil and one of the primary leaves was excised prior to application.

Test compounds were formulated and sprayed at 250 ppm and/or 50 ppm, and the tests were replicated three times as described for Test A. After spraying, the test units were allowed to dry for 1 h before they were post-infested with 5 potato leafhoppers (18-21-day-old adults). A black, screened cap was placed on the top of each test unit, and the test units were held for 6 days in a growth chamber at 24° C. and 70% relative humidity. Each test unit was then visually assessed for insect mortality.

Of the compounds of Formula 1 tested at 250 ppm the following provided very good to excellent levels of control efficacy (80% or more mortality): 11, 12, 22, 32, 33, 34, 41, 45, 46, 47, 50, 56, 57, 59, 62, 63, 71, 72, 74, 76, 78, 79, 80, 81, 83, 84, 95, 99, 102, 105, 106, 107, 108, 109, 112, 113, 114, 117, 121, 122, 124, 125, 126, 127, 129, 130, 132, 135, 136, 137, 209, 211, 213, 216, 218, 219, 220, 304, 311, 314, 408, 511, 525, 526, 527, 530, 531, 532, 534, 546, 547, 549, 550, 551, 553, 555, 557, 558, 560, 561, 568, 569, 570, 573, 581, 582, 584, 600, 602, 603, 605, 608, 609, 619, 620, 621, 622, 624, 630, 633, 634, 647, 650, 651, 660, 670, 685, 692, 694, 696, 702, 705, 720, 729, 733, 738, 742, 744, 747, 748, 749, 750, 751, 752, 753, 754, 761, 768, 770, 774, 781, 782, 783, 793, 794, 800, 801, 802, 803, 804, 805, 806, 810, 820, 821, 824, 829, 833, 837, 842, 843, 844, 845, 862, 868, 871, 874, 875, 876, 879, 880, 891, 892, 893, 894, 896, 900, 902 and 903.

Of the compounds of Formula 1 tested at 50 ppm the following provided very good to excellent levels of control efficacy (80% or more mortality): 62, 74, 76, 105, 106, 107, 108, 112, 113, 121, 136, 137, 525, 548, 549, 582, 584, 602, 603, 633, 647, 660, 685, 729, 744, 761, 800, 806, 879, 892 and 896.

Test G

For evaluating control of Western Flower Thrips (*Frankliniella occidentalis*) through contact and/or systemic means, the test unit consisted of a small open container with a 5-7-day-old Soleil bean plant inside.

Test compounds were formulated and sprayed at 250 and/or 50 ppm, and the tests were replicated three times as described for Test A. After spraying, the test units were allowed to dry for 1 hour, and then 22-27 adult thrips were added to the unit. A black, screened cap was placed on the top of each test unit, and the test units were held for 7 days at 25° C. and 45-55% relative humidity.

Of the compounds of Formula 1 tested at 250 ppm, the following provided very good to excellent levels of control efficacy (40% or less plant damage and/or 100% mortality): 50, 52, 56, 57, 63, 66, 67, 77, 79, 80, 81, 92, 102 and 211.

Of the compounds of Formula 1 tested at 50 ppm, the following provided very good to excellent levels of control efficacy (40% or less plant damage and/or 100% mortality): 86, 211 or 404.

What is claimed is:
1. A compound of Formula 1, an N-oxide, or salt thereof,

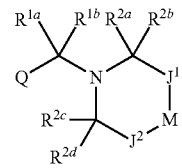

wherein
Q is

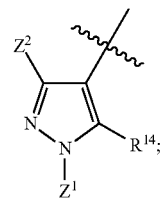

$R^{1a}$ is H, cyano, $C_1$-$C_6$ alkyl, $C_3$-$C_6$ cycloalkyl, $C_1$-$C_6$ haloalkyl, C(O)OH, C(O)$R^{5a}$, C(O)O$R^{6a}$ or C(O)N$R^{7a}R^{8a}$;

$R^{1b}$ is H or $C_1$-$C_6$ alkyl;

$R^{2a}$ and $R^{2c}$ are H;

$R^{2b}$ and $R^{2d}$ are H;

$J^1$ is —C($R^{3a}R^{3b}$)—;

$J^2$ is —C($R^{3c}R^{3d}$)—;

M is —C($R^{3e}$)(A)-;

A is cyano, C(X)$R^5$, C(O)O$R^6$, C(X)N$R^7R^8$ or N$R^9R^{10}$; or $C_1$-$C_6$ alkyl substituted with halogen; or phenyl or a 5- or 6-membered heteroaromatic ring, each ring unsubstituted or substituted with 1 to 3 $R^4$;

$R^{3a}$ and $R^{3c}$ are H;

$R^{3b}$ and $R^{3d}$ are H;

$R^{3e}$ is H or $C_1$-$C_6$ alkyl $Z^1$ is phenyl substituted with 1 to 4 $R^{4a}$; or $Z^1$ is a 5- or 6-membered heteroaromatic ring or an 8- to 10-membered heteroaromatic bicyclic ring system, each ring or ring system unsubstituted or substituted with 1 to 3 $R^{4a}$;

$Z^2$ is phenyl, unsubstituted or substituted with 1 to 4 $R^{4b}$; or $Z^2$ is a 5- or 6-membered heteroaromatic ring or an 8- to 10-membered heteroaromatic bicyclic ring system, each ring or ring system unsubstituted or substituted with 1 to 3 $R^{4b}$;

each $R^4$, $R^{4a}$ and $R^{4b}$ is independently halogen, cyano, nitro, C(X)$R^5$, C(O)O$R^6$, C(X)N$R^7R^8$, N$R^9R^{10}$, O$R^{12}$, S(O)$_n R^{11}$ or SO$_2$N$R^9R^{10}$; or $C_1$-$C_6$ alkyl, $C_2$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, O$R^{12a}$, $C_1$-$C_4$ alkyl, $C_1$-$C_4$ haloalkyl and S(O)$_n R^{11a}$; or phenyl or a 5- or 6-membered heteroaromatic ring, each ring unsubstituted or substituted with 1 to 3 $R^{13}$; provided that when two $R^4$, two $R^{4a}$ or two $R^{4b}$ groups are attached to adjacent carbon atoms, then said two $R^4$, two $R^{4a}$ or two $R^{4b}$ groups can be taken together with the carbon atoms to which they are attached to form a ring;

each $R^5$ is independently H; or $C_1$-$C_6$ alkyl, $C_2$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$; or phenyl or a 5- or 6-membered heteroaromatic ring, each ring unsubstituted or substituted with 1 to 3 $R^{13}$;

each $R^{5a}$ is independently $C_1$-$C_4$ alkyl, $C_1$-$C_4$ haloalkyl or $C_3$-$C_7$ cycloalkyl;

each $R^6$ is independently $C_1$-$C_6$ alkyl, $C_2$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$; or phenyl or a 5- or 6-membered heteroaromatic ring, each ring unsubstituted or substituted with 1 to 3 $R^{13}$;

each $R^{6a}$ is independently $C_1$-$C_4$ alkyl or $C_1$-$C_4$ haloalkyl;

each $R^7$ and $R^8$ is independently H; or $C_1$-$C_6$ alkyl, $C_2$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$; or phenyl or a 5- or 6-membered heteroaromatic ring, each ring unsubstituted or substituted with 1 to 3 $R^{13}$; or $R^7$ and $R^8$ can be taken together with the nitrogen atom to which they are attached to form a 5-, 6- or 7-membered ring;

each $R^{7a}$ and $R^{8a}$ is independently H, $C_1$-$C_4$ alkyl or $C_1$-$C_4$ haloalkyl;

each $R^{7b}$ is independently $N(R^{7a})_2$, OH or $OR^{12a}$;

each $R^9$ and $R^{10}$ is independently H, $C(X)R^5$, $C(O)OR^6$ or $C(X)NR^7R^8$; or $C_1$-$C_6$ alkyl, $C_2$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$; or phenyl or a 5- or 6-membered heteroaromatic ring, each ring unsubstituted or substituted with 1 to 3 $R^{13}$; or $R^9$ and $R^{10}$ can be taken together with the nitrogen atom to which they are attached to form a 5-, 6- or 7-membered ring;

each $R^{9a}$ and $R^{10a}$ is independently H, $C(X)R^{5a}$, $C(O)OR^{6a}$, $C(X)NR^{7a}R^{8a}$, $C_1$-$C_4$ alkyl or $C_1$-$C_4$ haloalkyl;

each $R^{11}$ is independently $C_1$-$C_6$ alkyl, $C_2$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, $OR^{12}a$, $C_1$-$C_4$ alkyl, $C_1$-$C_4$ haloalkyl and $S(O)_nR^{11a}$; or phenyl or a 5- or 6-membered heteroaromatic ring, each ring unsubstituted or substituted with 1 to 3 $R^{13}$;

each $R^{11a}$ is independently $C_1$-$C_4$ alkyl or $C_1$-$C_4$ haloalkyl;

each $R^{12}$ is independently H; or $C_1$-$C_6$ alkyl, $C_2$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, $oR^{12a}$, $C_1$-$C_4$ alkyl, $C_1$-$C_4$ haloalkyl and $S(O)_nR^{11a}$; or phenyl or a 5- or 6-membered heteroaromatic ring, each ring unsubstituted or substituted with 1 to 3 $R^{13}$;

each $R^{12}a$ is independently H, $C_1$-$C_4$ alkyl or $C_1$-$C_4$ haloalkyl;

each $R^{13}$ is independently halogen, cyano, nitro, $C(X)R^{5a}$, $C(O)OR^{6a}$, $C(X)NR^{7a}R^{8a}$, $NR^{9a}R^{10a}$, $OR^{12a}$, $s(O)_nR^{11a}$ or $SO_2NR^{9a}R^{10a}$; or $C_1$-$C_6$ alkyl, $C_2$-$C_6$ alkenyl, $C_2$-$C_6$ alkynyl, $C_3$-$C_7$ cycloalkyl or $C_4$-$C_8$ cycloalkylalkyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$; provided that when two $R^{13}$ groups are attached to adjacent carbon atoms, then said two $R^{13}$ groups can be taken together with the carbon atoms to which they are attached to form a ring;

$R^{14}$ is H, halogen, cyano, nitro, $C(X)R^5$, $C(O)OR^6$, $C(X)NR^7R^8$, $NR^9R^{10}$, $OR^{12}$, $S(O)_nR^{11}$ or $SO_2NR^9R^{10}$; or $C_1$-$C_6$ alkyl, $C_2$-$C_6$ alkenyl, $C_2$-$C_6$ alkynyl, $C_3$-$C_7$ cycloalkyl, $C_4$-$C_8$ cycloalkylalkyl or $C_3$-$C_6$ cycloalkenyl, each unsubstituted or substituted with at least one substituent independently selected from the group consisting of halogen, cyano, nitro, $OR^{12a}$, $C_1$-$C_4$ alkyl, $C_1$-$C_4$ haloalkyl and $S(O)_nR^{11a}$;

each X is independently O or S; and each n is independently 0, 1 or 2.

2. The compound of claim 1 wherein
X is O;
$R^{1a}$ is H; and
$R^{1b}$ is H.

3. The compound of claim 2 wherein
$R^{2a}$, $R^{2b}$, $R^{2c}$ and $R^{2d}$ are H;
$R^{3e}$ is H, halogen or $C_1$-$C_6$ alkyl; and
A is cyano, $C(X)R^5$, $C(O)OR^6$, $C(X)NR^7R^8$ or $NR^9R^{10}$; or phenyl or a 5- or 6-membered heteroaromatic ring, each ring unsubstituted or substituted with 1 to 3 $R^4$.

4. The compound of claim 2 wherein
A is cyano, $C(O)OR^{6a}$ or $NHC(O)R^{5a}$; or a 5-membered heteroaromatic ring, unsubstituted or substituted with 1 to 3 $R^4$.

5. The compound of claim 1 that is selected from the group consisting of:

methyl 1-[[3-(4-fluorophenyl)-1-[3-(trifluoromethyl)phenyl]-1H-pyrazol-4-yl]methyl]-4-piperidinecarboxylate;

1-[[3-(4-fluorophenyl)-1-[3-(trifluoromethyl)phenyl]-1H-pyrazol-4-yl]methyl]-4-piperidinecarbonitrile;

1-[[1-(3,4-dichlorophenyl)-3-(4-fluorophenyl)-1H-pyrazol-4-yl]methyl]-4-piperidinecarbonitrile;

1-[[3-(2-fluorophenyl)-1-[4-(trifluoromethoxy)phenyl]-1H-pyrazol-4-yl]methyl]-4-piperidinecarbonitrile;

1-[[3-(2,4-difluorophenyl)-1-[4-(trifluoromethoxy)phenyl]-1H-pyrazol-4-yl]methyl]-4-piperidinecarbonitrile;

1-[[1-(4-chlorophenyl)-3-(2-fluorophenyl)-1H-pyrazol-4-yl]methyl]-4-piperidinecarbonitrile;

1-[[1-(3-chloro-4-fluorophenyl)-3-(2-fluorophenyl)-1H-pyrazol-4-yl]methyl]-4-piperidinecarbonitrile;

1-[[1-(4-bromophenyl)-3-(2-fluorophenyl)-1H-pyrazol-4-yl]methyl]-4-piperidinecarbonitrile;

1-[[3-(2-fluorophenyl)-1-[4-(trifluoromethyl)phenyl]-1H-pyrazol-4-yl]methyl]-4-piperidinecarbonitrile;

1-[[3-(2-fluorophenyl)-1-[5-(trifluoromethyl)-2-pyridinyl]-1H-pyrazol-4-yl]methyl]-4-piperidinecarbonitrile;

1-[[3-(2,6-difluorophenyl)-1-[4-(trifluoromethoxy)phenyl]-1H-pyrazol-4-yl]methyl]-4-piperidinecarbonitrile;

N-[(3S)-1-[[1-(3,4-dichlorophenyl)-3-(4-fluorophenyl)-1H-pyrazol-4-yl]methyl]-3-pyrrolidinyl]cyclopropanecarboxamide;

1-[[1-(3-chloro-4-fluorophenyl)-3-(2-fluorophenyl)-1H-pyrazol-4-yl]methyl]-4-(1,3,4-oxadiazol-2-yl)piperidine;

1-[[1-(3,4-dichlorophenyl)-3-(2-fluorophenyl)-1H-pyrazol-4-yl]methyl]-4-(1,3,4-oxadiazol-2-yl)piperidine;

1-[[1-(5-chloro-2-pyridinyl)-3-(2,4,6-trifluorophenyl)-1H-pyrazol-4-yl]methyl]-4-piperidinecarbonitrile;

1-[[1-(4-chlorophenyl)-3-(2-fluorophenyl)-1H-pyrazol-4-yl]methyl]-4-(1,3,4-oxadiazol-2-yl)piperidine;

1-[[1-(3-chloro-4-fluorophenyl)-3-(2-fluorophenyl)-1H-pyrazol-4-yl]methyl]-4-piperidinecarbonitrile;

1-[[1-(4-chloro-3-fluorophenyl)-3-(2-fluorophenyl)-1H-pyrazol-4-yl]methyl]-4-piperidinecarbonitrile;

N-[(3S)-1-[[1-(3,4-dichlorophenyl)-3-(4-fluorophenyl)-1H-pyrazol-4-yl]methyl]-3-pyrrolidinyl]acetamide;

1-[[1-(4-chlorophenyl)-3-(2-fluorophenyl)-1H-pyrazol-4-yl]methyl]-4-piperidinecarbonitrile;

1-[[1-(5-chloro-2-pyridinyl)-3-(2-fluorophenyl)-1H-pyrazol-4-yl]methyl]-4-piperidinecarbonitrile;

1-[[3-(2-fluorophenyl)-1-[3-(trifluoromethyl)phenyl]-1H-pyrazol-4-yl]methyl]-4-(1,3,4-oxadiazol-2-yl)piperidine;

1-[[1-(3-bromophenyl)-3-(2-fluorophenyl)-1H-pyrazol-4-yl]methyl]-4-(1,3,4-oxadiazol-2-yl)piperidine;

1-[[1-(5-bromo-2-pyridinyl)-3-(2-fluorophenyl)-1H-pyrazol-4-yl]methyl]-4-piperidinecarbonitrile;

1-[[1-(5-chloro-2-pyridinyl)-3-(2,4-difluorophenyl)-1H-pyrazol-4-yl]methyl]-4-piperidinecarbonitrile; and 1-[[3-(2-fluorophenyl)-1-[4-(trifluoromethoxy)phenyl]-1H-pyrazol-4-yl]methyl]-4-(1,3,4-oxadiazol-2-yl)piperidine.

6. A composition comprising a compound of claim 1 and at least one additional component selected from the group consisting of surfactants, solid diluents and liquid diluents.

7. The composition of claim 6 further comprising at least one additional biologically active compound or agent.

8. The composition of claim 7 wherein the at least one additional biologically active compound or agent is selected from the group consisting of abamectin, acephate, acequinocyl, acetamiprid, acrinathrin, amidoflumet, amitraz, avermectin, azadirachtin, azinphos-methyl, benfuracarb, bensultap, bifenthrin, bifenazate, bistrifluron, borate, buprofezin, cadusafos, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyantraniliprole, cycloprothrin, cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenitrothion, fenothiocarb, fenoxycarb, fenpropathrin, fenvalerate, fipronil, flonicamid, flubendiamide, flucythrinate, flufenerim, flufenoxuron, fluvalinate, tau-fluvalinate, fonophos, formetanate, fosthiazate, halofenozide, hexaflumuron, hexythiazox, hydramethylnon, imidacloprid, indoxacarb, insecticidal soaps, isofenphos, lufenuron, malathion, meperfluthrin, metaflumizone, metaldehyde, methamidophos, methidathion, methiodicarb, methomyl, methoprene, methoxychlor, metofluthrin, monocrotophos, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, silafluofen, spinetoram, spinosad, spirodiclofen, spiromesifen, spirotetramat, sulprofos, sulfoxaflor, tebufenozide, tebufenpyrad, teflubenzuron, tefluthrin, terbufos, tetrachlorvinphos, tetramethrin, tetramethylfluthrin, thiacloprid, thiamethoxam, thiodicarb, thiosultap-sodium, tolfenpyrad, tralomethrin, triazamate, trichlorfon, triflumuron, *Bacillus thuringiensis* delta-endotoxins, entomopathogenic bacteria, entomopathogenic viruses and entomopathogenic fungi.

9. A method for controlling an invertebrate pest comprising contacting the invertebrate pest or its environment with a biologically effective amount of a compound of claim 1.

* * * * *